United States Patent
Medina et al.

(10) Patent No.: US 7,053,215 B2
(45) Date of Patent: May 30, 2006

(54) SUBSTITUTED QUINAZOLIN-4(3H)-ONE COMPOUNDS, COMPOSITIONS, AND METHODS FOR THEIR USE

(75) Inventors: Julio C. Medina, San Carlos, CA (US); Michael G. Johnson, San Francisco, CA (US); An-Rong Li, So. San Francisco, CA (US); Jiwen Liu, Belmont, CA (US); Alan Xi Huang, San Mateo, CA (US); Liusheng Zhu, Burlingame, CA (US); Andrew P. Marcus, San Francisco, CA (US)

(73) Assignee: Amgen SF, LLC, South San Francisco, CA (US)

( * ) Notice: Subject to any disclaimer, the term of this patent is extended or adjusted under 35 U.S.C. 154(b) by 54 days.

(21) Appl. No.: 10/231,895

(22) Filed: Aug. 29, 2002

(65) Prior Publication Data

US 2003/0055054 A1    Mar. 20, 2003

Related U.S. Application Data

(63) Continuation of application No. 10/015,532, filed on Dec. 11, 2001.

(60) Provisional application No. 60/296,499, filed on Jun. 6, 2001, provisional application No. 60/255,241, filed on Dec. 11, 2000.

(51) Int. Cl.
*C07D 403/12* (2006.01)
*A61K 31/517* (2006.01)

(52) U.S. Cl. ............... 544/284; 514/266.2; 514/266.23

(58) Field of Classification Search ............. 514/266.2, 514/266.23; 544/284
See application file for complete search history.

(56) References Cited

U.S. PATENT DOCUMENTS

| 5,202,322 A | 4/1993 | Allen et al. |
| 5,256,667 A | 10/1993 | Allen et al. |
| 5,719,144 A | 2/1998 | Hartman et al. |
| 5,756,502 A | 5/1998 | Padia |

(Continued)

FOREIGN PATENT DOCUMENTS

EP        0 481 614 A1    4/1992

(Continued)

OTHER PUBLICATIONS

Hawley, Gessner, "The Condensed Chemical Dictonary", 1977, Van Nostrand, New York, p. 480.*

(Continued)

*Primary Examiner*—Thomas C. McKenzie
(74) *Attorney, Agent, or Firm*—Jones Day

(57) ABSTRACT

Compounds are provided that have the formula:

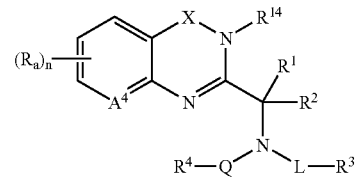

where X, $A^4$, $R_a$, $R^1$, $R^2$, $R^3$, $R^4$, $R^{14}$, L and Q are as described herein. These compounds are useful, for example, as modulators of a chemokine receptor and for treatment of inflammatory and immunoregulatory disorders and diseases. Pharmaceutical compositions and methods of using these compounds for the treatment of inflammatory and immunoregulatory disorders and diseases, such as multiple sclerosis, rheumatoid arthritis and type I diabetes, are also provided.

18 Claims, 12 Drawing Sheets

U.S. PATENT DOCUMENTS

| | | | |
|---|---|---|---|
| 5,869,665 | A | 2/1999 | Padia |
| 5,908,930 | A | 6/1999 | Dow |
| 6,140,064 | A | 10/2000 | Loetscher et al. |
| 6,545,005 | B1 | 4/2003 | Baxter et al. |
| 6,605,632 | B1 | 8/2003 | Lesieur et al. |
| 6,794,379 | B1 | 9/2004 | Medina et al. |
| 2002/0169159 | A1 | 11/2002 | Medina et al. |
| 2003/0134843 | A1 | 7/2003 | Lubisch et al. |

FOREIGN PATENT DOCUMENTS

| | | |
|---|---|---|
| WO | WO 92/01675 | 2/1992 |
| WO | WO9958495 | 11/1995 |
| WO | WO 97/04775 A1 | 2/1997 |
| WO | WO 98/13350 A1 | 4/1998 |
| WO | WO 98/26664 | 6/1998 |
| WO | WO 01 16114 A | 3/2001 |
| WO | WO 01/16114 A2 | 3/2001 |
| WO | WO 01/16114 A3 | 3/2001 |
| WO | WO 01/19800 A2 | 3/2001 |
| WO | WO 01/19800 A3 | 3/2001 |
| WO | WO 01/30768 | 5/2001 |
| WO | WO 01 30768 A | 5/2001 |
| WO | WO 01 62758 A | 8/2001 |
| WO | WO01057038 | 8/2001 |
| WO | WO 01 77087 A | 10/2001 |
| WO | WO 01/98278 A | 12/2001 |
| WO | WO 01/98278 A1 | 12/2001 |
| WO | WO02028831 | 4/2002 |

OTHER PUBLICATIONS

Wolff, Manfred E. "Burger's Medicinal Chemistry, 5ed, Part 1", John Wiley & Sons, 1995, pp. 975-977.*

Banker, G.S. et al, "Modern Pharmaceutics, 3ed.", Marcel Dekker, New York, 1996, p. 596.*

Carter, Percy H., Curr. Opin. Chem. Biol., 6, 2002, pp. 510-525.*

Onuffer, J.J. et al, TRENDS in Pharm. Sci., 23, 2002, pp. 459-467.*

Proudfoot, A.E.I. et al, Sem. Immun., vol. 15, 2003, pp. 57-65.*

Balashov et al., 1999 "CCR5$^+$ and CXCR3$^+$ T Cells are Increased in Multiple Sclerosis and Their Ligands MIP-1α and IP-10 are Expressed in Demyelinating Brain Lesions," Proc. Natl. Acad. Sci. USA, 96:6873-78.

Hancock et al., 2000 "Requirement of the Chemokine Receptor CXCR3 for Acute Allograft Rejection," J. Exp. Med., 192(10):1515-19.

Qin et al., 1998 "The Chemokine Receptors CXCR3 and CCR5 Mark Subsets of T Cells Associated with Certain Inflammatory Reactions," J. Clin. Invest. 101(4): 746-54.

Rabin et al., 1999 "Chemokine Receptor Responses on T Cells Achieved Through Regulation of Both Receptor Expression and Signaling," *The Journal of Immunology*, 162: 3840-50.

Bowdish et al. 2003 "Evaluation of An Oral CXCR3 Antagonist in a Rat Model of the Acute Allograft Rejection", *The Journal of the Heart and Lung Association* vol. 22 Supplement 1 p. S162.

Cecil's Textbook of Medicine, 20$^{th}$ Edition, vol. 1 (a996), pp. 1004-1010 (1996).

Cecil's Textbook of Medicine, 20$^{th}$ Edition, vol. 2, pp. 1992-1996 (1996).

Chabrier et al. Pubmed Abstract 10442086, also cited as Cell. Mol. Life Sci. 55/8-9 1029-35 (1999).

Chiang et al., Pubmed Abstract 12898413, also cited as Planta Med., 69/7, 600-4, (2003).

J.T. Coyle et al., 1983 Science 219, 1184-90.

Fife et al., 2001 "CXCL10 (IFN-γ-Inducible Protein-10) Control of Encephalitogenic CD4$^+$ T Cell Accumulation in the Central Nervous System During Experimental Autoimmune Encephalomyelitis", J. Immunol. 166: 7617-7624.

Goldbeerg et al., 2001 Pubmed Abstract 11437993, also cited as Neuropathol. Appl. Neurobiol. 27/2, 127-38.

Hancock et al., 2001 "Donor-Derived IP-10 Initiates Development of Acute Allograft Rejection", J. Exp. Med. 193: 975-980.

Liu et al., 2001 "Neutralization of the Chemokine CXCL10 Reduces Inflammatory Cell Invasion and Demyelination and Improves Neurological Function in a Viral Model of Multiple Sclerosis", J. Immunol. 167: 4091-4097.

Melter et al., 2001"Expression of the Chemokine Receptor CXCR3 and Its Ligand IP-10 During Cardiac Allograft Rejection", *Circulation* 104: 2558-2564.

Rottman et al., 2001 "Potential Role of the Chemokine Receptors CXCR3, CCR4, and the Integrin αEβ7 in the Pathogenesis of Psoriasis Vulgaris", *Lab Invest.* 81(3): 335-347.

Ruschpler et al., 2003 "Hign CXCR3 Expression in nSynovial Mast Cells Associated with CXCL9 and CXCL10 Expression in Inflammatory Synovial Tissues of Patients with Rheumatoid Arthritis", *Arthritis Res. Ther.* 5:R241-R252.

Sasaki et al., Nov. 2002 "Blockade of CXCL10 Protects Mice From Acute Colitis and Enhances Crypt Cell Survival", *Eur. J. Immunol.* 32:3197-31205.

Sorensen et al., 1999 "Expression of Specific Chemokines and Chemokine Receptors in the Central Nervous System of Multiple Sclerosis Patients", J. Clinical Invest. 103: 807-815.

Uckun et al., 2001 "Structure Based Design of Novel Anticancer Agents", Current Cancer Drug Targets, 1, 59-71.

Zhao et al., 2002 Pubmed Abstract 121133984, also cited as J. Immunol., 169/3 1556-60.

Padia, J.K. et al., "Design and synthesis of novel nonpeptide CCK-B receptor antagonists," Bioorganic & Medicinal Chemistry Letters, Oxford, GB, vol. 7, No. 7, Apr. 8, 1997, pp. 805-810.

* cited by examiner (a) DMF, RT (b) AcO$_2$, 118-130°C (c) i. CHCl$_3$, 80°C; ii. cat. NaOH, ethylene glycol, 130°C
(d) Br$_2$, NaOAc, HOAc, 40°C (e) EtOH, 80°C (f) NEt$_3$, cat. DMAP, 1,4-dioxane a Et$_2$Zn, AlCl3, CH2Cl2, -30°C- rt. b R'substituted-o-aminobenzaledehyde, 33% KOH, EtOH. c Br$_2$, NaOAc, HOAc. d EtOH, 80°C.

a. P(OPh)$_3$, pyridine, 55 °C, 14 h; b. R$^{III}$ substituted aniline, 55 °C, 1h;
c. TMSI, MeCN, 25 °C, 1 h; d. KI, K$_2$CO$_3$, DMPU; e. EDC, HOBT, CH$_2$Cl$_2$.
A$^4$=C or N

Scheme for the generic synthesis of benzimidazoles a $K_2CO_3$, DMF, 125°C, 16h.  b $H_2$, Pd/C, rt.  c D-Boc-Ala-OH, EDC, HOBt, NMM, DMF.
d HOAc, 90°C.  e 4M HCl in dioxane, EtOAc, rt.  f $NaBH_3CN$, MeOH, rt.  g Bop-Cl, $Et_3N$, THF, rt.

Part A

Part B

Ref. Nielsen, F.E.; Pedersen, E.B. Tetrahedron, 1982, 38, a. P(OPh)₃, pyridine, 80°C; b. p-Ethoxyaniline, 50°C; c. TFA, DCM; d. 3-Pyridylcarboxaldehyde, NEt₃, MgSO₄, DCM; e. 3-Fluoro-4-trifluoromethylphenylacetic acid, BOP-Cl.

a. NEt₃, DCM; b. EtOH, 90°C; c. BOP-Cl, DMF.

a. HCl (gas), EtOH; b. NH$_3$, EtOH; c. TBDMSCl, Imidazole, DMF; d. K$_2$CO$_3$, DMF, 50°C; e. HCl (conc.), EtOH; f. MnO$_2$, DCM.

R = OMe, COOEt, CN, 2-pyridyl a. CF$_3$CH$_2$CH$_2$I, K$_2$CO$_3$, DMF, 50°C; b. LiOH, H$_2$O; c. BOP-Cl, NEt$_3$.

a. iBuOCOCl, NEt$_3$, -20°C; b. iBuOCOCl, NEt$_3$, 0°C; c. TFA, DCM; d. 3-Pyridylcarboxaldehyde, NaBH(OAc)$_3$; e. 4-Fluoro-3-trifluoromethylphenylacetic acid, BOP-Cl, NEt$_3$.

FIGURE 19

Table

CXCR3 binding assay IC50≥10μM=X; 10μM>IC50≥1μM=XX; IC50<1μM=XXX

| Compound | IC50 |
|---|---|
| 1.01 | XX |
| 1.02 | XXX |
| 1.03 | XXX |
| 1.04 | XX |
| 1.05 | XXX |
| 1.06 | X |
| 1.07 | XXX |
| 1.08 | XXX |
| 1.09 | X |
| 1.1 | XXX |
| 1.11 | X |
| 1.12 | XX |
| 1.13 | XX |
| 1.14 | XX |
| 1.15 | XX |
| 1.16 | XXX |
| 1.17 | XXX |
| 1.18 | XXX |
| 1.19 | XXX |
| 1.2 | XX |
| 1.21 | XXX |
| 1.22 | XXX |
| 1.23 | XXX |
| 1.24 | XXX |
| 1.25 | XXX |
| 1.26 | XXX |
| 1.27 | XXX |
| 1.28 | XX |
| 1.29 | XXX |
| 1.3 | XXX |
| 1.31 | XX |
| 1.32 | XXX |
| 1.33 | XX |
| 1.34 | XXX |
| 1.35 | XX |
| 1.36 | XX |
| 1.37 | XX |
| 1.38 | XX |
| 1.39 | XXX |
| 1.4 | XX |
| 1.42 | XX |
| 1.43 | XXX |
| 1.44 | X |
| 1.45 | X |

| Compound | IC50 |
|---|---|
| 1.47 | XX |
| 1.48 | XXX |
| 1.49 | XXX |
| 1.5 | XX |
| 1.51 | X |
| 1.53 | XXX |
| 1.54 | XXX |
| 1.55 | X |
| 2.01 | XXX |
| 2.02 | XXX |
| 2.03 | XX |
| 2.04 | XX |
| 2.05 | XXX |
| 2.06 | XXX |
| 2.07 | XXX |
| 2.08 | XXX |
| 2.09 | XXX |
| 2.1 | XXX |
| 2.11 | XXX |
| 2.12 | XXX |
| 3.01 | XXX |
| 3.02 | XXX |
| 3.03 | XXX |
| 3.04 | XXX |
| 3.05 | XXX |
| 3.06 | XXX |
| 3.07 | XXX |
| 3.08 | XXX |
| 3.09 | XXX |
| 3.1 | XXX |
| 3.11 | XXX |
| 3.12 | XXX |
| 3.13 | XXX |
| 3.14 | XXX |
| 3.15 | XX |
| 3.16 | X |

| Compound | IC50 |
|---|---|
| 4.01 | XXX |
| 4.03 | X |
| 5.01 | X |
| 6.01 | XXX |
| 6.02 | XX |
| 7.01 | XX |
| 8.01 | X |
| 9.01 | XXX |
| 9.02 | XXX |
| 9.03 | XXX |
| 9.04 | XXX |
| 9.05 | XXX |
| 9.06 | XXX |
| 9.07 | XXX |
| 9.08 | XXX |
| 9.09 | X |
| 9.10 | |
| 10.01 | XXX |
| 10.02 | XX |
| 10.03 | XXX |
| 10.04 | XXX |
| 10.05 | XXX |

SUBSTITUTED QUINAZOLIN-4(3H)-ONE COMPOUNDS, COMPOSITIONS, AND METHODS FOR THEIR USE

CROSS-REFERENCES TO RELATED APPLICATIONS

This application is a continuation of U.S. patent application Ser. No. 10/015,532 filed Dec. 11, 2001, which claims the benefit of U.S. Provisional Application Nos. 60/255,241, filed Dec. 11, 2000 and Ser. No. 60/296,499 filed Jun. 6, 2001, which are each incorporated by reference herein in their entirety.

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine,* 3:165–183 (1991), Schall, et al., *Curr. Opin. Immunol.,* 6:865–873 (1994) and Murphy, *Rev. Immun.,* 12:593–633 (1994)). In addition to stimulating chemotaxis, other changes can be selectively induced by chemokines in responsive cells, including changes in cell shape, transient rises in the concentration of intracellular free calcium ions ($[Ca^{2+}]_i$), granule exocytosis, integrin upregulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

There are four classes of chemokines, CXC ($\alpha$), CC ($\beta$), C($\gamma$), and CX$_3$C ($\delta$), depending on whether the first two cysteines are separated by a single amino acid (C—X—C), are adjacent (C—C), have a missing cysteine pair (C), or are seperated by three amino acids (CXC$_3$). The $\alpha$-chemokines, such as interleukin-8 (IL-8), melanoma growth stimulatory activity protein (MGSA), and stromal cell derived factor 1 (SDF-1) are chemotactic primarily for neutrophils and lymphocytes, whereas $\beta$-chemokines, such as RANTES, MIP-1$\alpha$, MIP-1$\beta$, monocyte chemotactic protein-1 (MCP-1), MCP-2, MCP-3 and eotaxin are chemotactic for macrophages, T-cells, eosinophils and basophils (Deng, et al., *Nature,* 381:661–666 (1996)). The C chemokine lymphotactin shows specificity for lymphocytes (Kelner, et al., *Science,* 266:1395–1399 (1994)) while the CX$_3$C chemokine fractalkine shows specificity for lymphocytes and monocytes (Bazan, et al., *Nature,* 385:640–644 (1997).

Chemokines bind specific cell-surface receptors belonging to the family of G-protein-coupled seven-transmembrane-domain proteins (reviewed in Horuk, *Trends Pharm. Sci.,* 15:159–165 (1994)) termed "chemokine receptors." On binding their cognate ligands, chemokine receptors transduce an intracellular signal through the associated heterotrimeric G protein, resulting in a rapid increase in intracellular calcium concentration. There are at least twelve human chemokine receptors that bind or respond to $\beta$-chemokines with the following characteristic pattern: CCR1 (or "CKR-1" or "CC-CKR-1") MIP-1$\alpha$, MIP-1$\beta$, MCP-3, RANTES (Ben-Barruch, et al., *J. Biol. Chem.,* 270:22123–22128 (1995); Neote, et al., *Cell,* 72:415–425 (1993)); CCR2A and CCR2B (or "CKR-2A"/"CKR-2A" or "CC-CKR-2A"/"CC-CKR2A") MCP-1, MCP-3, MCP-4; CCR3 (or "CKR-3" or "CC-CKR-3") eotaxin, RANTES, MCP; (Ponath, et al., *J. Exp. Med.,* 183:2437–2448 (1996)); CCR4 (or "CKR4" or "CC-CKR-4") TARC, MDC (Imai, et al.,. *J. Biol. Chem.,* 273:1764–1768 (1998)); CCR5 (or "CKR-5" or "CC-CKR-5") MIP-1$\alpha$, RANTES, MIP-1$\beta$ (Sanson, et al., *Biochemistry,* 35:3362–3367 (1996)); CCR6 MIP-3 alpha (Greaves, et al., *J. Exp. Med.,* 186:837–844 (1997)); CCR7 MIP-3 beta and 6Ckine (Campbell, et al., *J. Cell. Biol.,* 141:1053–1059 (1998)); CCR8 I-309, HHV8 vMIP-I, HHV-8 vMIP-II, MCV vMCC-I (Dairaghi, et al., *J. Biol. Chem.,* 274:21569–21574 (1999)); CCR9 TECK (Zaballos, et al., *J. Immunol.,* 162:5671–5675 (1999)), D6 MIP-1 beta, RANTES, and MCP-3 (Nibbs, et al., *J. Biol. Chem.,* 272: 32078–32083 (1997)), and the Duffy blood-group antigen RANTES, MCP-1 (Chaudhun, et al., *J. Biol. Chem.,* 269: 7835–7838 (1994)).

Chemokine receptors, such as CCR1, CCR2, CCR2A, CCR2B, CCR3, CCR4, CCR5, CCR6, CCR7, CCR8, CCR9, CXCR1, CXCR2, CXCR3, CXCR4, CXCR5, CX$_3$CR1, and XCR1 have been implicated as being important mediators of inflammatory and immunoregulatory disorders and diseases, including asthma and allergic diseases, as well as autoimmune pathologies such as rheumatoid arthritis and atherosclerosis.

The CXCR3 chemokine receptor is expressed primarily in T lymphocytes, and its functional activity can be measured by cytosolic calcium elevation or chemotaxis. The receptor was previously referred to as GPR9 or CKR-L2. Its chromosomal location is unusual among the chemokine receptors in being localized to Xq13. Ligands that have been identified that are selective and of high affinity are the CXC chemokines, IP10, MIG and ITAC.

The highly selective expression of CXCR3 makes it an ideal target for intervention to interrupt inappropriate T cell trafficking. The clinical indications for such intervention are in T-cell mediated autoimmune diseases such as multiple sclerosis, rheumatoid arthritis, and type I diabetes. Inappropriate T-cell infiltration also occurs in psoriasis and other pathogenic skin inflammation conditions, although the diseases may not be true autoimmune disorders. In this regard, up-regulation of IP-10 expression in keratinocytes is a common feature in cutaneous immunopathologies. Inhibition of CXCR3 can be beneficial in reducing rejection in organ transplantation. Ectopic expression of CXCR3 in certain tumors, especially subsets of B cell malignancies indicate that selective inhibitors of CXCR3 will have value in tumor immunotherapy, particularly attenuation of metastasis.

In view of the clinical importance of CXCR3, the identification of compounds that modulate CXCR3 function represents an attractive avenue into the development of new therapeutic agents. Such compounds are provided herein.

SUMMARY OF THE INVENTION

The present invention provides compounds which are useful in the treatment or prevention of certain inflammatory and immunoregulatory disorders and diseases, including asthma and allergic diseases, as well as autoimmune pathologies such as rheumatoid arthritis and atherosclerosis. The compounds provided herein have the general formula (I):

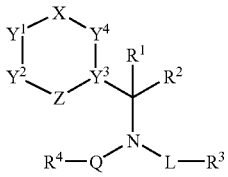

I wherein X represents a bond, —C(O)—, —C(R⁵)(R⁶)—, —C(R⁵)═, —S(O)—, —S(O)₂— or —N═; Z represents a bond, —N═, —O—, —S—, —N(R¹⁷)— or —C(R⁷)═, with the proviso that X and Z are not both a bond; L represents a bond, C(O)—(C₁–C₈)alkylene, (C₁–C₈)alkylene or (C₂–C₈)heteroalkylene, Q represents a bond, (C₁–C₈)alkylene, (C₂–C₈)heteroalkylene, —C(O)—, —OC(O)—, —N(⁸)C(O)—, —CH₂CO—, —CH₂SO— or —CH₂SO₂—, and optionally L and Q can be linked together to form a 5- or 6-membered heterocyclic group having from 1 to 3 heteroatoms. The symbols R¹ and R² independently represent H, (C₁–C₈)alkyl, (C₂–C₈)heteroalkyl, aryl or heteroaryl, or optionally are combined to form a 3 to 8-membered ring having from 0 to 2 heteroatoms as ring vertices, and optionally R² and L can be linked together to form a 5- or 6-membered heterocyclic group having from 1 to 4 heteroatoms. The symbol R³ represents hydroxy, (C₁–C₈) alkoxy, amino, (C₁–C₈)alkylamino, di(C₁–C₈)alkylamino, (C₂–C₈)heteroalkyl, (C₃–C₈)heterocyclyl, (C₁–C₈)acylamino, amidino, guanidino, ureido, cyano, heteroaryl, —CONR⁹R¹⁰ or —CO₂R¹¹. The symbol R⁴ represents (C₁–C₂₀)alkyl, (C₂–C₂₀)heteroalkyl, heteroaryl, aryl, heteroaryl(C₁–C₆)alkyl, heteroaryl(C₂–C₆)heteroalkyl, aryl(C₁–C₆)alkyl or aryl(C₂–C₆)heteroalkyl. The symbols R⁵ and R⁶ independently represent H, (C₁–C₈)alkyl, (C₂–C₈)heteroalkyl, heteroaryl or aryl, or optionally R⁵ and R⁶ are combined to form a 3- to 7-membered ring. The symbols R⁷ and R⁸ independently represent H, (C₁–C₈)alkyl, (C₂–C₈)heteroalkyl, heteroaryl or aryl. The symbols R⁹, R¹⁰ and R¹¹ each independently represent H, (C₁–C₈)alkyl, (C₂–C₈)heteroalkyl, heteroaryl, aryl, heteroaryl(C₁–C₆)alkyl, heteroaryl(C₂–C₈)heteroalkyl, aryl(C₁–C₈)alkyl or aryl(C₂–C₈)heteroalkyl.

Turning next to the ring vertices, Y¹, Y², Y³ and Y⁴, the symbols Y¹ and Y² independently represent —C(R¹²)═, —N═, —O—, —S—, or —N(R¹³)—. The symbol Y³ represents N or C wherein the carbon atom shares a double bond with either Z or Y⁴; and Y⁴ represents —N(R¹⁴)—, —C(R¹⁴)═, —N═ or —N(R¹⁴)—C(R¹⁵)(R¹⁶)—. In the above groups, the symbol R¹² represents H, halogen, hydroxy, amino, alkylamino, dialkylamino, (C₁–C₈)alkyl, (C₂–C₈)heteroalkyl, heteroaryl and aryl, or optionally when Y¹ and Y² are both —C(R¹²)═ the two R¹² groups can be combined to form a substituted or unsubstituted 5- to 6-membered cycloalkyl, heterocycloalkyl, aryl or heteroaryl ring; or optionally when Y¹ is —C(R¹²)═ and X is —C(R⁵)═ or —C(R⁵)(R⁶)—, R¹² and R⁵ can be combined to form a substituted or unsubstituted 5- to 6-membered cycloalkyl, heterocycloalkyl, aryl or heteroaryl ring. Additionally, the symbol R¹³ represents H, (C₁–C₈)alkyl, (C₂–C₈)heteroalkyl, heteroaryl, aryl, heteroaryl(C₁–C₆)alkyl, heteroaryl(C₂–C₈)heteroalkyl, aryl(C₁–C₈)alkyl or aryl(C₂–C₈)heteroalkyl. The symbol R¹⁴ represents (C₁–C₈)alkyl, (C₂–C₈)heteroalkyl, aryl(C₁–C₈)alkyl, aryl(C₂–C₈)heteroalkyl, heteroaryl(C₁–C₈)alkyl, heteroaryl(C₂–C₈)heteroalkyl, heteroalkyl, heteroaryl and aryl; R¹⁵ and R¹⁶ are independently selected from H, (C₁–C₈)alkyl and (C₂–C₈)heteroalkyl; and R¹⁷ is selected from H, (C₁–C₈)alkyl, (C₂–C₈)heteroalkyl, heteroaryl, aryl, heteroaryl(C₁–C₆)alkyl, heteroaryl(C₂–C₈)heteroalkyl, aryl(C₁–C₈)alkyl and aryl(C₂–C₈)heteroalkyl, or optionally when Y² is —C(R¹²)═ or —N(R¹³)—, R¹⁷ can be combined with R¹² or R¹³ to form a substituted or unsubstituted 5- to 6-membered cycloalkyl, heterocycloalkyl, aryl or heteroaryl ring; with the proviso that when the Y³-containing ring system is a quinazolinone or quinolinone ring system, and R⁴-Q- is substituted or unsubstituted (C₅–C₁₅)alkyl, then R³-L- is other than substituted or unsubstituted (C₂–C₈)alkylene or a substituted or unsubstituted (C₂–C₈)heteroalkylene attached to —NR'R", wherein R' and R" are independently selected from the group consisting of hydrogen and (C₁–C₈)alkyl, or optionally are combined with the nitrogen atom to which each is attached to form a 5-, 6- or 7-membered ring.

Unless otherwise indicated, the compounds provided in the above formula are meant to include pharmaceutically acceptable salts and prodrugs thereof.

The present invention also provides pharmaceutical compositions comprising a compound of formula I and a pharmaceutically acceptable excipient or carrier.

The present invention further provides methods for the treatment or prevention of an inflammatory or inmmune condition or disorder, comprising administering to a subject in need of such treatment or prevention a therapeutically effective amount of a compound of formula I.

The present invention also provides methods for the treatment or prevention of a condition or disorder mediated by the CXCR3 chemokine receptor, comprising administering to a subject in need of such treatment or prevention a therapeutically effective amount of a compound of formula I.

The present invention also provides methods for the modulation of CXCR3, comprising contacting a cell with a compound of formula I.

The present invention further provides methods for the modulation of CXCR3, comprising contacting a CXCR3 protein with a compound of formula I.

BRIEF DESCRIPTION OF THE DRAWINGS

FIG. 19 provides a table showing the CXCR3 antagonist activity for exemplary compounds of the invention.

DETAILED DESCRIPTION OF THE INVENTION

Definitions

Figure 1:
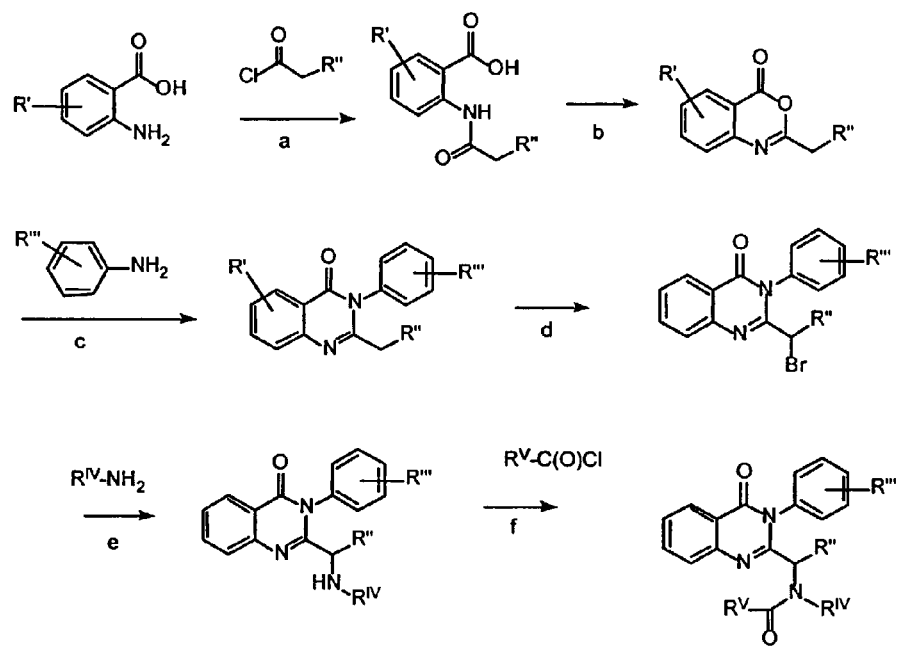
FIG. 1 illustrates a general synthesis scheme for racemic substituted quinazolinones of the invention.
Figure 2:
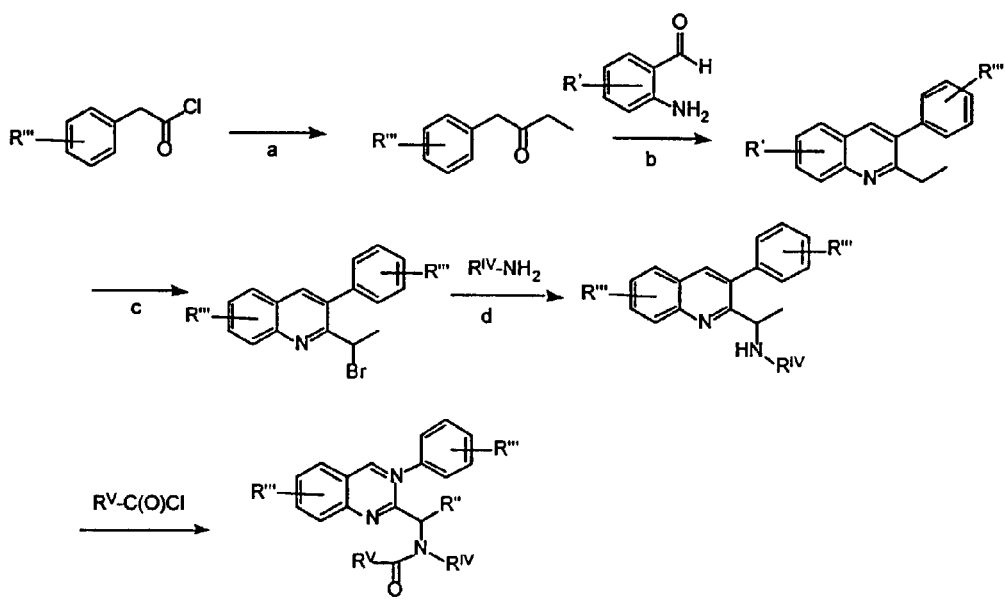
FIG. 2 illustrates the generic synthesis of substituted quinolines of the invention.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$–$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms, or more.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Similarly, the term dialkylamino refers to an amino group having two attached alkyl groups that can be the same or different.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. When a prefix such as ($C_2$–$C_8$) is used to refer to a heteroalkyl group, the number of carbons (2–8, in this example) is meant to include the heteroatoms as well. For example, a $C_2$-heteroalkyl group is meant to include, for example, —$CH_2OH$ (one carbon atom and one heteroatom replacing a carbon atom) and —$CH_2SH$. The term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo ($C_1$–$C_4$)alkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl4oxazolyl, 5-oxazolyl, 3-isoxazolyl, 4-isoxazolyl, 5-isoxazolyl, 2-thiazolyl, 4-thiazolyl, 5-thiazolyl, 2-fuiryl, 3-furyl, 2-thienyl, 3-thienyl, 2-pyridyl, 3-pryridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, allynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2m'+1), where m' is the total number of carbon atoms in such radical. R', R" and R"' each independently refer to H, unsubstituted ($C_1$–$C_8$)alkyl and heteroalkyl, unsubstituted aryl, aryl substituted with 1–3 halogens, alkoxy or thioalkoxy groups, or aryl-($C_1$–$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" in its broadest sense is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). Preferably, the alkyl groups will have from 0–3 substituents, more preferably 0, 1, or 2 substituents, unless otherwise specified.

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R"', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro($C_1$–$C_4$)alkoxy, and perfluoro($C_1$–$C_4$)alkyl, in a number ranging from zero to the total number of open valences on the aromatic ring system; and where R', R" and R"' are independently selected from H, ($C_1$–$C_8$)alkyl and heteroalkyl, unsubstituted aryl and heteroaryl, (unsubstituted aryl)-($C_1$–$C_4$)alkyl, and (unsubstituted aryl)oxy-($C_1$–$C_4$)alkyl.

Two of the substituents on adjacent atoms of the aryl or heteroaryl ring may optionally be replaced with a substituent of the formula -T-C(O)—(CH$_2$)q—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$–$C_6$)alkyl.

As used herein, the term "heteroatom" is meant to include oxygen (O), nitrogen (N), sulfuir (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, et al. (1977) *J. Pharm. Sci.* 66:1–19). Certain specific compounds of the present invention contain both basic and acidic functionalities that allow the compounds to be converted into either base or acid addition salts.

(1) The terms "treat", "treating" or "treatment", as used herein, refer to a method of alleviating or abrogating a disease and/or its attendant symptoms. The terms "prevent", "preventing" or "prevention", as used herein, refer to a method of barring a subject from acquiring a disease.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one, or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabled compounds are useful as therapeutic agents, e.g., cancer therapeutic agents, research reagents, e.g., binding assay reagents, and diagnostic agents, e.g., in vivo imaging agents. All isotopic variations of the compounds of the present invention, whether radioactive or not, are intended to be encompassed within the scope of the present invention.

EMBODIMENTS OF THE INVENTION

The present invention is directed to compounds, compositions and methods useful in the modulation of chemokine receptor activity, particularly CXCR3. Accordingly, the compounds of the present invention are those which inhibit at least one function or characteristic of a mammalian CXCR3 protein, for example, a human CXCR3 protein. The ability of a compound to inhibit such a function can be demonstrated in a binding assay (e.g., ligand binding or agonist binding), a signalling assay (e.g., activation of a mammalian G protein, induction of rapid and transient increase in the concentration of cytosolic free calcium), and/or cellular response function (e.g., stimulation of chemotaxis, exocytosis or inflammatory mediator release by leukocytes).

Compounds

The present invention provides compounds that are useful as antagonists of CXCR3, having particular utility for the treatment or prevention of inflammation. The compounds provided herein have the general formula (I):

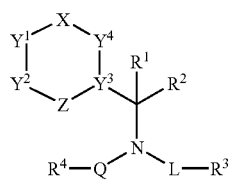

I wherein X represents a bond, —C(O)—, —C(R$^5$)(R$^6$)—, —C(R$^5$)═, —S(O)—, —S(O)$_2$— or —N═; Z represents a bond, —N═, —O—, —S—, —N(R$^{17}$)— or —C(R$^7$)═, with the proviso that X and Z are not both a bond; L represents a bond, C(O)—(C$_1$–C$_8$)alkylene, (C$_1$–C$_8$)alkylene or (C$_2$–C$_8$)heteroalkylene; Q represents a bond, (C$_1$–C$_8$)alkylene, (C$_2$–C$_8$)heteroalkylene, —C(O)—, —OC (O)—, —N(R$^8$)C(O)—, —CH$_2$CO—, —CH$_2$SO—, or —CH$_2$SO$_2$—; and optionally L and Q can be linked together to form a 5- or 6-membered heterocyclic group having from 1 to 3 heteroatoms. The symbols R$^1$ and R$^2$ independently represent H, (C$_1$–C$_8$)alkyl, (C$_2$–C$_8$)heteroalkyl, aryl or heteroaryl, or optionally are combined to form a 3 to 8-membered ring having from 0 to 2 heteroatoms as ring vertices, and optionally R$^2$ can be linked together with L to form a 5- or 6-membered heterocyclic group having from 1 to 4 heteroatoms. The symbol R$^3$ represents hydroxy, (C$_1$–C$_8$) alkoxy, amino, (C$_1$–C$_8$)alkylamino, di(C$_1$–C$_8$)alkylamino, (C$_2$–C$_8$)heteroalkyl, (C$_3$–C$_9$)heterocyclyl, (C$_1$–C$_8$)acylamino, amidino, guanidino, ureido, cyano, heteroaryl, —CONR$^9$R$^{10}$ or —CO$_2$R$^{11}$. The symbol R$^4$ represents (C$_1$–C$_{20}$)alkyl, (C$_2$–C$_{20}$)heteroalkyl, heteroaryl, aryl, heteroaryl(C$_1$–C$_6$)alkyl, heteroaryl(C$_2$–C$_6$)heteroalkyl, aryl (C$_1$–C$_6$)alkyl or aryl(C$_2$–C$_6$)heteroalkyl. The symbols R$^5$ and R$^6$ independently represent H, (C$_1$–C$_8$)alkyl, (C$_2$–C$_8$) heteroalkyl, heteroaryl or aryl, or optionally R$^5$ and R$^6$ are combined to form a 3- to 7-membered ring. The symbols R$^7$ and R$^8$ independently represent H, (C$_1$–C$_8$)alkyl, (C$_2$–C$_8$) heteroalkyl, heteroaryl or aryl. The symbols R$^9$, R$^{10}$ and R$^{11}$ each independently represent H, (C$_1$–C$_8$)alkyl, (C$_2$–C$_8$)heteroalkyl, heteroaryl, aryl, heteroaryl(C$_1$–C$_6$)alkyl, heteroaryl(C$_2$–C$_8$)heteroalkyl, aryl(C$_1$–C$_8$)alkyl or aryl(C$_2$–C$_8$) heteroalkyl.

Turning next to the ring vertices, Y$^1$, Y$^2$, Y$^3$ and Y$_4$, the symbols Y$^1$ and Y$^2$ independently represent —C(R$^{12}$)═, —N═, —O—, —S—, or —N(R$^{13}$)—. The symbol Y$^3$ represents N or C wherein the carbon atom shares a double bond with either Z or Y$^4$; and Y$^4$ represents —N(R$^{14}$)—, —C(R$^{14}$)═, —N═ or —N(R$^{14}$)—C(R$^{15}$)(R$^{16}$)—. In the above groups, the symbol R$^{12}$ represents H, halogen, hydroxy, amino, alkylamino, dialkylamino, (C$_1$–C$_8$)alkyl, (C$_2$–C$_8$)heteroalkyl, heteroaryl and aryl, or optionally when Y$^1$ and Y$^2$ are both —C(R$^{12}$)═ the two R$^{12}$ groups can be combined to form a substituted or unsubstituted 5- to 6-membered cycloalkyl, heterocycloalkyl, aryl or heteroaryl ring; or optionally when Y$^1$ is —C(R$^{12}$)═ and X is —C(R$^5$)═ or —C(R$^5$)(R$^6$)—, R$^{12}$ and R$^5$ can be combined to form a substituted or unsubstituted 5- to 6-membered cycloalkyl, heterocycloalkyl, aryl or heteroaryl ring. Additionally, the symbol R$^{13}$ represents H, (C$_1$–C$_8$)alkyl, (C$_2$–C$_8$)heteroalkyl, heteroaryl, aryl, heteroaryl(C$_1$–C$_6$) alkyl, heteroaryl(C$_2$–C$_8$)heteroalkyl, aryl(C$_1$–C$_8$)alkyl or aryl(C$_2$–C$_8$)heteroalkyl. The symbol R$^{14}$ represents (C$_1$–C$_8$) alkyl, (C$_2$–C$_8$)heteroalkyl, aryl(C$_1$–C$_8$)alkyl, aryl(C$_2$–C$_8$) heteroalkyl, heteroaryl(C$_1$–C$_8$)alkyl, heteroaryl(C$_2$–C$_8$)heteroalkyl, heteroaryl and aryl; R$^{15}$ and R$^{16}$ are independently selected from H, (C$_1$–C$_8$)alkyl and (C$_2$–C$_8$)heteroalkyl; and R$^{17}$ is selected from H, (C$_1$–C$_8$)alkyl, (C$_2$–C$_8$)heteroalkyl, heteroaryl, aryl, heteroaryl(C$_1$–C$_6$)alkyl, heteroaryl(C$_2$–C$_8$) heteroalkyl, aryl(C$_1$–C$_8$)alkyl and aryl(C$_2$–C$_8$)heteroalkyl, or optionally when Y$^2$ is —C(R$^{12}$)═ or —N(R$^{13}$)—, R$^{17}$ can be combined with R$^{12}$ or R$^{13}$ to form a substituted or unsubstituted 5- to 6-membered cycloalkyl, heterocycloalkyl, aryl or heteroaryl ring; with the proviso that when the Y$^3$-containing ring system is a quinazolinone or quinolinone ring system, and R$^4$-Q- is substituted or unsubstituted (C$_5$–C$_{15}$)alkyl, then R$^3$-L- is other than substituted or unsubstituted (C$_2$–C$_8$)alkylene or a substituted or unsubstituted (C$_2$–C$_8$)heteroalkylene attached to —NR'R", wherein R' and R" are independently selected from the group consisting of hydrogen and $(C_1-C_8)$alkyl, or optionally are combined with the nitrogen atom to which each is attached to form a 5-, 6- or 7-membered ring.

Embodiments represented by the above formula can be appreciated by replacing the ring system having vertices X, Z, $Y^1$, $Y^2$, $Y^3$ and $Y^4$ with an appropriate scaffold wherein the attachment points represent the attachment of a $R^{14}$ group and the carbon atom that bears the $R^1$ and $R^2$ groups:

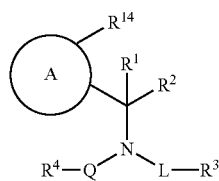

For example, the ring system or "scaffold" is meant to include the following (including substituted versions thereof) wherein the "A" ring is selected from those embodiments shown as:

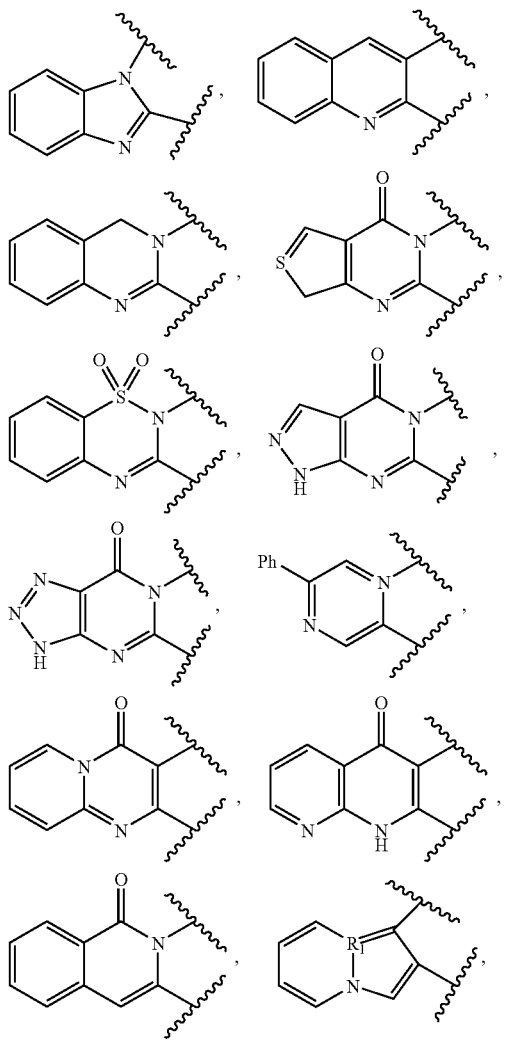

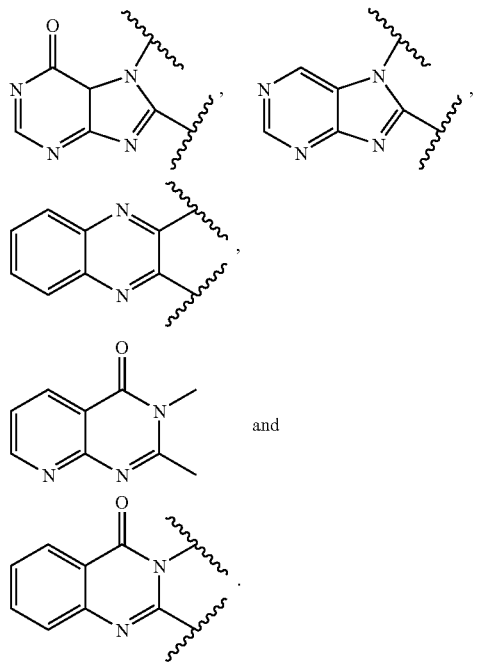

Still other A ring scaffolds are six-membered rings (without additional fused rings) and include:

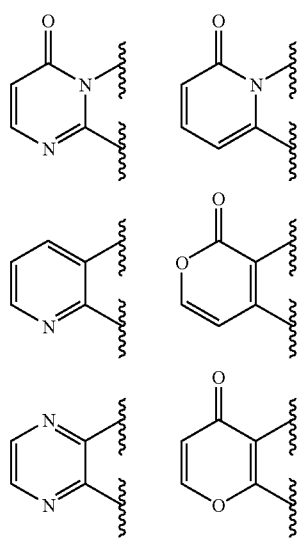

In other embodiments, the A ring scaffolds are five-membered rings (without additional fused rings) and include, for example:

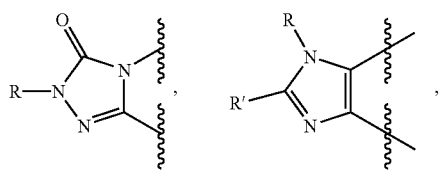

-continued

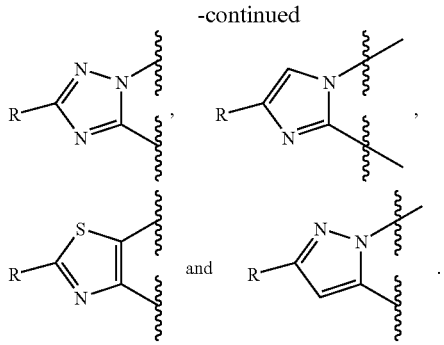

Typically, the ring substituents (shown as R and R' groups in the above five-membered rings, but not shown in the fused ring sets or six-membered rings above) are designed to provide electronic and/or additional hydrophobic or hydrophilic character to the molecule to bring the overall physical characters into conformity with those of the most preferred compounds in the series (see Examples).

Within each of the above groups of embodiments, $R^{14}$ is preferably a substituted or unsubstituted aryl group or a substituted or unsubstituted heteroaryl group. More preferably, the aryl or heteroaryl groups will have from 0 to 3 substituents. Still more preferably, 1 or 2 substituents. The aryl and heteroaryl groups are preferably selected from phenyl, substituted phenyl, pyridyl, substituted pyridyl, thiazolyl, substituted thiazolyl, pyrimidinyl, substituted pyrimidinyl, thienyl and substituted thienyl. For those embodiments having one substituent, the substituent will preferably be in a position para to the point of attachment to the heterocyclic scaffolding. In the most preferred embodiments, the substituents are selected from cyano, halogen, $(C_1–C_8)$alkoxy, $(C_1–C_8)$alkyl, $(C_2–C_8)$heteroalkyl, $CONH_2$, methylenedioxy and ethylenedioxy.

Returning to formula I, in one group of preferred embodiments, X is —C(O)—. In another group, Z is —N═. In still another group of preferred embodiments, $Y^1$ and $Y^2$ are each —C($R^{12}$)═, wherein the two $R^{12}$ groups are combined to form a fused 6-membered aryl or heteroaryl ring. Particularly preferred, are those embodiments that combine each of these preferred groups. Accordingly, in one group of particularly preferred embodiments, X is —C(O)—; Z is —N═; $Y^3$ is C; and $Y^1$ and $Y^2$ are each —C($R^{12}$)═ wherein the two $R^{12}$ groups are combined to form a fused 6-membered substituted or unsubstituted aryl or heteroaryl ring.

In other separate, but preferred embodiments, L is $(C_1–C_8)$alkylene; Q is —C(O)—, $R^4$ is $(C_5–C_{15})$alkyl, substituted or unsubstituted phenyl, or biphenyl; $R^3$ is $(C_1–C_8)$ alkoxy, $(C_1–C_8)$alkylamino, di$(C_1–C_8)$alkylamino, $(C_2–C_8)$ heteroalkyl, $(C_3–C_9)$heterocyclyl, $(C_1–C_8)$acylamino, cyano, heteroaryl, —CONR$^9$R$^{10}$ or —CO$_2$R$^{11}$; $R^1$ and $R^2$ are each independently H or $(C_1–C_4)$alkyl; $Y^3$ is C and the carbon atom shares a double bond with Z; and the $Y^3$-containing ring system is selected from quinoline, quinazoline, naphthalene, quinolinone, quinazolinone, triazolinone, pyrimidin-4-one, benzimidazole, thiazole, imidazole, pyridine, pyrazine and benzodiazepine.

Still other preferred embodiments can be defined according to the A ring scaffolding. For example, one group of preferred embodiments are those in which X is —C(O)—; Z is —N═; $Y^3$ is C; and $Y^1$ and $Y^2$ are each —C($R^{12}$)═. More preferably, the two $R^{12}$ groups are combined to form a fused 6-membered substituted or unsubstituted aryl or heteroaryl ring. Particularly preferred are those embodiments in which $Y^4$ is —N($R^{14}$)— or —C($R^{14}$)═ wherein the $R^{14}$ group is a substituted or unsubstituted aryl or heteroaryl. In another group of preferred embodiments, X is —C($R^5$)($R^6$)—; $Y^4$ is —N($R^{14}$)—, wherein $R^{14}$ is substituted or unsubstituted aryl or heteroaryl; $Y^3$ is C; Z is —N═; and $Y^1$ and $Y^2$ are each —C($R^{12}$)═. In another group of preferred embodiments, X is —C($R^5$)═; $Y^4$ is —C($R^{14}$)═, wherein $R^{14}$ is substituted or unsubstituted aryl or heteroaryl; $Y^3$ is C; Z is —N═; and $Y^1$ and $Y^2$ are each —C($R^{12}$)═. In another group of preferred embodiments, X is a bond; $Y^4$ is —N($R^{14}$)—, wherein $R^{14}$ is substituted or unsubstituted aryl or heteroaryl; $Y^3$ is C; Z is —N═; and $Y^1$ and $Y^2$ are each —C($R^{12}$)═. In another group of preferred embodiments, X is —C($R^5$)═; $Y^4$ is —C($R^{14}$)═, wherein $R^{14}$ is substituted or unsubstituted aryl or heteroaryl; $Y^3$ is C; Z is —C($R^7$)═; and $Y^1$ and $Y^2$ are each —C($R^{12}$)═. In another group of preferred embodiments, X is a bond; Z is —N═ or —N($R^{17}$)—; $Y^4$ is —C($R^{14}$)═, wherein $R^{14}$ is substituted or unsubstituted aryl or heteroaryl; $Y^1$ is selected from the group consisting of —O—, —S— and —N($R^{13}$)—; and $Y^2$ is —C($R^{12}$)═. In this group of embodiments, further preferred are those compounds in which $Y^1$ is —O— and Z is —N═; compounds in which $Y^1$ is —S— and Z is —N═; and compounds in which $Y^1$ is —N($R^{13}$)— and Z is —N═. In another group of preferred embodiments, X is —SO$_2$—; $Y^4$ is —N($R^{14}$)═, wherein $R^{14}$ is substituted or unsubstituted aryl or heteroaryl; $Y^3$ is C; Z is —N═ or —C($^7$)═; and $Y^1$ and $Y^2$ are each —C($R^{12}$). In another group of preferred embodiments, X is a bond; Z is —O—, —S— or —N($R^{17}$)—; $Y^1$ is —N═ or —N($R^{13}$)—; $Y^2$ is —C($R^{12}$)═; and $Y^4$ is —C($R^{14}$)═ wherein $R^{14}$ is substituted or unsubstituted aryl or heteroaryl. Particularly preferred embodiments in this group are those in which $Y^1$ is —N═ and Z is —O—; those in which $Y^1$ is —N═ and Z is —S—; and those in which Z is —N($R^{17}$)—. In another group of preferred embodiments, X is a bond; $Y^1$ is —N($R^{13}$)— or ═N—; $Y^2$ is —C($R^{12}$)═; $Y^3$ is C; $Y^4$ is —C($R^{14}$)═ wherein $R^{14}$ is substituted or unsubstituted aryl or heteroaryl; and Z is —N($R^{17}$)— or ═N—, with the proviso that $Y^1$ and Z are not both ═N—. In another group of preferred embodiments, X is a bond; $Y^1$ and $Y^2$ are each independently —C($R^{12}$)═; $Y^3$ is C; $Y^4$ is —C($R^{14}$)═ wherein $R^{14}$ is substituted or unsubstituted aryl or heteroaryl; and Z is —N($R^{17}$)—, O or S. More preferably, the two $R^{12}$ groups are combined to form a fused 5- or 6-membered substituted or unsubstituted aryl or heteroaryl ring. In another group of preferred embodiments, X is —C(O)—; $Y^1$ is —N($R^{13}$)—; $Y^2$ is —N═; $Y^3$ is C; $Y^4$ is —N($R^{14}$)— wherein $R^{14}$ is substituted or unsubstituted aryl or heteroaryl; and Z is a bond. In another group of preferred embodiments, X is —C(O)—; Z is —N($R^{17}$)— wherein $R^{17}$ is substituted or unsubstituted aryl or heteroaryl; $Y^1$ and $Y^2$ are each independently —C($R^{12}$)═; $Y^3$ is C; and $Y^4$ is —N═. In another group of preferred embodiments, X and Z are —N═, $Y^1$ and $Y^2$ are each independently —C($R^{12}$)═; $Y^3$ is C; and $Y^4$ is —C($R^{14}$)═ wherein $R^{14}$ is a substituted or unsubstituted aryl or heteroaryl group. In another group of preferred embodiments, wherein X is —C(O)—; $Y^4$ is —N($R^{14}$)—C($R^5$)($R^6$)—; wherein $R^{14}$ is substituted or unsubstituted aryl or heteroaryl; $Y^1$ and $Y^2$ are each independently —C($R^{12}$)═; $Y^3$ is C; and Z is —N═.

In each of the above groups of preferred embodiments, $R^1$ is most preferably H.

In one particularly preferred group of embodiments, the A ring is a fused 6,6 or 6,5-member ring system having the indicated nitrogen vertices (see formula II).

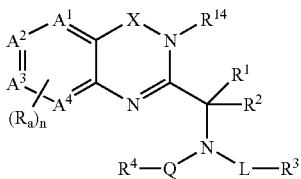

In formula II, each of $A^1$, $A^2$, $A^3$ and $A^4$ is independently C or N. Preferably, no more than two of $A^1$–$A^4$ are N. Additionally, X is —CO—, —CH$_2$— or a bond; $R^1$ and $R^2$ are each independently H or (C$_1$–C$_4$)alkyl; $R^{14}$ is a substituted or unsubstituted phenyl, pyridyl, thiazolyl, thienyl or pyrimidinyl group; Q is —CO—; L is (C$_1$–C$_8$)alkylene; the subscript n is an integer of from 0 to 4; and each R$_a$ is independently selected from halogen, —OR', —OC(O)R', —NR'R'', —SR', —R', —CN, —NO$_2$, —CO$_2$R', —CONR'R'', —C(O)R', —OC(O)NR'R'', —NR''C(O)R', —NR''C(O)$_2$R', —NR'—C(O)NR''R''', —NH—C(NH$_2$)=NH, —NR'C(NH$_2$)=NH, —NHC(NH$_2$)=NR', —S(O)R', —S(O)$_2$R', —S(O)$_2$NR'R'', —N$_3$, —CH(Ph)$_2$, perfluoro(C$_1$–C$_4$)alkoxy, and perfluoro(C$_1$–C$_4$)alkyl, wherein R', R'' and R''' are each independently selected from H, (C$_1$–C$_8$) alkyl, (C$_2$–C$_8$)heteroalkyl, unsubstituted aryl, unsubstituted heteroaryl, (unsubstituted aryl)-(C$_1$–C$_4$)alkyl, and (unsubstituted aryl)oxy-(C$_1$–C$_4$)alkyl. The remaining symbols, $R^3$ and $R^4$, have the meanings (and preferred groupings) provided above.

Still more preferably, the compound has the formula (III):

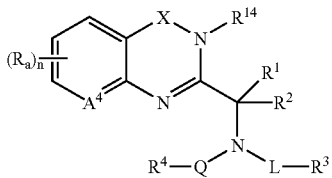

wherein $A^4$ is C or N; X is —CO—, —CH$_2$— or a bond; $R^1$ and $R^2$ are each independently H or (C$_1$–C$_4$)alkyl; $R^{14}$ is a substituted or unsubstituted phenyl, pyridyl, thiazolyl, thienyl or pyrimidinyl group; Q is —CO—; L is (C$_1$–C$_8$) alkylene; the subscript n is an integer of from 0 to 4; and each R$_a$ is independently selected from the group consisting of halogen, —OR', —OC(O)R', —NR'R'', —SR', —R', —CN, —NO$_2$, —CO$_2$R', —CONR'R'', —C(O)R', —OC(O)NR'R'', —NR''C(O)R', —NR''C(O)$_2$R', —NR'—C(O)NR''R''', —NH—C(NH$_2$)=NH, —NR'C(NH$_2$)=NH, —NHC(NH$_2$)=NR', —S(O)R', —S(O)$_2$R', —S(O)$_2$NR'R'', —N$_3$, —CH(Ph)$_2$, perfluoro(C$_1$–C$_4$)alkoxy, and perfluoro(C$_1$–C$_4$)alkyl, wherein R', R'' and R''' are each independently selected from H, (C$_1$–C$_8$)alkyl, (C$_2$–C$_8$)heteroalkyl, unsubstituted aryl, unsubstituted heteroaryl, (unsubstituted aryl)-(C$_1$–C$_4$)alkyl, and (unsubstituted aryl)oxy-(C$_1$–C$_4$)alkyl. The remaining symbols, $R^3$ and $R^4$, have the meanings (and preferred groupings) provided above.

In one group of preferred embodiments, X is —CO—. In another group of preferred embodiments, X is —CH$_2$—. In yet another group of preferred embodiments, X is a bond.

Further preferred compounds of formula III are those in which $R^1$ is methyl, ethyl or propyl and $R^2$ is hydrogen or methyl. More preferably, $R^1$ and $R^2$ are each methyl. Still other preferred compounds of formula III are those in which $R^3$ is selected from substituted or unsubstituted pyridyl or substituted or unsubstituted imidazolyl. Also preferred are those compounds of formula III in which $R^4$ is a substituted or unsubstituted benzyl group, wherein the substituents are selected from halogen, halo(C$_1$–C$_4$)alkyl, halo(C$_1$–C$_4$) alkoxy, cyano, nitro, and phenyl. A preferred group for L is (C$_1$–C$_4$)alkylene. Also preferred are those compounds of formula III in which $R^{14}$ is selected from substituted phenyl, substituted pyridyl, substituted thiazolyl and substituted thienyl, wherein the substituents are selected from cyano, halogen, (C$_1$–C$_8$)alkoxy, (C$_1$–C$_8$)alkyl, (C$_2$–C$_8$)heteroalkyl, CONH$_2$, methylenedioxy and ethylenedioxy. Still further preferred are those compounds that combine two or more of the preferred groups listed above.

In particularly preferred embodiments for compounds of formula III, X is —CO—; $R^1$ and $R^2$ are each independently selected from the group consisting of H, methyl and ethyl; $R^{14}$ is selected from the group consisting of substituted or unsubstituted phenyl; Q is —CO—; L is methylene, ethylene or propylene, $R^3$ is selected from the group consisting of substituted or unsubstituted pyridyl and substituted or unsubstituted imidazolyl; $R^4$ is substituted or unsubstituted benzyl, wherein said substituents are selected from the group consisting of halogen, halo(C$_1$–C$_4$)alkyl, halo(C$_1$–C$_4$) alkoxy, cyano, nitro, and phenyl; and each R$_a$ is selected from the group consisting of halogen, —OR', —OC(O)R', —NR'R'', —SR', —R', —CN, —NO$_2$, —CO$_2$R', —CONR'R'', —C(O)R', —NR''C(O)R', —NR'—C(O)NR''R''', perfluoro(C$_1$–C$_4$)alkoxy, and perfluoro(C$_1$–C$_4$) alkyl, wherein R', R' and R'''' are each independently selected from the group consisting of H, (C$_1$–C$_8$)alkyl, (C$_2$–C$_8$)heteroalkyl, unsubstituted aryl, unsubstituted heteroaryl, (unsubstituted aryl)-(C$_1$–C$_4$)alkyl, and (unsubstituted aryl)oxy-(C$_1$–C$_4$)alkyl.

Exemplary structures within this preferred group of embodiments are:

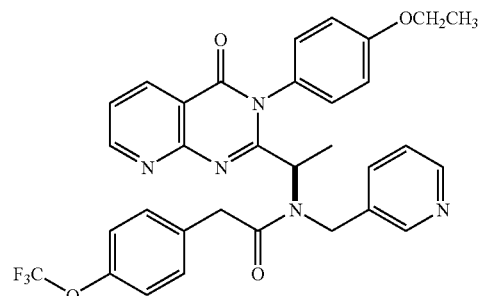

3.16a

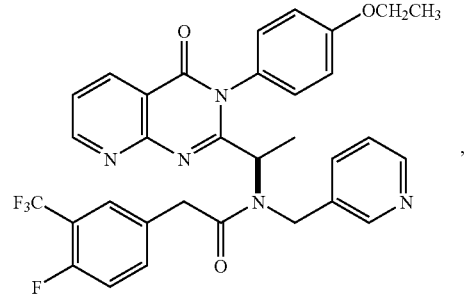

3.16b

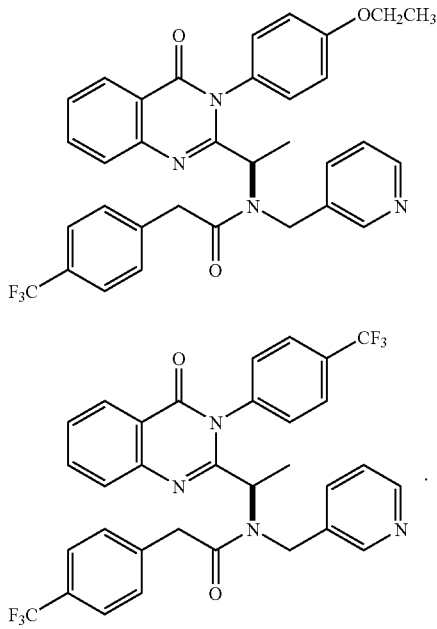

Preparation of the Compounds

FIGS. 1–18 provide a variety of synthesis routes to the compounds provided herein. One of skill in the art will appreciate that the substituents (e.g., R', R'', R''', $R^{iv}$, etc.) can be altered before, during or after preparation of the heterocyclic scaffolding and that suitable adjustments in the exemplary conditions (e.g., temperatures, solvents, etc.) can be made. Additionally, one of skill in the art will recognize that protecting groups may be necessary for the preparation of certain compounds and will be aware of those conditions compatible with a selected protecting group.

The exemplary methods and the examples described herein are illustrative of the present invention and are not be construed as limiting the scope thereof Compositions In another aspect, the present invention provides pharmaceutical compositions for modulating chemokine receptor activity in humans and animals. The compositions comprise a compound of the present invention with a pharmaceutically acceptable carrier or diluent.

"Modulation" or modulating of chemokine receptor activity, as used herein in its various forms, is intended to encompass antagonism, agonism, partial antagonism and/or partial agonism of the activity associated with a particular chemokine receptor, preferably the CXCR3 receptor. The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,166,452 and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphafide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. As used herein, topical application is also meant to include the use of mouth washes and gargles.

The pharmaceutical composition and method of the present invention may further comprise other therapeutically active compounds as noted herein which are usually applied in the treatment or prevention of the above mentioned pathological conditions.

Methods of Use

In yet another aspect, the present invention provides methods of treating CXCR3-mediated conditions or diseases by administering to a subject having such a disease or condition, a therapeutically effective amount of a compound or composition of the invention. The "subject" is defined herein to include animals such as mammals, including, but not limited to, primates (e.g., humans), cows, sheep, goats, horses, dogs, cats, rabbits, rats, mice and the like.

As used herein, the phrase "CXCR3-mediated condition or disease" and related phrases and terms refer to a condition characterized by inappropriate, e.g., less than or greater than normal, CXCR3 activity. Inappropriate CXCR3 activity might arise as the result of CXCR3 expression in cells which normally do not express CXCR3, increased CXCR3 expression (leading to, e.g., inflammatory and immunoregulatory disorders and diseases), or, decreased CXCR3 expression (leading to, e.g., certain cancers and angiogenic and vasculogenic-related disorders). Inappropriate CXCR3 functional activity might arise as the result of CXCR3 expression in cells which normally do not express CXCR3, increased CXCR3 expression (leading to, e.g., inflammatory and immunoregulatory disorders and diseases) or decreased CXCR3 expression. Inappropriate CXCR3 functional activity might also arise as the result of chemokine secretion by cells which normally do not secrete a CXC chemokine, increased chemokine expression (leading to, e.g., inflammatory and immunoregulatory disorders and diseases) or decreased chemokine expression. A CXCR3-mediated condition or disease may be completely or partially mediated by inappropriate CXCR3 functional activity. However, a CXCR3 -mediated condition or disease is one in which modulation of CXCR3 results in some effect on the underlying condition or disease (e.g., a.CXCR3 antagonist results in some improvement in patient well-being in at least some patients).

The term "therapeutically effective amount" means the amount of the subject compound that will elicit the biological or medical response of a tissue, system, animal or human that is being sought by the researcher, veterinarian, medical doctor or other clinician or that is sufficient to prevent development of or alleviate to some extent one or more of the symptoms of the disease being treated.

Diseases and conditions associated with inflammation, infection and cancer can be treated with the present compounds and compositions. In one group of embodiments, diseases or conditions, including chronic diseases, of humans or other species can be treated with inhibitors of CXCR3 function. These diseases or conditions include: (1) inflammatory or allergic diseases such as systemic anaphylaxis or hypersensitivity responses, drug allergies, insect sting allergies and food allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis; spondyloarthropathies; scleroderma; asthma and respiratory allergic diseases such as allergic rhinitis, hypersensitivity lung diseases, and the like, (2) autoimmune diseases, such as arthritis (rheumatoid and psoriatic), multiple sclerosis, systemic lupus erythematosus, type I diabetes, glomerulonephritis, and the like, (3) graft rejection (including allograft rejection and graft-v-host disease) and conditions associated therewith, and (4) other diseases in which undesired inflammatory responses are to be inhibited, e.g., atherosclerosis, myositis, neurodegenerative diseases (e.g., Alzheimer's disease), encephalitis, meningitis, hepatitis, nephritis, sepsis, sarcoidosis, conjunctivitis, otitis, chronic obstructive pulmonary disease, sinusitis and Behcet's syndrome. In another group of embodiments, diseases or conditions are treated with agonists of CXCR3 function. Examples of diseases to be treated with CXCR3 agonists include cancers, diseases in which angiogenesis or neovascularization play a role (neoplastic diseases, retinopathy and macular degeneration), infectious diseases and immunosuppressive diseases.

Preferably, the present methods are directed to the treatment or prevention of diseases or conditions selected from neurodegenerative diseases (e.g., Alzheimer's disease), multiple sclerosis, systemic lupus erythematosus, rheumatoid arthritis, atherosclerosis, encephalitis, meningitis, hepatitis, nephritis, sepsis, sarcoidosis, psoriasis, eczema, uticaria, type I diabetes, asthma, conjunctivitis, otitis, allergic rhinitis, chronic obstructive pulmonary disease, sinusitis, dermatitis, inflammatory bowel disease, ulcerative colitis, Crohn's disease, Behcet's syndrome, gout, cancer, viral infections (e.g., HIV), bacterial infections, and organ transplant conditions or skin transplant conditions. The term "organ transplant conditions" is meant to include bone marrow transplant conditions and solid organ (e.g., kidney, liver, lung, heart, pancreas or combination thereof) transplant conditions.

Diseases or conditions that can be treated with the present compounds and compositions include diseases commonly associated with (1) inflammatory or allergic diseases, (2) autoimmune diseases, (3) graft rejection and (4) other diseases in which undesired inflammatory responses are to be inhibited, as described above. For example, restenosis following a procedure such as balloon angioplasty, is commonly associated with atherosclerosis and can be treated with the present compounds and compositions.

Depending on the disease to be treated and the subject's condition, the compounds of the present invention may be administered by oral, parenteral (e.g., intramuscular, intraperitoneal, intravenous, ICV, intracistemal injection or infusion, subcutaneous injection, or implant), inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the present invention can be combined with other compounds having related utilities to treat or prevent inflammatory and immune disorders and diseases, including asthma and allergic diseases, as well as autoimmune pathologies such as rheumatoid arthritis and atherosclerosis, and those pathologies noted above. In many instances, compositions which include a compound of the invention and an alternative or second therapeutic agent have additive or synergistic effects when administered.

For example, in the treatment or prevention of inflammation, the present compounds may be used in conjunction or combination with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antitussive such as codeine, hydrocodone, caramiphen, carbetapentane, or dextromethorphan; a diuretic; and a sedating or non-sedating antihistamine. Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists, (b) steroids such as beclomethasone, methylprednisolone, betamethasone, prednisone, dexamethasone, and hydrocortisone; (c) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as .beta.2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors such as celecoxib (Celebrex®) and rofecoxib (Vioxx®); (h) inhibitors of phosphodiesterase type IV (PDE-IV); (i) gold compounds such as auranofin and aurothioglucose, (j) inhibitors of phosphodiesterase type IV (PDE-IV); (k) other antagonists of the chemokine receptors, especially CCR1, CCR2, CCR3, CCR5, CCR6, CCR8 and CCR10; (l) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (m) anti-diabetic agents such as insulin, sulfonylureas, biguanides (metformin), α-glucosidase inhibitors (acarbose) and glitazones (troglitazone and pioglitazone); (n) preparations of interferon beta (interferon β-1 α, interferon β-1 β); (o) etanercept (Enbrel®), (p) antibody therapies such as orthoclone (OKT3), daclizumab (Zenapax®), infliximab (Remicade®), basiliximnab (Simulect®) and anti-CD40 ligand antibodies (e.g., MRP-1); and (q) other compounds such as 5-aminosalicylic acid and prodrugs thereof, hydroxychloroquine, D-penicillamine, antimetabolites such as azathioprene and 6-mercaptopurine, and cytotoxic cancer chemotherapeutic agents. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Immunosuppressants within the scope of the present invention further include, but are not limited to, leflunomide, RAD001, ERL080, FTY720, CTLA-4, antibody therapies such as orthoclone (OKT3), daclizumab (Zenapax®) and basiliximab (Simulect®), and antithymocyte globulins such as thymoglobulins.

In particularly preferred embodiments, the present methods are directed to the treatment or prevention of multiple sclerosis using a compound of the invention either alone or in combination with a second therapeutic agent selected from betaseron, avonex, azathioprene (Imurek®, Imuran®), capoxone, prednisolone and cyclophosphamide. When used in combination, the practitioner can administer a combination of the therapeutic agents, or administration can be sequential.

In still other particularly preferred embodiments, the present methods are directed to the treatment or prevention of rheumatoid arthritis, wherein the compound of the invention is administered either alone or in combination with a second therapeutic agent selected from the group consisting of methotrexate, sulfasalazine, hydroxychloroquine, cyclosporine A, D-penicillamine, infliximab (Remicade®), etanercept (Enbrel®), auranofin and aurothioglucose.

In yet other particularly preferred embodiments, the present methods are directed to the treatment or prevention of an organ transplant condition wherein the compound of the invention is used alone or in combination with a second therapeutic agent selected from the group consisting of cyclosporine A, FK-506, rapamycin, mycophenolate, prednisolone, azathioprene, cyclophosphamide and an antilymphocyte globulin.

In yet another aspect, the present invention includes methods to evaluate putative specific agonists or antagonists of CXCR3 function. Accordingly, the present invention is directed to the use of these compounds in the preparation and execution of screening assays for compounds which modulate the activity of the CXCR3 chemokine receptor. For example, the compounds of this invention are useful for isolating receptor mutants, which are excellent screening tools for more potent compounds. Furthermore, the compounds of this invention are useful in establishing or determining the binding site of other compounds to the CXCR3 chemokine receptor, e.g., by competitive inhibition. The compounds of the instant invention are also useful for the evaluation of putative specific modulators of the CXCR3 chemokine receptor, relative to other chemokine receptors including CCR1, CCR2, CCR2A, CCR2B, CCR3, CCR4, CCR5, CCR6, CCR8, CCR10, CXCR3 and CXCR4,. One of skill in the art will appreciate that thorough evaluation of specific agonists and antagonists of the above chemokine receptors has been hampered by the lack of availability of non-peptidyl (metabolically resistant) compounds with high binding affinity for these receptors. Thus the compounds provided herein are particularly useful in this context. Combinatorial libraries of putative CXCR3 agonists or antagonists can be screened for pharmacological activity in in vitro or in vivo assays. Conventionally, new chemical entities with useful properties are generated by identifying a chemical compound (called a "lead compound") with some desirable property or activity, e.g., CXCR3 chemokine receptor modulation activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of potential therapeutic compounds (candidate compounds). Such "combinatorial chemical libraries" are then screened in one or more assays to identify those library members (particular chemical species or subclasses) that display a desired characteristic activity. The compounds thus identified can serve conventional "lead compounds" or can themselves be used as potential or actual therapeutics.

A combinatorial chemical library is a collection of diverse chemical compounds generated by either chemical synthesis or biological synthesis by combining a number of chemical "building blocks" such as reagents. For example, a linear combinatorial chemical library, such as a polypeptide (e.g., mutein) library, is formed by combining a set of chemical building blocks called amino acids in every possible way for a given compound length (i.e., the number of amino acids in a polypeptide compound). Millions of chemical compounds can be synthesized through such combinatorial mixing of chemical building blocks (Gallop et. al. (1994) *J. Med. Chem.* 37(9):1233–1251).

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.* 37:487–493, Houghton et. al. (1991) *Nature* 354: 84–88), peptoid libraries (PCT Publication No WO 91/19735), encoded peptide libraries (PCT Publication WO 93/20242), random bio-oligomer libraries (PCT Publication WO 92/00091), benzodiazepine libraries (U.S. Pat. No. 5,288,514), libraries of diversomers, such as hydantoins, benzodiazepines and dipeptides (Hobbs et. al. (1993) *Proc. Nat. Acad. Sci. USA* 90:6909–6913), vinylogous polypeptide libraries (Hagihara et al. (1992) *J. Amer. Chem. Soc.* 114:6568), libraries of nonpeptidyl peptidomimetics with a Beta-D-Glucose scaffolding (Hirschmann et al. (1992) *J. Amer. Chem. Soc.* 114:9217–9218), analogous organic syntheses of small compound libraries (Chen et. al. (1994) *J. Am. Chem. Soc.* 116:2661), oligocarbamate libraries (Cho et al. (1993) *Science* 261:1303) and/or peptidyl phosphonate libraries (Campbell et al. (1994) *J. Org. Chem.* 59:658). See, generally, Gordon et al. (1994) *J. Med. Chem.* 37:1385–1401, nucleic acid libraries (see, e.g., Stratagene Corp.), peptide nucleic acid libraries (see, e.g., U.S. Pat. No. 5,539,083), antibody libraries (see, e.g., Vaughn et. al. (1996) *Nature Biotechnology* 14(3):309–314), and PCT/US96/10287), carbohydrate libraries (see, e.g., Liang et al. (1996) *Science* 274:1520–1522, and U.S. Pat. No. 5,593,853), and small organic molecule libraries (see, e.g., benzodiazepines, Baum (1993) *C&EN* January 18, page 33; isoprenoids, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514; and the like).

Devices for the preparation of combinatorial libraries are commercially available (see, e.g., 357 MPS, 390 MPS, Advanced Chem Tech, Louisville Ky.; Symphony, Rainin, Woburn Mass.; 433A Applied Biosystems, Foster City Calif.; 9050 Plus, Millipore, Bedford, Mass.).

A number of well known robotic systems have also been developed for solution phase chemistries. These systems includes automated workstations like the automated synthesis apparatus developed by Takeda Chemical Industries, LTD. (Osaka, Japan) and many robotic systems utilizing robotic arms (Zymate II, Zymark Corporation, Hopkinton Mass.; Orca, Hewlett-Packard, Palo Alto Calif.), which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see e.g., ComGenex, Princeton N.J.; Asinex, Moscow, Russia; Tripos, Inc., St. Louis Mo.; ChemStar, Ltd, Moscow, Russia; 3D Pharmaceuticals, Exton Pa.; Martek Biosciences, Columbia Md.; etc.).

High throughput assays for the presence, absence, quantification, or other properties of particular compounds may be used to test a combinatorial library that contains a large number of potential therapeutic, compounds (potential modulator compounds). The assays are typically designed to screen large chemical libraries by automating the assay steps and providing compounds from any convenient source to assays, which are typically run in parallel (e.g., in microtiter formats on microtiter plates in robotic assays). Preferred assays detect enhancement or inhibition of CXCR3 receptor function.

High throughput screening systems are commercially available (see e.g., Zymark Corp., Hopkinton Mass.; Air Technical Industries, Mentor Ohio; Beckman Instruments, Inc., Fullerton Calif.; Precision Systems, Inc., Natick Mass.; etc.). These systems typically automate entire procedures, including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

EXAMPLES

Reagents and solvents used below can be obtained from commercial sources such as Aldrich Chemical Co. (Milwaukee, Wis., USA). $^1$H-NMR spectra were recorded on a Varian Gemini 400 MHz NMR spectrometer. Significant peaks are tabulated in the order: number of protons, multiplicity (s, singlet; d, doublet; t, triplet; q, quartet; m, multiplet; br s, broad singlet) and coupling constant(s) in Hertz (Hz). Electron Ionization (EI) mass spectra were recorded on a Hewlett Packard 5989A mass spectrometer. Mass spectrometry results are reported as the ratio of mass over charge, followed by the relative abundance of each ion (in parentheses). In tables, a single mn/e value is reported for the M+H (or, as noted, M–H) ion containing the most common atomic isotopes. Isotope patterns correspond to the expected formula in all cases. Electrospray ionization (ESI) mass spectrometry analysis was conducted on a Hewlett-Packard 1100 MSD electrospray mass spectrometer using the HP1 1100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using 1:1 acetonitrile/water with 1% acetic acid as the delivery solvent. The compounds provided below could also be analyzed in the negative ESI mode, using 2 mM $NH_4OAc$ in acetonitrile/water as delivery solvent.

Example 1

Synthesis of Compound 1.01

The synthesis of compound 1.01 in six steps from commercially available anthinllic acid provides an example of 3H-quinazolin4-one synthesis by Method 1. Scheme 1 provides an overview of the synthetic route, for which the experimental details follow.

Scheme 1

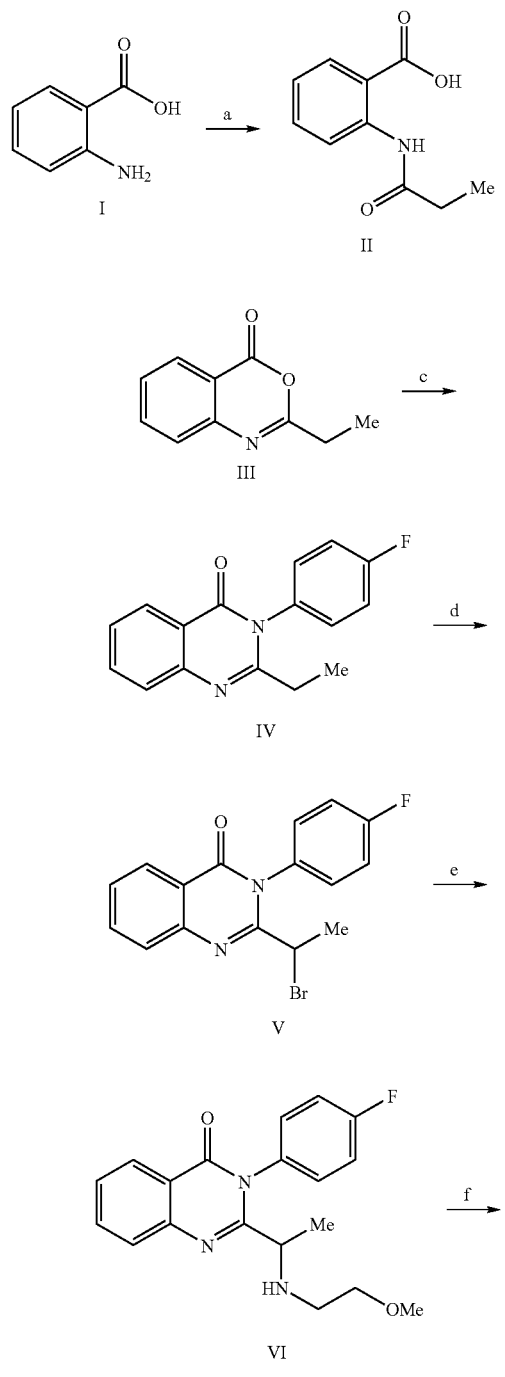

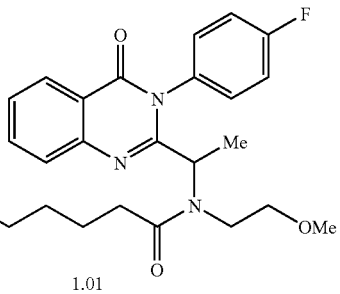

1.01

(a) propionyl chloride, DMF, RT
(b) AcO$_2$, 118–130° C.
(c) i. 4-fluoroaniline, CHCl$_3$, 80° C.; ii, cat. NaOH, ethylene glycol, 130° C.
(d) Br$_2$, NaOAc, HOAc, 40° C.
(e) 1-amino-2-ethoxyethane, EtOH, 80° C.
(f) decanoyl chloride, NEt$_3$, cat. DMAP, 1,4-dioxane.

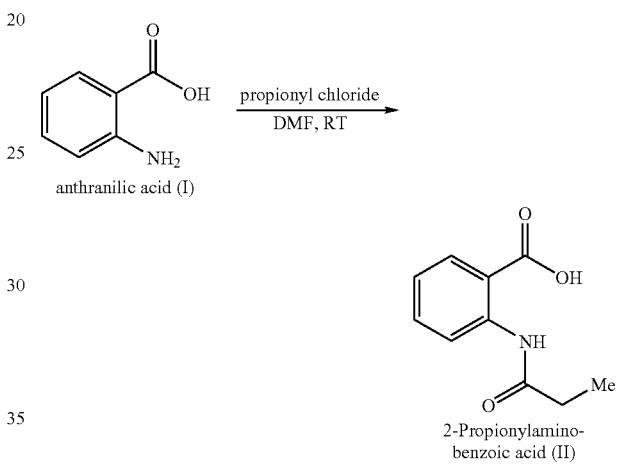

anthranilic acid (I)

2-Propionylamino-benzoic acid (II)

2-Propionylamino-benzoic acid (II). To a room temperature solution of 50.22 g anthranilic acid (I) (370 mmol, 1.00 equiv) dissolved in 200 mL dry DMF was added 35.0 mL propionyl chloride (400 mmol, 1.10 equiv) dropwise by addition funnel over 1.5 h. The addition rate was slow enough to maintain internal temperature of the reaction below 38° C. Upon completed addition of the acid chloride, the heterogeneous reaction mixture was stirred for 2.5 h at ambient temperature and then poured into 1600 mL water. The resulting water/DMF mixture, with white precipitate, was stirred vigorously at ambient temperature for one h, after which time the solid was collected by vacuum filtration, rinsing the solid with cold water (2×100 mL). The product was dried in vacuo over phosphorous pentoxide overnight affording 48.04 g of a white solid. m.p. 120.1° C. $^1$H NMR (CDCl$_3$) δ 1.30 (t, 3H, J=7.4 Hz), 2.52 (q, 2H, J=7.4 Hz), 7.12 (t, 1H, J=7.2 Hz), 7.60 (t, 1H, J=7.1 Hz), 8.13 (d, 1H, J=6.3 Hz), 8.76 (d, 1H, J=7.8 Hz) ppm. MS (ESI$^-$) 192.1 [M–H]$^-$.

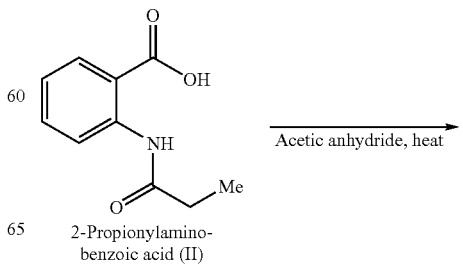

2-Propionylamino-benzoic acid (II)

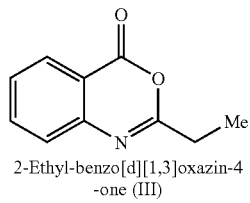

2-Ethyl-benzo[d][1,3]oxazin-4-one (III)

2-Ethyl-benzo[d][1,3oxazin-4-one (III). A mixture of 46.66 g 2-propionylamino-benzoic acid (II) (240 mmol, 1.00 equiv) suspended in 180 mL acetic anhydride was heated to reflux (external temperature 170° to 180° C., oil bath) in a reaction vessel fitted with a distillation head. Acetic acid was distilled from the reaction (b.p. 116 to 118° C.) over 1.5 to 2 h, after which time acetic anhydride began to distill (b.p. 136 to 138° C.). The reaction was equilibrated to room temperature and acetic anhydride removed by vacuum distillation; a light yellow solid resulted from concentration of the reaction solution. The solid was triturated with hexane, collected by filtration (3×100 mL volumes of hexane), and then dried in vacuo over phosphorous pentoxide to afford 33.26 g of a light yellow solid. m.p. 83.9° C. $^1$H NMR (CDCl$_3$) δ 1.37 (t, 3H, J=7.6 Hz), 2.73 (q, 2H, J=7.6 Hz), 7.49 (t, 1H, J$_1$=1.1 Hz, J$_2$=7.6 Hz), 7.56 (d, 1H, J=8.4 Hz), 7.78 (t, 1H, J$_1$=1.5 Hz, J$_2$=7.2 Hz), 8.18 (d, 1H, J=7.0 Hz) ppm. MS (ESI$^+$) 176.1 [MH]$^+$.

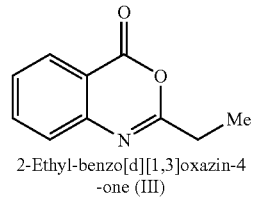

2-Ethyl-benzo[d][1,3]oxazin-4-one (III)

i. 4-Fluoroaniline, CHCl$_3$, heat
ii. ethylene glycol, cat. NaOH, heat

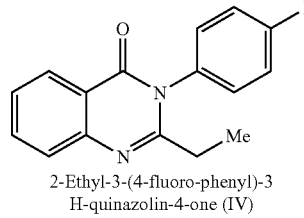

2-Ethyl-3-(4-fluoro-phenyl)-3H-quinazolin-4-one (IV)

2-Ethyl-3-(4-fluorophenyl)-3H-quinazolin-4-one (IV) A solution of 8.50 2-ethyl-benzo[d]1,3]oxazin-4-one (III) (48.5 mmol, 1.00 equiv) and 6.27 g 4-fluoroaniline (50.9 mmol, 1.05 equiv) dissolved in 35 mL chloroform was heated to reflux for 12 h, after which time TLC indicated no compound III remained (R$_f$=0.51, 20% acetone in hexane). The chloroform was removed in vacuo and the resulting solid suspended in 18 mL ethylene glycol. A catalytic amount of sodium hydroxide (86 mg, 2.2 mmol, 0.045 equiv) was added to the mixture, which was heated to 140 to 150° C. (external temperature, oil bath). After 10 h, the reaction was removed from heat and equilibrated to room temperature; upon cooling a precipitate formed. The cooled reaction product mixture was acidified with 2 mL aqueous 5% hydrochloric acid solution and suspended in 20 mL cold water. The solid was collected by vacuum filtration, rinsing with cold water (2×50 mL) and cold isopropyl alcohol (2×50 mL). The air-dried solid was recrystallized from isopropyl alcohol, affording 10.62 g tan-white needles. m.p. 178.3° C. $^1$H NMR (CDCl$_3$) δ 1.25 (t, 3H, J=7.4 Hz), 2.46 (q, 2H, J=7.4 Hz), 7.26 (d, 2H, J=6.4 Hz), 7.27 (d, 2H, J=6.4 Hz), 7.48 (t, 1H, J=6.8 Hz), 7.73–7.81 (m, 2H), 8.27 (d, 1H, J=7.96 Hz) ppm. MS (ESI$^+$) 269.1 [MH]$^+$.

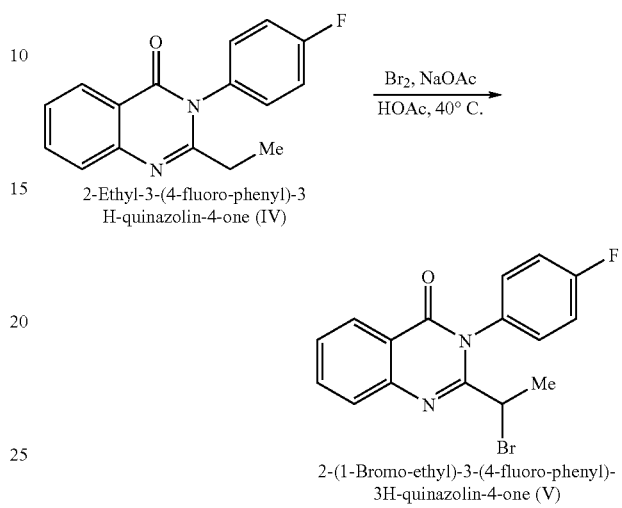

2-Ethyl-3-(4-fluoro-phenyl)-3H-quinazolin-4-one (IV)

Br$_2$, NaOAc
HOAc, 40° C.

2-(1-Bromo-ethyl)-3-(4-fluoro-phenyl)-3H-quinazolin-4-one (V)

2-(1-Bromoethyl)-3-(4-fluorophenyl)-3H-quinazolin4-one (V). To a solution of 7.084 g 2-ethyl-3-(4-fluorophenyl)-3H-quinazoline-4-one (IV) (26.40 mmol, 1.000 equiv) and 2.60 g sodium acetate (31.7 mmol, 1.20 equiv) dissolved in 30 mL glacial acetic acid at 40° C. (external temperature; oil bath) was added dropwise by addition funnel a solution of 1.36 mL bromine (26.4 mmol, 1.00 equiv) in 5 mL glacial acetic acid over 60 min. Upon completed addition of the bromine solution, the reaction was stirred an additional 60 min, after which time TLC indicated no IV remained (R$_f$=0.44; 40% ethyl acetate in hexane) and the heterogeneous mixture was poured into 400 mL water. The resulting aqueous, acidic mixture, with precipitate, was stirred vigorously at ambient temperature for two h. The precipitate was collected by vacuum filtration, rinsing with warm (ca. 40° C.) water (2×50 mL) and cold isopropyl alcohol (50 mL). The solid was dried in vacuo over phosphorous pentoxide overnight, affording 8.81 g of a white solid.m.p. 179.8° C. $^1$H NMR (CDCl$_3$) δ 2.06 (d, J=0.016p, 3H), 4.55 (q, 0.016 p, 2H), 7.16 (ddd, 1H, J$_1$=2.4 Hz, J$_2$=4.8 Hz, J$_3$=8.4 Hz), 7.24 (dt, 1H, J$_1$=2.8 Hz, J$_2$=8.0 Hz), 7.28 (dt, 1H, J$_1$=2.8 Hz, J$_2$=8.4 Hz), 7.51–7.58 (m, 2H), 7.80–7.81 (m, 2H), 8.28 (dt, 1H, J$_1$=0.8 Hz, J$_2$=8.0 Hz) ppm. MS (ESI$^+$) 348.0 [MH]$^+$.

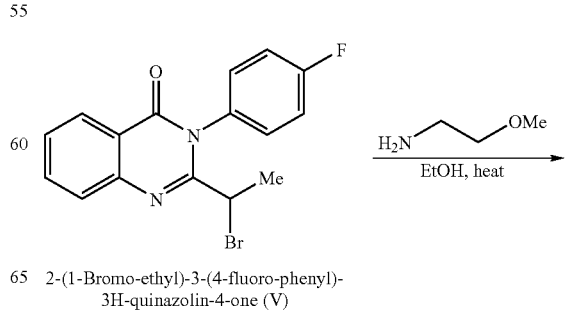

2-(1-Bromo-ethyl)-3-(4-fluoro-phenyl)-3H-quinazolin-4-one (V)

H$_2$N⁀OMe
EtOH, heat

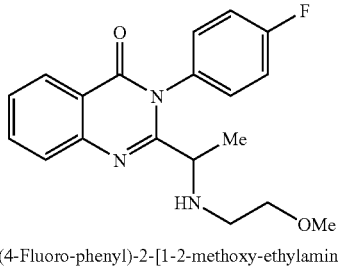

3-(4-Fluoro-phenyl)-2-[1-2-methoxy-ethylamino)-
ethyl]-3H-quinazolin-4-one (VI)

3-(4-Fluorophenyl)-2-[1-(2-methoxy-ethylamino)-ethyl]-3H-quinazolin-4-one (VI). A solution of 242 mg from 2-(1-bromoethyl)-3-(4-fluorophenyl)-3H-quinazolinon-4-one (V) (0.697 mmol, 1.00 equiv) and 160 μL 1-amino-2-methoxyethane (1.81 mmol, 2.60 equiv) in 5 mL absolute ethanol was heated to reflux for 26 h then concentrated in vacuo to remove the ethanol. The resulting yellow foam was partitioned between dichloromethane and aqueous saturated sodium bicarbonate solution (25 mL each). The separated aqueous layer was extracted again with dichloromethane (20 mL). Combined organic extracts were dried over sodium sulfate, filtered, and concentrated in vacuo to yield a yellow foam. The crude product was purified by chromatography on silica gel (3.5 cm o.d.×12 cm h) eluting with 5% methanol in chloroform. Fractions containing product at $R_f$=0.31, 5% methanol in chloroform, were combined and concentrated in vacuo to afford 220 mg product as a light yellow foam. $^1$H NMR (CDCl$_3$) δ 1.26 (d, 3H, J=6.4 Hz), 2.35 (br s, 1H), 2.54 (ddd, 1H, $J_1$=4.4 Hz, $J_2$=6.0Hz, $J_3$=10.4 Hz), 2.71 (ddd, 1H, $J_1$=4.0 Hz, $J_2$=7.2 Hz, $J_3$=11.2 Hz), 3.27 (s, 3H), 3.36–3.45 (m, 2H), 3.47 (q, 1H, J=6.4 Hz), 7.22–7.26 (m, 4H), 7.46 (ddd, 1H, $J_1$=1.6 Hz, $J_2$=6.8 Hz, $J_3$=8.0 Hz), 7.71–7.78 (m, 2H), 8.25 (dd, 1H, $J_1$=1.2 Hz, $J_2$=8.0 Hz) ppm. MS (ESI$^+$) 342.2 [MH]$^+$ Compound 1.01. To a solution of 130 mg 3-(4-fluorophenyl)-2-[1-(2-ethoxy-ethylamino)-ethyl]-3H-quinazolin-4-one (VI) (0.381 mmol, 1.00 equiv), 59 μL triethylamine (0.419 mmol, 1.10 equiv), and 2 mg DMAP (16 μmol, 0.04 equiv) dissolved in 3 mL 1,4-dioxane at room temperature was added 79 μL neat decanoyl chloride (0.381 mmol, 1.00 equiv); a colorless precipitate developed. The reaction mixture was stirred overnight at room temperature then concentrated in vacuo to remove the dioxaxie. The resulting concentrate was partitioned between dichloromethane and aqueous saturated sodium bicarbonate solution (20 mL each). The separated aqueous layer was extracted again with dichloromethane (15 mL) and the combined organic extracts dried over sodium sulfate, filtered, and concentrated in vacuo to yield a yellow, glassy oil. The crude product was purified by chromatography on silica gel (2.5 cm o.d.×10 cm h) eluting with a gradient of 20 to 25% ethyl acetate in hexane. Fractions containing product at $R_f$=0.84, 5% methanol in chloroform, were combined and concentrated in vacuo to afford 120 mg of a colorless solid. m.p. 71.4° C. $^1$H NMR (d$_6$-DMSO; T=140° C.) δ 0.90 (t, 3H, J=7.2 Hz), 1.18–1.44 (m, 14H), 1.44 (d, 3H, J=7.2 Hz), 1.98–2.08 (m, 2H), 3.11 (s, 3H), 3.33–3.52 (m, 4H), 5.11 (br q, 1H, J=6.0 Hz), 7.32 (br m, 3H), 7.49 (br m, 1H), 7.55 (ddd, 1H, $J_1$=1.2 Hz, $J_2$=7.6 Hz, $J_3$=8.0 Hz), 7.73 (d, 1H, J=8.0 Hz), 7.85 (ddd, 1H, $J_1$=1.2 Hz, $J_2$=7.2 Hz, $J_3$=8.4 Hz), 8.15 (dd, 1H, $J_1$=1.6 Hz, $J_2$=8.0 Hz) ppm. At room temperature, compound exists as a mixture of cis/trans amide rotamers, ca. 1:1 determined by integration of characteristic $^1$H NMR peaks (CDCl$_3$, T=25° C.) at δ$_{minor}$ 4.78 (q, 1.0H, J=7.2 Hz) and δ$_{major}$ 5.33 (q, 1.2H, J=7.2 Hz) ppm. MS (ESI$^+$) 496.4 [MH]$^+$ Synthesis of Compound 1.02

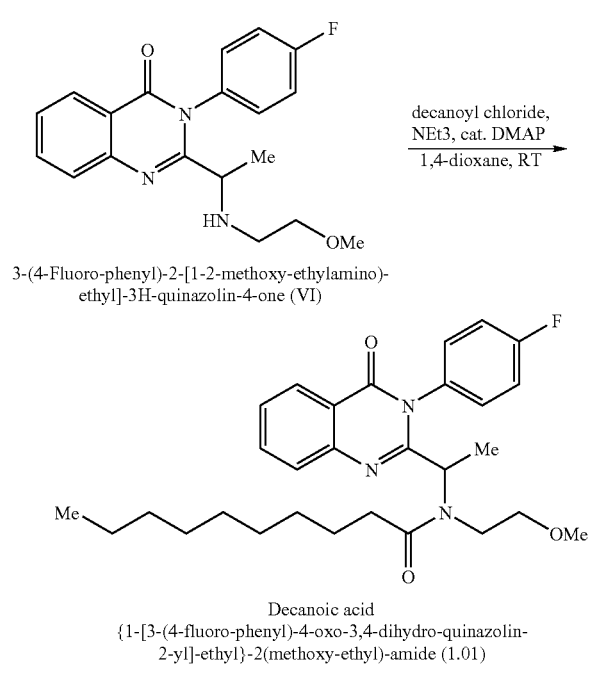

Decanoic acid
{1-[3-(4-fluoro-phenyl)-4-oxo-3,4-dihydro-quinazolin-2-yl]-ethyl}-2(methoxy-ethyl)-amide (1.01)

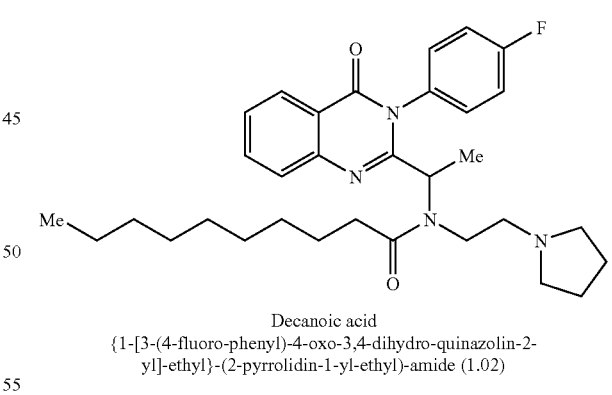

Decanoic acid
{1-[3-(4-fluoro-phenyl)-4-oxo-3,4-dihydro-quinazolin-2-yl]-ethyl}-(2-pyrrolidin-1-yl-ethyl)-amide (1.02)

Compound 1.02 was prepared following the synthesis of compound 1.01 described above. Method 1 was followed for the synthetic sequence, wherein 1-(2-aminoethyl)pyrrolidine was used in step e instead of 2-(dimethylamino)-1-aminoethane. Characterization data for compound 1.02 follows: colorless, viscous oil. $^1$H NMR similar to spectrum for compound 1.01: a mixture of cis/trans amide rotamers in ca. 2:1 (CDCl$_3$; T=25° C.) characteristic resonance peaks at δ$_{minor}$ 4.78 (q, 1.0H, J=6.8 Hz) and δ$_{major}$ 5.33 (q, 1.8H, J=7.6 Hz) ppm. MS (ESI$^+$) 535.4 [MH]$^+$

Synthesis of Compound 1.03

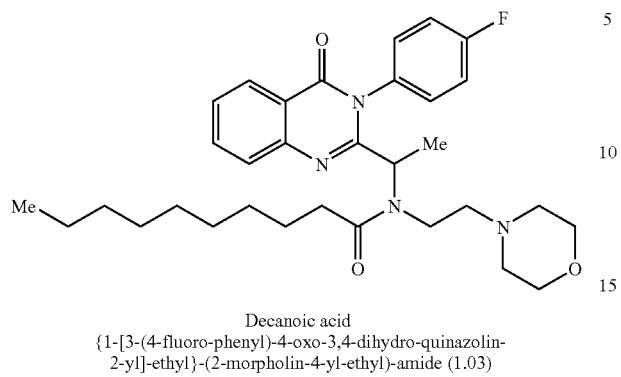

Decanoic acid
{1-[3-(4-fluoro-phenyl)-4-oxo-3,4-dihydro-quinazolin-
2-yl]-ethyl}-(2-morpholin-4-yl-ethyl)-amide (1.03)

Compound 1.03 was prepared following the synthesis of compound 1.01 described above. Method 1 was followed for the synthetic sequence, wherein 1-(2-Aminoethyl)morpholine was used in step e instead of 2-(dimethylamino)-1-aminoethane. Characterization data for compound 1.03 follows: colorless, viscous oil. $^1$H NMR (d$_6$-DMSO; T=140° C.) δ 0.89 (t, 3H, J=6.8 Hz), 1.18–1.46 (m, 14H), 1.46 (d, 3H, J=6.4 Hz), 1.98–2.08 (m, 2H), 2.23–2.34 (m, 5H), 2.47 (ddd, 1H, , $J_1$=6.0 Hz, $J_2$=8.8 Hz, $J_3$=14.4 Hz), 3.31 (ddd, 1H, , $J_1$=5.6 Hz, $J_2$=8.4 Hz, $J_3$=14.4 Hz), 3.39–3.49 (m, 5H), 5.10 (br q, 1H), 7.32 (br m, 3H), 7.51 (br m, 1H), 7.56 (ddd, 1H, $J_1$=0.8 Hz, $J_2$=$J_3$=8.0 Hz), 7.72 (d, 1H, J=7.6 Hz), 7.86 (ddd, 1H, $J_1$=1.6 Hz, $J_2$=7.2 Hz, $J_3$=8.4 Hz), 8.15 (dd, 1H, $J_1$=0.8 Hz, $J_2$=7.2 Hz) ppm. At room temperature, compound exists as a mixture of cis/trans amide, ca. 4:3 (CDCl$_3$; T=25° C.) characteristic resonance peaks at δ$_{minor}$ 4.77 (q, 1.0H, J=6.4 Hz) and δ$_{major}$ 5.33 (q, 1.3H, J=6.8 Hz) ppm. MS (ESI$^+$) 551.5 [MH]$^+$

Synthesis of Compound 1.04

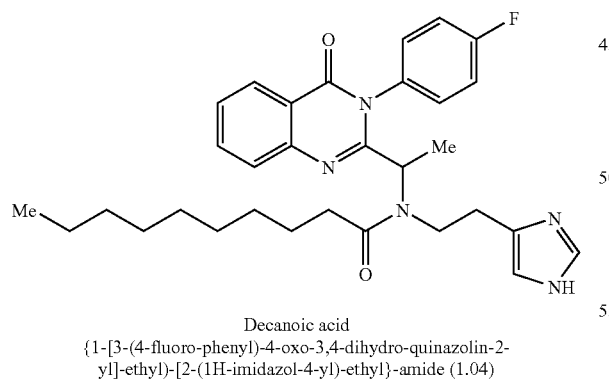

Decanoic acid
{1-[3-(4-fluoro-phenyl)-4-oxo-3,4-dihydro-quinazolin-2-
yl]-ethyl)-[2-(1H-imidazol-4-yl)-ethyl]-amide (1.04)

Compound 1.04 was prepared following the synthesis of compound 1.01 described above. Method 1 was followed for the synthetic sequence, wherein 5-(2-Aminoethyl)imidazole was used in step e instead of 2-(dimethylamino)-1-aminoethane. Characterization data for compound 1.04 follows: colorless, viscous oil. $^1$H NMR similar to spectrum for compound 1.01: a mixture of cis/trans amide rotamers in ca. 3:1 (CDCl$_3$; T=25° C.) characteristic resonance peaks at δ$_{minor}$ 4.81 (q, 1.0H, J=6.8 Hz) and δ$_{major}$ 5.05 (q, 2.7H, J=7.2 Hz) ppm. MS (ESI$^+$) 532.3 [MH]$^+$.

Synthesis of Compound 1.05

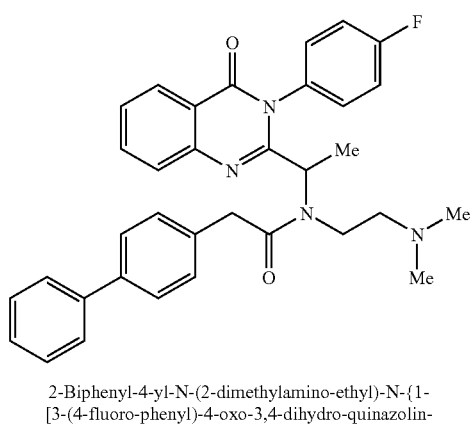

2-Biphenyl-4-yl-N-(2-dimethylamino-ethyl)-N-{1-
[3-(4-fluoro-phenyl)-4-oxo-3,4-dihydro-quinazolin-
2-yl]-ethyl}-acetamide (1.05)

Compound 1.05 was prepared following the synthesis of compound 1.01 described above. Method 1 was followed for the synthetic sequence, wherein biphenylacetyl chloride was used in step f instead of decanoyl chloride. Characterization data for compound 1.05 follows: yellow, viscous oil. $^1$H NMR similar to spectrum for compound 1.01: a mixture of cis/trans amide rotamers in ca. 2:1 (CDCl$_3$; T=25° C.) characteristic resonance peaks at δ$_{minor}$ 4.89 (q, 1.0H, J=6.8 Hz) and δ$_{major}$ 5.32 (q, 1.8H, J=6.8 Hz) ppm. MS (ESI$^+$) 549.2 [MH]$^+$

Synthesis of Compound 1.06

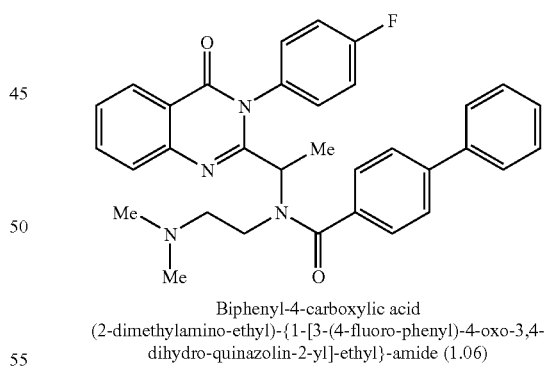

Biphenyl-4-carboxylic acid
(2-dimethylamino-ethyl)-{1-[3-(4-fluoro-phenyl)-4-oxo-3,4-
dihydro-quinazolin-2-yl]-ethyl}-amide (1.06)

Compound 1.06 was prepared following the synthesis of 1.01 described above. Method 1 was followed for the synthetic sequence, wherein biphenylcarbonyl chloride was used in step f instead of decanoyl chloride. Characterization data for compound 1.06 follows: white solid. m.p.=147.3° C. $^1$H NMR similar to spectrum for compound 1.01: a mixture of cis/trans amide rotamers in ca. 3:1 (CDCl$_3$; T=25° C.) determined by integration of characteristic resonance peaks at δ$_{minor}$ 5.02 (br q, 1.0H) and δ$_{major}$ 5.43 (br q, 3.0H) ppm. MS (ESI$^+$) 535.2 [MH]$^+$

Synthesis of Compound 1.07

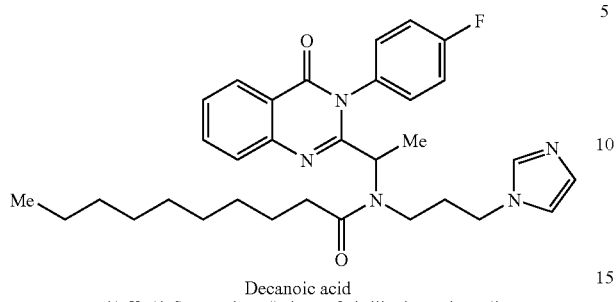

Decanoic acid
{1-[3-(4-fluoro-phenyl)-4-oxo-3,4-dihydro-quinazolin-2-yl]-ethyl}-(3-(imidazol-1-yl-propyl)-amide (1.07)

Compound 1.07 was prepared following the synthesis of 1.01 described above. Method 1 was followed for the synthetic sequence, wherein 3-(3-Aminopropyl)-(3H)-imidazole was used in step e instead of 2-(Dimethylamino)-1-aminoethane. Characterization data for compound 1.07 follows: colorless, viscous oil. $^1$H NMR similar to spectrum for compound 1.01: a mixture of cis/trans amide rotamers in ca. 1:1 (CDCl$_3$; T=25° C.) determined by integration of characteristic resonance peaks at $\delta_{minor}$ 4.77 (q, 1.0H, J=6.8 Hz) and $\delta_{major}$ 5.28 (q, 1.1H, J=7.6 Hz) ppm. MS (ESI$^+$) 546.3 [MH]$^+$

Synthesis of Compound 1.08

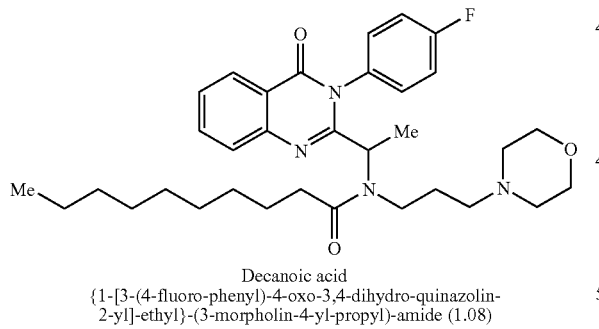

Decanoic acid
{1-[3-(4-fluoro-phenyl)-4-oxo-3,4-dihydro-quinazolin-2-yl]-ethyl}-(3-morpholin-4-yl-propyl)-amide (1.08)

Compound 1.08 was prepared following the synthesis of compound 1.01 described above. Method 1 was followed for the synthetic sequence, wherein 1-(3-Aminopropyl)morpholine was used in step e instead of 2-(Dimethylamino)-1-aminoethane. Characterization data for compound 1.08 follows: pale yellow glass. $^1$H NMR similar to spectrum for compound 1.01: a mixture of cis/trans amide rotamers in ca. 2:1 (CDCl$_3$; T=25° C.) determined by integration of characteristic resonance peaks at $\delta_{minor}$ 4.77 (q, 1.0H, J=6.4 Hz) and $\delta_{major}$ 5.38 (q, 1.8H, J=7.2 Hz) ppm. MS (ESI$^+$) 565.4 [MH]$^+$

Synthesis of Compound 1.09

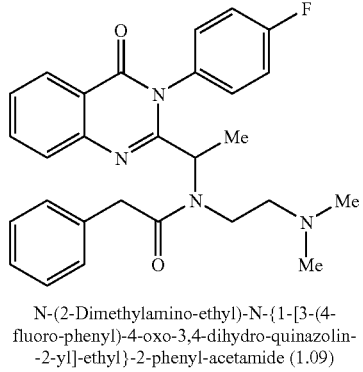

N-(2-Dimethylamino-ethyl)-N-{1-[3-(4-fluoro-phenyl)-4-oxo-3,4-dihydro-quinazolin-2-yl]-ethyl}-2-phenyl-acetamide (1.09)

Compound 1.09 was prepared following the synthesis of 1.01 described above. Method 1 was followed for the synthetic sequence, wherein biphenylcarbonyl chloride was used in step f instead of decanoyl chloride. Characterization data for compound 1.09 follows: white solid. m.p.=153.0° C. $^1$H NMR (d$_6$-DMSO; T=140° C.) δ 1.42 (d, 3H, J=7.2 Hz), 2.07 (s, 6H), 2.26 (ddd, 1H, J$_1$=5.6 Hz, J$_2$=9.2 Hz, J$_3$=12.4 Hz), 2.46 (ddd, 1H, J$_1$=5.2 Hz, J$_2$=9.2 Hz, J$_3$=14.4 Hz), 3.36 (d, 1H, J=15.2 Hz), 3.38 (ddd, 1H, J$_1$=5.2 Hz, J$_2$=8.8 Hz, J$_3$=14.8 Hz), 3.49 (ddd, 1H, J$_1$=6.0 Hz, J$_2$=9.2 Hz, J$_3$=15.2 Hz), 3.50 (d, 1H, J=15.2 Hz), 5.15 (q, 1H, J=6.8 Hz), 7.12 (d, 2H, J=7.6 Hz), 7.20 (t, 1H, J=7.2 Hz), 7.26 (dd, 2H, J$_1$=7.2 Hz, J$_2$=7.6 Hz), 7.36 (br m, 3H), 7.53 (br m, 1H), 7.56 (ddd, 1H, J$_1$=1.2 Hz, J$_2$=7.2 Hz, J$_3$=8.0 Hz), 7.72 (d, 1H, J=7.2 Hz), 7.87 (ddd, 1H, J$_1$=1.6 Hz, J$_2$=7.2 Hz, J$_3$=8.4 Hz), 8.16 (dd, 1H, J$_1$=1.6 Hz, J$_2$=8.0 Hz) ppm. At room temperature, compound exists as a mixture of cis/trans amide rotamers, ca. 2:1 (CDCl$_3$; T=25° C.) determined by integration of characteristic resonance peaks at $\delta_{minor}$ 4.84 (q, 1.0H, J=6.8 Hz) and $\delta_{major}$ 5.30 (q, 2.1H, J=6.8 Hz) ppm. MS (ESI$^+$) 473.3 [MH]$^+$

Synthesis of Compound 1.10

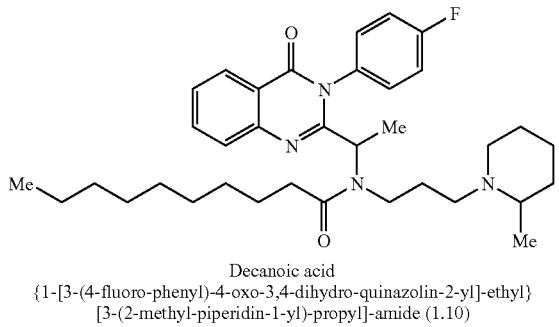

Decanoic acid
{1-[3-(4-fluoro-phenyl)-4-oxo-3,4-dihydro-quinazolin-2-yl]-ethyl}
[3-(2-methyl-piperidin-1-yl)-propyl]-amide (1.10)

Compound 1.10 was prepared following the synthesis of 1.01 described above. Method 1 was followed for the synthetic sequence, wherein 5-(2-Aminoethyl)imidazole was used in step e instead of 2-(Dimethylamino)-1-aminoethane. Characterization data for compound 1.10 follows: yellow, viscous oil. $^1$H NMR similar to spectrum for compound 1.01: a mixture of cis/trans amide rotamers in ca. 3:2 (CDCl$_3$; T=25° C.) determined by integration of characteristic resonance peaks at δ$_{minor}$ 4.77 (q, 1.0H, J=6.8 Hz) and δ$_{major}$ 5.37 (q, 1.6H, J=6.8 Hz) ppm. MS (ESI$^+$) 577.4 [MH]$^+$

Synthesis of Compound 1.11

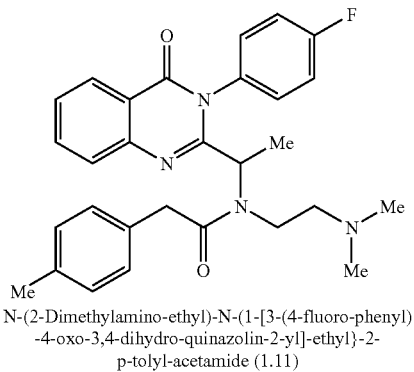

N-(2-Dimethylamino-ethyl)-N-(1-[3-(4-fluoro-phenyl)-4-oxo-3,4-dihydro-quinazolin-2-yl]-ethyl}-2-p-tolyl-acetamide (1.11)

Compound 1.11 was prepared following the synthesis of compound 1.01 described above. Method 1 was followed for the synthetic sequence, wherein (4-methylphenyl)acetyl chloride was used in step f instead of decanoyl chloride. Characterization data for compound 1.11 follows: white solid. m.p. 188.3° C. $^1$H NMR similar to spectrum for compound 1.09: a mixture of cis/trans amide rotamers in ca. 2:1 (CDCl$_3$; T=25° C.) determined by integration of characteristic resonance peaks at δ$_{minor}$ 5.02 (q, 1.0H, J=6.8 Hz) and δ$_{major}$ 5.47 (q, 1.9H, J=7.2 Hz) ppm. MS (ESI$^+$) 487.3 [MH]$^+$

Synthesis of Compound 1.12

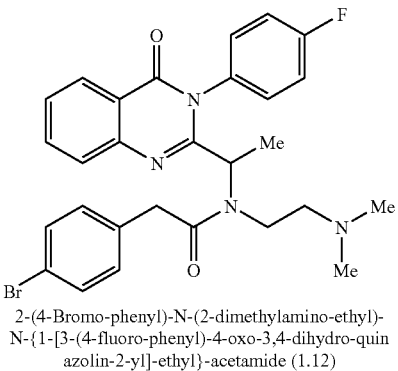

2-(4-Bromo-phenyl)-N-(2-dimethylamino-ethyl)-N-{1-[3-(4-fluoro-phenyl)-4-oxo-3,4-dihydro-quinazolin-2-yl]-ethyl}-acetamide (1.12)

Compound 1.12 was prepared following the synthesis of compound 1.01 described above. Method 1 was followed for the synthetic sequence, wherein (4-bromophenyl)acetyl chloride was used in step f instead of decanoyl chloride. Characterization data for compound 1.12 follows: colorless glass. $^1$H NMR similar to spectrum for compound 1.09: a mixture of cis/trans amide rotamers in ca. 2:1 (CDCl$_3$;  T=25° C.) determined by integration of characteristic resonance peaks at δ$_{minor}$ 4.82 (q, 1.0H, J=7.2 Hz) and δ$_{major}$ 5.27 (q, 2.3H, J=6.8 Hz) ppm. MS (ESI$^+$) 551.2 [MH]$^+$

Synthesis of Compound 1.13

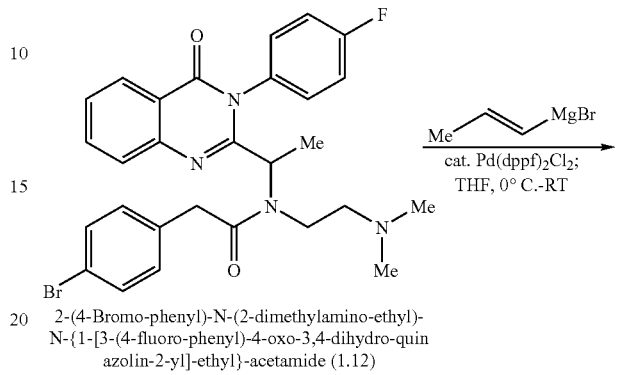

2-(4-Bromo-phenyl)-N-(2-dimethylamino-ethyl)-N-{1-[3-(4-fluoro-phenyl)-4-oxo-3,4-dihydro-quinazolin-2-yl]-ethyl}-acetamide (1.12)

N-(2-Dimethylamino-ethyl)-N-{1-[3-(4-fluoro-phenyl)-4-oxo-3,4-dihydro-quinazolin-2-yl]-ethyl}-2-(4-Z-propenyl-phenyl)-acetamide (1.13)

To a solution of 112 mg zinc(II) bromide (500 μmol 10 equiv) at 0° C. was added 1.0 mL 1-propenylmagnesium bromide solution in 0.5 mL THF (0.5 M; 500 μmol, 10 equiv). The resulting white, cloudy mixture was stirred at 0° C. for 60 min before a solution of 27 mg 1.12 (49 μmol, 1.0 equiv) and 4 mg bis-dppf palladium(II) dichloride (5 μmol, 0.1 equiv) dissolved in 0.5 mL THF was added all at once by cannulation. The reaction mixture was stirred at room temperature for 14 h, then heated to 60° C. (external temperature, oil bath) to drive the reaction toward completion. After 2 h at 60° C., 5 mL saturated aqueous ammonium chloride solution was added to the cooled (0° C.) reaction mixture. The aqueous layer was extracted with ethyl acetate (3×15 mL) and the combined organic separations dried over magnesium sulfate, filtered, and concentrated in vacuo to yield a yellow film. The crude product was purified by flash column chromatography on silica gel (3.5 cm o.d.×10 cm h) eluting with 5% methanol in chloroform to yield 8 mg product olefin as a colorless film. The product was isolated as a mixture of olefin isomers, which were separated by preparative HPLC (reverse phase, CH$_3$CN:H$_2$O). Compound 1.13 eluted before the trans olefin isomer 1.14. $^1$H NMR similar to spectrum for compound 1.09: a mixture of cis/trans amide rotamers in ca. 2:1 (CDCl$_3$; T=25° C.) determined by integration of characteristic resonance peaks at δ$_{major}$ 4.85 (q, 1.9H, J=6.8 Hz) and δ$_{minor}$ 5.13 (q, 1.0H, J=7.2 Hz) ppm. MS (ESI$^+$) 513.2 [MH]$^+$

Synthesis of Compound 1.14

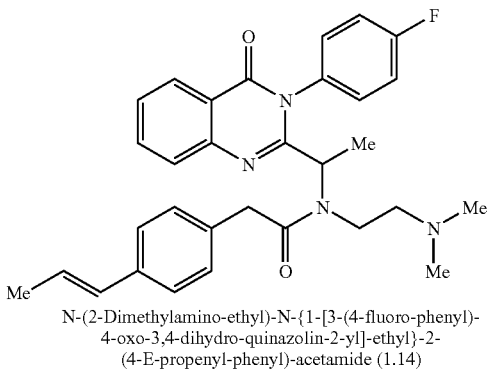

N-(2-Dimethylamino-ethyl)-N-{1-[3-(4-fluoro-phenyl)-
4-oxo-3,4-dihydro-quinazolin-2-yl]-ethyl}-2-
(4-E-propenyl-phenyl)-acetamide (1.14)

Compound 1.14 was prepared coincidentally with compound 1.12 and isolated by preparative HPLC as the second product to elute. $^1$H NMR similar to spectrum for compound 1.09: a mixture of cis/trans amide rotamers in ca. 2:1 (CDCl$_3$; T=25° C.) determined by integration of characteristic resonance peaks at $\delta_{major}$ 4.83 (q, 1.8H, J=7.2 Hz) and $\delta_{minor}$ 5.12 (q, 1.0H, J=7.6 Hz) ppm. MS (ESI$^+$) 513.2 [MH]$^+$

Synthesis of Compound 1.15

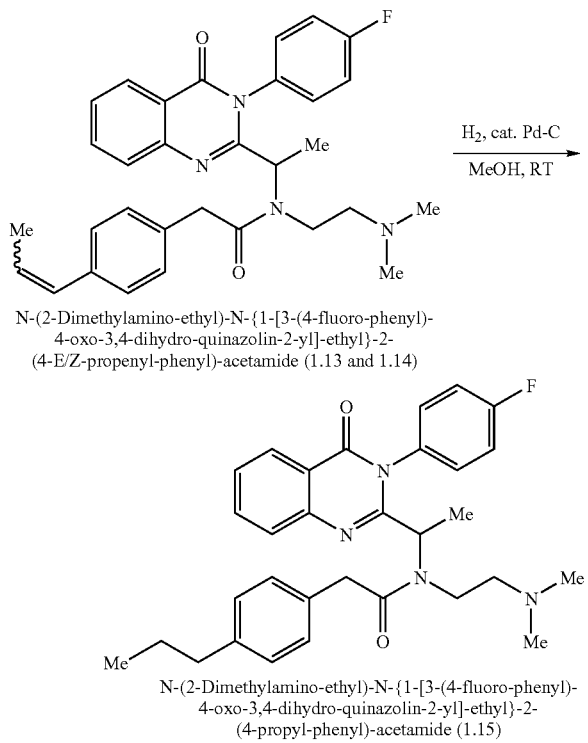

N-(2-Dimethylamino-ethyl)-N-{1-[3-(4-fluoro-phenyl)-
4-oxo-3,4-dihydro-quinazolin-2-yl]-ethyl}-2-
(4-E/Z-propenyl-phenyl)-acetamide (1.13 and 1.14)

N-(2-Dimethylamino-ethyl)-N-{1-[3-(4-fluoro-phenyl)-
4-oxo-3,4-dihydro-quinazolin-2-yl]-ethyl}-2-
(4-propyl-phenyl)-acetamide (1.15)

Hydrogen gas was introduced by balloon to a nitrogen-purged, evacuated flask charged with 4.8 mg 1.13 and 1.14 (9.4 μmol, 1.0 equiv) and 5.0 mg palladium on activated carbon (10% wt Pd; 4.7 μmol, 0.5 equiv) suspended in 2.0 mL methanol at room temperature. The reaction was stirred at room temperature for 18 h then filtered through a pad of celite. The filtrate was concentrated in vacuo then purified by column chromatography on silica gel (2.0 cm o.d.×8 cm h) eluting with 5% methanol in chloroform. Fractions containing product were concentrated in vacuo to afford 4.5 mg of a colorless film. $^1$H NMR similar to spectrum for compound 1.09: a mixture of cis/trans amide rotamers in ca. 3:2 (CDCl$_3$; T=25° C.) determined by integration of characteristic resonance peaks at $\delta_{major}$ 4.83 (q, 1.4H, J=6.8 Hz) and $\delta_{minor}$ 5.20 (q, 1.0H, J=7.2 Hz ppm. MS (ESI$^+$) 515.3 [MH]$^+$

Synthesis of Compound 1.16

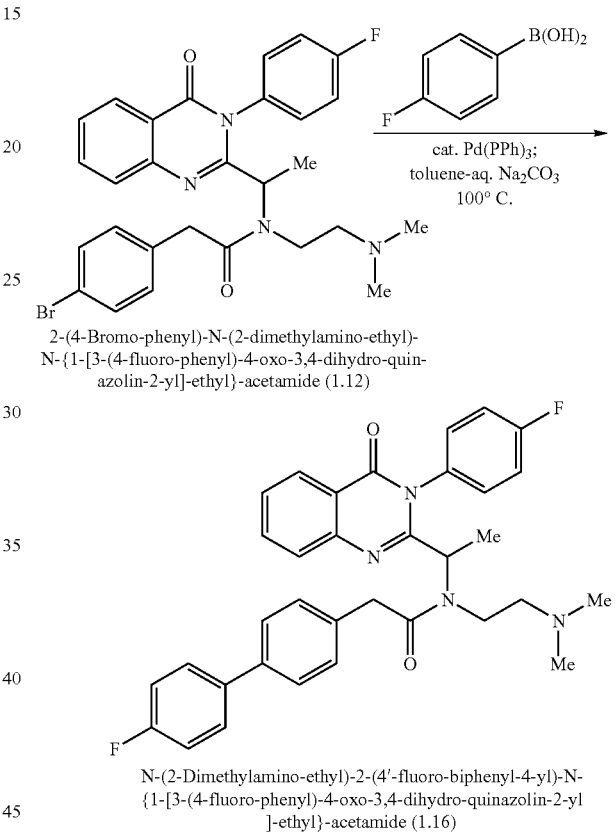

2-(4-Bromo-phenyl)-N-(2-dimethylamino-ethyl)-
N-{1-[3-(4-fluoro-phenyl)-4-oxo-3,4-dihydro-quin-
azolin-2-yl]-ethyl}-acetamide (1.12)

N-(2-Dimethylamino-ethyl)-2-(4'-fluoro-biphenyl-4-yl)-N-
{1-[3-(4-fluoro-phenyl)-4-oxo-3,4-dihydro-quinazolin-2-yl
]-ethyl}-acetamide (1.16)

A degassed (3× freeze-evacuate-thaw cycles) biphasic mixture of 27.0 mg 1.12 (49.0 μmol, 1.00 equiv), 34.0 mg 4-fluorophenylboronic acid (245 μmol, 5.00 equiv), and 3.0 mg tetrakistriphenylphosphine palladium(0) (2.5 μmol, 0.05 equiv) in 3.0 mL toluene and 3.0 mL 2M aqueous sodium carbonate was heated to 100° C. (external temperature, oil bath). After 4 h, MS indicated no compound 1.12 remained and the separated aqueous layer was extracted with 50% ethylacetate in hexane (2×15 mL). Combined organic extracts were dried over magnesium sulfate, filtered, and concentrated in vacuo to yield a yellow oil. The crude material was purified by chromatography on silica gel (3.5 cm o.d.×12 cm h) eluting with 5% methanol in chloroform. Fractions containing product were combined and concentrated in vacuo to afford 27.0 mg product as a colorless, viscous oil. $^1$H NMR similar to spectrum for compound 1.09: a mixture of cis/trans amide rotamers in ca. 3:2 (CDCl$_3$; T=25° C.) determined by integration of characteristic resonance peaks at $\delta_{major}$ 4.90 (q, 1.3H, J=7.2 Hz) and $\delta_{minor}$ 5.30 (q, 1.0H, J=7.2 Hz) ppm. MS (ESI$^+$) 567.2 [MH]$^+$.

Synthesis of Compound 1.17

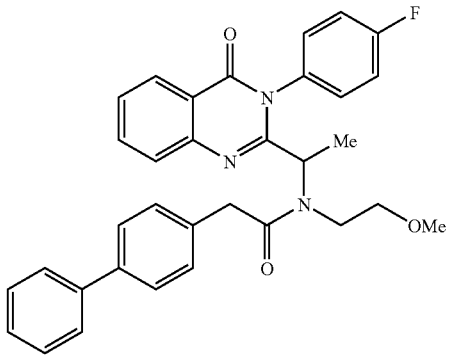

2-Biphenyl-4-yl-N-{1-[3-(4-fluoro-phenyl)-4-oxo-3,4-dihydro-quinazolin-2-yl]-ethyl}-N-(2-methoxy-ethyl)-acetamide (1.17)

Compound 1.17 was prepared following the synthesis of 1.01 described above. Method 1 was followed for the synthetic sequence, wherein 2-methoxy-1-aminoethane was used in step e instead of 2-(N,N-dimethylamino)-1-aminoethane, and biphenylacetyl chloride was used in step f instead of decanoyl chloride. Characterization data for compound 1.17 follows: beige solid. m.p.=153.8° C. $^1$H NMR similar to spectrum for compound 1.09: a mixture of cis/trans amide rotamers in ca. 2:1 (CDCl$_3$; T=25° C.) determined by integration of characteristic resonance peaks at $\delta_{minor}$ 4.89 (q, 1.0H, J=6.4 Hz) and $\delta_{major}$ 5.33 (q, 1.8H, J=6.8 Hz) ppm. MS (ESI$^+$) 536.2 [MH]$^+$

Synthesis of Compound 1.18

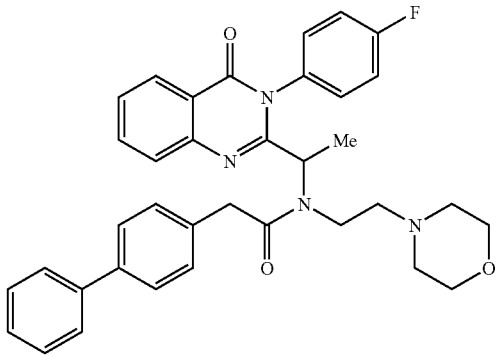

2-Biphenyl-4-yl-N-{1-[3-(4-fluoro-phenyl)-4-oxo-3,4-dihydro-quinazolin-2-yl]-ethyl}-N-(2-morpholin-4-yl-ethyl)-acetamide (1.18)

Compound 1.18 was prepared following the synthesis of compound 1.01 described above. Method 1 was followed for the synthetic sequence, wherein 1-(2-aminoethyl)morpholine was used in step e instead of 2-(N,N-dimethylamino)-1-aminoethane, and biphenylacetyl chloride was used in step f instead of decanoyl chloride. Characterization data for compound 1.18 follows: colorless, viscous oil. $^1$H NMR similar to spectrum for compound 1.09: a mixture of cis/trans amide rotamers in ca. 2:1 (CDCl$_3$; T=25° C.) determined by integration of characteristic resonance peaks at $\delta_{minor}$ 4.88 (q, 1.0H, J=6.8 Hz) and $\delta_{major}$ 5.32 (q, 1.7H, J=7.2 Hz) ppm. MS (ESI$^+$) 591.3 [MH]$^+$

Synthesis of Compound 1.19

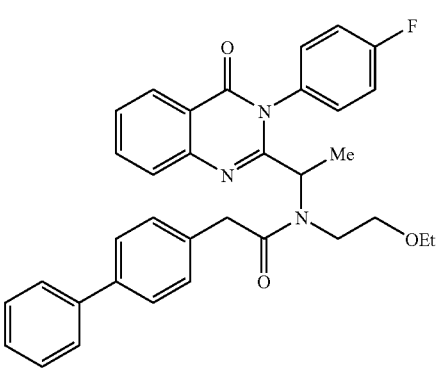

2-Biphenyl-4-yl-N-(2-ethoxy-ethyl)-N-{1-[3-(4-fluoro-phenyl)-4-oxo-3,4-dihydro-quinazolin-2-yl]-ethyl}-acetamide (1.19)

Compound 1.19 was prepared following the synthesis of compound 1.01 described above. Method 1 was followed for the synthetic sequence, wherein 2-ethoxy-1-aminoethane was used in step e instead of 2-(N,N-dimethylamino)-1-aminoethane, and biphenylacetyl chloride was used in step f instead of decanoyl chloride. Characterization data for compound 1.19 follows: light yellow, glassy solid. m.p.=150.6° C. $^1$H NMR (d$_6$-DMSO; T=140° C.) δ 0.98 (t, 3H, J=6.8 Hz), 1.43 (d, 3H, J=6.8 Hz), 3.29–3.63 (m, 8H), 5.18 (q, 1H, J=6.0 Hz), 7.20 (d, 2H, J=7.6 Hz), 7.27–7.36 (m, 3H), 7.41–7.47 (m, 3H), 7.49–7.64 (m, 6H), 7.72 (d, 1H, J=8.0 Hz), 7.85 (ddd, 1H, J$_1$=1.6 Hz, J$_2$=8.2 Hz, J$_3$=8.6 Hz), 8.15 (d, 1H, J=8.0 Hz) ppm. At room temperature, compound exists as a mixture of cis/trans amide rotamers, ca. 2:1 (CDCl$_3$; T=25° C.) determined by integration of characteristic resonance peaks at $\delta_{minor}$ 4.87 (q, 1.0H, J=6.8 Hz) and $\delta_{major}$ 5.33 (q, 2.1H, J=7.2 Hz) ppm. MS (ESI$^+$) 550.2 [MH]$^+$

Synthesis of Compound 1.20

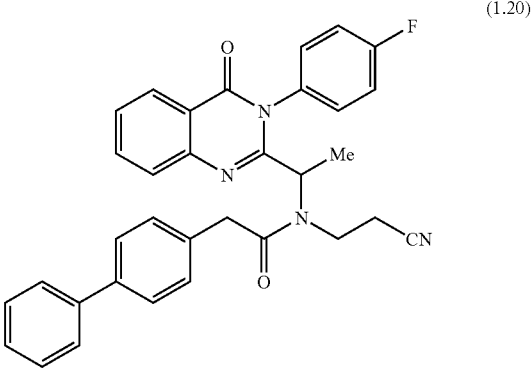

(1.20)

2-Biphenyl-4-yl-N-(2-cyano-ethyl)-N-{1-[3-(4-fluoro-phenyl)-4-oxo-3,4-dihydro-quinazolin-2-yl]-ethyl}-acetamide Compound 1.20 was prepared following the synthesis of compound 1.01 described above. Method 1 was followed for the synthetic sequence, wherein 3-aminopropionitrile was used in step e instead of 2-(N,N-dimethylamino)-1-aminoethane, and biphenylacetyl chloride was used in step f instead of decanoyl chloride. Characterization data for compound 1.20 follows: colorless glass. $^1$H NMR similar to spectrum for compound 1.19: a mixture of cis/trans amide rotamers in ca. 1:1 (CDCl$_3$; T=25° C.) determined by integration of characteristic resonance peaks at $\delta_A$ 4.94 (q, 1.0H, J=6.8 Hz) and $\delta_B$ 5.14 (q, 1.0H, J=7.6 Hz) ppm. MS (ESI$^+$) 530.2 [MH]$^+$ Synthesis of Compound 1.21

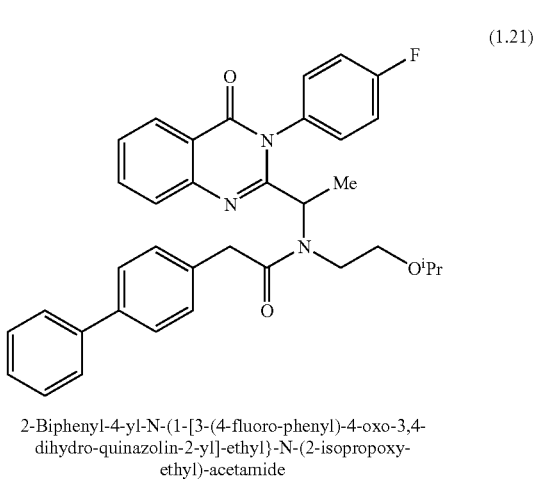

2-Biphenyl-4-yl-N-(1-[3-(4-fluoro-phenyl)-4-oxo-3,4-dihydro-quinazolin-2-yl]-ethyl}-N-(2-isopropoxy-ethyl)-acetamide Compound 1.21 was prepared following the synthesis of compound 1.01 described above. Method 1 was followed for the synthetic sequence, wherein 2-isopropoxy-1-aminoethane was used in step e instead of 2-(N,N-dimethylamino)-1-aminoethane, and biphenylacetyl chloride was used in step f instead of decanoyl chloride. Characterization data for compound 1.21 follows: faint yellow glass. $^1$H NMR similar to spectrum for compound 1.19: a mixture of cis/trans amide rotamers in ca. 3:1 (CDCl$_3$; T=25° C.) determined by integration of characteristic resonance peaks at $\delta_{minor}$ 4.88 (q, 1.0H, J=6.7 Hz) and $\delta_{major}$ 5.30 (q, 2.9H, J=7.0 Hz) ppm. MS (ESI$^+$) 564.2 [MH]$^+$ Synthesis of Compound 1.22

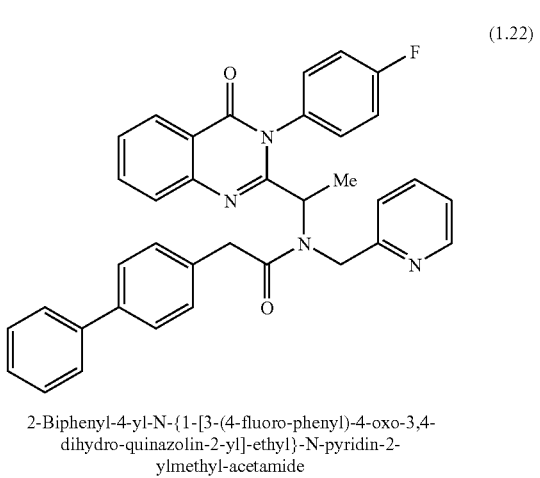

2-Biphenyl-4-yl-N-{1-[3-(4-fluoro-phenyl)-4-oxo-3,4-dihydro-quinazolin-2-yl]-ethyl}-N-pyridin-2-ylmethyl-acetamide Compound 1.22 was prepared following the synthesis of compound 1.01 described above. Method 1 was followed for the synthetic sequence, wherein 2-aminomethyl pyridine was used in step e instead of 2-(N,N-dimethylamino)-1-aminoethane, and biphenylacetyl chloride was used in step f instead of decanoyl chloride. Characterization data for compound 1.22 follows: colorless glass. $^1$H NMR similar to spectrum for compound 1.19: a mixture of cis/trans amide rotamers in ca. 1:1 (CDCl$_3$; T=25° C.) determined by integration of characteristic resonance peaks at $\delta_A$ 5.13 (q, 1.0H, J=6.4 Hz) and $\delta_B$ 5.46 (q, 1.0H, J=8.0 Hz) ppm. MS (ESI$^+$) 569.3 [MH]$^+$ Synthesis of Compound 1.23

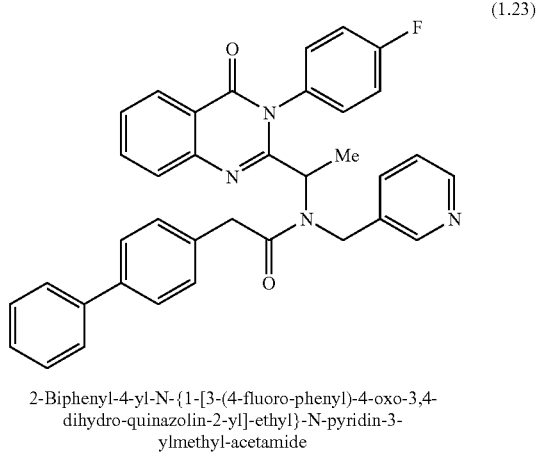

2-Biphenyl-4-yl-N-{1-[3-(4-fluoro-phenyl)-4-oxo-3,4-dihydro-quinazolin-2-yl]-ethyl}-N-pyridin-3-ylmethyl-acetamide Compound 1.23 was prepared following the synthesis of compound 1.01 described above. Method 1 was followed for the synthetic sequence, wherein 2-aminomethyl pyridine was used in step e instead of 2-(N,N-dimethylamino)-1-aminoethane, and biphenylacetyl chloride was used in step f instead of decanoyl chloride. Characterization data for compound 1.23 follows: colorless glass. $^1$H NMR similar to spectrum for compound 1.19: a mixture of cis/trans amide rotamers in ca. 1:1 (CDCl$_3$; T=25° C.) determined by integration of characteristic resonance peaks at $\delta_A$ 5.13 (q, 1.0H, J=6.4 Hz) and $\delta_B$ 5.46 (q, 1.0H, J=8.0 Hz) ppm. MS (ESI$^+$) 569.3 [MH]$^+$ Synthesis of Compound 1.24

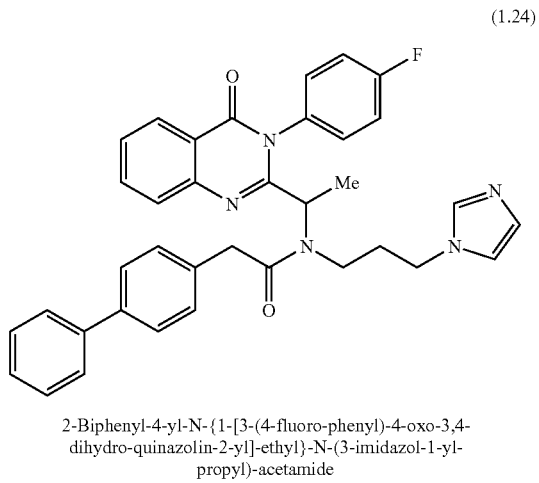

2-Biphenyl-4-yl-N-{1-[3-(4-fluoro-phenyl)-4-oxo-3,4-dihydro-quinazolin-2-yl]-ethyl}-N-(3-imidazol-1-yl-propyl)-acetamide Compound 1.24 was prepared following the synthesis of compound 1.01 described above. Method 1 was followed for the synthetic sequence, wherein 3-(3-aminopropyl)imidazole was used in step e instead of 2-(N,N-dimethylamino)-1-aminoethane, and biphenylacetyl chloride was used in step f instead of decanoyl chloride. Characterization data for compound 1.24 follows: colorless oil. $^1$H NMR similar to spectrum for compound 1.19: a mixture of cis/trans amide rotamers in ca. 1:1 (CDCl$_3$; T=25° C.) determined by integration of characteristic resonance peaks at $\delta_A$ 4.89 (q, 1.0H, J=6.6 Hz) and $\delta_B$ 5.29 (q, 1.1H, J=7.1 Hz) ppm. MS (ESI$^+$) 569.3 [MH]$^+$.

Synthesis of Compound 1.25

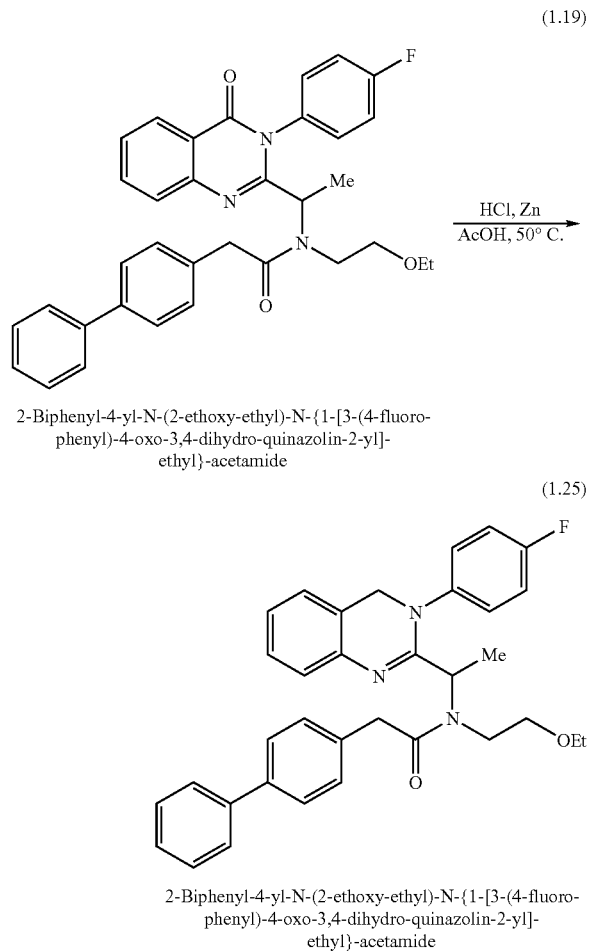

2-Biphenyl-4-yl-N-(2-ethoxy-ethyl)-N-{1-[3-(4-fluoro-phenyl)-4-oxo-3,4-dihydro-quinazolin-2-yl]-ethyl}-acetamide 2-Biphenyl-4-yl-N-(2-ethoxy-ethyl)-N-{1-[3-(4-fluoro-phenyl)-4-oxo-3,4-dihydro-quinazolin-2-yl]-ethyl}-acetamide To a mixture of 175 mg 1.19 (318 μmol, 1.00 equiv) and 500 mg zinc powder (7.65 mmol, 24.0 equiv) suspended in 3.0 mL glacial acetic acid at 40° C. (external temperature, oil bath) was added ca. 200 μL concentrated aqueous hydrochloric acid (5 drops by pipet, 18 M; 3.6 mmol). The resulting beige, cloudy reaction mixture evolved gas and was stirred at 40° C. for 15 min, then decanted from the suspended solids/zinc and neutralized with concentrated aqueous sodium hydroxide to pH>12. The aqueous, alkaline solution was extracted with dichloromethane (3×20 mL). Combined organic extracts were dried over magnesium sulfate, filtered, and concentrated in vacuo to yield a colorless oil. The crude material was purified by chromatography on silica gel (3.5 cm o.d.×10 cm h) eluting with 2% methanol in chloroform. Fractions containing product at R$_f$=0.52, 10% methanol in chloroform, were combined and concentrated in vacuo to afford 83 mg of a colorless oil. $^1$H NMR similar to spectrum for compound 1.19: a mixture of cis/trans amide rotamers in ca. 2:1 (CDCl$_3$; T=25° C.) determined by integration of characteristic resonance peaks at $\delta_{minor}$ 4.62 (q, 1.0H, J=7.1 Hz) and $\delta_{major}$ 5.31 (q, 2.1H, J=7.0 Hz) ppm. MS (ESI$^+$) 536.3 [MH]$^+$ Synthesis of Compound 1.26

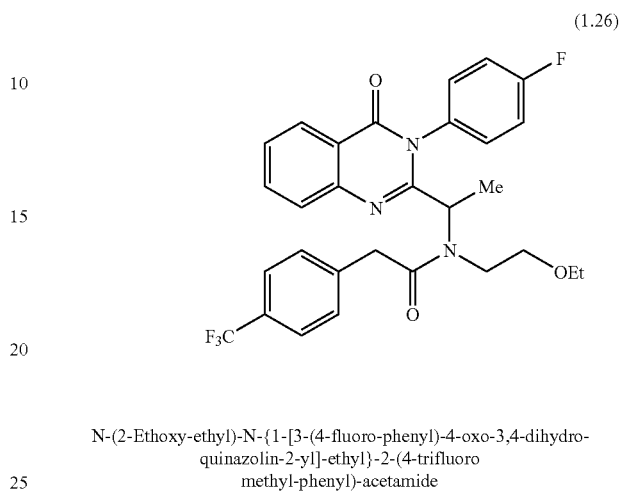

N-(2-Ethoxy-ethyl)-N-{1-[3-(4-fluoro-phenyl)-4-oxo-3,4-dihydro-quinazolin-2-yl]-ethyl}-2-(4-trifluoro methyl-phenyl)-acetamide Compound 1.26 was prepared following the synthesis of compound 1.01 described above. Method 1 was followed for the synthetic sequence, wherein 2-ethoxy-1-aminoethane was used in step e instead of 2-(N,N-dimethylamino)-1-aminoethane, and (4-trifluoromethylphenyl)acetic acid was used, with EDC and catalytic HOBT, in step f instead of decanoyl chloride. Characterization data for compound 1.26 follows: colorless oil. $^1$H NMR similar to spectrum for compound 1.19: a mixture of cis/trans amide rotamers in ca. 5:2 (CDCl$_3$; T=25° C.) determined by integration of characteristic resonance peaks at $\delta_{minor}$ 4.85 (q, 1.0H, J=6.8 Hz) and $\delta_{major}$ 5.33 (q, 2.6H, J=6.8 Hz) ppm. MS (ESI$^+$) 542.2 [MH]$^+$ Synthesis of Compound 1.27

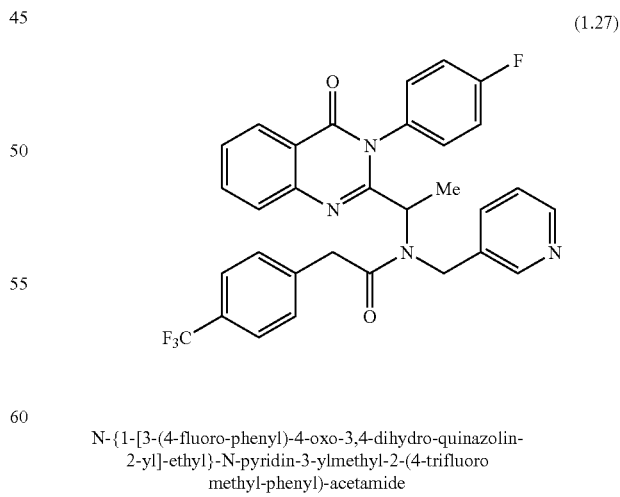

N-{1-[3-(4-fluoro-phenyl)-4-oxo-3,4-dihydro-quinazolin-2-yl]-ethyl}-N-pyridin-3-ylmethyl-2-(4-trifluoro methyl-phenyl)-acetamide Compound 1.27 was prepared following the synthesis of compound 1.01 described above. Method 1 was followed for the synthetic sequence, wherein 3-methylaminopyridine was used in step e instead of 2-(N,N-dimethylamino)-1-amino-ethane, and (4-trifluoromethylphenyl)acetic acid was used, with EDC and catalytic HOBT, in step f instead of decanoyl chloride. Characterization data for compound 1.27 follows: colorless oil. $^1$H NMR similar to spectrum for compound 1.19: a mixture of cis/trans amide rotamers in ca. 6:5 (CDCl$_3$; T=25° C.) determined by integration of characteristic resonance peaks at $\delta_{minor}$ 4.99 (q, 1.0H, J=6.6 Hz) and $\delta_{major}$ 5.37 (q, 1.2H, J=7.2 Hz) ppm. MS (ESI$^+$) 561.2 [MH]$^+$ Synthesis of Compound 1.28

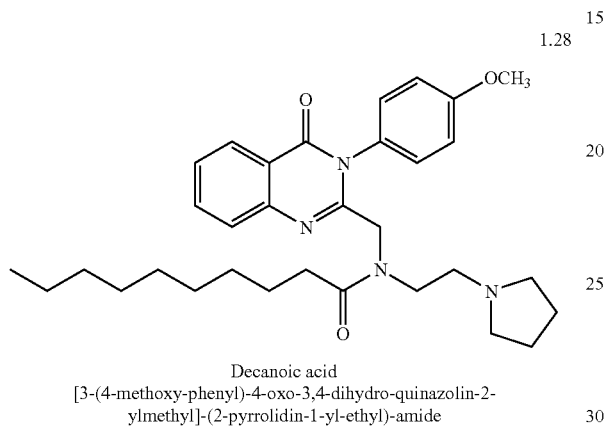

Decanoic acid
[3-(4-methoxy-phenyl)-4-oxo-3,4-dihydro-quinazolin-2-ylmethyl]-(2-pyrrolidin-1-yl-ethyl)-amide Compound 1.28 was prepared following the synthesis of compound 1.01. MS(ESI$^+$) 533.3, 534.3. $^1$H NMR (DMSO, T=140° C.) 0.87 (t, 3H, J=7.0 Hz), 1.26 (m, 14H), 1.66 (m, 4H), 2.22 (m, 2H), 2.49–2.76 (m, 6H), 3.51 (t, 2H, J=3.3 Hz), 3.87 (s, 3H), 4.24 (s, 2H), 7.11 (m, 2H), 7.31 (m, 2H), 7.51 (m, 1H), 7.60 (m, 1H), 7.80 (m, 1H), 8.13 (m, 1H). MS(ESI$^+$) 533.8 (MH$^+$).

Synthesis of Compound 1.29

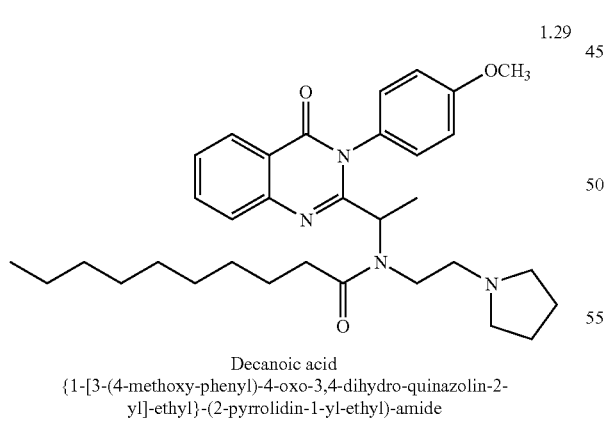

Decanoic acid
{1-[3-(4-methoxy-phenyl)-4-oxo-3,4-dihydro-quinazolin-2-yl]-ethyl}-(2-pyrrolidin-1-yl-ethyl)-amide Compound 1.29 was prepared following the synthesis of compound 1.01. Colorless viscous oil; mixture of cis/trans amide rotamers (1/1), determined by $^1$H NMR (CDCl$_3$) 4.82 (q, 1H, J=7.5 Hz), 5.37 (q, 1H, J=7.5 Hz). MS(ESI$^+$) 547.2 (MH$^+$). Anal. (C$_{23}$H$_{28}$N$_4$O$_2$) cal. C, 72.49; H, 8.48, N, 10.25. Found C, 72.62, H, 8.44, N, 10.12.

Synthesis of Compound 1.30

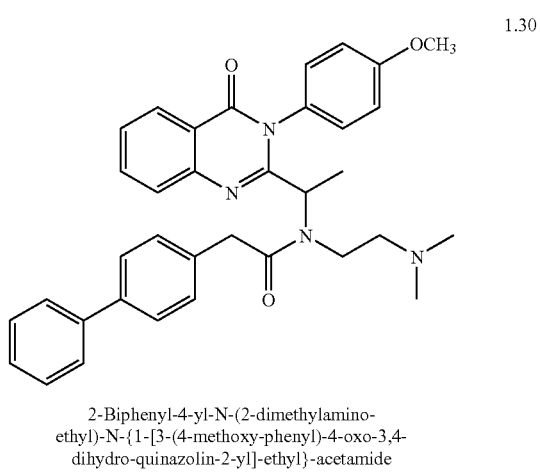

2-Biphenyl-4-yl-N-(2-dimethylamino-ethyl)-N-{1-[3-(4-methoxy-phenyl)-4-oxo-3,4-dihydro-quinazolin-2-yl]-ethyl}-acetamide Compound 1.30 was prepared following the synthesis of 1.01. Yellow solid. Mixture of cis/trans amide rotamers(1/1), determined by $^1$H NMR (CDCl$_3$) 1.40 (d, 3H, J=6.8 Hz), 1.46 (d, 3H, J=6.8 Hz). MS(ESI$^+$) 561.2 (MH$^+$).

Synthesis of Compound 1.31

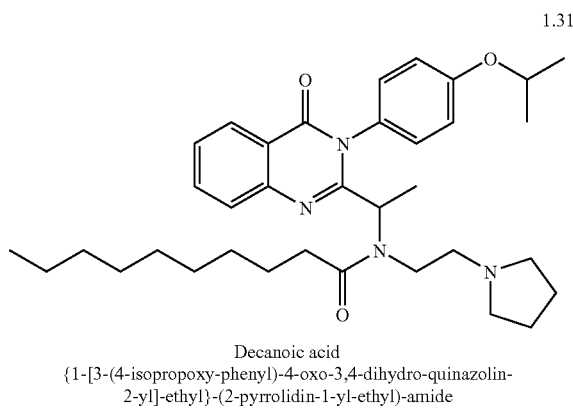

Decanoic acid
{1-[3-(4-isopropoxy-phenyl)-4-oxo-3,4-dihydro-quinazolin-2-yl]-ethyl}-(2-pyrrolidin-1-yl-ethyl)-amide Compound 1.31 was prepared following the synthesis of 1.01. Colorless viscous oil; mixture of cis/trans amide rotamers (1/1), determined by $^1$H NMR (CDCl$_3$) 4.88(q, 1H, J=7.2 Hz), 5.38 (q, 1H, J=7.2 Hz). MS(ESI$^+$) 575.5 (MH$^+$). Anal. (C$_{35}$H$_{50}$N$_4$O$_3$) cal. C, 73.14; H, 8.77, N, 9.75. Found C, 72.45, H, 8.75, N, 9.08.

Synthesis of Compound 1.32

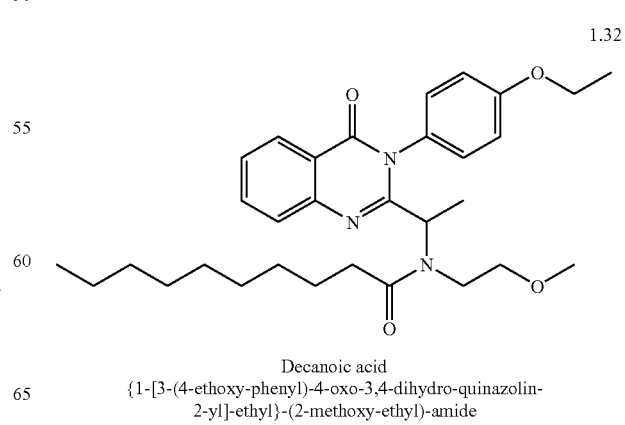

Decanoic acid
{1-[3-(4-ethoxy-phenyl)-4-oxo-3,4-dihydro-quinazolin-2-yl]-ethyl}-(2-methoxy-ethyl)-amide Compound 1.32 was prepared following the synthesis of 1.01. Colorless viscous oil; mixture of cis/trans amide rotamers (2/3), determined by $^1$H NMR (CDCl$_3$) 4.87(q, 1H, J=7.2 Hz), 5.38 (q, 1H, J=7.2 Hz). MS(ESI$^+$) 522.3 (MH$^+$). Anal. (C$_{31}$H$_{43}$N$_3$O$_4$) cal. C, 71.37; H, 8.31, N, 8.05. Found C, 71.13, H, 8.42, N, 8.02.

Synthesis of Compound 1.33

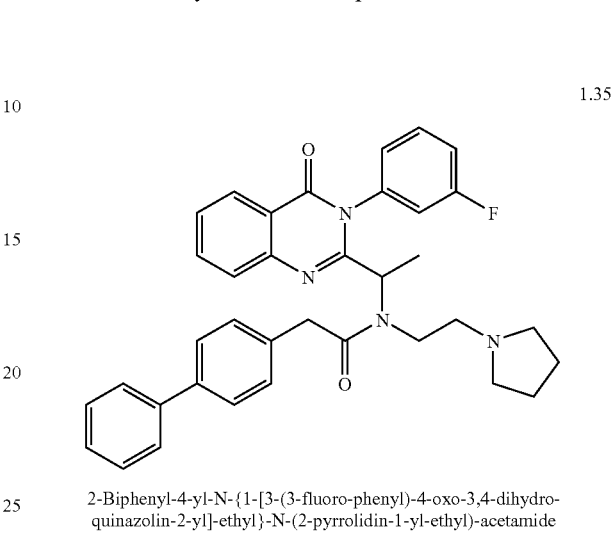

2-Biphenyl-4-yl-N-{1-[3-(3-fluoro-4-methoxy-phenyl)-4-oxo-3,4-dihydro-quinazolin-2-yl]-ethyl}-N-(2-pyrrolidin-1-yl-ethyl)-acetamide Compound 1.33 was prepared following the synthesis of 1.01. Yellow solid. m.p. 96.9° C. mixture of cis/trans amide rotamers (1/1), determined by $^1$H NMR (CDCl$_3$) 4.87(q, 1H, J=7.2 Hz), 5.38 (q, 1H, J=7.2 Hz). MS(ESI$^+$) 605.3 (MH$^+$). Anal. (C$_{37}$H$_{37}$FN$_4$O$_3$C$_4$H$_8$O$_2$) cal. C, 71.08H, 6.55, N, 8.09. Found C, 71.96, H, 6.19, N, 8.47.

Synthesis of Compound 1.34

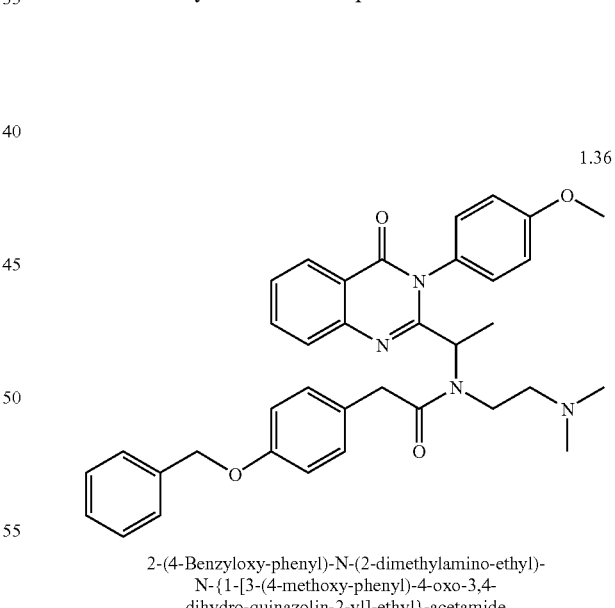

2-Biphenyl-4-yl-N-{1-[3-(4--methoxy-phenyl)-4-oxo-3,4-dihydro-quinazolin-2-yl]-ethyl}-N-(2-pyrrolidin-1-yl-ethyl)-acetamide Compound 1.34 was prepared following the synthesis of 1.01. white solid. m.p. 116.3° C. mixture of cis/trans amide rotamers (1/1), determined by $^1$H NMR (CDCl$_3$) 4.96(q, 1H, J=7.2 Hz), 5.38 (q, 1H, J=7.2 Hz). MS(ESI$^+$) 587.3 (MH$^+$). Anal. (C$_{37}$H$_{38}$N$_4$O$_3$) cal. C, 75.74; H, 6.53, N, 9.55. Found C, 75.05, H, 6.56, N, 9.35.

Synthesis of Compound 1.35

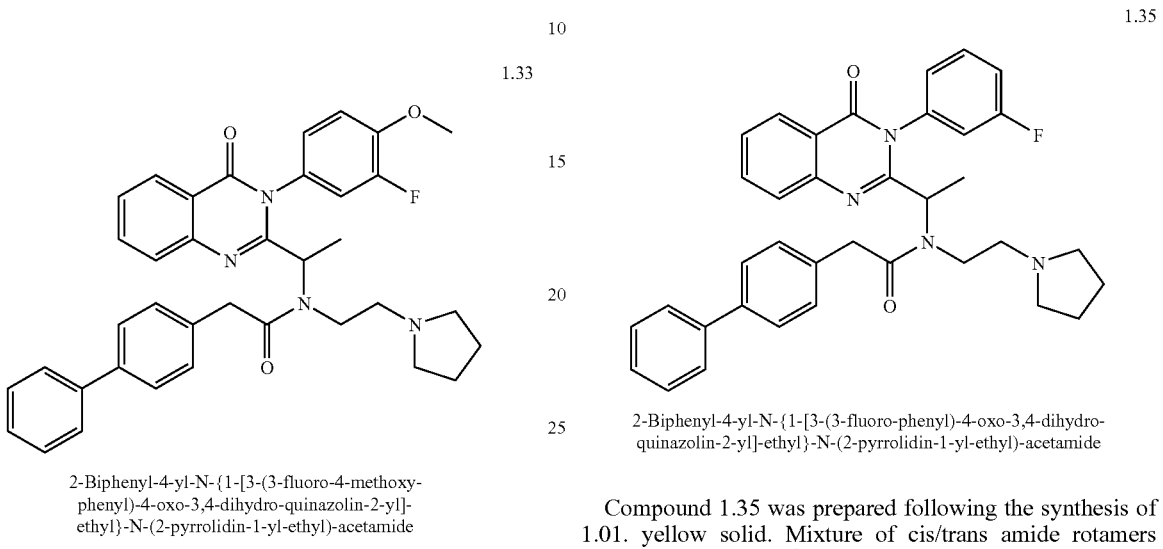

2-Biphenyl-4-yl-N-{1-[3-(3-fluoro-phenyl)-4-oxo-3,4-dihydro-quinazolin-2-yl]-ethyl}-N-(2-pyrrolidin-1-yl-ethyl)-acetamide Compound 1.35 was prepared following the synthesis of 1.01. yellow solid. Mixture of cis/trans amide rotamers (3/8), determined by $^1$H NMR (CDCl$_3$) 4.89(m, 1H), 5.38 (m, 1H). MS(ESI$^+$) 575.3 (MH$^+$). Anal. (C$_{36}$H$_{35}$FN$_4$O$_2$.C$_4$H$_8$O$_2$) cal. C, 72.49; H, 6.54, N, 8.45. Found C, 72.77, H, 6.10, N, 8.89.

Synthesis of Compound 1.36

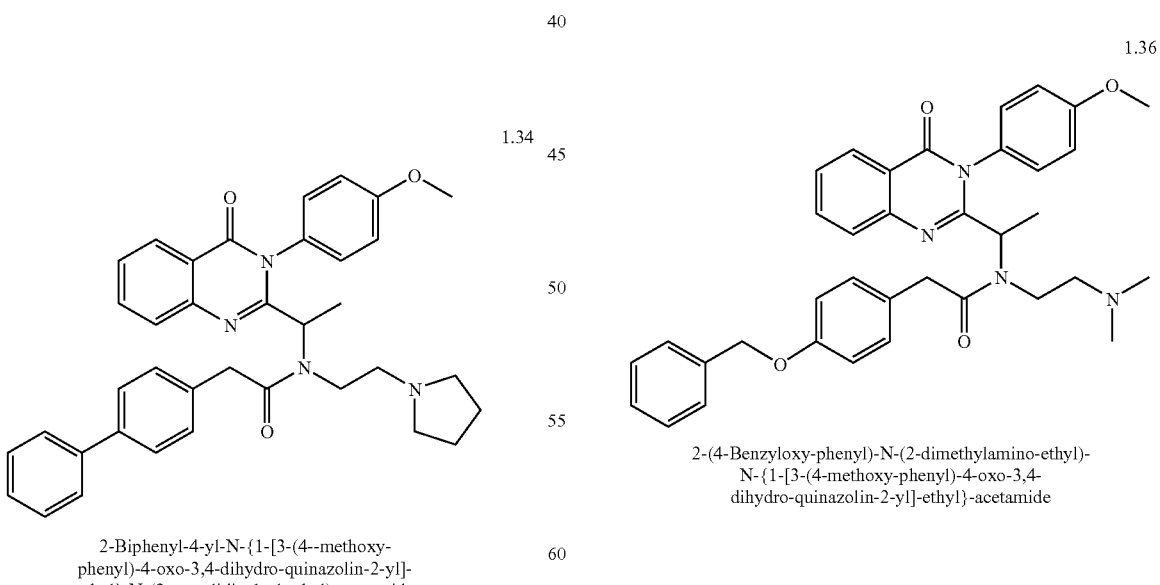

2-(4-Benzyloxy-phenyl)-N-(2-dimethylamino-ethyl)-N-{1-[3-(4-methoxy-phenyl)-4-oxo-3,4-dihydro-quinazolin-2-yl]-ethyl}-acetamide Compound 1.36 was prepared following the synthesis of 1.01. white solid; m.p. 61.3° C. mixture of cis/trans amide rotamers (1/1), determined by $^1$H NMR (CDCl$_3$) 4.92(q, 1H, J=7.2 Hz), 5.32 (q, 1H, J=7.2 Hz). MS(ESI$^+$) 591.3 (MH$^+$). Anal. (C$_{36}$H$_{38}$N$_4$O$_4$) cal. C, 73.20; H, 6.48, N, 9.48. Found C, 72.92, H, 6.46, N, 9.29.

Synthesis of Compound 1.37

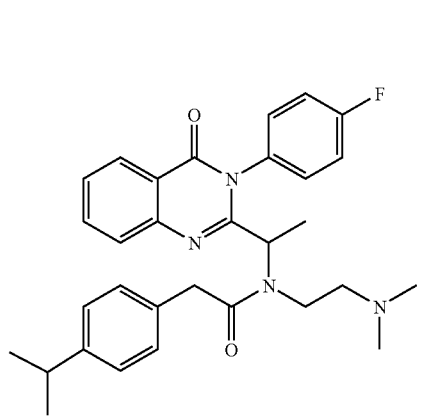

N-(2-Dimethylamino-ethyl)-N-{1-[3-(4-fluoro-phenyl)-4-oxo-3,4-dihydro-quinazolin-2-yl]-ethyl}-2-(4-isopropyl-phenyl)-acetamide Compound 1.37 was prepared following the synthesis of 1.01. white solid; mixture of cis/trans amide rotamers (1/2), determined by $^1$H NMR (CDCl$_3$) 4.86(q, 1H, J=7.2 Hz), 5.32 (q, 1H, J=7.2 Hz). MS(ESI$^+$) 515.3 (MH$^+$). Anal. (C$_{31}$H$_{35}$FN$_4$O$_2$) cal. C, 72.35; H, 6.85, N, 10.89. Found C, 72.11, H, 6.92, N, 10.71.

Synthesis of Compound 1.38

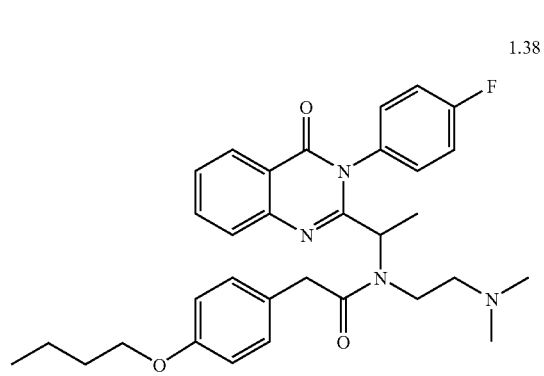

2-(4-Butoxy-phenyl)-N-(2-dimethtlamino-ethyl)-N-{1-[3-(4-fluoro-phynyl)-4-oxo-3,4-dihydro-quinazolin-2-yl]-ethyl}-acetamide Compound 1.38 was prepared following the synthesis of 1.01. white solid; mixture of cis/trans amide rotamers (1/1.7), determined by $^1$H NMR (CDCl$_3$) 4.85 (q, 1H, J=7.2 Hz), 5.30 (q, 1H, J=7.2 Hz). MS(ESI$^+$) 545.3 (MH$^+$). Anal. (C$_{32}$H$_{37}$FN$_4$O$_3$) cal. C, 70.57; H, 6.85, N, 10.29. Found C, 70.33, H, 6.90, N, 10.13.

Synthesis of Compound 1.39

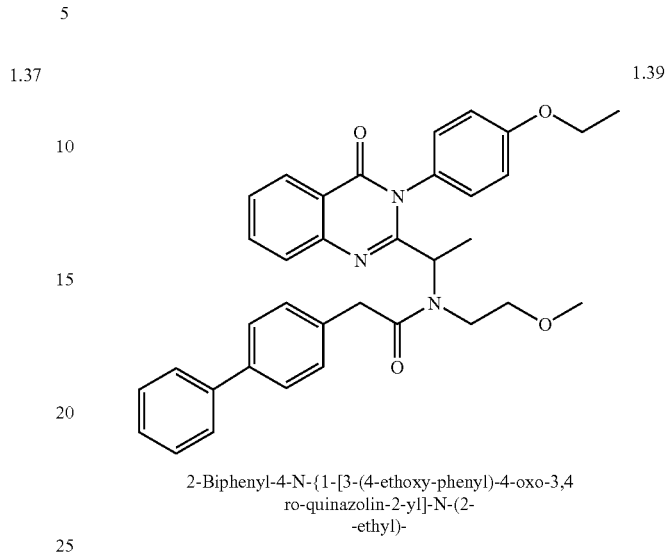

2-Biphenyl-4-N-{1-[3-(4-ethoxy-phenyl)-4-oxo-3,4 ro-quinazolin-2-yl]-N-(2- -ethyl)-

Compound 1.39 was prepared following the synthesis of 1.01. white solid; mixture of cis/trans amide rotamers (1/1), determined by $^1$H NMR (CDCl$_3$) 4.95 (q, 1H, J=7.2 Hz), 5.32 (q, 1H, J=7.2 Hz). MS(ESI$^+$) 562.3 (MH$^+$). Anal. (C$_{35}$H$_{35}$N$_3$O$_4$) cal. C, 74.84; H, 6.28, N, 7.48. Found C, 74.56, H, 6.26, N, 7.30.

Synthesis of Compound 1.40

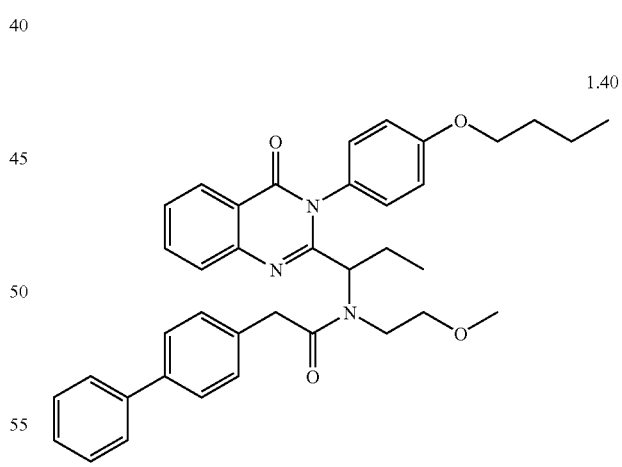

2-Biphenyl-4-yl-N-{1-[3-(4-butoxy-phenyl)-4-oxo-3,4-dihydro-quinazolin-2-yl]-propyl}-N-(2-methoxy-ethyl)-acetamide Compound 1.40 was prepared following the synthesis of 1.01. White solid; mixture of cis/trans amide rotamers (2/1), determined by $^1$H NMR (CDCl$_3$) 4.70 (m, 1H), 5.38 (t, 1H, J=7.0 Hz). MS(ESI$^+$) 604.3 (M$^+$). Anal. (C$_{38}$H$_{41}$N$_3$O$_4$) Cal. C, 75.60; H, 6.84, N, 6.96. Found C, 74.98, H, 6.82, N, 6.72.

Synthesis of Compound 1.42

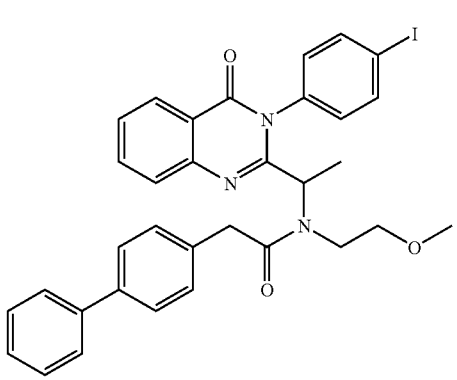

2-Biphenyl-4-yl-N-{1-[3-(4-iodo-phenyl)-4-oxo-3,4-dihydro-quinazolin-2-yl]-ethyl}-N-(2-methoxy-ethyl)-acetamide Compound 1.42 was prepared following the synthesis of 1.01. white solid; mixture of cis/trans amide rotamers (1/2), determined by $^1$H NMR (CDCl$_3$) 4.86 (q, 1H, J=7.3 Hz), 5.30 (q, 1H, J=7.3 Hz). MS(ESI$^+$) 644.2 (MH$^+$). Anal. (C$_{33}$H$_{30}$IN$_3$O$_3$) cal. C, 61.59; H, 4.70, N, 6.53. Found C, 61.63, H, 4.73, N, 6.36.

Synthesis of Compound 1.43

1.43

2-Biphenyl-4-yl-N-{1-[3-(4-cyano-phenyl)-4-oxo-3,4-dihydro-quinazolin-2-yl]-ethyl}-N-(2-methoxy-ethyl)-acetamide The mixture of 1.42 (1 mmol, 0.643 g) and CuCN (3 mmol, 0.27 g) in 0.10 ml of DMF was heated to 130° C. for 10 h. After evaporating the solvent, the residue was dissolved in CH$_2$Cl$_2$, the organic layer was washed by water, brine, dried over NaSO$_4$ and removed in vacuo to give a sticky oil which was purified by chromatography to afford a white solid; mixture of cis/trans amide rotamers (1/2), determined by $^1$H NMR (CDCl$_3$) 4.75 (q, 1H, J=7.3 Hz), 5.28 (q, 1H, J=7.3 Hz). MS(ESI$^+$) 543.2 (MH$^+$). Anal. (C$_{34}$H$_{30}$N$_4$O$_3$) cal. C, 75.26; H, 5.57, N, 10.32. Found C, 75.00, H, 5.59, N, 10.19.

Synthesis of Compound 1.44

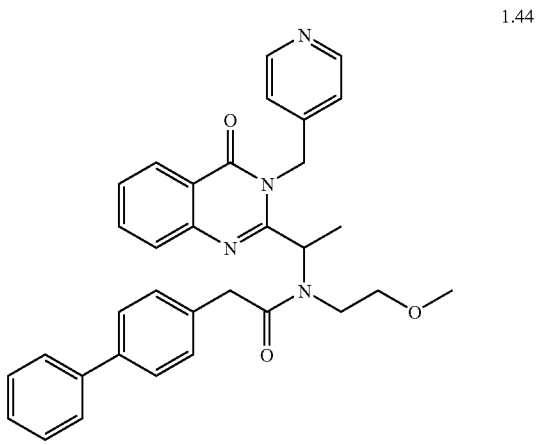

2-Biphenyl-4-yl-N-(2-methoxy-ethyl)-N-[1-(4-oxo-3-pyridin-4-ylmethyl-3,4-dihydro-quinazolin-2-yl)-ethyl]-acetamide Compound 1.44 was prepared following the synthesis of 1.01. White solid. $^1$H NMR (CDCl$_3$) 1.40 (d, 3H, J=7.3 Hz), 3.05 (m, 1H), 3.12 (s, 3H), 3.25 (m, 1H), 3.55–3.70 (m, 2H), 3.77 (d, 1H, J=15 Hz), 3.9 (d, 1H, J=15 Hz), 5.08 (d, 1H, 12Hz), 5.88 (m, 2H), 7.28–7.35 (m, 5H), 7.42 (m, 2H), 7.57 (m, 5H), 7.72 (m, 1H), 7.80(m, 1H), 8.32(m, 1H), 8.55 (m, 2H). MS(ESI$^+$) 533.3 (MH$^+$).

Synthesis of Compound 1.45

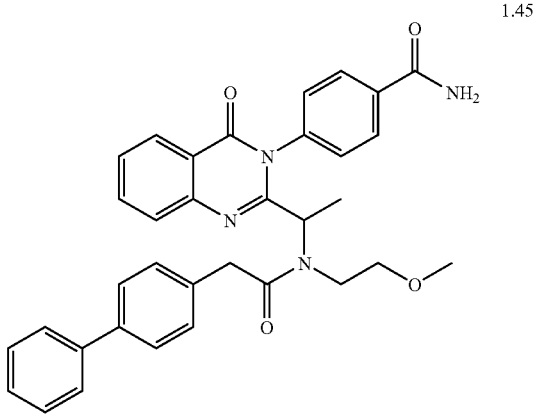

4-(2-{1-[(Biphenyl-4-yl-acetyl)-(2-methoxy-ethyl)-amino]-ethyl}-4-oxo-4H-quinazolin-3-yl)-benzamide The mixture of 1.43 (0.1 mmol, 0.054 g) and 30% H$_2$O$_2$ (0.6 mmol) in 1 mL of DMF and 1 ml of dioxane was stirred at room temperature for 1 h. Usual work up gave the give a white solid; mixture of cis/trans amide rotamers (1/2), determined by $^1$H NMR (CDCl$_3$) 4.95 (q, 1H, J=7.3 Hz), 5.15 (q, 1H J=7.3 Hz). MS(ESI$^+$) 561.3(MH$^+$). Anal. (C$_{34}$H$_{32}$N$_4$O$_4$·C$_4$H$_8$O) cal. C, 70.35; H, 6.21 N, 8.64. Found C, 70.98, H, 5.99, N, 9.14.

Synthesis of Compound 1.47

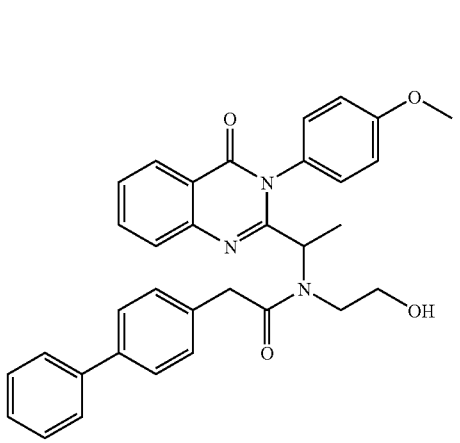

2-Biphenyl-4-yl-N-(2-hydroxy-ethyl)-N-{1-[3-(4-methoxy-phenyl-4-oxo-3,4-dihydro-quinazolin-2-yl]-ethyl}-acetamide Compound 1.47 was prepared following the synthesis of 1.01, mixture of cis/trans amide rotamers (1/17), determined by $^1$H NMR (CDCl$_3$) 1.35 (d, 3H, J=7.3 Hz), 1.42(d, 3H, J=7.3 Hz). MS(ESI$^+$) 534.2 (MH$^+$). Anal. (C$_{33}$H$_{31}$N$_3$O$_4$) cal. C, 74.28; H, 5.86, N, 7.87. Found C, 73.83, H, 5.93, N, 7.73.

Synthesis of compound 1.48

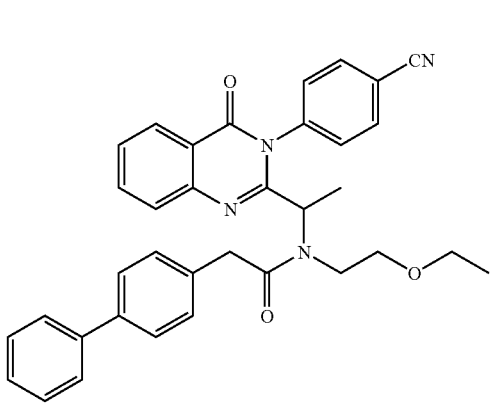

2-Biphenyl-4-yl-N-{1-[3-(4-cyano-phenyl)-4-oxo-3,4-dihydro-quinazolin-2-yl]-ethyl}-N-(2-ethoxy-ethyl)-acetamide Compound 1.48 was prepared following the synthesis of 21. white solid, mixture of cis/trans amide rotamers (1/5), determined by $^1$H NMR (CDCl$_3$) 4.72 (q, 1H, J=7.0 Hz), 5.25 (q, 1H, J=7.0 Hz). MS(ESI$^+$) 557.3 (MH$^+$). Anal. (C$_{35}$H$_{32}$N$_4$O$_3$) cal. C, 75.52; H, 5.79, N, 10.06. Found C, 75.03, H, 5.92, N, 9.96.

Synthesis of Compound 1.49

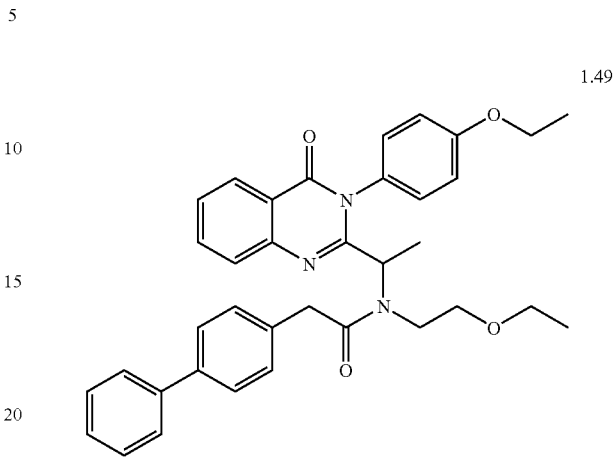

2-Biphenyl-4-yl-N-(2-ethoxy-ethyl)-N-{1-[3-(4-ethoxy-phenyl)-4-oxo-3,4-dihydro-quinazolin-2-yl]-ethyl}-acetamide Compound 1.49 was prepared following the synthesis of 1.01, white solid, m.p. 98.1° C., mixture of cis/trans amide rotamers (1/1), determined by $^1$H NMR (CDCl$_3$) 4.72 (q, 1H, J=7.0 Hz), 5.25 (q, 1H, J=7.0 Hz). MS(ESI$^+$) 576.3 (MH$^+$). Anal. (C$_{36}$H$_{37}$N$_3$O$_4$) cal. C, 75.11; H, 6.48, N, 7.30. Found C, 75.08, H, 6.59, N, 7.27.

Synthesis of Compound 1.50

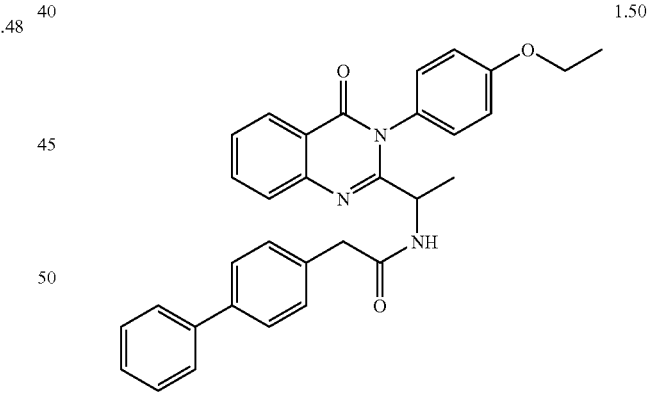

2-Biphenyl-4-yl-N-{1-[3-(4-ethoxy-phenyl)-4-oxo-3,4-dihydro-quinazolin-2-yl]-ethyl}-acetamide Compound 1.50 was prepared following the synthesis of 1.01, white solid, $^1$H NMR (CDCl$_3$) 1.24 (d, 3H, J=6.8 Hz), 1.46 (t, 3H, J=6.9 Hz), 3.64 (s, 2H), 4.09 (q, 2H, J=6.9 Hz), 4.83 (m, 1H), 6.90 (m, 1H), 7.05 (m, 2H), 7.17 (m, 1H), 7.35–7.61 (m, 7H), 7.63 (m, 5H), 8.25 (m, 1H). MS(ESI$^+$) 504.2 (MH$^+$). Anal. (C$_{32}$H$_{29}$N$_3$O$_3$) cal. C, 76.32; H, 5.80, N, 8.34. Found C, 75.85, H, 5.88, N, 8.14.

Synthesis of Compound 1.51

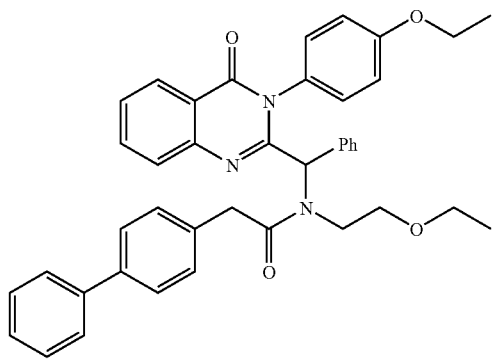

2-Biphenyl-4-yl-N-(2-ethoxy-ethyl)-N-{[3-(4-ethoxy-phenyl)-4-oxo-3,4-dihydro-quinazolin-2-yl]-phenyl-methyl}-acetamide Compound 1.51 was prepared following the synthesis of 1.01, white solid, $^1$H NMR (CDCl$_3$) 1.05 (t, 3H, J=7.0 Hz), 1.40 (t, 3H, J=6.92 Hz), 2.81 (m, 2H), 3.18 (m, 2H), 3.80 (m, 2H), 3.91 (d, 1H, J=15 Hz), 4.0 (m, 2H), 4.03 (d, 1H, J=15 Hz), 6.11 (m, 1H), 6.42 (m, 1H), 6.47 (m, 1H), 7.01 (m, 3H), 7.22–7.58 (m, 14H), 7.64 (m, 1H), 7.75 (m, 1H), 8.27 (d, 1H, J=8 Hz). MS(ESI$^+$) 638.3 (MH$^+$). Anal. (C$_{41}$H$_{39}$N$_3$O$_4$) cal. C, 77.21; H, 6.16, N, 6.59. Found C, 77.28, H, 6.15, N, 6.58.

Synthesis of Compound 1.52

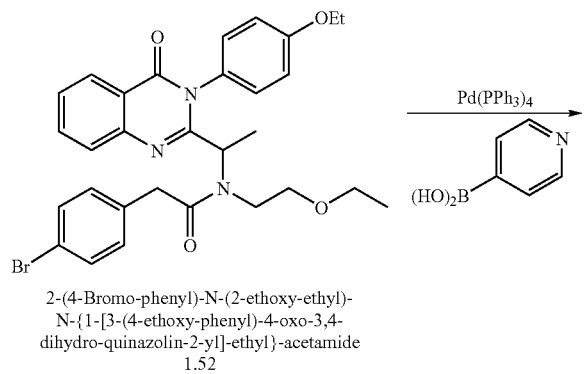

2-(4-Bromo-phenyl)-N-(2-ethoxy-ethyl)-N-{1-[3-(4-ethoxy-phenyl)-4-oxo-3,4-dihydro-quinazolin-2-yl]-ethyl}-acetamide
1.52

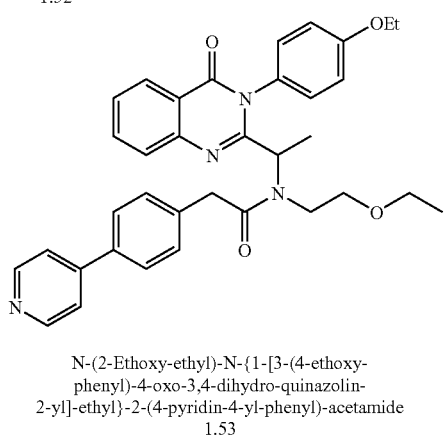

N-(2-Ethoxy-ethyl)-N-{1-[3-(4-ethoxy-phenyl)-4-oxo-3,4-dihydro-quinazolin-2-yl]-ethyl}-2-(4-pyridin-4-yl-phenyl)-acetamide
1.53

Compound 1.53 was synthesized in a manner similar to that used for the synthesis of 1.01. Under N$_2$, the mixture of pyridine-4-boronic acid (0.053 g, 0.43 mmol), 1.52 (0.050 g, 0.087 mmol) and Pd(PPh$_3$)$_4$ (0.010 g, 0.009 mmol) in toluene (4 mL) and 3M Na$_2$CO$_3$ (4 mL) was heated to 110° C. for 3 h. The organic layer was washed with water, dried over NaSO$_4$ and evaporated to give a oil which was purified by chromatography to afford compound 1.53 as a white solid (15 mg). MS(ESI$^+$) 577.3 (MH$^+$).

Synthesis of Compound 1.54

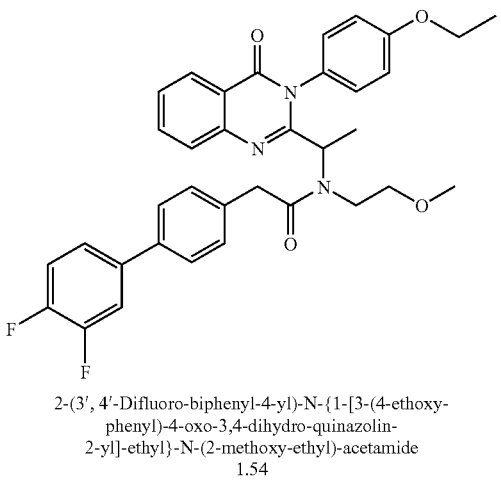

2-(3',4'-Difluoro-biphenyl-4-yl)-N-{1-[3-(4-ethoxy-phenyl)-4-oxo-3,4-dihydro-quinazolin-2-yl]-ethyl}-N-(2-methoxy-ethyl)-acetamide
1.54

Under N$_2$, the mixture of 3,4-difluorophenylboronic acid (0.131 g, 0.83 mmol), compound 1.52 (0.050 g, 0.087 mmol) and Pd(OAc)$_2$ (0.016 g, 0.071 mmol) in DME (3 mL) and 3M Na$_2$CO$_3$ (2 mL) was heated to 90° C. for 3 h. The aqueous layer was extracted with CH$_2$Cl$_2$, the combined organic extracts was dried over Na$_2$SO$_4$, filtered and concentrated. The residue was purified by chromatography to give a white solid (71 mg,). $^1$H NMR (DMSO, T=140° C.) 0.96 (d, 3H, J=6.8 Hz), 1.36 (t, 3H, J=7.2 Hz), 1.42 (d, 3H, J=6.4 Hz), 3.31–3.56 (m, 8H), 4.13 (q, 2H, J=6.8 Hz), 5.16 (g, 1H, J=6.4 Hz), 7.05 (br, 2H), 7.18–7.61 (m 10H), 7.70 (d, 1H, J=8 Hz), 7.84 (t, 1H, J=6.8 Hz), 8.13 (d, 1H, J=8.4 Hz). At room temperature, mixture of cis/trans amide rotamers (1/1), determined by $^1$H NMR (CDCl$_3$) 4.95 (q, 1H, J=6.8 Hz), 5.35 (q, 1H, J=6.8 Hz). MS(ESI$^+$) 612.2(MH$^+$). Anal. (C$_{36}$H$_{35}$F$_2$N$_3$O$_4$) cal. C, 70.69; H, 5.77; N, 6.87. Found C, 70.22, H, 5.71, N, 6.81.

Synthesis of Compound 1.55

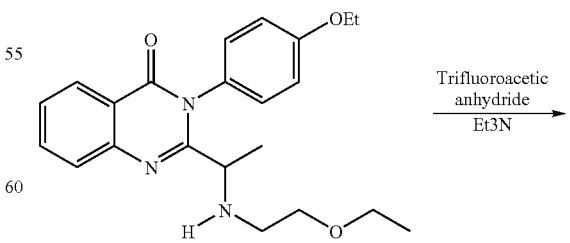

2-[1-(2-Ethoxy-ethylamino)-ethyl]-3-(4-ethoxy-phenyl)-3H-quinazolin-4-one

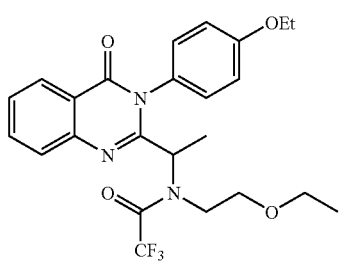

N-(2-Ethoxy-ethyl)-N-{1-[3-(4-ethoxy-phenyl)-4-oxo-3,4-dihydro-quinazolin-2-yl]-ethyl}-2,2,2-trifluoro-acetamide
1.55

Trifluoroacetic anhydride (0.024 g, 0.113 mmol) was added dropwise to a mixture of the amine (0.036 g, 0.094 mmol) and Et₃N (0.014 g, 0.142 mmol) in CH₂Cl₂ at room temperature. After stirring for 1 h, the organic layer was washed by water, brine, dried over NaSO₄ and removed in vacuo to give a oil which was purified by chromatography to afford a colorless oil, compound 1.55. ¹H NMR (CDCl₃) 1.06 (t, 3H, J=7.04 Hz), 1.45(t, 3H, J=7.0 Hz), 1.54(d, 3H, J=7 Hz), 3.38 (m, 2H), 3.58 (t, 2H, J=6.2 Hz), 3.70 (t, 2H, J=6.2 Hz), 4.08 (m, 2H), 5.19 (q, 1H, J=7 Hz), 7.01 (m, 2H), 7.14 (m, 1H), 7.32 (m, 1H), 7.51(m, 1H), 7,77(m, 2H), 8.27 (d, 1H, J=7.3 Hz) MS(ESI⁺) 478.3 (MH⁺).

Example 2

Synthesis of Compound 2.01

The synthesis of 2.01 in five steps from commercially available 2-amino-6-methyl-benzoic acid is an example of 3H-quinazolin-4-one synthesis by Method 2 (see Scheme 2, below).

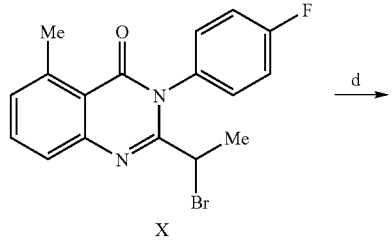

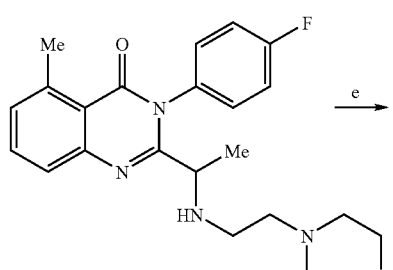

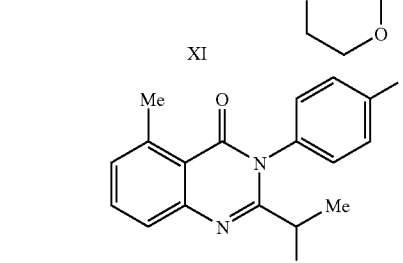

2.01

(a) propionyl chloride, DMF, RT
(b) PCl₃, 4-fluoroaniline, toluene, 110° C.
(c) Br₂, NaOAc, HOAc, 40° C.
(d) 1-(3-aminoethyl)morpholine, EtOH, 80° C.
(e) biphenylacetyl chloride, NEt₃, cat. DMAP, 1,4-dioxane Scheme 2

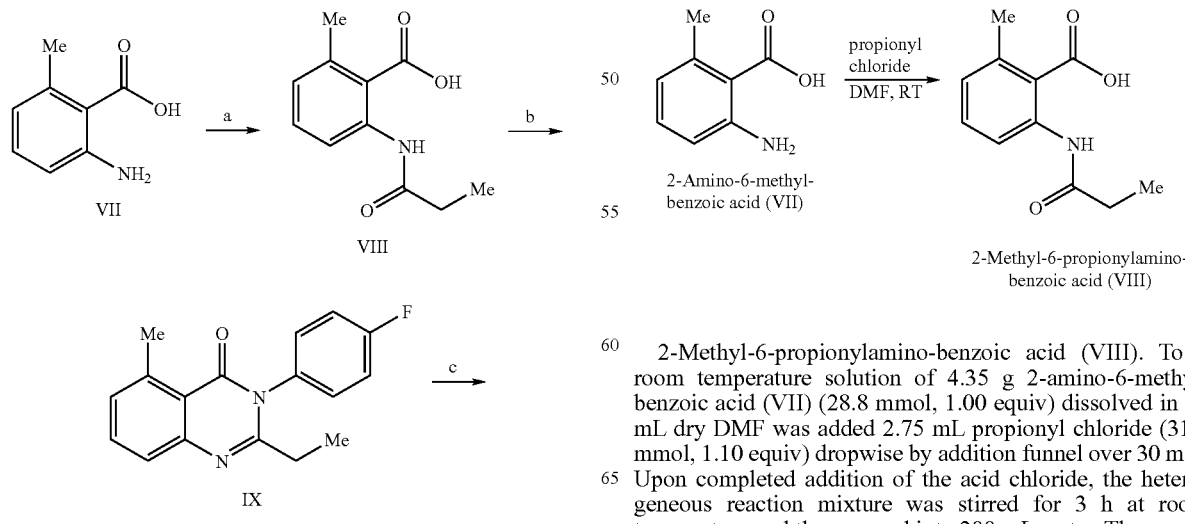

2-Methyl-6-propionylamino-benzoic acid (VIII). To a room temperature solution of 4.35 g 2-amino-6-methyl-benzoic acid (VII) (28.8 mmol, 1.00 equiv) dissolved in 25 mL dry DMF was added 2.75 mL propionyl chloride (31.7 mmol, 1.10 equiv) dropwise by addition funnel over 30 min. Upon completed addition of the acid chloride, the heterogeneous reaction mixture was stirred for 3 h at room temperature and then poured into 200 mL water. The resulting water/DMF mixture, with white precipitate, was stirred vigorously at ambient temperature for one h, after which time the solid was collected by vacuum filtration, rinsing the solid with cold water (2×50 mL). The white solid was dried in vacuo over phosphorous pentoxide overnight to afford 4.65 g of a white solid. m.p. 152.5° C. $^1$H NMR (d$_6$-DMSO) δ 1.06 (t, 3H, J=7.6 Hz), 2.29 (q, 2H, J=7.6 Hz), 2.35 (s, 3H), 7.04 (d, 1H, J=7.6 Hz), 7.30 (dd, 1H, J$_1$=7.6 Hz, J$_2$=8.0 Hz), 7.47 (d, 1H, J=8.0 Hz), 9.57 (s, 1H), 13.18 (br s, 1H) ppm. MS (ESI$^-$) 206.1 [M−H]$^-$.

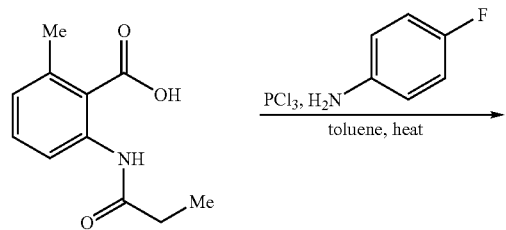

2-Methyl-6-propionylamino-benzoic acid (VIII)

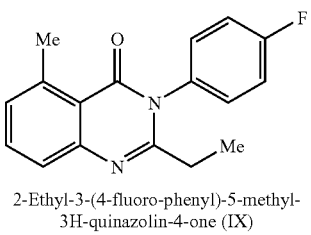

2-Ethyl-3-(4-fluoro-phenyl)-5-methyl-3H-quinazolin-4-one (IX)

2-Ethyl-3-(4-fluoro-phenyl)-5-methyl-3H-quinazolin-4-one (IX)). To a mixture of 4.266 g 2-methyl-6propionylamino-benzoicacid (VIII) (20.58 mmol, 1.00 equiv) and 2.14 mL 4-fluoroaniline (22.6 mmol, 1.10 equiv) suspended in 35 mL toluene was added a solution of 1.08 mL phosphorous trichloride (12.3 mmol, 0.598 equiv) dissolved in 10 mL toluene dropwise by addition funnel over 30 min. The resulting heterogeneous mixture was heated to reflux for 20 h and then cooled to room temperature and diluted with 100 mL toluene. To the room temperature reaction mixture was added 100 mL aqueous 10% sodium carbonate solution and the resulting biphase was stirred vigorously until all solids dissolved. The toluene was removed in vacuo and a precipitate developed. The solid was collected by filtration, rinsing with water (2×75 mL). The air-dried solid was purified by recrystallization from isopropyl alcohol to afford 3.31 g colorless flakes, dried in vacuo over phosphorous pentoxide. m.p. 170.0° C. $^1$H NMR (CDCl$_3$) δ 1.24 (t, 3H, J=7.6 Hz), 2.44 (q, 2H, J=7.6 Hz), 2.84 (s, 3H), 7.25 (dd, 1H, J$_1$=1.6 Hz, J$_2$=6.4 Hz), 7.27 (2×d, 2×2H, J=6.4 Hz), 7.58 (dd, 1H, J$_1$=1.2 Hz, J$_2$=8.0 Hz), 7.63 (dd, 1H, J$_1$=J$_2$=8.0 Hz) ppm. MS (ESI$^+$) 283.2 [MH]$^+$.

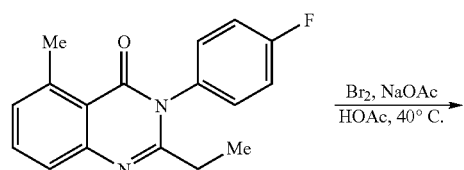

2-Ethyl-3-(4-fluoro-phenyl)-5-methyl-3H-quinazolin-4-one (IX)

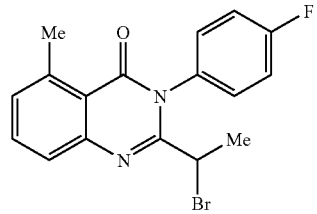

2-(1-Bromo-ethyl)-3-(4-fluoro-phenyl)-5-methyl-3H-quinazolin-4-one (X)

2-(1-Bromo-ethyl)-3-(4-fluoro-phenyl)-5-methyl-3H-quinazolin-4-one (X). To a mixture of 1.969 g 2-ethyl-3-(4-fluoro-phenyl)-5-methyl-3H-quinazolin-4-one (X) (6.974 mmol, 1.000 equiv) and 0.687 g sodium acetate (8.37 mmol, 1.20 equiv) in 28 mL glacial acetic acid at 40° C. (external temperature, oil bath) was added a solution of 0.372 mL bromine (7.32 mmol, 1.05 equiv) dissolved in 5 mL glacial acetic acid dropwise by addition funnel over 30 min. After 2 h the reaction solution was poured into 250 mL water. The resulting mixture was stirred vigorously at room temperature for 1 h, after which time the precipitate was collected by vacuum filtration, rinsing with warm (ca. 40° C.) water (3×50 mL). The solid was dried in vacuo over phosphorous pentoxide overnight, affording 2.19 g of a white solid. m.p. decomposes upon heating. $^1$H NMR (CDCl$_3$) δ 2.04 (d, 3H, J=6.8 Hz), 2.82 (s, 3H), 4.51 (q, 1H, J=6.8 Hz), 7.15 (ddd, 1H), J$_1$=2.4 Hz, J$_2$=4.4 Hz, J$_3$=8.4 Hz), 7.23 (dd, 1H, J$_1$=2.8 Hz, J$_2$=10.8 Hz), 7.25–7.31 (m, 2H), 7.56 (ddd, J$_1$=2.8 Hz, J$_2$=4.8 Hz, J$_3$=8.8 Hz), 7.64 (2×d, 2×1H, J=5.2 Hz) ppm. MS (ESI$^+$) 361.1 [MH]$^+$.

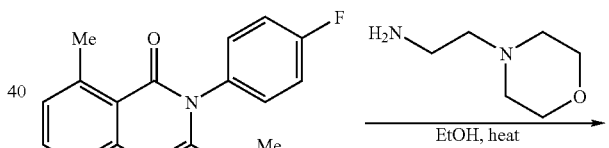

2-(1-Bromo-ethyl)-3-(4-fluoro-phenyl)-5-methyl-3H-quinazolin-4-one
X

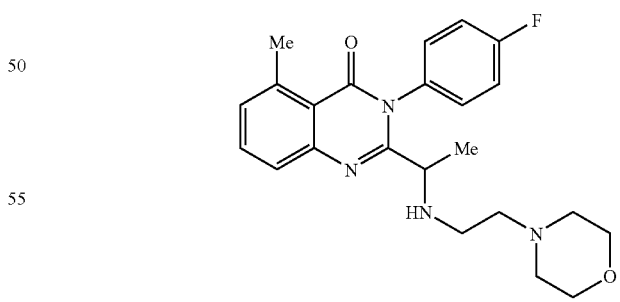

3-(4-Fluoro-phenyl)-5-methyl-2-[1-(2-morpholin-4-yl-ethylamino)-ethyl]-3H-quinazolin-4-one
XI 3-(4-Fluoro-phenyl)-5methyl-2-[1-(2-morpholin4-yl-ethylamino)-ethyl]-3H-quinazolin4-one (XI). A mixture of 0.283 g 2-(1-bromo-ethyl)-3-(4-fluoro-phenyl)-5-methyl- 3H-quinazolin-4-one (X) (0.784 mmol, 1.00 equiv) and 0.165 mL 1-(2-aminoethyl)morpholine (1.25 mmol, 1.60 equiv) in 5 mL ethanol was heated to reflux. After 20 h, the ethanol was removed in vacuo and the concentrate partitioned between dichloromethane and saturated aqueous sodium bicarbonate solution (20 mL ea.). The separated aqueous layer was extracted again with dichloromethane (15 mL) and the combined organic extracts dried over magnesium sulfate, filtered, and concentrated in vacuo to yield a yellow foam. The crude material was purified by chromatography on silica gel (3.5 cm o.d.×12 cm h) eluting with 5% methanol in chloroform. Fractions containing product were combined and concentrated in vacuo to afford 257 mg of a pale yellow solid. m.p. 192.9° C. $^1$H NMR (CDCl$_3$) δ 1.27 (d, 3H, J=6.4 Hz), 2.26–2.34 (m, 3H), 2.38–2.44 (m, 1H), 2.46–2.52 (m, 2H), 2.56–2.70 (m, 2H), 2.82 (s, 3H), 3.39 (q, 1H, J=6.4 Hz), 3.70–3.80 (m, 4H), 7.18–7.29 (m, 5H), 7.46 (dd, 1H, J$_1$=0.8 Hz, J$_2$=8.0 Hz), 7.61 (dd, 1H, J$_1$=7.6 Hz, J$_2$=7.8 Hz), ppm. MS (ESI$^+$) 411.2 [MH]$^+$

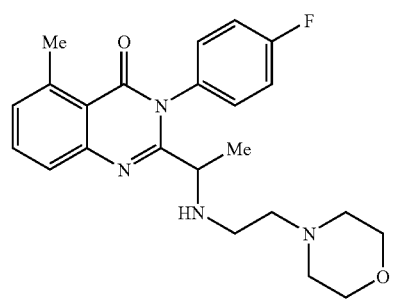

3-(4-Fluoro-phenyl)-5-methyl-2-[1-(2-morpholin-4-yl-ethylamino)-ethyl]-3H-quinazolin-4-one (XI)

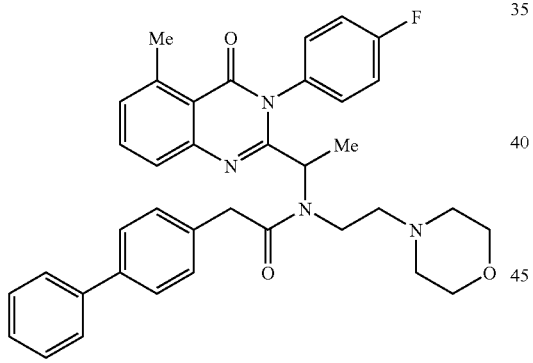

2-Biphenyl-4-yl-N-{1-[3-(4-fluoro-phenyl)-5-methyl-4-oxo-3,4-dihydro-quinazolin-2-yl]-ethyl}-N-(2-morpholin-4-yl-ethyl)-acetamide (2.01)

Compound 2.01. To a room temperature solution of 127 mg 3-(4-fluoro-phenyl)-5-methyl-2-[1-(2-morpholin-4-yl-ethylamino)-ethyl]-3H-quinazolin-4-one (XI) (0.309 mmol, 1.00 equiv), 0.084 mL triethylamine (0.618 mmol, 2.00 equiv), and 2.0 mg DMAP (0.016 mmol, 0.052 equiv) dissolved in 3 mL dichloromethane was added 107 mg biphenylacetyl chloride (0.463 mmol, 1.50 equiv). The clear, faint yellow-colored reaction mixture was stirred for 12 h at room temperature then poured into 10 mL saturated aqueous sodium bicarbonate solution. The separated aqueous layer was extracted with a second volume of dichloromethane (20 mL). The combined organic extracts dried over magnesium sulfate, filtered, and concentrated in vacuo to yield an orange oil. The crude product was purified by chromatography on silica gel (3.5 cm o.d.×10 cm h) eluting with 2% methanol in chloroform. Fractions containing product at R$_f$=0.48, 5% methanol in chloroform, were combined and concentrated in vacuo to afford 115 mg product as a faint yellow, viscous oil. $^1$H NMR (d$_6$-DMSO; T=140° C.) δ 1.44 (d, 3H, J=6.4 Hz), 2.28–2.42 (m, 5H), 2.50–2.60 (m, 1H), 2.77 (s, 3H), 3.38–3.64 (m, 8H), 5.12 (q, 1H, J=6.8 Hz), 7.20 (m, 2H), 7.27–7.38 (m, 5H), 7.40–7.47 (m, 3H), 7.51–7.56 (m, 3H), 7.58–7.64 (m, 2H), 7.68 (dd, 1H, J$_1$=J$_2$=7.6 Hz)ppm. At room temperature, compound exists as a mixture of cis/trans amide rotamers, ca. 3:2 by $^1$H NMR (CDCl$_3$; T=25° C.) δ 4.84 (q, 1.0H, J=6.8 Hz) & 5.28 (q, 1.4H, J=6.8 Hz) ppm. MS (ESI$^+$) 605.3 [MH]$^+$ Synthesis of Compound 2.02

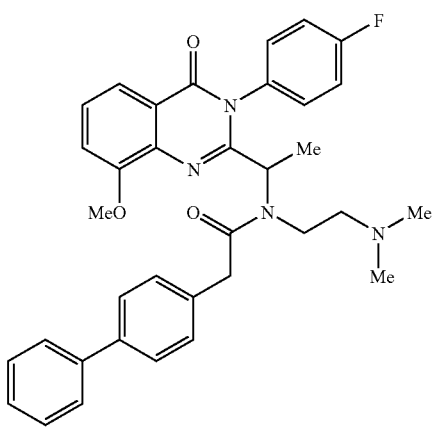

2-Biphenyl-4-yl-N-(2-dimethylamino-ethyl)-N-{1-[3-(4-fluoro-phenyl)-8-methoxy-4-oxo-3,4-dihydro-quinazolin-2-yl]-ethyl}acetamide (2.02)

Compound 2.02 was prepared following the synthesis of 2.01 described above. Method 2 was followed for the synthetic sequence, wherein 2-amino-3-methoxy-benzoic acid was used in step a instead of 2-amino-6-methylbenzoic acid. Characterization data for compound 2.02 follows: colorless, viscous oil. $^1$H NMR similar to spectrum for compound 2.01: a mixture of cis/trans amide rotamers in ca. 3:1 (CDCl$_3$; T=25° C.) characteristic resonance peaks at δ$_{minor}$ 4.89 (q, 1.0H, J=6.8 Hz) and δ$_{major}$ 5.28 (q, 2.8H, J=7.6 Hz) ppm. MS (ESI$^+$) 579.3 [MH]$^+$ Synthesis of Compound 2.03

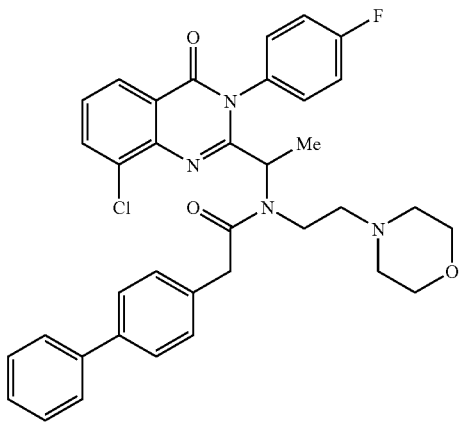

2-Biphenyl-4-yl-N-{1-[8-chloro-3-(4-fluoro-phenyl)-4-oxo-3,4-dihydro-quinazolin-2-yl]-ethyl}-N-(2-morpholin-4-yl-ethyl)-acetamide (2.03)

Compound 2.03 was prepared following the synthesis of compound 2.01 described above. Method 2 was followed for the synthetic sequence, wherein 2-amino-3-chloro-benzoic acid was used in step a instead of 2-amino-6-methylbenzoic acid. Characterization data for compound 2.03 follows: colorless, viscous oil. $^1$H NMR similar to spectrum for compound 2.01: a mixture of cis/trans amide retainers in ca. 3:1 (CDCl$_3$; T=25° C.) characteristic resonance peaks at $\delta_{minor}$ 4.89 (q, 1.0H, J=6.4 Hz) and $\delta_{major}$ 5.23 (q, 2.7H, J=6.8 Hz) ppm. MS (ESI$^+$) 625.3 [MH]$^+$ Synthesis of Compound 2.04

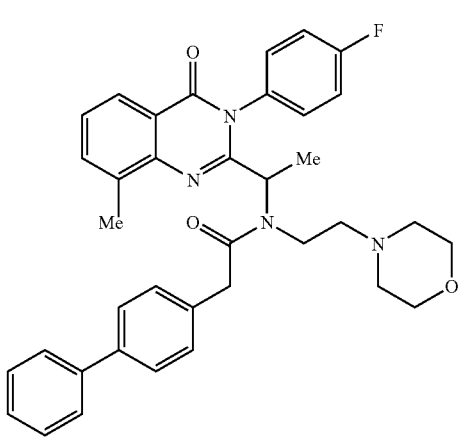

(2.04)

Compound 2.04 was prepared following the synthesis of compound 2.01 described above. Method 2 was followed for the synthetic sequence, wherein 2-amino-3-methyl-benzoic acid was used in step a instead of 2-amino-6-methyl-benzoic acid. Characterization data for compound 2.04 follows: colorless, viscous oil. $^1$H NMR similar to spectrum for compound 2.01: a mixture of cis/trans amide rotamers in ca. 3:2 (CDCl$_3$; T=25° C.) characteristic resonance peaks at $\delta_{minor}$ 4.92 (q, 1.0H, J=6.7 Hz) and $\delta_{major}$ 5.35 (q, 1.7H, J=7.3 Hz) ppm. MS (ESI$^+$) 605.3 [MH]$^+$ Synthesis of Compound 2.05

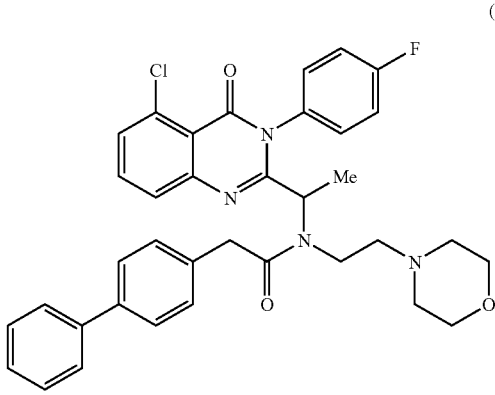

(2.05)

Compound 2.05 was prepared following the synthesis of compound 2.01 described above. Method 2 was followed for the synthetic sequence, wherein 2-amino-6-chloro-benzoic acid was used in step a instead of 2-amino-6-methyl-benzoic acid. Characterization data for compound 2.05 follows: colorless, viscous oil. $^1$H NMR similar to spectrum for compound 2.01: a mixture of cis/trans amide rotamers in ca. 2:1 (CDCl$_3$; T=25° C.) characteristic resonance peaks at $\delta_{minor}$ 4.84 (q, 1.0H, J=6.8 Hz) and $\delta_{major}$ 5.21 (q, 2.0H, J=6.8 Hz) ppm. MS (ESI$^+$) 625.3 [MH]$^+$ Synthesis of Compound 2.06

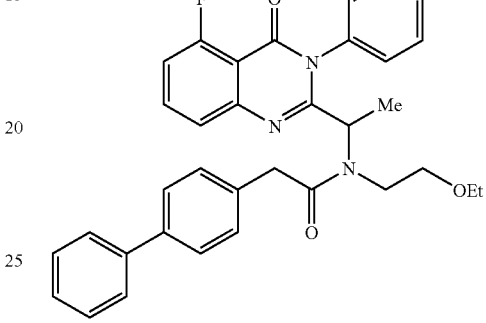

(2.06)

2-Bipheny-4-yl-N-(2-ethoxy-ethyl)-N-{1-[5-fluoro-3-(4-fluoro-phenyl)-4-oxo-3,4-dihydro-quinazolin-2-yl]-ethyl}-acetamide Compound 2.06 was prepared following the synthesis of compound 2.01 described above. Method 2 was followed for the synthetic sequence, wherein 2-amino-6-fluoro-benzoic acid was used in step a instead of 2-amino-6-methyl-benzoic acid and 2-ethoxy-1-aminoethane was used in step d instead of 1-(2-aminoethyl)morpholine. Characterization data for compound 2.06 follows: colorless, viscous oil. $^1$H NMR similar to spectrum for compound 2.01: a mixture of cis/trans amide rotamers in ca. 5:2 (CDCl$_3$; T=25° C.) characteristic resonance peaks at $\delta_{minor}$ 4.87 (q, 1.0H, J=6.7 Hz) and $\delta_{major}$ 5.27 (q, 2.5H, J=7.0 Hz) ppm. MS (ESI$^+$) 568.2 [MH]$^+$ Synthesis of Compound 2.07

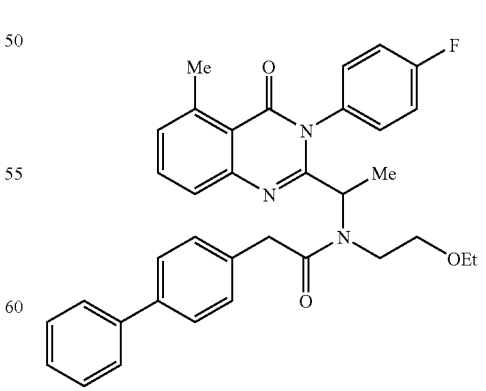

(2.07)

2-Biphenyl-4-yl-N-(2-ethoxy-ethyl)-N-{1-[5-methyl-3-(4-fluoro-phenyl)-4-oxo-3,4-dihydro-quinazolin-2-yl]-ethyl}-acetamide Compound 2.07 was prepared following the synthesis of compound 2.01 described above. Method 2 was followed for the synthetic sequence, wherein 2-ethoxy-1-aminoethane was used in step d instead of 1-(2-aminoethyl)morpholine. Characterization data for compound 2.07 follows: colorless, viscous oil. $^1$H NMR similar to spectrum for compound 2.01: a mixture of cis/trans amide rotamers in ca. 2:1 (CDCl$_3$; T=25° C.) characteristic resonance peaks at $\delta_{minor}$ 4.85 (q, 0.1H, J=6.8 Hz) and $\delta_{major}$ 5.29 (q, 1.8H, J=6.6 Hz) ppm. MS (ESI$^+$) 564.3 [MH]$^+$ Synthesis of Compound 2.08

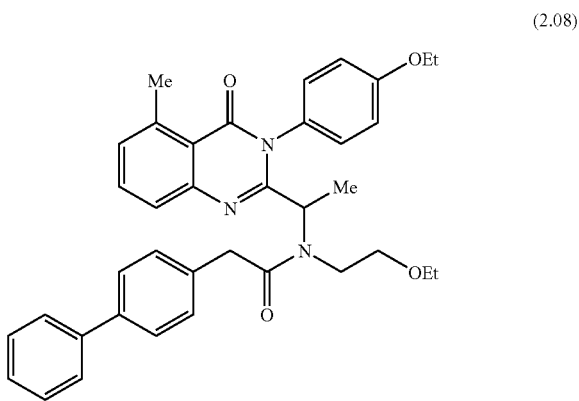

(2.08)

2-Biphenyl-4-yl-N-(2-ethoxy-ethyl)-N-{1-[3-(4-ethoxy-phenyl)-5-methyl-4-oxo-3,4-dihydro-quinazolin-2-yl]-ethyl}-acetamide Compound 2.08 was prepared following the synthesis of compound 2.01 described above. Method 2 was followed for the synthetic sequence, wherein 4-ethoxyaniline was used in step b instead of 4-fluoroaniline and 2-ethoxy-1-aminoethane was used in step d instead of 1-(2-aminoethyl)morpholine. Characterization data for compound 2.08 follows: colorless, viscous oil. $^1$H NMR similar to spectrum for compound 2.01: a mixture of cis/trans amide rotamers in ca. 1:1 (CDCl$_3$; T=25° C.) characteristic resonance peaks at $\delta_A$ 4.95 (q, 1.1H, J=6.8 Hz) and $\delta_B$ 5.35 (q, 1.0H, J=6.8 Hz) ppm. MS (ESI$^+$) 590.3 [MH]$^+$ Synthesis of Compound 2.09

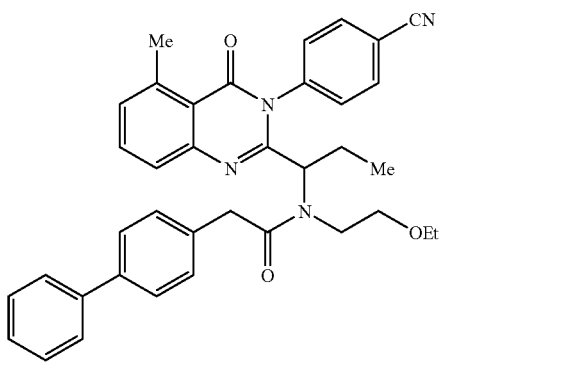

(2.09)

2-Biphenyl-4-yl-N-(1-[3-(4-cyano-phenyl)-5-methyl-4-oxo-3,4-dihydro-quinazolin-2-yl]-propyl)-N-(2-ethoxy-ethyl)-acetamide Compound 2.09 was prepared following the synthesis of compound 2.01 described above. Method 2 was followed for the synthetic sequence wherein butyryl chloride was used in step a instead of propionyl chloride, 4-cyanoaniline was used in step b instead of 4-fluoroaniline, and 2-ethoxy-1-aminoethane was used in step d instead of 1-(2-aminoethyl)morpholine. Characterization data for compound 2.09 follows: colorless, viscous oil. $^1$H NMR similar to spectrum for compound 2.01: a mixture of cis/trans amide rotamers in ca. 4:1 (CDCl$_3$; T=25° C.) characteristic resonance peaks at $\delta_{minor}$ 4.39 (dd, 1.0H, J$_1$=4.4 Hz, J$_2$=10.0 Hz) and $\delta_{major}$ 5.31 (dd, 3.9H, J$_1$=J$_2$=7.2 Hz) ppm. MS (ESI$^+$) 585.3 [MH]$^+$.

Synthesis of Compound 2.10

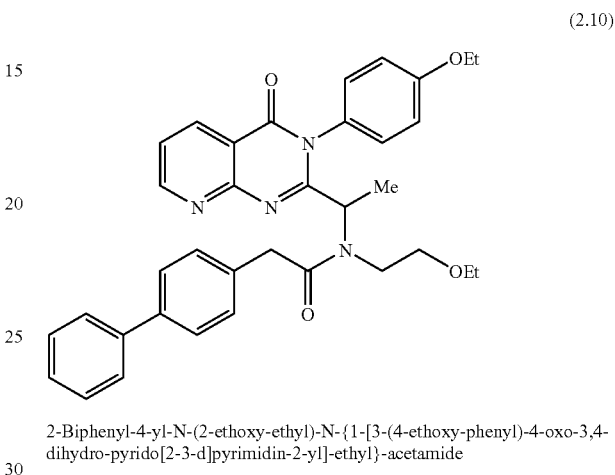

(2.10)

2-Biphenyl-4-yl-N-(2-ethoxy-ethyl)-N-{1-[3-(4-ethoxy-phenyl)-4-oxo-3,4-dihydro-pyrido[2-3-d]pyrimidin-2-yl]-ethyl}-acetamide Compound 2.10 was prepared following the synthesis of compound 2.01 described above. Method 2 was followed for the synthetic sequence, wherein 2-aminonicotinic acid was used in step a instead of 2-amino-6-methylbenzoic acid, 4-ethoxyaniline was used in step b instead of 4-fluoroaniline, and 2-ethoxy-1-aminoethane was used in step d instead of 1-(2-aminoethyl)morpholine. Characterization data for compound 2.10 follows: light yellow, viscous oil. $^1$H NMR similar to spectrum for compound 2.01: a mixture of cis/trans amide rotamers in ca. 1:1 (CDCl$_3$; T=25° C.) characteristic resonance peaks at $\delta_{minor}$ 5.04 (q, 1.0H, J=6.4 Hz) and $\delta_{major}$ 5.41 (q, 1.0H, J=7.2 Hz) ppm. MS (ESI$^+$) 577.3 [MH]$^+$ Synthesis of Compound 2.11

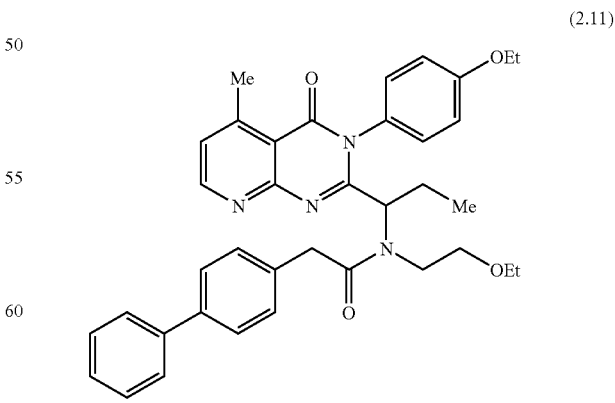

(2.11)

2-Biphenyl-4yl-N-(2-ethoxy-ethyl)-N-{1-[3-(4-ethoxy-phenyl)-5-methyl-4-oxo-3,4-dihydro-quinazolin-2-yl]-propyl}-acetamide Compound 2.11 was prepared following the synthesis of compound 2.01 described above. Method 2 was followed for the synthetic sequence, wherein butyryl chloride was used in step a instead of propionyl chloride, 4-ethoxyaniline was used in step b instead of 4-fluoroaniline, and 2-ethoxy-1-aminoethane was used in step d instead of 1-(2-aminoethyl)morpholine. Characterization data for compound 2.11 follows: colorless, viscous oil. $^1$H NMR (d$_6$-DMSO; T=140° C.) δ 0.80 (t, 3H, J=7.6 Hz), 0.94 (t, 3H, J=6.8 Hz), 1.35 (t, 3H, J=6.8 Hz), 1.59–1.70 (m, 1H), 2.20–2.30 (m, 1H), 2.77 (s, 3H), 3.22–3.42 (m, 4H), 3.47–3.65 (m, 2H), 4.10 (q, 2H, J=6.8 Hz, 5.01 (br q, 1H), 6.98–7.12 (m, 2H), 7.15–7.27 (m, 4H), 7.29–7.36 (m, 2H), 7.41–7.47 (m, 2H), 7.51–7.56 (m, 3H), 7.59–7.63 (m, 2H), 7.67 (dd, 1H, J$_1$=7.6 Hz, J$_2$=7.8 Hz) ppm. At room temperature, compound exists as a mixture of cis/trans amide rotamers, ca. 5:3 by $^1$H NMR (CDCl$_3$; T=25° C.) δ$_{major}$ 4.65 (dd, 1.7H, J$_1$=4.8 Hz, J$_2$=10.0 Hz) and δ$_{minor}$ 5.39 (dd, 1.0H, J$_1$=J$_2$=7.2 Hz) ppm. MS (ESI$^+$) 604.2 [MH]$^+$ Synthesis of Compound 2.12

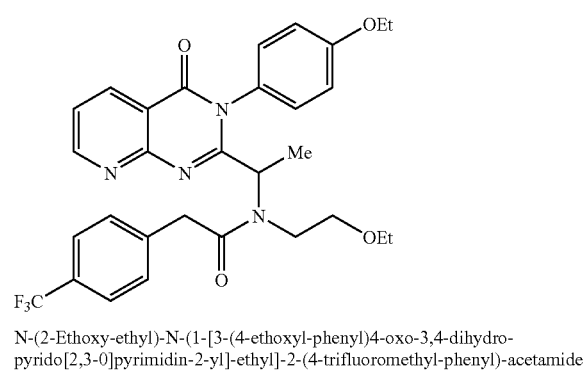

(2.12)

N-(2-Ethoxy-ethyl)-N-(1-[3-(4-ethoxyl-phenyl)4-oxo-3,4-dihydro-pyrido[2,3-0]pyrimidin-2-yl]-ethyl]-2-(4-trifluoromethyl-phenyl)-acetamide Compound 2.12 was prepared following the synthesis of compound 2.01 described above. Method 2 was followed for the synthetic sequence, wherein 2-aminonicotinic acid was used in step a instead of 2-amino-6-methylbenzoic acid, 4-ethoxyaniline was used in step b instead of 4-fluoroaniline, 2-ethoxy-1-aminoethane was used in step d instead of 1-(2-aminoethyl)morpholine, and 4-trifluoromethylphenylacetic acid was used in step e instead of biphenylacetyl chloride. Characterization data for compound 2.12 follows: colorless, viscous oil. $^1$H NMR (d$_6$-DMSO; T=140° C.) δ 0.96 (t, 3H, J=7.2 Hz), 1.36 (t, 3H, J=7.2 Hz), 1.47 (d, 3H, J=6.4 Hz), 3.29–3.40 (m, 2H), 3.42–3.51 (m, 2H), 3.54–3.64 (m, 2H), 4.11 (q, 2H, J=6.8 Hz), 5.20 (q, 1H, J=7.2 Hz), 7.00–7.10 (m, 2H), 7.23–7.41 (m, 4H), 7.53–7.60 (m, 3H), 8.50 (dd, 1H, J$_1$=2.4 Hz, J$_2$=8.4 Hz), 9.00 (dd, 1H, J$_1$=2.0 Hz, J$_2$=4.4 Hz) ppm. At room temperature, compound exists as a mixture of cis/trans amide rotamers, ca. 3:2 by $^1$H NMR (CDCl$_3$; T=25° C.) δ$_{minor}$ 5.00 (q, 1.0H, J=6.0 Hz) and δ$_{major}$ 5.38 (q, 1.4H, J=7.2 Hz) ppm. MS (ESI$^+$) 569.3 [MH]$^+$.

Example 3

Synthesis of 3.01

The synthesis of compound 3.01 in five steps from commercially available starting materials provides an example of a 3H-quinazolin-4-one synthesis in enantiomerically enriched form. Scheme 3 provides an overview of the synthetic route, for which the experimental details follow.

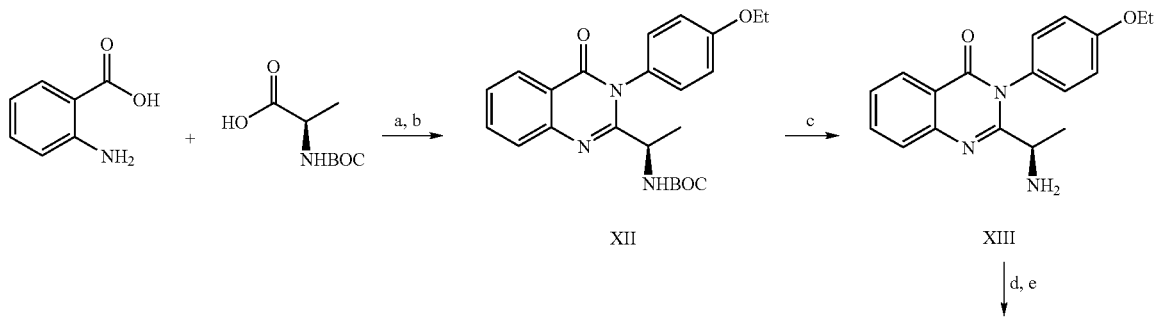

Scheme 3

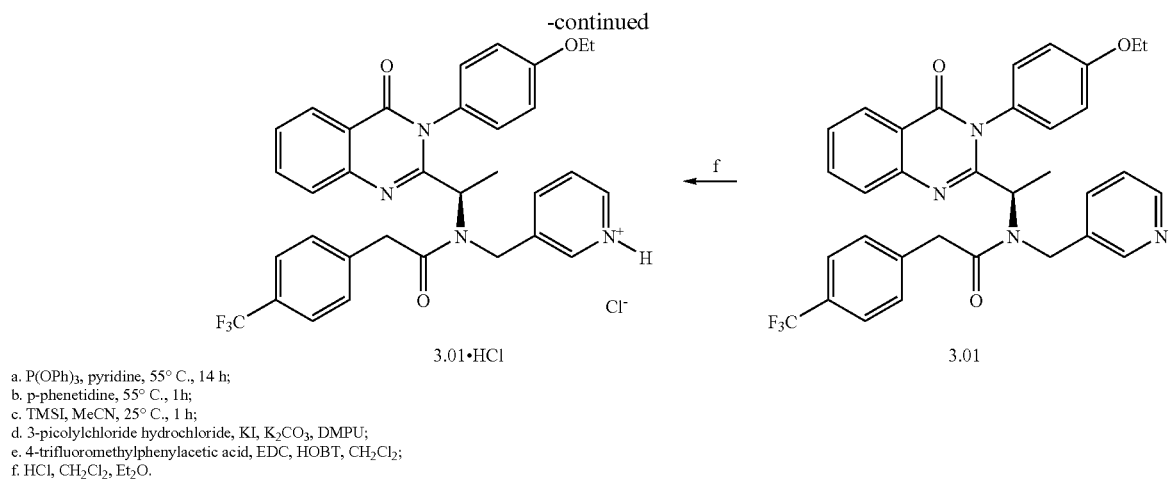

3.01•HCl          3.01 a. P(OPh)₃, pyridine, 55° C., 14 h;
b. p-phenetidine, 55° C., 1h;
c. TMSI, MeCN, 25° C., 1 h;
d. 3-picolylchloride hydrochloride, KI, K₂CO₃, DMPU;
e. 4-trifluoromethylphenylacetic acid, EDC, HOBT, CH₂Cl₂;
f. HCl, CH₂Cl₂, Et₂O.

(R)-2-(1-N-BOC-aminoethyl)-3-(4-ethoxyphenyl)-3H-quinazoline-4-one (XII). To a solution of anthranilic acid (411 mg, 3.0 mmol, 1.0 equiv) and N-BOC-D-alanine (568 mg, 3.0 mmol, 1.0 equiv) in 3.0 mL of anhydrous pyridine was added 0.96 mL of triphenylphosphite (1.14 g, 3.6 mmol, 1.2 equiv) at room temperature. The resulting yellow solution was stirred at 50° C. for 20 h. p-Phenetidine (453 mg, 3.3 mmol, 1.1 equiv) was added via syringe. The reaction mixture was stirred for another 2 h at 50° C., cooled to room temperature, and evaporated in vacuo to remove most of pyridine. The residue in 15 mL of diethyl ether was washed successively twice with 9 mL of 5% aqueous phosphoric acid, twice with 9 mL of 1 M NaOH, once with 5 mL of pH 7 phosphate buffer (0.5 M KH₂PO₄ and 0.5 M K₂HPO₄), and once with 9 mL of brine. The organic layer was dried over Na₂SO₄ and evaporated in vacuo to give a brown residue, which was recrystallized from a mixture of 3 mL of EtOAc and 12 mL of heptane to give 0.51 g of compound XII as a white solid. The mother liquor was concentrated in vacuo to give a brown residue, which was recrystallized from a mixture of 1 mL of EtOAc and 4 mL of heptane to give a second crop of 0.13 g of XII as a light yellow solid. m.p. 143.7° C. $^1$H NMR (DMSO-d₆) δ 1.19 (d, J=6.4 Hz, 3H), 1.32 (s, 9H), 1.37 (t, J=6.8 Hz, 3H), 4.10 (q, J=6.9 Hz, 2H), 4.24 (m, 1H), 7.09 (m, 2H), 7.28 (d, J=8.0 Hz, 2H), 7.39 (dd, J=8.4, 2.0 Hz, 1H), 7.54 (t, J=7.6 Hz, 1H), 7.69 (d, J=8.0 Hz, 1H), 7.85 (t, J=8.0 Hz, 1H), 8.11 (d, J=8.0 Hz, 1H) ppm. MS (ESI⁺) m/z 410.2 [M+H]⁺.

(R)-2-(1-Aminoethyl)-3-(4-ethoxyphenyl)-3H-quinazoline-4-one (XIII). To a suspension of XII (9.39 g, 22.9 mmol, 1.0 equiv) in 45 mL of anhydrous acetonitrile was added 3.43 mL of iodotrimethylsilane (4.82 g, 24.1 mmol, 1.05 equiv) dropwise via syringe over 15 min. After stirring for another 45 min at room temperature, all starting material XII had been consumed. The resulting mixture was partitioned between 50 mL of 1 M NH₄OH and 90 mL of ether. The aqueous layer was extracted two more times with 30 mL of ether. The combined ether extract was washed once with 40 mL of brine. The organic layer was dried over Na₂SO₄ and evaporated in vacuo to give a light gray solid. Recrystallization of this crude product from 25 mL of dioxane gave 4.2 g of XIII as a white solid. The mother liquor was concentrated in vacuo to give a light gray solid which was triturated with 15 mL of ether to give 1.8 g of additional product as a off-white solid. Total yield was 6.0 g. m.p. 179.9° C. $^1$H NMR (DMSO-d₆) δ 1.16 (d, J=6.4 Hz, 3H), 1.38 (t, J=7.0 Hz, 3H), 2.25 (br s, 2H), 3.51 (q, J=6.4 Hz, 1H), 4.11 (q, J=6.9 Hz, 2H), 7.08 (m, 2H), 7.36 (m, 2H), 7.52 (t, J=7.6 Hz, 1H), 7.70 (d, J=8.0 Hz, 1H), 7.85 (t, J=7.8 Hz, 1H), 8.11 (d, J=8.0 Hz, 1H) ppm. MS (ESI⁺) m/z 310.1 [M+H]⁺.

(R)-2-((N-3-Picolyl)-N-(4-trinfluoromethylphenylacetyl)-1-aminoethyl)-3-(4-ethoxyphenyl)-3H-quinazoline-4-one (3.01). 3-Picolylchloride hydrochloride (4.27 g, 26 mmol, 1.15 equiv), KI (4.32 g, 26.0 mmol, 1.15 equiv), and 60 mL of DMPU were mixed in a 200 mL flask. The mixture was vigorously stirred for 1 h at room temperature. To the resulting yellow mixture was added compound MII (7.0 g, 22.6 mmol, 1.0 equiv) and K₂CO₃ (9.38 g, 67.9 mmol, 3.0 equiv). The mixture was stirred at room temperature for 14 h. Additional 3-picolylchloride hydrochloride (740 mg, 4.51 mmol, 0.2 equiv) was added and the mixture was stirred for another 8 h at room temperature.

To the above reaction mixture was added 4-trifluoromethylphenylacetic acid (5.08 g, 24.9 mmol, 1.1 equiv), HOBT (4.58 g, 33.9 mmol, 1.5 equiv), and 20 mL of dichloromethane at room temperature. EDC (13.0 g, 67.8 mmol, 3.0 equiv) was then added portionwise over 15 min. After the initial gas evolution had subsided, the mixture was stirred vigorously at room temperature for another 14 h. The reaction mixture was poured into a mixture of 180 mL of 10% citric acid and 150 mL of ether. The aqueous layer was extracted twice with 100 mL of ether. The combined ether extract was washed twice with 60 mL of 2% citric acid, twice with 50 mL of saturated NaHCO₃, and once with 100 mL of brine. The organic layer was dried over Na₂SO₄ and evaporated in vacuo to give a orange foam, which was recrystallized from 20 mL of 1:1 heptane/i-PrOH to give 6.50 g of compound 3.01 as a light yellow solid. m.p. 176.3° C. $^1$H NMR (DMSO-d₆, T=140° C.) δ 1.36 (t, J=6.9 Hz, 3H), 1.41 (d, J=6.9 Hz, 3H), 1.53 (d, J=19.6 Hz, 1H), 3.18 (br, 1H), 4.12 (q, J=6.9 Hz, 2H), 4.70 (d, J=16.7 Hz, 1H), 4.76 (d, J=16.6 Hz, 1H), 5.28 (q, J=6.6 Hz, 1H), 7.08 (br, 3H), 7.15 (dd, J=7.7, 4.8 Hz, 1H), 7.27 (d, J=8.0 Hz, 2H), 7.37 (br, 1H), 7.48–7.58 (m, 4H), 7.68 (d, J=7.7 Hz, 1H), 7.85 (m, 1H), 8.10 (m, 1H), 8.34 (d, J=4.5 Hz, 1H), 8.37 (s, 1H) ppm. At room temperature, this compound exists as a mixture of cis/trans amide rotamers, ca. 1.83:1 by $^1$H NMR (DMSO-d₆, T=25° C.) δ 5.11 (q, J=6.8 Hz, 1H) & 5.28 (q, J=6.8 Hz, 1H) ppm. MS (ESI⁺) m/z 587.3 [M+H]⁺.

(R)-2-((N-3-Picolyl)-N-(4-trifluoromethylphenylacetyl)-1-aminoethyl)-3-(4-ethoxyphenyl)-3H-quinazoline-4-one hydrochloride (3.01.HCl). To a solution of compound 3.01 (3.55 g, 6.05 mmol, 1.0 equiv) in 25 mL of ether and 25 mL of dichloromethane was added a 1.0 M solution of HCl in ether (12.1 mL, 12.1 mmol, 2.0 equiv) dropwise via syringe, followed by another 50 mL of ether. The resulting suspension was stirred at room temperature for 1 h. The precipitates were collected by filtration. The solids were washed twice with 30 mL of ether and air dried in the dark to give 3.74 g of the product as a white powder. m.p. 186.2° C. At room temperature, this compound exists as a mixture of cis/trans amide rotamers, ca. 1.78:1 by $^1$H NMR (DMSO-$d_6$, T=25° C.) δ 1.48 (d, J=6.4 Hz, 3H) & 1.22 (d, J=7.2 Hz, 3H) ppm. At 140° C., the $^1$H NMR spectra of 3.01.HCl was identical to that of 3.01. MS (ESI$^+$) m/z 587.3 [M+H]$^+$. Chiral HPLC showed the enantiomeric ratio of this product to be 98:2 R/S.

Synthesis of Compound 3.02

The synthesis of compound 3.02 in five steps from commercially available starting materials provides an example of a 3H-quinazolin-4-one synthesis in racemic form. Scheme 4 provides an overview of the synthetic route, for which the experimental details follow.

2—(1-N-BOC-aminoethyl)-3-(4fluorophenyl)3H-quinazoline-4-one (XIV). To a solution of anthranilic acid (2.74 g, 20 mmol, 1.0 equiv) and N-BOC-D-alanine (3.78 g, 20 mmol, 1.0 equiv) in 20 mL of anhydrous pyridine was added 5.24 mL of triphenylphosphite (6.21 g, 20 mmol, 1.0 equiv) at room temperature. The resulting yellow solution was stirred at 100° C. for 4 h. 4-Fluoroaniline (2.22 g, 20 mmol, 1.0 equiv) was added via syringe. The reaction mixture was stirred for another 3 h at 100° C., cooled to room temperature, and evaporated in vacuo to give a brown residue. This residue was dissolved in 50 mL of EtOAc. The mixture was washed successively twice with 40 mL of 5% aqueous phosphoric acid, once with 20 mL of saturated NaHCO$_3$, and once with 40 mL of brine. The organic layer was dried over Na$_2$SO$_4$ and evaporated in vacuo to give a brown residue, which was purified by silica gel chromatography to give 2.40 g of compound XIV as a light yellow solid. $^1$H NMR (DMSO-$d_6$) δ 1.22 (d, J=6.8 Hz, 3H), 1.31 (s, 9H), 4.21 (m, 1H), 7.30 (m, 1H), 7.42 (m, 3H), 7.58 (m, 2H), 7.71 (d, J=8.0 Hz, 1H), 7.88 (t, J=7.8 Hz, 1H), 8.11 (d, J=8.0 Hz, 1H) ppm. MS (ESI$^+$) m/z 384.0 [M+H]$^+$.

2-(1-Aminoethyl)-3-(4-fluorophenyl)-3H-quinazoline-4-one hydrochloride (XV). To a solution of compound XIV (2.30 g, 6.0 mmol, 1.0 equiv) in 6.0 mL of EtOAc was added 6.0 mL of a 4.0 M solution of HCl in dioxane (24 mmol, 4.0 equiv) at room temperature. After the resulting solution was stirred at room temperature for 1.5 h, it was evaporated in Scheme 4

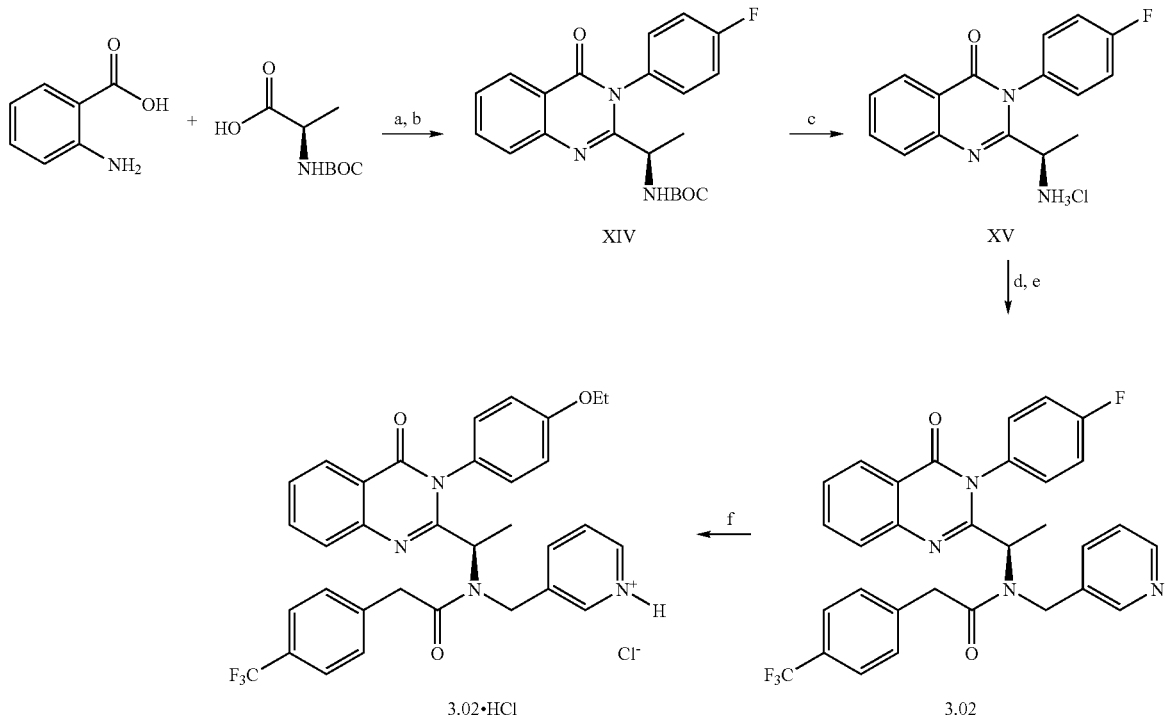

XIV

XV 3.02•HCl 3.02 a. P(OPh)$_3$, pyridine, 100° C., 4 h;
b. 4-fluoroaniline, 100° C., 3h;
c. HCl, dioxane, EtOAc, 25° C., 1.5 h;
d. 3-picolylchloride hydrochloride, KI, K$_2$CO$_3$, DMF;
e. 4-trifluoromethylphenylacetic acid, EDC, HOBT, NMM, CH$_2$Cl$_2$;
f. HCl, CH$_2$Cl$_2$, Et$_2$O.

vacuo to give a light gray solid. This crude product was dissolved in 9 mL of dichloromethane. To this stirring solution was added a total of 36 mL of ether via an additional funnel. The precipitates were collected by vacuum filtration, washed twice with 10 mL of ether, and air-dried to give 1.1 g of compound XV as a slightly off-white solid. $^1$H NMR (DMSO-d$_6$) δ 1.31 (d, J=6.8 Hz, 3H), 3.89 (m, 1H), 7.20 (t, J=4.8 Hz, 1H), 7.48 (m, 2H), 7.67 (m, 2H), 7.77 (d, J=8.0 Hz, 1H), 7.95 (t,J=7.6 Hz, 1H), 8.18 (d, J=8.0 Hz, 1H), 8.53 (br, 3H) ppm. MS (ESI$^+$) m/z 284.0 [M+H]$^+$.

2-((N-3-Picolyl)-N-(4-trifluoromethylphenylacetyl)-1-aminoethyl)-3-(4-fluorophenyl)-3H-quinazoline-4-one (3.02). 3-Picolylchloride hydrochloride (333 mg, 2.03 mmol, 1.15 equiv), KI (59 mg, 0.35 mmol, 0.20 equiv), compound XV (0.56 g, 1.77 mmol, 1.0 equiv), and K$_2$CO$_3$ (513 mg, 3.71 mmol, 2.1 equiv) were added to 2.5 mL of DMF. The mixture was vigorously stirred for 14 h at room temperature. The mixture was poured into 20 mL of 10% Na$_2$CO$_3$ and extracted four times with 10 mL of EtOAc. The combined EtOAc extract was washed once with 20 mL of brine, dried over Na$_2$SO$_4$, and evaporated in vacuo to give an orange colored foam, which was used without further purification.

To the above crude product was added 4-trifluoromethylphenylacetic acid (542 mg, 2.66 mmol, 1.5 equiv), EDC (594 mg, 3.10 mmol, 1.75 equiv) HOBT (419 mg, 3.00 mmol, 1.7 equiv), N-methylmorpholine (304 mg, 3.00 mmol, 1.7 equiv), and 6.0 mL of dichloromethane at room temperature. The mixture was stirred at room temperature for 14 h. The reaction mixture was poured into a 20 mL of 10% citric acid, and extracted twice with 15 mL of EtOAc. The combined EtOAc extract was washed once with 20 mL of saturated NaHCO$_3$, and once with 20 mL of brine. The organic layer was dried over Na$_2$SO$_4$ and evaporated in vacuo to give a brown residue, which was purified by silica gel chromatography to give 169 mg of compound 3.02 as a white solid. m.p. 167.0° C. $^1$H NMR (DMSO-d$_6$, T=140° C.) δ 1.40 (d, J=6.7 Hz, 3H), 3.32 (br, 1H), 3.59 (d, J=15.8 Hz, 1H), 4.73 (d, J=17.6 Hz, 1H), 4.81 (d, J=17.2 Hz, 1H), 5.26 (q, J=6.5 Hz, 1H), 7.18 (dd, J=7.7 Hz, 4.8 Hz, 1H), 7.29 (d, J=8.1 Hz, 2H), 7.34 (m, 3H), 7.55 (m, 5H), 7.67 (d, J=8.0 Hz, 1H), 7.86 (dd, J=7.6, 1.6 Hz, 1H), 8.11 (d, J=8.0 Hz, 1H), 8.36 (d, J=4.8 Hz, 1H), 8.40 (s, 1H) ppm. At room temperature, this compound exists as a mixture of cis/trans amide rotamers, ca. 0.96:1 molar ratio (DMSO-d$_6$, T=25° C.) d 5.10 (q, J=6.8 Hz, 1H) & 5.31 (q, J=6.8 Hz, 1H) ppm. MS (ESP$^+$) m/z 561.2 [M+H]$^+$. Chiral HPLC showed the enantiomeric ratio of this product to be ca. 1:1 R/S.

2-((N-3-Picolyl)-N-(4-trifluoromethylphenylacetyl)-1-aminoethyl)-3-(4-fluorophenyl)-3H-quinazoline-4-one hydrochloride (3.02.HCl). To a solution of compound 3.02 (50 mg, 89 µmol, 1.0 equiv) in 2 mL of dichloromethane was added a 1.0 M solution of HCl in ether (180 µL, 0.18 mmol, 2.0 equiv) dropwise via syringe, followed by another 5 mL of ether. The resulting suspension was stirred at room temperature for 1 h. The precipitates were collected by filtration. The solids were washed twice with 30 mL of ether and air dried in the dark to give 47 mg of the product as a white powder. mp 122.7° C. At room temperature, this compound exists as a mixture of cis/trans amide rotamers, ca. 0.93:1 by $^1$H NMR (DMSO-d$_6$, T=25° C.) δ 5.05 (q, J=6.8 Hz, 1H) & 5.18 (q, J=6.8 Hz, 1H) ppm. MS (ESI$^+$) m/z 561.2 [M+H]$^+$.

Synthesis of Compound 3.03 and Compound 3.03.HCl

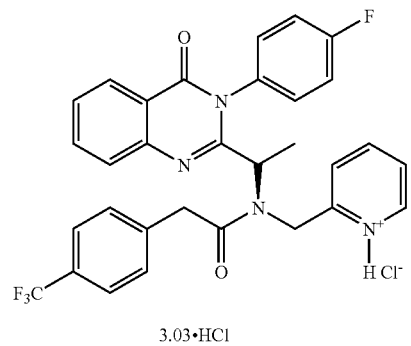

3.03·HCl

The synthesis of compound 3.03 followed the method described for compound 3.02. 2-Picolylchloride hydrochloride was used in place of 3-picolylchloride hydrochloride in step 3 of the synthetic sequence. Characterization of the products follows.

2-((N-(2-Picolyl)-N-(4-trifluoromethylphenylacetyl)-1-aminoethyl)-3-(4-fluorophenyl)3H-quinazoline-4-one (3.03) was obtained as a white solid from compound XV. Mp 159.2° C. At room temperature, this compound exists as a mixture of cis/trans amide rotamers, ca. 0.23:1 by $^1$H NMR (DMSO-d$_6$, T=25° C.) δ 5.05 (q, J=6.8 Hz, 1H) & 5.36 (q, J=6.8 Hz, 1H) ppm. MS (ESI$^+$) m/z 561.2 [M+H]$^+$.

2-((N-2-Picolyl)-N-(4-trifluoromethylphenylacetyl)-1-aminoethyl)-3-(4-fluorophenyl)-3H-quinazoline-4-one hydrochloride (3.03.HCl) was obtained as a white solid from compound 3.03. At room temperature, this compound exists as a mixture of cis/trans amide rotamers, ca. 0.64:1 by $^1$H NMR (DMSO-d$_6$, T=25° C.) δ 5.04 (q, J=6.8 Hz, 1H) & 5.35 (q, J=6.8 Hz, 1H) ppm. MS (ESI$^+$) m/z 561.2 [M+H]$^+$.

Synthesis of Compounds 3.04 and 3.04.HCl

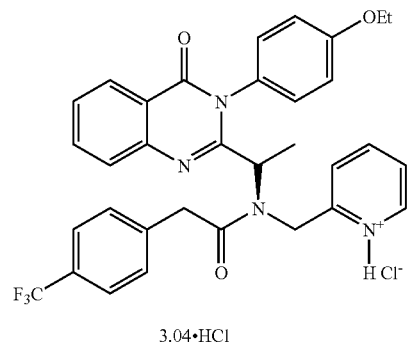

3.04·HCl

The synthesis of compound 3.04 followed the method described for compound 3.02. p-Phenetidine was used in place of 4-fluoroaniline in step 1 of the synthetic sequence. 2-Picolylchloride hydrochloride was used in place of 3-picolylchloride hydrochloride in step 3 of the synthetic sequence. Characterization of the products follows.

2-((N-2-Picolyl)-N-(4-trifluoromethylphenylacetyl)-1-aminoethyl)-3-(4-ethoxyphenyl) 3H-quinazoline-4-one (3.04) was obtained as a white solid from the hydrochloride salt of racemic compound XIII. Mp 167.5° C. $^1$H NMR (DMSO-d$_6$, T=140° C.) δ 1.35 (d, J=6.9 Hz, 3H), 1.37 (t, J=7.4 Hz, 3H), 3.49 (br, 1H), 3.64 (m, 1H), 4.10 (q, J=9.1 Hz, 2H), 4.78 (d, J=17.2 Hz, 1H), 4.84 (d, J=17.2 Hz, 1H), 5.38 (q, J=6.2 Hz, 1H), 7.02 (br, 2H), 7.09 (dd, J=6.7, 4.8 Hz, 1H), 7.18 (d, J=7.9 Hz, 1H), 7.30 (m, 4H), 7.46–7.58 m, 4H), 7.61 (d, J=8.3 Hz, 1H), 7.79 (m, 1H), 8.07 (dd, J=8.0, 1.4 Hz, 1H), 8.36 (m, 1H) ppm. At room temperature, this compound exists as a mixture of cis/trans amide rotamers, ca. 0.42:1 molar ratio (DMSO-d$_6$, T=25° C.) d 5.12 (q, J=6.8 Hz, 1H) & 5.34 (q, J=6.8 Hz, 1H) ppm. MS (ESI$^+$) m/z 587.2 [M+H]$^+$.

2-((N-(2-Picolyl)-N-(4-trifluoromethylphenylacetyl)-1-aminoethyl)-3-(4-ethoxyphenyl)-3H-quinazoline-4-one hydrochloride (3.04.HCl) was obtained as a white solid from compound 3.04. Mp 162.6° C. At room temperature, this compound exists as a mixture of cis/trans amide rotamers, ca. 1.45:1 molar ratio DMSO-d6, T.=25° C.) d 1.51 (d, J=6.4 Hz, 1H) & 1.24 (d, J=7.2 Hz, 1H) ppm. MS (ESI$^+$) m/z 587.2 [M+H]$^+$.

Synthesis of Compound 3.05

The synthesis of compound 3.05 is closely related to that of compound 3.02 described above. Scheme 5 provides an overview of synthetic route. Compound 3.05 also served as a common precursor for a series of closely related compounds.

2-(1-Aminoethyl)-3-(4-iodophenyl)-3H-quinazoline-4-one hydrochloride (XVI) The product was a white solid. $^1$H NMR (DMSO-d$_6$) δ 1.31 (d, J=6.8 Hz, 3H), 3.89 (m, 1H), 7.31 (d, J=7.6 Hz, 1H), 7.42 (d, J=7.2 Hz, 1H), 7.63 (t, J=7.6 Hz, 1H), 7.76 (d, J=8.0 Hz, 1H), 7.97 (m, 3H), 8.14 (d, J=8.0 Hz, 1H), 8.51 (br, 3H) ppm. MS (ESI$^+$) m/z 392.0 [M+H]$^+$.

2-((N-2-Ethoxyethyl)-N-(4-trifluoromethylphenylacetyl)-1-aminoethyl) 3-(4-iodophenyl)-3H-quinazoline-4-one (3.05) was obtained as a white solid from compound XVI. Mp 181.8° C. At room temperature, this compound exists as a mixture of cis/trans amide rotamers, ca. 0.64:1 by $^1$H NMR (DMSO-d$_6$, T=25° C.) δ 4.89 (q, J=6.0 Hz, 1H) & 5.22 (q, J=6.4 Hz, 1H) ppm. MS (ESI$^+$) m/z 650.2 [M+H]$^+$.

Scheme 6

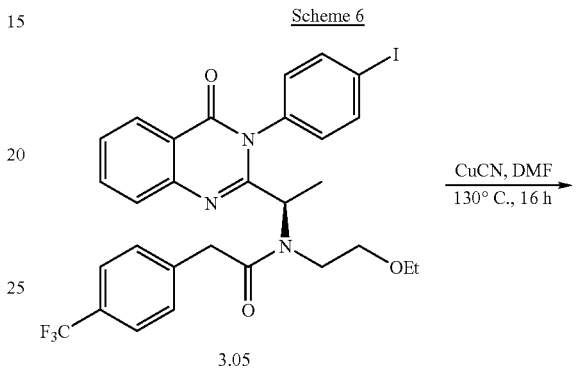

Scheme 5

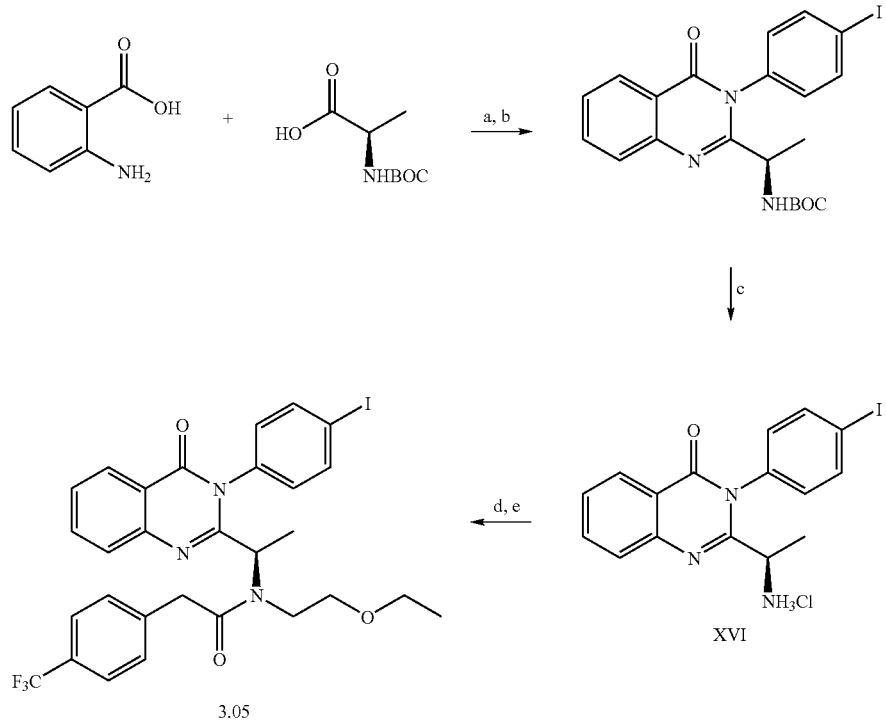

a. P(OPh)$_3$, pyridine, 100° C., 4 h;
b. 4-iodoaniline, 100° C., 3h;
c. HCl, dioxane, EtOAc, 25° C., 1.5 h;
d. 2-bromoethyl ethyl ether, KI, K$_2$CO$_3$, DMF;
e. 4-trifluoromethylphenylacetic acid, EDC, HOBT, CH$_2$Cl$_2$.

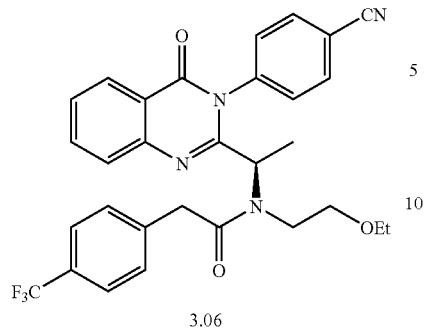

3.06

2-((N-2-Ethoxyethyl)-N-(4-trinfluoromethylphenylacetyl)-1-aminoethyl)3-(4-cyanophenyl)3H-quinazoline-4-one (3.06). 3.05 (150 mg, 0.23 mmol, 1.0 equiv) was dissolved in 0.5 mL of anhydrous DMF. CuCN (31 mg, 0.35 mmol, 1.5 equiv) was added. The resulting mixture was heated to 130° C. for 16 h. The mixture was cooled to room temperature and diluted with 15 mL of EtOAc. The mixture was filtered through a short column of silica gel, which was further eluted with 50 mL of EtOAc. The eluent was concentrated in vacuo to give a yellow residue, which was purified by preparative TLC to give 95 mg of compound 3.06 as a white solid. Mp 197.0° C. $^1$H NMR (DMSO-$d_6$, T=140° C.) δ 0.98 (t, J=6.9 Hz, 3H), 1.44 (d, J=6.8 Hz, 3H), 3.30–3.65 m, 8H), 5.16 (q, J=6.2 Hz, 1H), 7.33 (d, J=8.0 Hz, 2H), 7.50–7.77 (m, 6H), 7.72–7.95 (m, 3H), 8.15 (dd, J=7.9, 1.5 Hz, 1H) ppm. At room temperature, this compound exists as a mixture of cis/trans amide rotamers, ca. 0.64:1 molar ratio in DMSO. $^1$H NMR (DMSO-$d_6$, T=25° C.) δ 4.84 (q, J=6.4 Hz, 1H) & 5.22 (q, J=6.4 Hz, 1H) ppm. MS (ESI$^+$) m/z 650.2 [M+H]$^+$.

Scheme 7

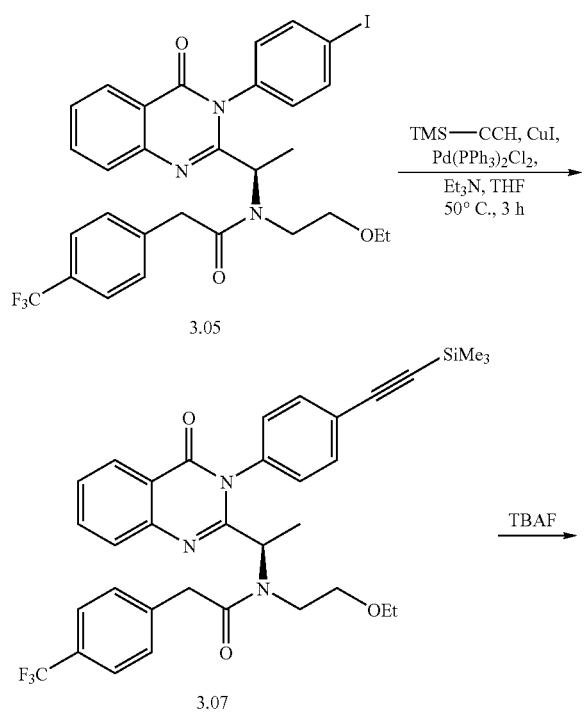

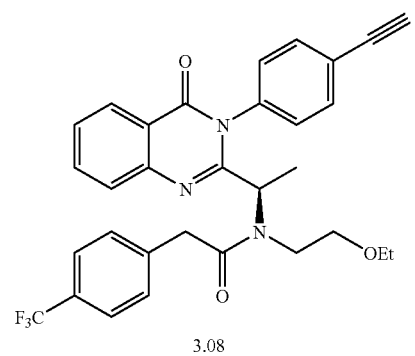

3.08

2-((N-2-Ethoxyethyl)-N-(4-trifluoromethylphenylacetyl)-1-aminoethyl)-3-(4-trimethylsilylethynylphenyl)-3H-quinazoline-4-one (3.07). Compound 3.05 (150 mg, 0.23 mmol, 1.0 equiv) was dissolved in 1.0 mL of anhydrous THF. Trimethylsilylacetylene (45 mg, 0.46 mmol, 2.0 equiv), CuI (87 mg, 0.46 mmol, 2.0 equiv), Pd(PPh$_3$)$_2$Cl$_2$ (32 mg, 0.046 mmol, 0.20 equiv), and triethylamine (92 mg, 0.91 mmol, 4.0 equiv) were added sequentially. The resulting mixture was heated to 50° C. for 3 h. The mixture was cooled to room temperature and diluted with 15 mL of EtOAc. The mixture was filtered through a short column of silica gel, which was further eluted with 50 mL of EtOAc. The eluent was concentrated in vacuo to give a yellow residue, which was purified by preparative TLC to give 105 mg 3.07 as a white solid. Mp 185.3° C. At room temperature, this compound exists as a mixture of cis/trans amide rotamers, ca. 0.54:1 molar ratio in DMSO. $^1$H NMR (DMSO-$d_6$, T=25° C.) δ 4.88 (q, J=6.8 Hz, 1H) & 5.25 (q, J=6.8 Hz, 1H) ppm. MS (ESI$^+$) m/z 620.2 [M+H]$^+$.

2-((N-2-Ethoxyethyl)-N-(4-trifluoromethylphenylacetyl)-1-aminoethyl)-3-(4-ethynylphenyl)-3H-quinazoline-4-one (3.08). Compound 3.07 (57 mg, 92 μmol, 1.0 equiv) was dissolved in 1.0 mL of anhydrous THF. A 1.0 M solution of tetrabutylammonium fluoride in THF (101 μL, 0.101 mmol, 1.1 equiv) was added at room temperature. The resulting mixture was stirred at room temperature for 15 min. To the reaction mixture was added 100 μL of saturated aqueous NH$_4$Cl and 15 mL of EtOAc. After stirring at room temperature for another 15 min, the mixture was dried over Na2SO4, and filtered through a short column of silica gel, which was further eluted with 50 mL of EtOAc. The eluent was concentrated in vacuo to give a yellow residue, which was purified by preparative TLC to give 39 mg of compound 3.08 as a white solid. Mp 186.7° C. At room temperature, this compound exists as a mixture of cis/trans amide rotamers, ca. 0.54:1 molar ratio in DMSO. $^1$H NMR (DMSO-$d_6$, T=25° C.) δ 4.87 (q, J=6.0 Hz, 1H) & 5.20 (q, J=6.8 Hz, 1H) ppm. MS (ESI$^+$) m/z 548.2 [M+H]$^+$.

Synthesis of Compounds 3.09 and 3.10

Synthesis of Compounds 3.11 and 3.12

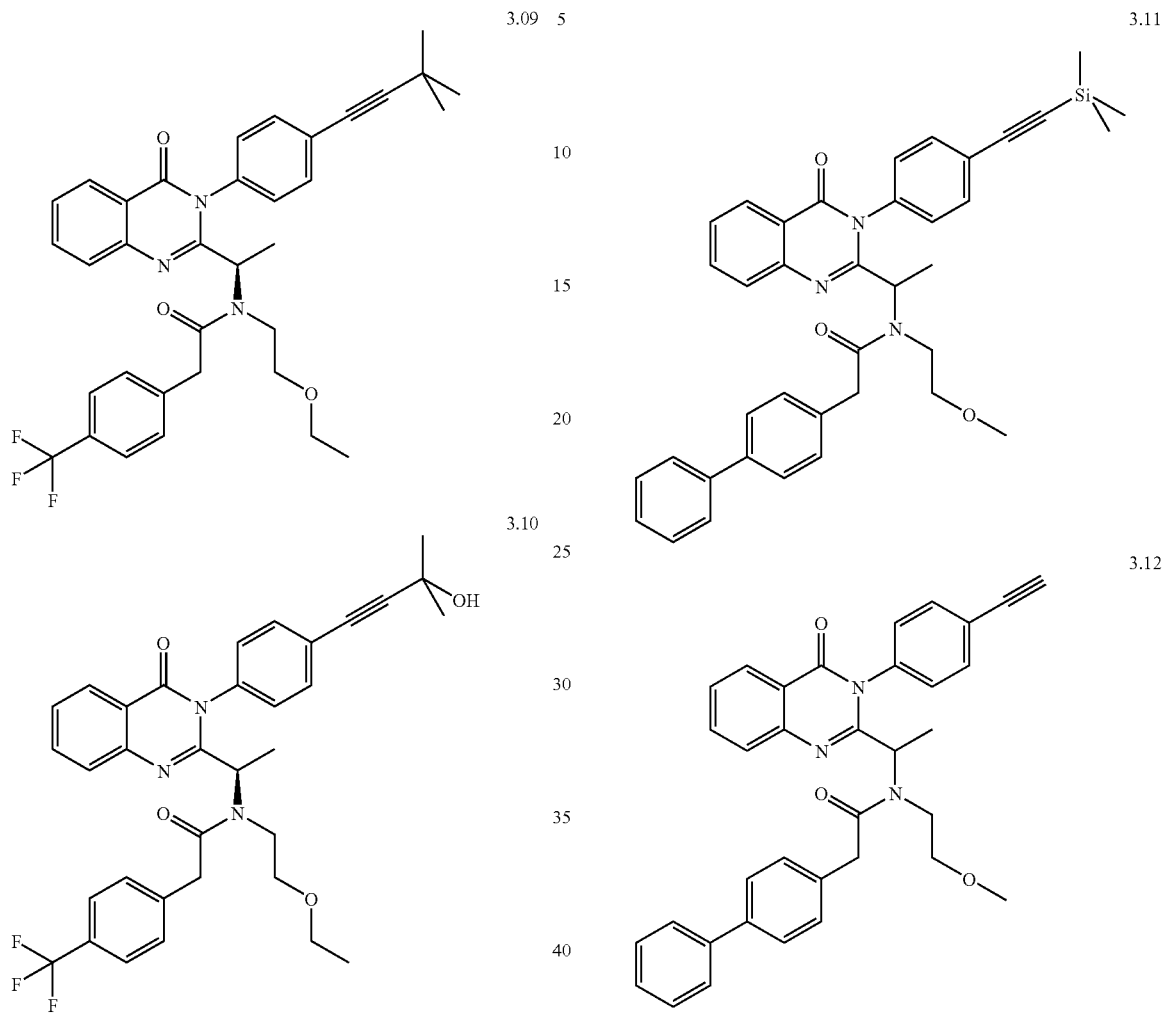

Compounds 3.09 and 3.10 were synthesized in the same manner as compound 3.07 (See Scheme 7). 3,3-Dimethyl-1-butyne, and 2-methyl-3-butyn-2-ol were used respectively, instead of trimethylsilylacetylene. Characterization of the products follows.

2-((N-2-Ethoxyethyl)-N-(4-trifluoromethylphenylacetyl)-1-aminoethyl)-3-(4-(t-butylethynyl)phenyl)-3H-quinazoline-4-one (3.09) was obtained from compound 3.05 in as a white solid. Mp 189.9° C. At room temperature, this compound exists as a mixture of cis/trans amide rotamers, ca. 0.69:1 molar ratio in DMSO. $^1$H NMR (DMSO-$d_6$, T=25° C.) δ 4.89 (q, J=6.4 Hz, 1H) & 5.25 (q, J=6.4 Hz, 1H) ppm. MS (ESP$^+$) m/z 604.2 [M+H]$^+$.

2-((N-2-Ethoxyethyl)-N-(4-trifluoromethylphenylacetyl)-1-aminoethyl)-3-(4-(3-hydroxy-3-methyl-1-butynyl)phenyl)-3H-quinazoline-4-one (3.10) was obtained from compound 3.05 as a white solid. Mp 162.2° C. At room temperature, this compound exists as a mixture of cis/trans amide rotamers, ca. 0.69:1 molar ratio in DMSO. $^1$H NMR (DMSO-$d_6$, T=25° C.) δ 4.89 (q, J=6.8 Hz, 1H) & 5.24 (q, J=6.4 Hz, 1H) ppm. MS (ESI$^+$) m/z 606.3 [M+H]$^+$.

Compounds 3.11 and 3.12 were synthesized in the same manner as compounds 3.07 and 3.08 (Scheme 7). Compound 1.42 was used as starting material in both cases, instead of compound 3.05. Characterization of the products follows.

2-((N-2-Methoxyethyl)-N-(4-phenylphenylacetyl)-1-aminoethyl)-3-(4-trimethylsilylethynyl)phenyl)-3H-quinazoline-4-one (3.11) was obtained from compound 1.42 as a white solid. At room temperature, this compound exists as a mixture of cis/trans amide rotamers, ca. 0.61:1 molar ratio in DMSO. $^1$H NMR (DMSO-$d_6$, T=25° C.) δ 4.91 (q, J=6.4 Hz, 1H) & 5.21 (q, J=6.4 Hz, 1H) ppm. MS (ESI$^+$) m/z 614.3 [M+H]$^+$.

2-((N-2-Methoxyethyl)-N-(4-phenylphenylacetyl)-1-aminoethyl)-3-(4-ethynylphenyl)-3H-quinazoline-4-one (3.12) was obtained from compound 1.42 as a white solid. Mp 73.3° C. At room temperature, this compound exists as a mixture of cis/trans amide rotamers, ca. 0.67:1 molar ratio in DMSO. $^1$H NMR (DMSO-$d_6$, T=25° C.) δ 4.92 (q, J=6.4 Hz, 1H) & 5.17 (q, J=6.8 Hz, 1H) ppm. MS (ESI$^+$) m/z 542.2 [M+H]$^+$.

Synthesis of Compounds 3.13 and 3.14. Compounds 3.13 and 3.14 were synthesized in the same reaction from compound 3.05. Experimental details follow.

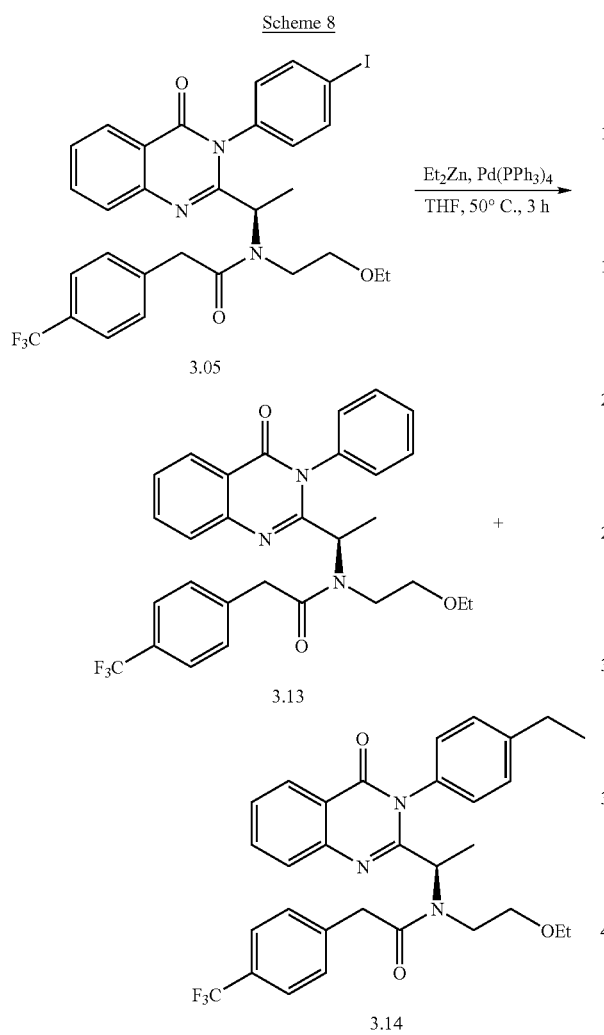

2-((N-2-Ethoxyethyl)-N-(4-trifluoromethylphenylacetyl)-1-aminoethyl)-3-phenyl-3H-quinazoline-4-one (3.13) and 2-((N-2-Ethoxyethyl)-N-(4-trifluoromethylphenylacetyl)-1-aminoethyl)-3-(4-ethylphenyl)-3H-quinazoline-4-one (3.14) To a solution of compound 3.05 (98 mg, 0.15 mmol, 1.0 equiv) and Pd(PPh$_3$)$_4$ (35 mg, 30 μmol, 0.20 equiv) in 1.0 mL of THF was added Et$_2$Zn (37 mg, 0.30 mmol, 2.0 equiv) via syringe. The darkened reaction mixture was stirred at 50° C. for 3 h. After cooling to room temperature, the reaction mixture was diluted with 20 mL of EtOAc, and washed successively with 10 mL of 1 M HCl, 10 mL of saturated NaHCO$_3$, and 10 mL of brine. The organic layer was dried over Na2SO4, and evaporated in vacuo to give a brown residue, which was purified by preparative TLC to give 18 mg of compound 3.13 and 27 mg of compound 3.14. Both are white solids. Characterization of these two products follows.

Compound 3.13. At room temperature, this compound exists as a mixture of cis/trans amide rotamers, ca. 0.69:1 molar ratio in CDCl$_3$. $^1$H NMR (CDCl$_3$, T=25° C.) δ 0.71 (d, J=7.0 Hz, 3H) & 1.15 (d, J=7.0 Hz, 1H) ppm. MS (ESI$^+$) m/z 524.3 [M+H]$^+$.

Compound 3.14. At room temperature, this compound exists as a mixture of cis/trans amide rotamers, ca. 0.69:1 molar ratio in CDCl$_3$. $^1$H NMR (CDCl$_3$, T=25° C.) δ 4.88 (q, J=6.8 Hz, 1H) & 5.34 (q, J=6.8 Hz, 1H) ppm. MS (ESI$^+$) m/z 552.2 [M+H]$^+$.

Synthesis of Compound 3.15

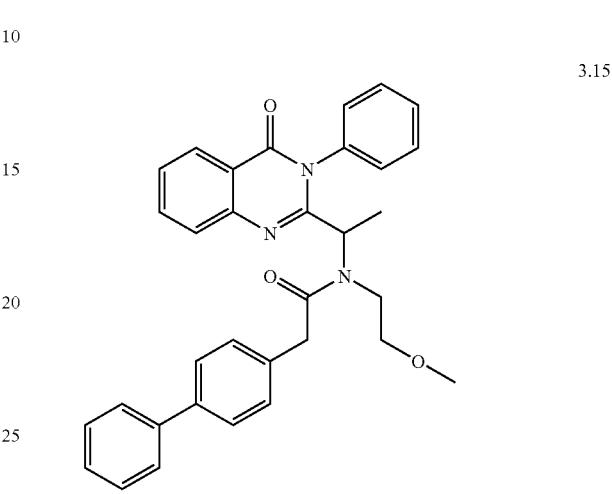

Compound 3.15 was synthesized from compound 1.42 using Pd catalyzed hydrogenation. Experimental details follow.

2-((N-2-Methoxyethyl)-N-(4-phenylphenylacetyl)-1-aminoethyl)-3-phenyl-3H-quinazoline-4-one (3.15) To a solution of compound 1.42 (25 mg, 39 μmol, 1.0 equiv) in a mixture of 1.0 mL of MeOH and 1.0 mL of dichloromethane, was added 10% Pd on carbon (83 mg, 78 μmol, 2.0 equiv). Excess hydrogen was introduced using a balloon. After stirring at room temperature for 2 h. The reaction mixture was diluted with 5 mL of dichloromethane, and filtered through a pad of Celite. The filtrate was concentrated in vacuo to give a yellow oil, which was passed through a short column of silica gel, eluted with EtOAc. The eluent was concentrated in vacuo to give 17 mg of compound 3.15 as a colorless oil. At room temperature, this compound exists as a mixture of cis/trans amide rotamers, ca. 1.06:1 molar ratio in DMSO. $^1$H NMR (DMSO-d$_6$, T=25° C.) δ 4.94 (q, J=6.4 Hz, 1H) & 5.08 (q, J=6.8 Hz, 1H) ppm. MS (ESI$^+$) m/z 518.3 [M+H]$^+$.

Synthesis of Compound 3.16

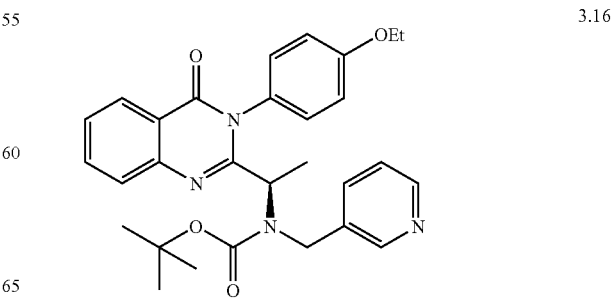

Compound 3.16 was synthesized from the racemic form of compound XII as described in the experimental details below.

2-((N-3-Picolyl)-N-(t-butoxycarbonyl)-1-aminoethyl)-3-(4-ethoxyphenyl)-3H-quinazoline-4-one (3.16). To a solution of racemic compound XII (124 mg, 0.30 mmol, 1.0 equiv) in 0.60 mL of DMF, was added 3-picolylchloride hydrochloride (55 mg, 0.33 mmol, 1.1 equiv), KI (50 mg, 0.30 mmol, 1.0 equiv), and NaH (60% suspension in mineral oil, 25 mg, 0.62 mmol, 2.05 equiv). After stirred at room temperature for 16 h, the reaction mixture was poured into 10 mL of 5% aqueous $H_3PO_4$. The resulting mixture was extracted twice with 10 mL of EtOAc. The organic layer was washed with 10 mL of $NaHCO_3$ and 10 mL of brine, dried over $Na_2SO_4$ and concentrated in vacuo to give a yellow oil, which was purified by preparative TLC to give 33 mg of compound 3.16 as a white solid. Mp 67.5° C. At room temperature, this compound exists as a mixture of cis/trans amide rotamers, ca. 1.11:1 molar ratio in DMSO. $^1$H NMR (DMSO-$d_6$, T=25° C.) δ 5.03 (m, 1H) & 5.12 (m, 1H) ppm. MS (ESI$^+$) m/z 510.3 [M+H]$^+$.

Synthesis of Compound 3.16a

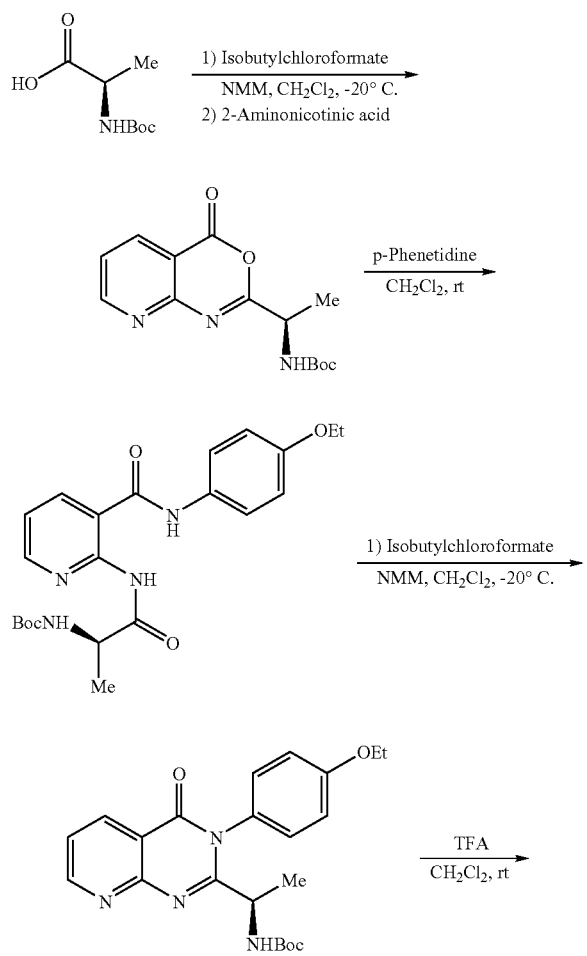

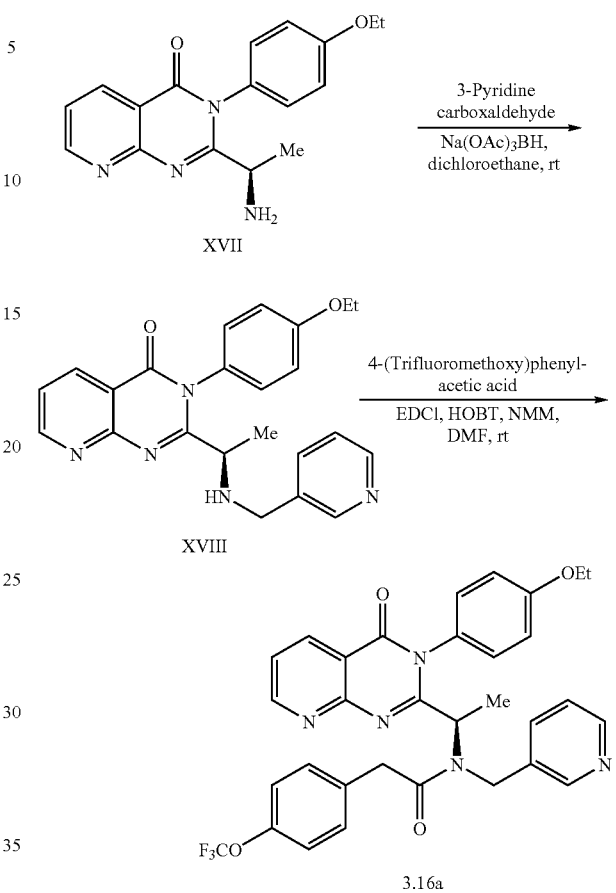

(1-N-BOC-aminoethyl)-3-(4-ethoxyphenyl)-2-{(1R)-1-[(pyridin-3-ylmethyl)-amino]-ethyl}-3H-pyrido[2,3-d]pyrimidin-4-one (XVII precursor). To a 3 L round bottom flask equipped with addition funnel, mechanical stirrer and temperature probe was added 102.60 g (542.26 mmol) of N-(tert-butoxycarbonyl)-D-alanine in 1.2 L of dichloromethane (DCM) under a nitrogen atmosphere. The solution was cooled to −20° C. and 150.00 ml (1364.31 mmol) of N-methyl morpholine added followed by the addition of a solution containing 140.1 ml (1084 mmol) of iso-butylchloroformate in 360 ml of DCM over 40 min. while maintaining the reaction temperature below −20° C. After complete addition, the reaction was allowed to stir for 45 min. and 75.00 g (542.97 mmol) of 2-aminonicotinic acid added. The reaction was allowed to warm to room temperature overnight. The reaction was diluted with 1.5 L DCM and washed with 1.0 N hydrochloric acid (2×750 ml) and brine (1×500 ml). The organic phase was dried over magnesium sulfate, filtered, and concentrated in vacuo to give 175.0 g of a yellow-orange oil. The material was used without further purification in the next step.

A solution containing the crude material from above dissolved in 2 L DCM was cooled to −20° C. under a nitrogen atmosphere and 69.00 ml (535.68 mmol) of p-phenetidine was added over 5 minutes. After stirring with gradual warming to 0° C. the reaction mixture was transferred to a separatory funnel and washed with 1.0 N hydrochloric acid (2×500 ml), saturated sodium bicarbonate solution (2×1 L), and brine (1×1 L). The organic phase was dried over magnesium sulfate, filtered, and concentrated in vacuo to give 175.2 g of crude bis-amide. The material was used without further purification in the next step.

A solution containing the crude bis-amide prepared above in 2.3 L of DCM and 50.0 ml (454.7 mmol) of N-methyl morpholine was cooled to −20° C. under a nitrogen atmosphere and 53.0 ml (408.6 mmol) of iso-butylchloroformate was added dropwise over a period of 5 minutes. Upon completed addition of the chloroformate HPLC analysis indicated no bis-amide remained. The reaction mixture was transferred to a separatory funnel and washed with 1.0 N hydrochloric acid (2×1 L), saturated bicarbonate solution (1×1 L), and brine (1×1 L). The organic phase was dried over magnesium sulfate, filtered, and concentrated in vacuo to give 205 g of a brown, viscous oil. This product was dissolved in 500 ml of methyl tert-butyl ether and allowed to stir until the product began to precipitate from the solution. Heptane was then added (1000 ml) and stirring continued. The resulting precipitate was collected by filtration, washed with heptane, and dried to afford 78.9 g of product as an off-white solid. $^1$H NMR (CDCl$_3$) δ 8.99 (dd, J$_1$=2.0 Hz, J$_2$=4.4 Hz, 1H), 8.60 (dd, J$_1$=2.0 Hz, J$_2$=8.0 Hz, 1H), 7.44 (dd, J$_1$=4.4 Hz, J$_2$=8.0 Hz, 1H), 7.33 (dd, J$_1$=1.6 Hz, J$_2$=8.8 Hz, 1H), 7.16 (dd, J$_1$=2.8 Hz, J$_2$=8.8 Hz, 1H), 7.20 (dd, J$_1$=2.4 Hz, J$_2$=8.8 Hz, 1H), 7.04 (dd, J$_1$=2.8 Hz, J$_2$=8.8 Hz, 1H), 5.80 (d, J=8.8 Hz, 1H), 4.63–4.70 (m, 1H), 4.06–4.13 (q, J=7.2 Hz, 2H), 1.46 (t, J=7.2 Hz, 3H), 1.40 (s, 9H), 1.31 (d, J=6.8 Hz, 3H) ppm.

Intermediate XVII. To a solution containing 77.00 g (187.59 mmol) of the compound prepared above in 2.1 L of DCM was added 290 mL trifluoroacetic acid. The reaction was allowed to stir for 3.5 h at room temperature then concentrated in vacuo. The concentrate was dissolved in 1.4 L DCM and washed with 1.0 N hydrochloric acid (3×500 ml). The combined aqueous washes were made alkaline by addition of concentrated ammonium hydroxide until pH=10. The resulting cloudy solution was extracted with DCM (2×700 ml) and the combined organic extracts dried over magnesium sulfate, filtered, and concentrated in vacuo to afford 58.40 g of product as a tan solid. $^1$H NMR (DMSO-d$_6$) δ 8.94 (dd, J$_1$=2.0 Hz, J$_2$=4.8 Hz, 1H), 8.44 (dd, J$_1$=2.0 Hz, J$_2$=8.0 Hz, 1H), 7.49 (dd, J$_1$=4.8 Hz, J$_2$=8.0 Hz, 1H), 7.34–7.39 (m, 2H), 7.04–7.10 (m, 2H), 4.08 (q, J=6.8 Hz, 2H), 3.52 (q, J=6.4 Hz, 1H), 1.94 (br s, 2H), 1.34 (t, J=6.8 Hz, 3H), 1.15 (d, J=6.4 Hz, 3H) ppm.

Intermediate XVIII. To a solution containing 57.70 g (185.92 mmol) of intermediate XVII prepared above dissolved in 1.7 L of dichloroethane was added 18.5 ml (196.04 mmol) pyridine carboxaldehyde followed by 55.20 g (260.45 mmol) of sodium triacetoxy borohydride. The reaction was allowed to stir at room temperature overnight. The reaction was diluted with 1 L of DCM and washed with 1.0 M ammonium hydroxide (2×500 ml). The organic phase was dried over magnesium sulfate, filtered, and concentrated in vacuo to afford 79.20 g of product as a pale yellow solid. $^1$H NMR (DMSO-d$_6$) δ 8.96–8.98 (m, 1H), 8.42–8.48 (m, 1H), 8.45 (br s, 1H), 8.37 (d, J=4.8 Hz, 1H), 7.64 (d, J=8.0 Hz, 1H), 7.52 (dd, J$_1$=4.8 Hz, J$_2$=8.0 Hz, 1H), 7.33 (dd, J$_1$=2.4 Hz, J$_2$=8.4 Hz, 1H), 7.24 (dd, J$_1$=4.8 Hz, J$_2$=8.0 Hz, 1H), 7.14 (dd, J$_1$=2.4 Hz, J$_2$=8.4 Hz, 1H), 6.99 (dd, J$_1$=2.8 Hz, J$_2$=8.4 Hz, 1H), 6.83 (dd, J$_1$=2.8 Hz, J$_2$=8.8 Hz, 1H), 3.97–4.10 (m, 2H), 3.87 (s, 1H), 3.72 (d, J=14.0 Hz, 1H), 3.52 (d, J=13.6 Hz, 1H), 3.28 (q, J=6.4 Hz, 1H), 1.31 (t, J=7.2 Hz, 3H), 1.17 (d, J=6.4 Hz, 3H) ppm.

Compound 3.16a. To a solution containing 54.00 g (245.29 mmol) of 4-(trifluoromethoxy)phenylacetic acid in 1.1 L of DMF was added 61.30 g (319.77 mmol) of EDCI, 43.20 g (319.69 mmol) HOBT and 42.00 ml (382.01 mmol) of N-methyl morpholine. After stirring for 30 min., 74.60 g (185.82 mmol) of intermediate XVIII was added. The reaction was allowed to stir at room temperature overnight. The reaction was diluted with 3 L DCM and washed with water (2×3 L), saturated sodium bicarbonate solution (2×2 L), and brine (1×2 L). The organic extract was dried over magnesium sulfate, filtered, and concentrated in vacuo to afford 121.7 g of a yellow solid. The solids were triturated with 700 ml of methyl tert-butyl ether, collected by filtration, rinsed, and dried to afford 88.46 g of product as an off-white solid.

The product was recrystallized from 10% ethyl acetate in heptane to afford a colorless, microcrystalline (small needles) solid, m.p. 161.2° C. $^1$H NMR (T=120° C.; DMSO-d$_6$) δ 9.01 (dd, J$_1$=1.6 Hz, J$_2$=4.4 Hz, 1H), 8.46 (dd, J$_1$=2.0 Hz, J$_2$=7.6 Hz, 1H), 8.35 (m, 2H), 7.57 (dd, J$_1$=4.8 Hz, J$_2$=8.4 Hz, 1H), 7.55 (d, J=8.0 Hz, 1H), 7.43 (d, J=8.0 Hz, 1H), 7.06–7.22 (m, 7H), 5.28 (q, J=6.0 Hz, 1H), 4.76 (br s, 2H), 4.13 (q, J=6.8 Hz, 2H), 3.48 (br s, 0.5–1H [H$_2$O]), 2.91 (br s, 2H), 1.42 (d, J=6.8 Hz, 3H), 1.36 (t, J=6.8 Hz, 3H), ppm. HPLC>99%, chiral HPLC>96% ee). MS (ESI, positive mode): 626 (MH$^+$).

Synthesis of Compound 3.16b

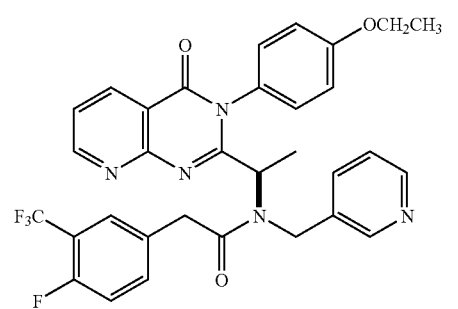

3.16b

Compound 3.16b was prepared following the synthetic procedure for compound 3.16a, wherein 3-trifluoromethyl-4-fluorophenylacetic acid was used instead of 4-(trifluoromethoxy)phenylacetic acid.

Synthesis of Compound 3.17

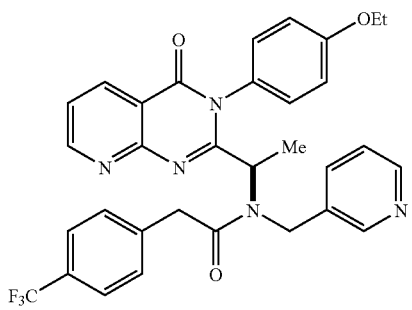

3.17

N-{1R-[3-(4-Ethoxy-phenyl)-4-oxo-3,4-dihydro-pyrido(2,3-d]pyrimidin-2-yl]-ethyl)-N-pyridin-3-ylmethyl-2-(4-trifluoromethyl-phenyl)-acetamide Compound 3.17 was prepared following the synthesis of compound 3.01 described above. Example 3.02 was followed for the synthetic sequence, wherein 2-aminonicotinic acid was used in step a instead of 2-aminobenzoic acid. Characterization data for compound 3.17 follows: colorless, viscous oil. ¹H NMR similar to spectrum for compound 3.01: a mixture of cis/trans amide rotamers in ca. 2:1 (CDCl₃; T=25° C.) characteristic resonance peaks at $\delta_{minor}$ 5.16 (q, 1.0H, J=6.8 Hz) and $\delta_{major}$ 5.40 (q, 2.0H, J=7.2 Hz) ppm. MS (ESI³⁰) 588.2 [MH]⁺

Synthesis of Compound 3.17a

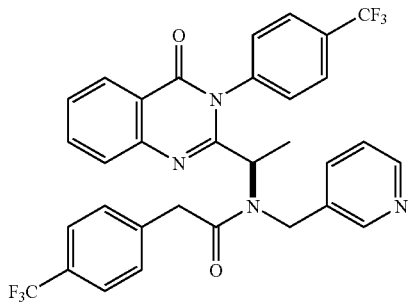

3.17a

Compound 3.17a was prepared following the synthetic procedure for compound 3.17, wherein 4-trifluoromethyl-benzenamine was used instead of p-phenetidine.

Synthesis of Compound 3.18

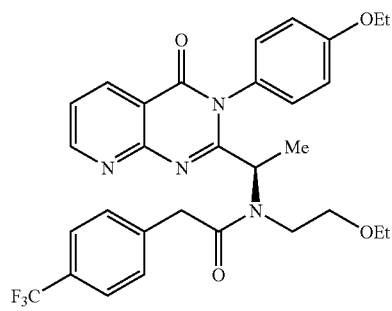

3.18

N-(2-Ethoxy-ethyl)-N-{1R-[3-(4-ethoxy-phenyl)-4-oxo-3,4-dihydro-pyrido[2,3-d]pyrimidin-2-yl]-ethyl}-2-(4-trifluoromethyl-phenyl)-acetamide Compound 3.18 was prepared following the synthesis of compound 3.01 described above. Example 3.02 was followed for the synthetic sequence, wherein 2-aminonicotinic acid was used in step a instead of 2-aminobenzoic acid, and 2-bromoethyl ethyl ether was used in step c instead of 3-picolyl chloride. Characterization data for compound 3.18 follows: colorless, viscous oil. ¹H NMR similar to spectrum for compound 3.01: a mixture of cis/trans amide rotamers in ca. 3:2 (CDCl₃; T=25° C.) characteristic resonance peaks at $\delta_{minor}$ 5.00 (q, 1.0H, J=6.4 Hz) and $\delta_{minor}$ 5.00 (q, 1.5H, J=6.8 Hz) ppm. MS (ESI⁺) 569.3 [MH]⁺

Synthesis of Compound 3.19

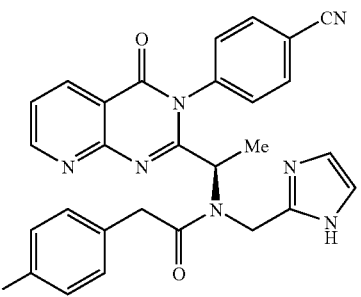

3.19

N-(1R-[3-(4-Cyano-phenyl)-4-oxo-3,4-dihydro-pyrido[2,3-d]pyrimidin-2-yl]-ethyl)N-(1H-imidazol-2-ylmethyl)-2-(4-trifluoromethyl-phenyl)-acetamide Compound 3.19 was prepared following the synthesis of compound 3.01 described above. Example 3.02 was followed for the synthetic sequence, wherein 2-aminonicotinic acid and 4-cyanoanilne were used in step a instead of 2-aminobenzoic acid and 4-ethoxyaniline, and imidazole-2-carboxaldehyde was used in step c via reductive amination instead of 3-picolyl chloride via amine alkylation. Characterization data for compound 3.19 follows: colorless, viscous oil. ¹H NMR single amide rotamer (CDCl₃; T=25° C.) δ 1.45 (d, 3H, J=7.6 Hz), 3.69 (d, 1H, J=15.2 Hz), 3.79 (d, 1H, J=15.2 Hz), 4.74 (q, 1H, J=7.2 Hz), 4.76 (d, 1H, J=19.6 Hz), 5.39 (d, 1H, J=19.6 Hz), 7.02 (t, 1H, J=1.6 Hz), 7.07 (d, 1H, J=2.0 Hz), 7.14 (d, 2H, J=8.0 Hz), 7.40 (d, 2H, J=8.0 Hz), 7.47 (dd, 1H, J₁=2.0 Hz, J₂=8.4 Hz), 7.60 (dd, 1H, J₁=4.8 Hz, J₂=8.0 Hz), 7.95 (dd, 1H, J₁=2.0 Hz, J₂=6.8 Hz), 8.00 (dd, 1H, J₁=2.0 Hz, J₂=8.4 Hz), 8.11 (dd, 1H, J₁=2.0 Hz, J₂=8.4 Hz), 8.66 (dd, 1H, J₁=1.6 Hz, J₂=7.6 Hz), 9.04 (dd, 1H, J₁=1.6 Hz, J₂=4.4 Hz) ppm. MS (ESI⁺) 569.3 [MH]⁺

Synthesis of Compound 3.20

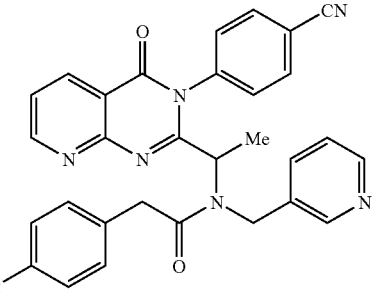

3.20

N-{1R-[3-(4-Cyano-phenyl)-4-oxo-3,4-dihydro-pyrido(2,3-d]pyrimidin-2-yl]-ethyl)-N-pyridin-3-yimethyl-2-(4-trifluoromethyl-phenyl)-acetamide Compound 3.20 was prepared following the synthesis of compound 3.01 described above. Example 3.02 was followed for the synthetic sequence, wherein 2-aminonicotinic acid and 4-cyanoaniline were used in step a instead of 2-aminobenzoic acid and 4-ethoxyaniline, and 3-pyridinecarboxaldehyde was used in step c via reductive amination instead of 3-picolyl chloride via amine alkylation. Characterization data for compound 3.20 follows: colorless, viscous oil. $^1$H NMR single amide rotamer (CDCl$_3$; T=25° C.) δ 1.33 (d, 3H, J=7.2 Hz), 3.66 (d, 1H, J=15.6 Hz), 3.79 (d, 1H, J=15.6 Hz), 5.16 (d, 1H, J=18.0 Hz), 5.19 (q, 1H, J=7.2 Hz), 5.24 (d, 1H, J=18.0 Hz), 7.23–7.32 (m, 3H), 7.45 (dd, 1H, J$_1$=1.6 Hz, J$_2$=8.0 Hz), 7.49–7.55 (m, 4H), 7.89 (dd, 1H, J$_1$=1.6 Hz, J$_2$=8.4 Hz), 7.95 (dd, 1H, J$_1$=1.2 Hz, J$_2$=8.0 Hz), 8.02 (dd, 1H, J$_2$=8.4 Hz), 8.52–8.58 (m, 2H), 8.62 (dd, 1H, J$_1$=2.0 Hz, J$_2$=8.0 Hz), 9.07 (dd, 1H, J$_1$=2.0 Hz, J$_2$=4.8 Hz) ppm. MS (ESI$^+$) 569.2 [MH]$^+$ Synthesis of Compound 3.21

(3.21)

{1R-[3-(4-Cyano-phenyl)-4-oxo-3,4-dihydro-pyrido[2,3-d]rimidin-2-yl]-ethyl}-N-(1-methyl-1H--Imidazol-2-ylmethyl)-2-(4-trifluoromethyl-phenyl)-acetamide Compound 3.21 was prepared following the synthesis of compound 3.01 described above. Example 3.02 was followed for the synthetic sequence, wherein 2-aminonicotinic acid and 4-cyanoaniline were used in step a instead of 2-aminobenzoic acid and 4-ethoxyaniline, and 3-methyl-4-carboxaldehyde-(3H)imidazole was used in step c via reductive amination instead of 3-picolyl chloride via amine alkylation. Characterization data for compound 3.21 follows: colorless, viscous oil. $^1$H NMR single amide rotamer (CDCl$_3$; T=25° C.) δ 1.41 (d, 3H, J=7.2 Hz), 3.66 (s, 3H), 3.75 (d, 1H, J=16.0 Hz), 3.84 (d, 1H, J=16.0 Hz), 4.98 (s, 2H), 5.17 (q, 1H, J=7.2 Hz), 6.86 (s, 1H), 7.30 (s, 1H), 7.40–7.50 (m, 3H), 7.50–7.58 (m, 3H), 7.80–8.05 (m, 3H), 8.63 (dd, 1H, J$_1$=2.0 Hz, J$_2$=8.0 Hz), 9.06 (dd, 1H, J$_1$=2.0 Hz, J$_2$=4.4 Hz) ppm. MS (ESI$^+$) 572.2 [MH]$^+$ Synthesis of Compound 3.22

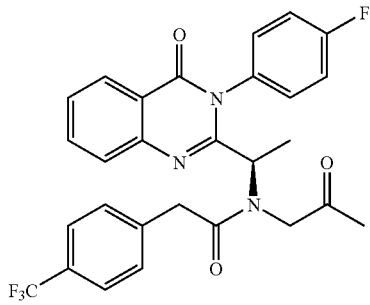

3.22

Compound 3.22 was prepared following the synthetic procedure for compound 3.02, described above. $^1$H NMR (d$_6$-DMSO, T=140° C.) δ 8.13 (d, J=8.1 Hz, 1H), 7.85 (t, J=8.0 Hz, 1H), 7.70 (d, J=8.1 Hz, 1H), 7.65–7.45 (m, 5H), 7.40–7.20 (m, 4H), 5.30 (bs, 1H), 4.40 (bs, 2H), 3.40 (bs, 2H), 1.99 (s, 3H), 1.34 (d, J=6.6 Hz, 3H). m.p. 220–221° C. MS (ESI$^+$) 526.2 [MH]$^+$.

Synthesis of Compound 3.23

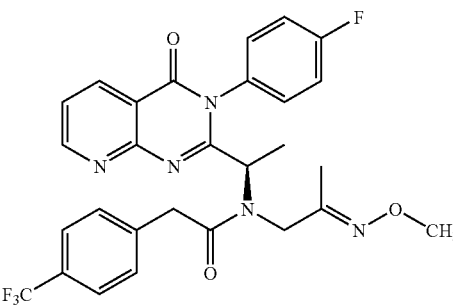

3.23

A mixture of compound 3.22 (11 mg, 0.021 mmol) and methoxylamine hydrochloride (0.08 mL, 25–30% aqueous solution) in methanol (4 mL) and pyridine (0.1 mL) was stirred at room temperature for three days. The solvents were evaporated, and the residue was purified by column (30% EtOAc in Hexane) to give 12 mg of 3.23 as white solid. MS (ESI$^+$) 555.2 [MH]$^+$.

Synthesis of Compound 3.24

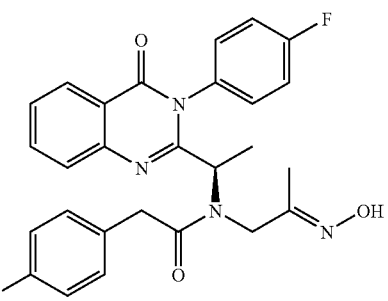

3.24

Compound 3.24 was prepared following the synthetic procedure for compound 3.23, described above. MS (ESI$^+$) 541.3 [MH]$^+$.

Synthesis of Compound 3.25

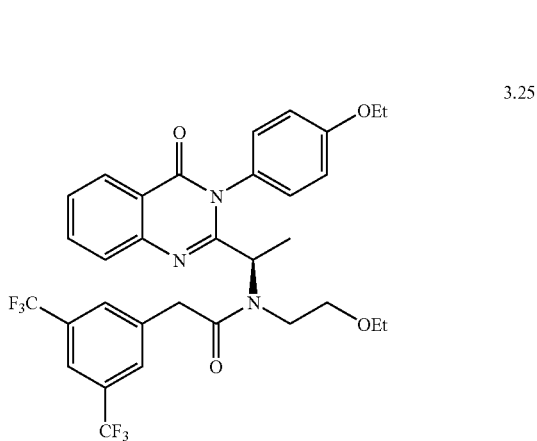

3.25

Compound 3.25 was prepared following the synthetic procedure for compound 3.02, described above. $^1$H NMR (d$_6$-DMSO, T=140° C.) δ 8.14 (d, J=8.1 Hz, 1H), 7.84 (m, 2H), 7.74 (m, 3H), 7.55 (t, J=8.2 Hz, 1H), 7.30 (m, 2H), 7.00 (m, 2H), 5.20 (q, J=6.9 Hz, 1H), 4.05 (dd, J=6.9, 7.0 Hz, 2H), 3.80–3.25 (m, 8H), 1.49 (d, J=6.9 Hz, 3H), 1.31 (t, J=7.0 Hz, 3H), 0.95 (t, J=7.0 Hz, 3H). m.p. 57–60° C. MS (ESI$^+$) 636.2 [MH]$^+$. Anal. Calcd. for C$_{32}$H$_{31}$F$_6$N$_3$O$_4$: C, 60.47; H, 4.92; N, 6.61. Found: C, 60.36; H, 4.99; N, 6.51.

Synthesis of Compound 3.26

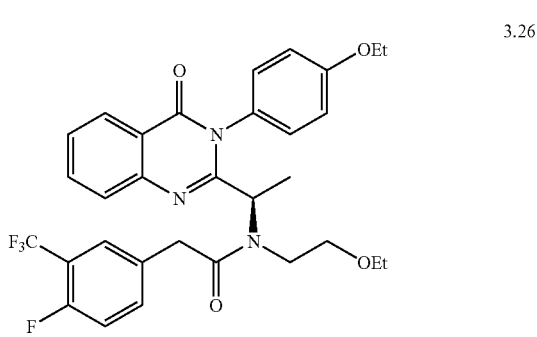

3.26

Compound 3.26 was prepared following the synthetic procedure for compound 3.02, described above. $^1$H NMR (d$_6$-DMSO, T=140° C.) δ 8.13 (d, J=8.0 Hz, 1H), 7.84 (t, J=8.1 Hz, 1H), 7.70 (d, J=8.0 Hz, 1H), 7.54 (t, J=8.2 Hz, 1H), 7.42 (m, 2H), 7.28–7.19 (m, 3H), 7.15 (m, 2H), 5.15 (q, J=6.8 Hz, 2H), 4.08 (q, J=7.0 Hz, 2H), 3.65–3.20 (m, 8H), 1.46 (d, J=6.8 Hz, 3H), 1.34 (t, J=7.0 Hz, 3H), 0.96 (t, J=7.0 Hz, 3H). m.p. 137–138° C. MS (ESI$^+$) 586.2 [MH]$^+$. Anal. Calcd. for C$_{31}$H$_{31}$F$_4$N$_3$O$_4$: C, 63.58; H, 5.34; N, 7.18. Found: C, 63.47; H, 5.45; N, 7.40.

Synthesis of Compound 3.27

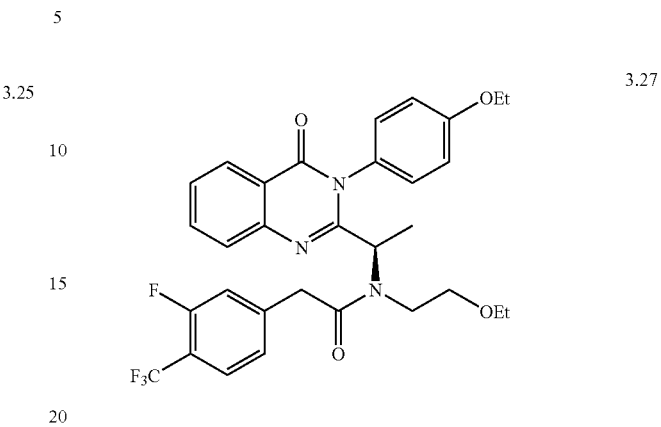

3.27

Compound 3.27 was prepared following the synthetic procedure for compound 3.02, described above. $^1$H NMR (d$_6$-DMSO, T=140° C.) δ 8.13 (d, J=8.0 Hz, 1H), 7.84 (t, J=8.1 Hz, 1H), 7.70 (d, J=8.0 Hz, 1H), 7.57 (m, 2H), 7.40–7.20 (m, 2H), 7.13 (m, 1H), 7.05 (m, 2H), 6.84 (d, J=8.8 Hz, 1H), 5.17 (q, J=6.9 Hz, 2H), 4.09 (q, J=7.0 Hz, 2H), 3.65–3.20 (m, 8H), 1.46 (d, J=6.8 Hz, 3H), 1.35 (t, J=7.0 Hz, 3H), 0.96 (t, J=7.0 Hz, 3H). m.p. 146–148° C. MS (ESI$^+$) 586.2 [MH]$^+$. Anal. Calcd. for C$_{31}$H$_{31}$F$_4$N$_3$O$_4$: C, 63.58; H, 5.34; N, 7.18. Found: C, 63.76; H, 5.43; N, 7.19.

Synthesis of Compound 3.28

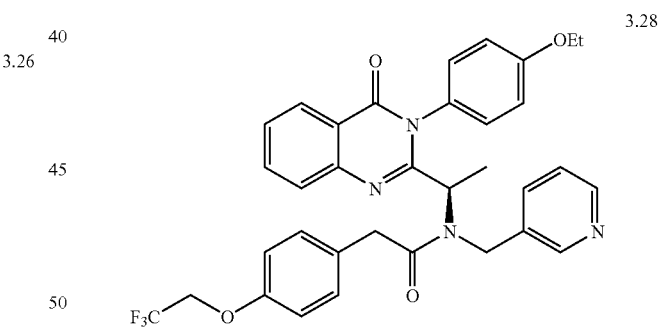

3.28

Compound 3.28 was prepared following the synthetic procedure for compound 3.02, described above. $^1$H NMR (d$_6$-DMSO, T=140° C.) δ 8.33 (m, 2H), 8.09 (d, J=8.1 Hz, 1H), 7.84 (t, J=8.0 Hz, 1H), 7.67 (d, J=8.0 Hz, 1H), 7.54 (t, J=8.1 Hz, 1H), 7.48 (m, 1H), 7.36 (m, 1H), 7.18–7.04 (m, 4H), 7.01 (d, J=8.7 Hz, 2H), 6.92 (d, J=8.7 Hz, 2H), 5.25 (q, J=6.8 Hz, 2H), 4.70 (s, 2H), 4.60 (q, J=8.9 Hz, 2H), 4.14 (q, J=7.0 Hz, 2H), 3.35–3.00 (bm, 2H), 1.37 (m, 6H). m.p. 103–104° C. MS (ESI$^+$) 617.3 [MH]$^+$. Anal. Calcd. for 2H), 4.70 (s, 2H), 4.60 (q, J=8.9 Hz, 2H), 4.14 (q, J=7.0 Hz, 2H), 3.35–3.00 (bm, 2H), 1.37 (m, 6H). m.p. 103–104° C. MS (ESI$^+$) 617.3 [MH]$^+$. Anal. Calcd. for C$_{34}$H$_{31}$F$_3$N$_4$O$_4$.1/2H$_2$O: C, 65.27; H, 5.16; N, 8.96. Found: C, 65.01; H, 5.12; N, 8.96.

Synthesis of Compound 3.29

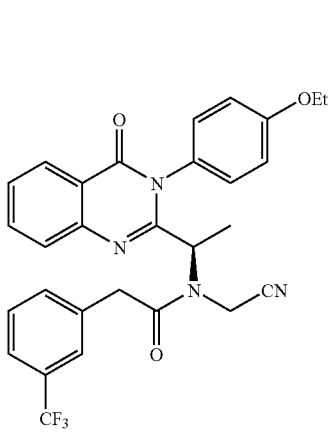

3.29

Compound 3.29 was prepared in a manner similar to that used for compound 3.02. Light yellow solid, $^1$H NMR (DMSO, T=140° C.) 1.35 (t, 3H, J=6.8 Hz), 1.50 (d, 3H, J=6.8 Hz), 3.58 (m, 2H), 4.10 (q, 2H, J=6.8 Hz), 4.50 (m, 2H), 5.23 (q, 1H, J=6.8 Hz), 7.11 (m, 2H), 7.29–7.62 (m, 6H), 7.78 (m, 2H), 7.88 (t, 1H, J=8 Hz), 8.15 (dd, 1H, $J_1$=1.2 Hz, $J_2$=8.0 Hz). At room temperature, mixture of cis/trans amide rotamers (2/1), determined by $^1$H NMR (CDCl$_3$) 5.02 (q, 1H, J=6.8 Hz ), 5.51 (q, 1H, J=6.8 Hz). MS(ESI$^+$) 535.2 (MH$^+$).

Synthesis of Compound 3.30

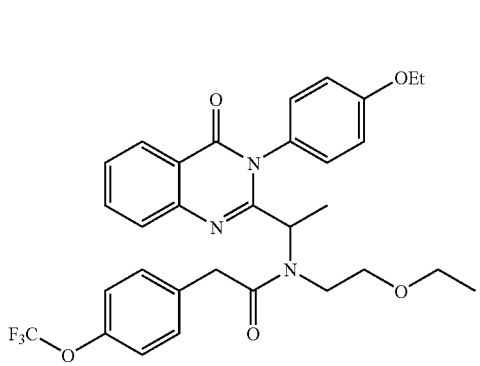

3.30

Compound 3.30 was prepared in a manner similar to that used for compound 3.02. Light yellow solid, m.p. 153° C. $^1$H NMR (DMSO, T=140° C.) 0.97 (t, 3H, J=6.8 Hz), 1.37 (t, 3H, J=6.8 Hz), 1.44 (d, 3H, J=6.8 Hz), 3.31–3.59 (m, 8H), 4.10 (q, 2H, J=6.8 Hz), 5.17 (q, 1H, J=6.8 Hz), 7.05–7.33 (m, 8H), 7.55 (t, 1H, J=8 Hz), 7.71 (d, 1H, J=8 Hz), 7.85 (t, 1H, J=8 Hz), 8.15 (dd, 1H, $J_1$=1.2 Hz, $J_2$=8.0 Hz). At room temperature, mixture of cis/trans amide rotamers (1/1), determined by $^1$H NMR (CDCl$_3$) 4.92 (q, 1H, J=6.9 Hz), 5.35 (q, 1H, J=6.9 Hz). MS(ESI$^+$) 584.3 (MH$^+$). Anal. (C$_{31}$H$_{32}$F$_3$N$_3$O$_5$) cal. C, 63.80; H, 5.53; N, 7.20. Found C, 63.92, H, 5.61, N, 7.20.

Synthesis of Compound 3.31

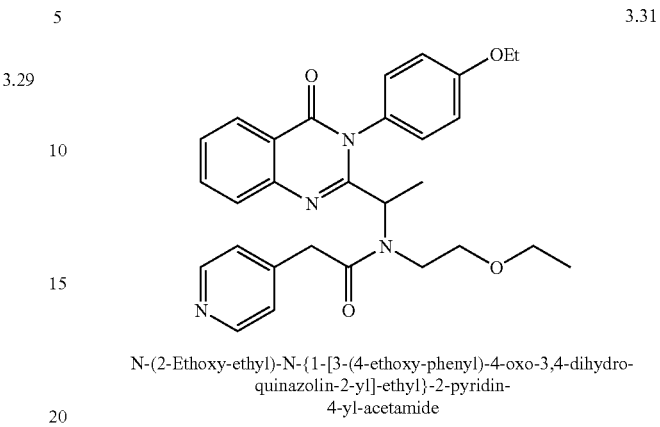

3.31

N-(2-Ethoxy-ethyl)-N-{1-[3-(4-ethoxy-phenyl)-4-oxo-3,4-dihydro-quinazolin-2-yl]-ethyl}-2-pyridin-4-yl-acetamide Compound 3.31 was prepared in a manner similar to that used for compound 3.02. Colorless oil, $^1$H NMR (CD$_3$OD) 1.18 (t, 3H, J=7.0 Hz), 1.37 (t, 3H, J=7.0 Hz), 1.41 (d, 3H, J=6.6 Hz), 3.30 (s, 2H), 3.36 (m, 1H), 3.52 (q, 2H, J=7.0 Hz), 3.62 (m, 2H), 3.91 (m, 1H), 4.02 (q, 2H, J=7.0 Hz ), 4.75 (q, 1H, J=6.6 Hz), 6.85 (m, 1H), 6.90 (d, 2H, J=9 Hz), 7.06 (m, 1H), 7.13 (m, 1H), 7.34 (d, 2H, J=4.8 Hz), 7.53 (d, 2H, J=9 Hz), 7.70 (m, 1H), 8.28 (d, 2H, J=4.8 Hz) MS(ESI$^+$) 501.2 (MH$^+$).

Synthesis of Compound 3.32

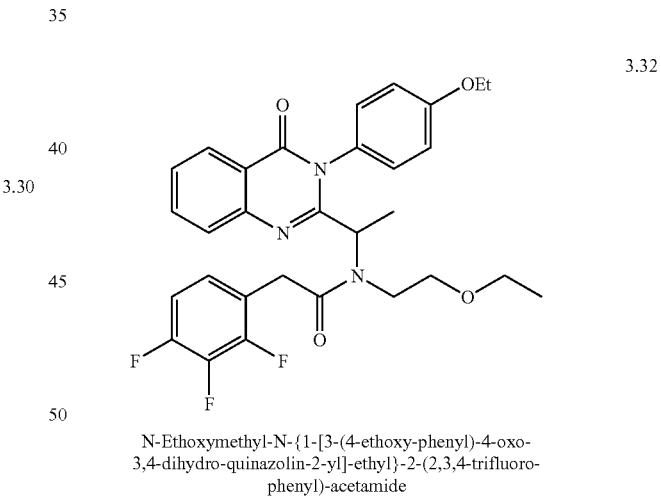

3.32

N-Ethoxymethyl-N-{1-[3-(4-ethoxy-phenyl)-4-oxo-3,4-dihydro-quinazolin-2-yl]-ethyl}-2-(2,3,4-trifluoro-phenyl)-acetamide Compound 3.32 was prepared in a manner similar to that used for compound 3.02. Light yellow solid, m.p. 146.3° C. $^1$H NMR (DMSO, T=140° C.) 0.97 (t, 3H, J=6.8 Hz), 1.36 (t, 3H, J=6.8 Hz), 1.46 (d, 3H, J=6.4 Hz), 3.32–3.59 (m, 8H), 4.09 (q, 2H, J=6.8 Hz), 5.17 (q, 1H, J=6.4 Hz), 6.95–7.11 (m, 4H), 7.26 (m, 2H), 7.54 (t, 1H, J=8 Hz), 7.71 (d, 1H, $J_2$=7.6 Hz), 7.85 (dt, 1H, $J_1$=1.6 Hz, $J_2$=8.2 Hz), 8.15 (dd, 1H, $J_1$=1.2 Hz, $J_2$=7.6 Hz). At room temperature, mixture of cis/trans amide rotamers (1/1), determined by $^1$H NMR (CDCl$_3$) 4.92 (q, 1H, J=6.8 Hz), 5.38 (q, 1H, J=6.8 Hz). MS(ESI$^+$) 554.3 (MH$^+$). Anal. (C$_{30}$H$_{30}$F$_3$N$_3$O$_4$) cal. C, 65.09; H, 5.46; N, 7.59. Found C, 64.93, H, 5.55, N, 7.62.

Synthesis of Compound 3.33

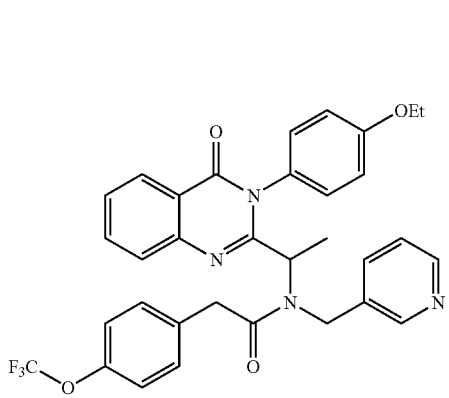

N-{1-[3-(4-Ethoxy-phenyl)-4-oxo-3,4-dihydro-quinazolin-2-yl]-ethyl}-N-pyridin-3-ylmethyl-2-(4-trifluoromethoxy-phenyl)-acetamide Compound 3.33 was prepared in a manner similar to that used for compound 3.02. Light yellow solid, m.p. 77.7° C. $^1$H NMR (DMSO, T=140° C.) 1.38 (m, 6H), 3.05 (br, 1H), 3.42 (m, 1H), 4.12 (q, 2H, J=7.2 Hz), 4.71 (m, 2H), 5.26 (q, 1H, J=6.4 Hz), 7.09–7.51 (m, 9H), 7.39 (m, 1H), 7.51–7.56 (m, 2H), 7.67 (d, 1H, $J_2$=8.4 Hz), 7.85 (t, 1H, J=8 Hz), 8.09 (d, 1H, J=8.0 Hz), 8.34 (m, 1H). At room temperature, mixture of cis/trans amide rotamers (2/1), determined by $^1$H NMR (CDCl$_3$) 5.09 (m, 1H), 5.40 (m, 1H). MS(ESI$^+$) 604.2 (MH$^+$). Anal. (C$_{33}$H$_{29}$F$_3$N$_4$O$_4$) cal. C, 65.77; H, 4.85; N, 9.30. Found C, 65.32, H, 4.87, N, 9.12.

Synthesis of Compound 3.34

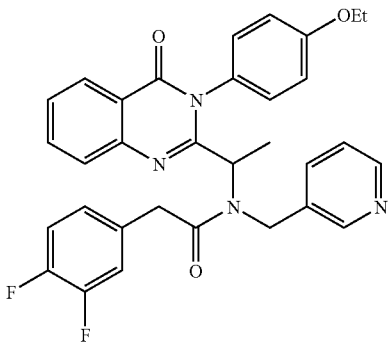

2-(3,4-Difluoro-phenyl)-N-{1-[3-(4-ethoxy-phenyl)-4-oxo-3,4-dihydro-quinazolin-2-yl]-ethyl}-N-pyridin-3-ylmethyl-acetamide Compound 3.34 was prepared in a manner similar to that used for compound 3.02. Light yellow solid, m.p. 75.5° C. mixture of cis/trans amide rotamers (2/1), determined by $^1$H NMR (CD$_3$OD) 5.20 (m, 1H), 5.45 (m, 1H). MS(ESI$^+$) 556.3 (MH$^+$). Anal. (C$_{32}$H$_{28}$F$_2$N$_4$O$_3$) cal. C, 69.30; H, 5.09; N, 10.10. Found C, 68.83, H, 5.15, N, 9.99.

Synthesis of Compound 3.35

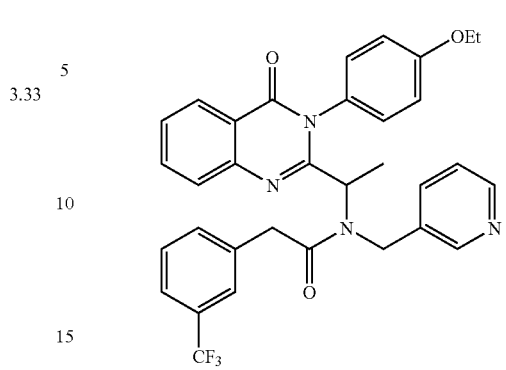

N-{1-[3-(4-Ethoxy-phenyl)-4-oxo-3,4-dihydro-quinazolin-2-yl]-ethyl}-N-pyridin-3-ylmethyl-2-(3-trifluoromethyl-phenyl)-acetamide Compound 3.35 was prepared in a manner similar to that used for compound 3.02 White solid. $^1$H NMR (DMSO, T=140° C.) 1.36(t, 3H, J=6.8 Hz), 1.42 (d, 3H, J=6.4 Hz), 3.05 (m, 1H), 3.53(m, 1H ), 4.11 (m, 2H), 4.73 (m, 2H), 5.27 (q, 1H, J=6.4 Hz), 7.11 (m, 4H), 7.33–7.51 (m, 8H), 7.68 (d, 1H, J=8 Hz), 7.83 (t, 1H, J=7.2 Hz), 8.10 (m, 1H), 8.34 (m, 1H). At room temperature, mixture of cis/trans amide rotamers (7/1), determined by $^1$H NMR (CDCl$_3$) 5.11 (q, 1H, J=6.4 Hz), 5.42 (m, 1H). MS(ESI$^+$) 587.3 (MH$^+$). Anal. (C$_{33}$H$_{29}$F$_3$N$_4$O$_3$) cal. C, 67.57; H, 4.98; N, 9.55. Found C, 67.15, H, 5.12, N, 9.81.

Synthesis of Compound 3.36

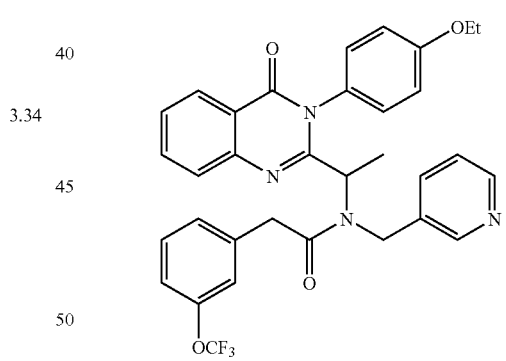

N-{1-[3-(4-Ethoxy-phenyl)-4-oxo-3,4-dihydro-quinazolin-2-yl]-ethyl}-N-pyridin-3-ylmethyl-2-(3-trifluoromethoxy-phenyl)-acetamide Compound 3.36 was prepared in a manner similar to that used for compound 3.02. Light yellow solid, $^1$H NMR (DMSO, T=140° C.) 1.39 (m, 6H), 3.05 (br, 1H), 3.45 (m, 1H), 4.13 (q, 2H, J=6.8 Hz), 4.71 (m, 2H), 5.26 (q, 1H, J=6.4 Hz), 7.00–7.16 (m, 8H), 7.35 (m, 2H), 7.37–7.60 (m, 2H), 7.68 (d, 1H, $J_2$=8.4 Hz), 7.84 (t, 1H, J=8 Hz), 8.09 (d, 1H, J=8.0 Hz), 8.34 (m, 1H). At room temperature mixture of cis/trans amide rotamers (1/2), determined by $^1$H NMR (CDCl$_3$) 1.25 (d, 1H, J=6.4 Hz), 1.32 (d, 1H, J=6.4 Hz). MS(ESI$^+$) 603.2 (MH$^+$). Anal. (C$_{33}$H$_{29}$F$_3$N$_4$O$_4$) cal. C, 65.77; H, 4.85; N, 9.30. Found C, 65.48, H, 4.98, N, 9.39.

Synthesis of Compound 3.37

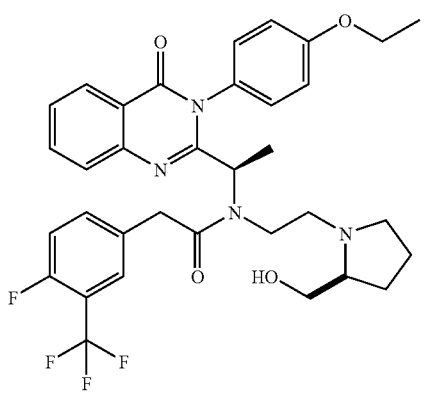

(s)-N-{1-[3-(4-Ethoxy-phenyl)-4-oxo-3,4-dihydro-quinazolin-2-yl]-ethyl}-2-(4-fluoro-3-trifluoromethyl-phenyl)-N-[2-(2-hydroxymethyl-pyrrolidin-1-yl)-ethyl]-acetamide Compound 3.37 was prepared following the synthesis procedure for compound 3.02. White solid. $^1$H NMR (DMSO, T=120° C.) 1.32 (t, 3H, J=7.07 Hz), 1.49–1.55 (m, 6H), 1.70 (m, 1H), 2.26 (m, 1H), 2.58 (m, 1H), 2.78–2.88 (m, 4H), 3.12–3.15 (m, 1H), 3.20 (m, 1H), 3.40 (m, 1H), 3.49 (m, 1H), 3.50–3.85 (m, 2H), 4.07 (q, 2H, J=7.07 Hz), 5.16 (q, 1H, J=6.67 Hz), 7.02 (m, 2H), 7.24 (m, 1H), 7.29–7.44 (m, 4H), 7.56 (t, 1H, J=7.33 Hz), 7.72 (d, 1H, J=8 Hz), 7.86 (t, 1H, J=7.6 Hz), 8.14 (d, 1H, J=7.60 Hz). MS(ESI$^+$) 641.2 (MH$^+$).

Synthesis of Compound 3.38

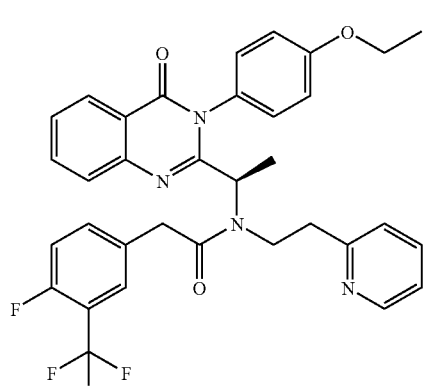

N-{1-[3-(4-Ethoxy-phenyl)-4-oxo-3,4-dihydro-quinazolin-2-yl]-ethyl}-2-(4-fluoro-3-trifluoromethyl-phenyl)-N-(2-pyridin-2-yl-ethyl)-acetamide Compound 3.38 was prepared following the synthesis of compound 3.02. Pale yellow solid. $^1$H NMR (DMSO, T=120° C.) 1.33 (t, 3H, J=6.67 Hz), 1.51 (d, 3H, J=6.67 Hz), 2.95 (m, 1H), 3.19(m, 1H), 3.69 (m, 1H), 3.83 (m, 1H), 4.09 (q, 2H, J=6.67 Hz), 5.11–5.23 (m, 3H), 7.06 (m, 2H), 7.27–7.45 (m, 7H), 7.56 (t, 1H, J=7.33 Hz), 7.70 (d, 1H, J=8 Hz), 7.85 (m, 2H), 8.13 (d, 1H, J=7.60 Hz), 8.48 (s, 1H). MS(ESI$^+$) 619.30 (MH$^+$).

Synthesis of Compound 3.39.HCl

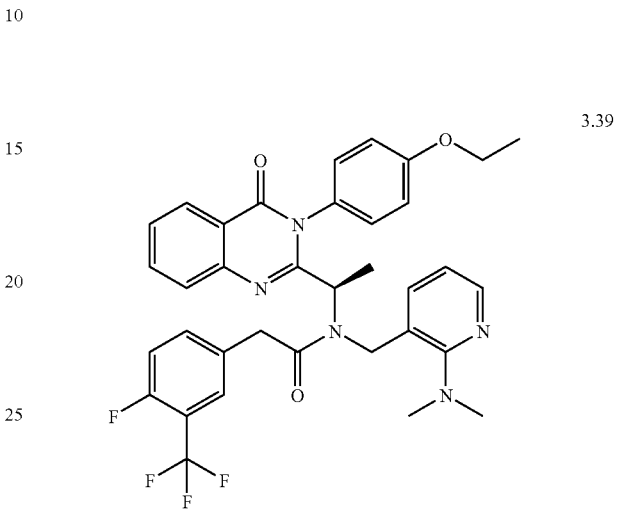

N-(2-Dimethylamino-pyridin-3-ylmethyl)-N-{1-[3-(4-ethoxy-phenyl)-4-oxo-3,4-dihydro-quinazolin-2-yl]-ethyl}-2-(4-fluoro-3-trifluoromethyl-phenyl)-acetamide Compound 3.39 was prepared following the synthesis of compound 3.02. White solid. $^1$H NMR (DMSO, T=120° C.) 1.36 (m, 6H), 2.88 (s, 6H), 3.61 (d, 1H, J=14.67 Hz), 4.12 (q, 2H, J=6.93 Hz), 4.78 (m, 3H), 5.26 (m, 1H), 6.93 (m, 1H), 7.10 (m, 2H), 7.28–7.43 (m, 5H), 7.51–7.59 (m, 3H), 7.83 (t, 1H, J=7.33 Hz), 7.97 (m, 1H), 8.08 (d, 1H, J=7.73 Hz). MS(ESI$^+$) 648.2 (MH$^+$).

Scheme 10

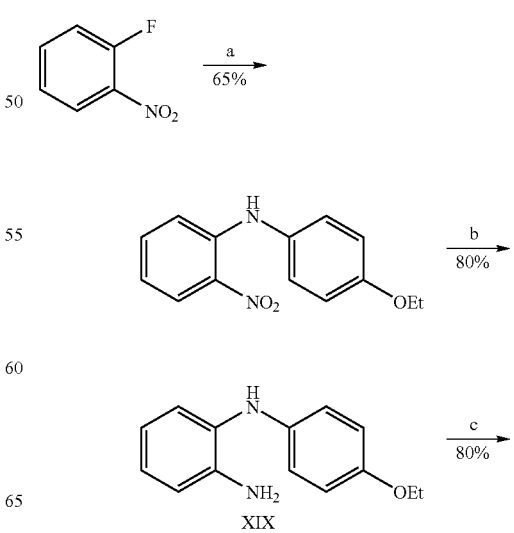

-continued

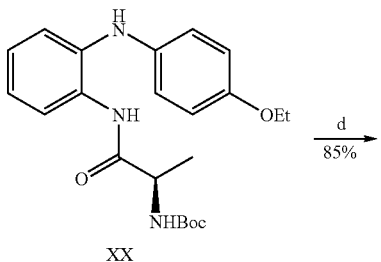

XX

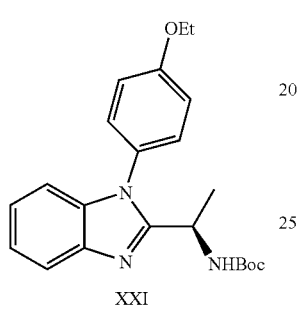

XXI a p-phenetidine, K₂CO₃, DMF, 125° C., 16h.
b H2, Pd/C, rt
c D-Boc-Ala-OH, EDC, HOBt, NMM, DMF.
d HOAc, 90° C.

N-(4-Ethoxy-phenyl)-benzene-1,2-diamine (XIX). In the presence of K₂CO₃ (13.0 g, 94.2 mmol), the mixture of 1-fluoro-2-nitrobenzene (8.46 g, 60 mmol) and phenylamine (8.22 g, 60 mmol) in DMF (40 ml) was heated to 125° C. for 16 h. and then poured into water, the aqueous layer was extracted with EtOAc three times, the combined organic layer was then washed by water, brine and dried over Na₂SO4. The solvent was evaporated and the crude product was recrystallized from EtOH to afford a brown solid (4-ethoxy-phenyl)-(2-nitro-pheny)1-amine (10 g).

In the presence of 10% Pd—C (2.1 g, 2 mmol), under hydrogen atmosphere, a solution of (4-ethoxy-phenyl)-(2-nitro-pheny)1-amine (5.16 g, 20 mmol) in MeOH/Et₂O (30 ml/30 ml) was stirred overnight. The solid was filtered, the filtrate was evaporated to give a orange solid N-(4-ethoxy-phenyl)-benzene-1,2-diamine (3.6 g) (XIX). ¹H NMR (CDCl₃) 1.39 (t, 3H, J=6.93 Hz), 3.98 (q, 2H, J=6.93 Hz), 6.78 (m, 6H), 6.94 (m, 1H), 7.03 (m, 1H). MS(ESI⁺) 229.2 (MH⁺).

{1-[2-(4-Ethoxy-phenylamino)-phenylcarbamoyl]-ethyl}-carbamic acid tert-butyl ester (XX). To a solution containing (R)-Boc-Ala-OH (4.92 g, 26 mmol) and above diamine (5.4 g, 23.68 mmol) in 50 ml of DMF, was added EDCI (9.08 g, 47.3 mmol), HOBt (3.62 g, 23.68 mmol) and NMM (3.59 g, 35.52 mmol). The mixture was stirred at room temperature overnight. The reaction was diluted with dichloromethane and washed with water (three times), brine and dried over Na₂SO₄. Removal of solvent afforded a oil which was subjected to flash column. A yellow solid (7.55 g) was obtained. ¹H NMR (CDCl₃) 1.37 (m, 15H), 3.98 (q, 2H, J=5.2 Hz), 4.21 (m, 1H), 4.92 (m, 1H), 5.65 (br, 1H), 6.81 (m, 4H), 6.97 (m, 1H), 7.08 (m, 2H), 7.68 (d, 1H, J=8 Hz), 8.16 (s, 1H). MS(ESI⁺) 400.2 (MH⁺).

{1-[1-(4-Ethoxy-phenyl)-1H-benzoimidazol-2-yl]-ethyl}-carbamic acid tert-butyl ester (XXI). A solution of above solid (6 g, 15.03 mmol) in HOAc (60 ml) was heated to 80° C. for 4 h. The solvent was evaporated, the residue was dissolved in EtOAc and washed by sat. NaHCO₃, water, brine and dried over Na₂SO4. The solvent was removed and the crude residue was subjected by flash column to afford a white solid (4.1 g). ¹H NMR (CDCl₃) 1.36 (s, 9H), 1.43 (m, 6H), 4.10 (q, 2H, J=6.93 Hz), 4.84 (m, 1H), 7.03 (m, 1H), 7.06 (m, 2H), 7.21 (m, 2H), 7.38 (m, 2H), 7.66 (d, 1H, J=7.73 Hz). MS(ESI⁺) 382.3 (MH⁺).

Synthesis of Compound 3.40.HCl

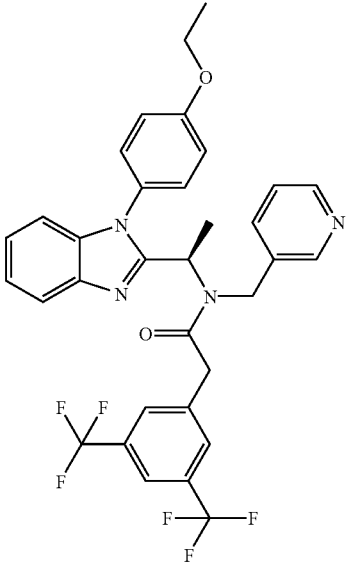

3.40

2-(3,5-Bis-trifluoromethyl-phenyl)-N-{1-[1-(4-ethoxy-phenyl)1H-benzoimidazol-2-yl]-ethyl}-N-pyridin-3-ylmethyl-acetamide Starting from {1-[1-(4-ethoxy-phenyl)-1H-benzoimidazol-2-yl]-ethlyl}-carbamic acid tert-butyl ester, compound 3.40 was prepared following the synthesis of compound 3.02. Yellow solid. ¹H NMR (DMSO, T=120° C.) 1.35 (t, 3H, J=6.93 Hz), 1.66 (m, 3H), 3.29 (br, 1H), 3.93 (d, 1H, J=16 Hz), 4.11 (q, 2H, J=6.93 Hz), 4.65 (m, 1H), 4.75 (m, 1H), 5.70 (m, 1H), 7.03 (d, 1H, J=7.73 Hz ), 7.14 (d, 2H, J=8.27 Hz), 7.26–7.44 (m, 5H), 7.70–7.84 (m, 5H), 8.45 (s, 2H). MS(ESI⁺) 627.2 (MH⁺).

Synthesis of Compound 3.41

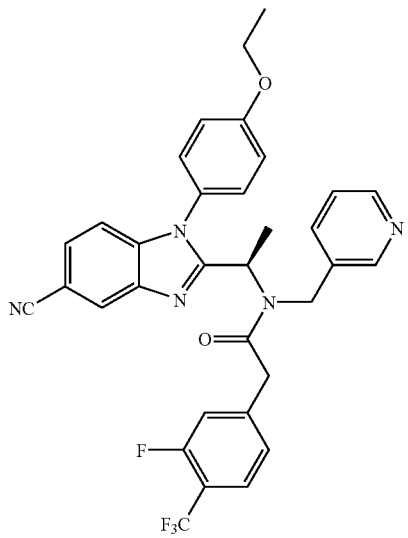

N-{1-[5-Cyano-1-(4-ethoxy-phenyl)-1H-benzoimidazol-2-yl]-ethyl}-2-(3-fluoro-4-trifluoromethyl-phenyl)-N-pyridin-3-ylmethyl-acetamide Compound 3.41 was prepared following the synthesis of compound 3.40. White solid. $^1$H NMR (DMSO, T=120° C.) 1.41 (t, 3H, J=6.93 Hz), 1.59 (m, 3H), 3.30 (br, 1H), 3.69 (d, 1H, J=16 Hz), 4.15 (q, 2H, J=6.93 Hz), 4.49–4.63 (m, 2H), 5.74 (m, 1H), 7.02–7.15 (m, 6H), 7.30–7.41 (m, 3H), 7.58 (m, 2H), 8.18–8.32 (m, 3H). MS(ESI$^+$) 602.3 (MH$^+$).

Synthesis of Compound 3.42.HCl

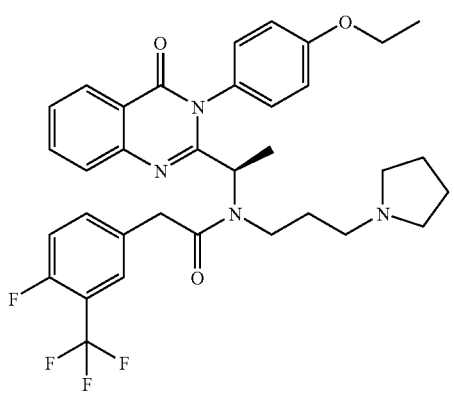

N-{1-[3-(4-Ethoxy-phenyl)-4-oxo-3,4-dihydro-quinazolin-2-yl]-ethyl}-2-(4-fluoro-3-trifluoromethyl-phenyl)-N-(3-pyrrolidin-1-yl-propyl)-acetamide Compound 3.42 was prepared following the synthesis of compound 3.02. White solid. $^1$H NMR (DMSO, T=120° C.) 1.35 (t, 3H, J=6.93 Hz), 1.52 (m, 3H), 1.9 (m, 6H), 2.85–3.05 (m, 3H), 3.36–3.57 (m, 4H), 3.95 (m, 3H), 4.08 (q, 2H, J=6.93 Hz), 5.17 (m, 1H), 7.02–7.10 (m, 2H), 7.24–7.46 (m, 5H), 7.58 (t, 1H, J=7.6 Hz), 7.75 (d, 1H, J=7.73 Hz), 7.88 (t, 1H, J=7.73 Hz), 8.15 (d, 1H, J=8 Hz). MS(ESI$^+$) 625.3 (MH$^+$).

Synthesis of Compound 3.43

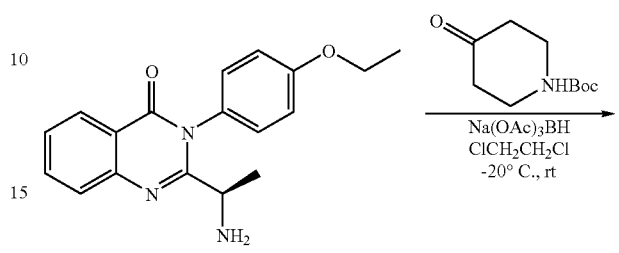

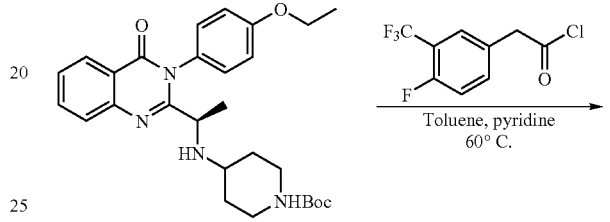

I

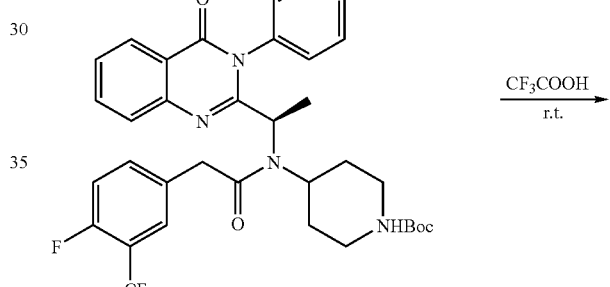

II

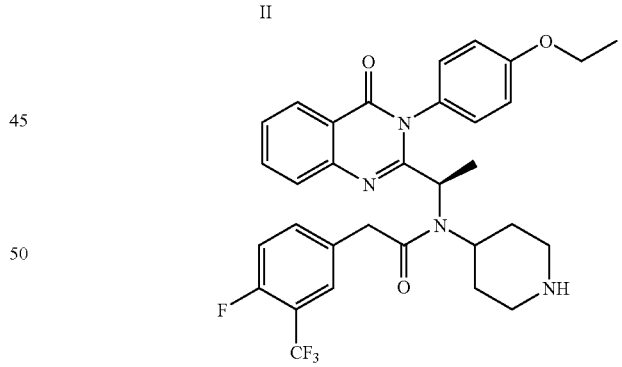

3.43

4-{1-[3-(4-Ethoxy-phenyl)-4-oxo-3,4-dihydro-quinazolin-2-yl]-ethylamino}-piperidine-1-carboxylic acid tert-butyl ester (I). 4-Oxo-Piperidine-1-carboxylic acid tert-butyl ester (0.468 g, 2.35 mmol) was added to a solution of amine (0.6 g, 1.96 mmol) in dichloroethane (10 ml) at −10° C., followed by Na(OAC)$_3$BH (0.602 g, 2.84 mmol). The mixture was kept at that temperature for 1.5 h, then warmed slowly to room temperature and stirred overnight. The solution was diluted with DCM, washed by sat.NaHCO$_3$, water, brine and dried over Na$_2$SO$_4$. The solvent was evaporated and a white solid (1.1 g) was obtained, which was used in the next step. MS(ESI$^+$) 493.3 (MH$^+$).

4-{{1-[3-(4-Ethoxy-phenyl)-4-oxo-3,4-dihydro-quinazoin-2-yl]-ethyl}-[(4-fluoro-3-trifluoromethyl-phenyl)-acetyl]-amino}-piperidine-1-carboxylic acid ester (II). Pyridine (0.289 g, 3.66 mmol) was added to a mixture of I (0.6 g, 1.22 mmol) and phenylacetyl chloride (0.44 g, 1.83 mmol) in toluene (15 ml). The solution was heated to 60° C. for 3 h, and then poured into 1N HCl. The aqueous layer was extracted with EtOAc three times, the combined organic layer was then washed by sat. NaHCO$_3$, water, brine and dried over Na$_2$SO4. The solvent was evaporated and the crude oil was subjected by flash column to afford a yellow solid (540 mg). MS(ESI$^+$) 697.3 (MH$^+$).

{1-[3-(4-Ethoxy-phenyl)-4-oxo-3,4-dihydro-quinazolin-2-yl]-ethyl}-2-(4-fluoro-3-trifluoromethyl-phenyl)-piperidin-4-yl-acetamide (3.43). Trifluoroacetic acid (1.77 g, 15.5 mmol) was added to a solution of II (0.54 g, 0.77 mmol) in dichloromethane. The mixture was stirred at room temperature for 3 h. The solvent was evaporated, the residue was dissolved in EtOAc and washed with sat. NaHCO$_3$, water, brine and dried over Na$_2$SO4. The solvent was evaporated and the crude oil was subjected by flash column to afford a white solid (440 mg). $^1$H NMR (DMSO, T=120° C.) 1.21 (m, 1H), 1.34 (m, 4H), 1.48 (d, 3H, J=6.8 Hz), 2.16 (m, 3H), 2.70–2.97 (m, 4H), 3.28 (d, 1H, J=16 Hz), 3.64 (m, 1H), 4.09 (q, 2H, J=6.8 Hz), 5.04 (m, 1H), 7.07–7.20 (m, 3H), 7.30–7.44 (m, 4H), 7.58 (t, 1H, J=7.33 Hz), 7.76 (d, 1H, J=8 Hz), 7.88 (d, 1H, J=7.07 Hz), 8.14 (d, 1H, J=7.73 Hz), MS(ESI$^+$) 597.3 (MH$^+$).

Synthesis of Compound 3.44

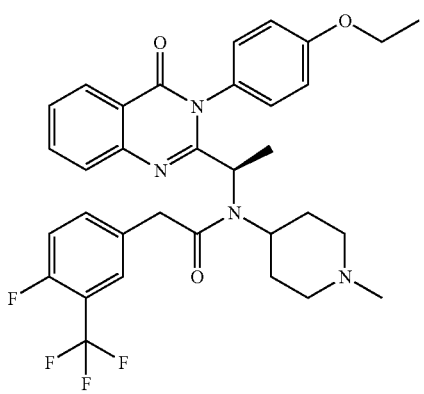

N-{1-[3-(4-Ethoxy-phenyl)-4-oxo-3,4-dihydro-quinazolin-2-yl]-ethyl}-2-(4-fluoro-3-trifluoromethyl-phenyl)-N-(1-methyl-piSperidin-4-yl)-acetamide Formaldehyde (37% in water) (0.016 g, 0.20 mmol) was added to a solution of T0913409 (0.06 g, 0.1 mmol) in dichloroethane (5 ml), followed by Na(OAC)$_3$BH (0.127 g, 0.60 mmol) at room temperature. The mixture was stirred overnight. The solution was diluted with DCM, washed by sat.NaHCO$_3$, water, brine and dried over Na$_2$SO$_4$. The solvent was evaporated and the residue was purified by flash column to afford a white solid (58 mg). $^1$H NMR (DMSO, T=120° C.) 1.18 (m, 1H), 1.33 (m, 3H, J=6.8 Hz), 1.48 (d, 3H, J=6.67 Hz), 1.61 (m, 1H), 1.95 (m, 1H), 2.10 (s, 3H), 2.38 (m, 2H), 2.64 (m, 1H), 2.76 (m, 1H), 2.88 (s, 2H), 3.26 (d, 1H, J=16 Hz), Hz), 3.58 (m, 1H), 4.09 (d, 2H, J=6.8 Hz), 5.04 (m, 1H), 7.08–7.45 (m, 7H), 7.58 (m, 1H), 7.76 (d, 1H, J=8 Hz), 7.89 (m, 1H), 8.14 (d, 1H, J=7.73 Hz). MS(ESI$^+$) 611.3 (MH$^+$).

Synthesis of Compound 3.45

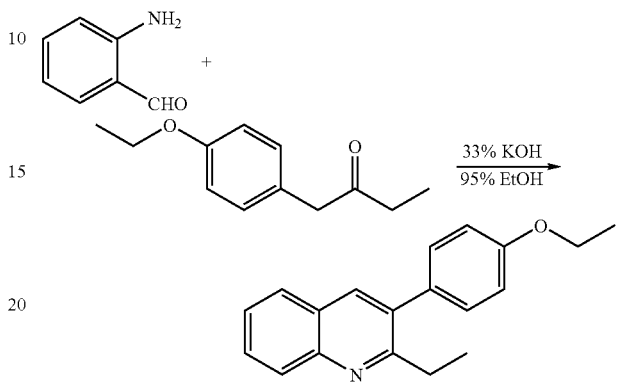

3-(4-Ethoxyphenyl)-2-ethyl-quinoline. 33% Potassium hydroxide (1.3 ml) was added to a mixture of o-amino aldehyde (0.31 g, 2.6 mmol) and ketone (0.5 g, 2.6 mmol) in 95% EtOH. The solution was heated to reflux for 2 h and then poured into water. The aqueous layer was extracted with EtOAc three times, the combined organic layer was then washed by water, brine and dried over Na$_2$SO$_4$. The solvent was evaporated and the crude oil was subjected by flash column to afford a white solid (170 mg). $^1$H NMR (CDCl$_3$) 1.23 (t, 3H, J=7.5 Hz), 1.47 (t, 3H, J=6.93 Hz), 2.98 (q, 2H, J=7.47 Hz), 4.11 (q, 2H, J=6.93 Hz), 6.98 (m, 2H, J=6.8 Hz), 7.31 (m, 2H), 7.49 (m, 1H), 7.68 (m, 1H), 7.77 (d, 1H, J=8 Hz), 7.92 (s, 1H), 8.08 (d, 1H, J=8 Hz). MS(ESI$^+$) 278.3 (MH$^+$).

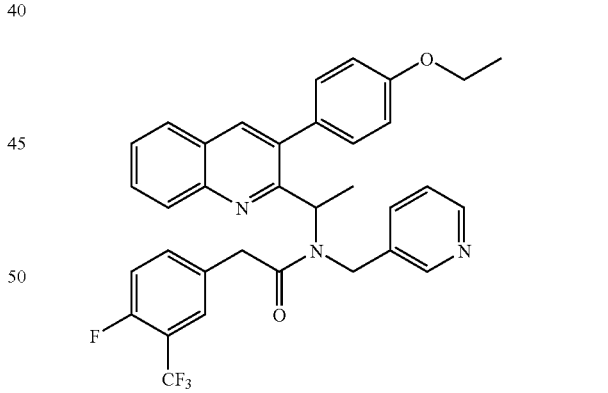

N-{1-[3-(4-Ethoxy-phenyl)-quinolin-2-yl]-ethyl}-2-(4-fluoro-3-trifluoromethyl-phenyl)-N-pyridin-3-ylmethyl-acetamide Starting from 3-(4-ethoxy-phenyl)-2-ethyl-quinoline, compound 3.45 was prepared following the synthesis of compound 1.01 (IV-1.01). yellow solid. $^1$H NMR (DMSO, T=120° C.) 1.35 (t, 3H, J=6.80 Hz), 1.57 (m, 3H), 2.94 (br, 1H), 3.63 (d, 1H, J=16 Hz ), 4.11 (q, 2H, J=6.80 Hz ), 4.63 (m, 2H ), 5.88 (m, 1H), 7.07 (m, 5H), 7.22–7.33 (m, 3H), 7.58 (m, 2H), 7.76 (t, 1H, J=7.6 Hz), 7.90 (d, 1H, J=8 Hz), 7.80–8.12 (m, 3H), 8.24 (m, 1H). MS(ESI$^+$) 588.3 (MH$^+$).

Synthesis of Compound 3.46

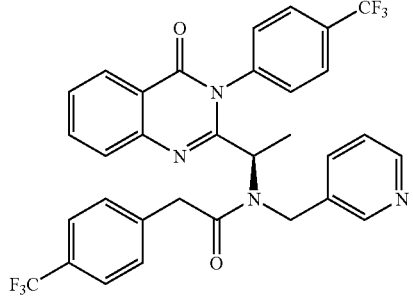

3.46

(R)-2-((N-3-Picolyl)-N-(4-trifluoromethylphenylacetyl)-1-aminoethyl)-3-(4-trifluoroethyl)-3H-quinazoline-4-one (3.46). Compound 1 was synthesized using the method described in FIG. 4, except that 4-trifluoromethylaniline was used in place of p-phenetidine. $^1$H NMR (DMSO-$d_6$, T=120° C.) 1.40 (m, 3H), 2.89 (m, 1H), 3.58 (m, 1H), 4.78 (m, 2H), 5.24 (m, 1H), 7.21 (d, J=4.0 Hz, 1H), 7.26 (m, 2H), 7.55 (m, 5H), 7.71 (m, 1H), 7.80 (br s, 1H), 7.90 (m, 3H), 8.12 (d, J=7.8 Hz, 1H), 8.38 (t, J=5.1 Hz, 2H) ppm. MS (ESI$^+$) m/z 611.3 [M+H]$^+$.

Synthesis of Compound 3.47

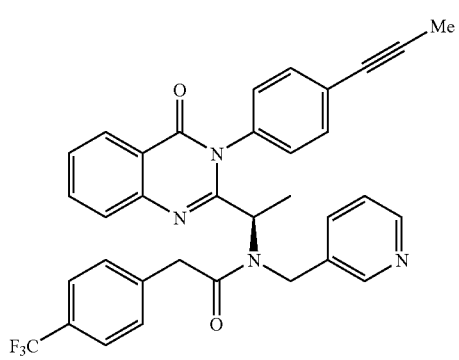

3.47

(R)-2-((N-3-Picolyl)-N-(4-trifluoromethylphenylacetyl)-1-aminoethyl)-3-(4-(1-propynyl))-3H-quinazoline-4-one (3.47). Compound 3.47 was synthesized using the method described for the synthesis of compound 3.07, except that excess amount of propyne gas was used in place of trimethylsilylacetylene. $^1$H NMR (DMSO-$d_6$, T=120° C.) 1.41 (m, 3H), 2.09 (s, 3H), 2.89 (m, 1H), 3.55 (m, 1H), 4.72 (m, 2H), 5.23 (m, 1H), 7.18 (m, 1H), 7.28 (m, 2H), 7.55 (m, 8H), 7.71 (m, 1H), 7.87 (m, 1H), 8.11(d, J=7.8 Hz, 1H), 8.37 (m, 2H) ppm. MS (ESI$^+$) m/z 581.2 [M+H]$^+$.

Synthesis of Compound 3.48

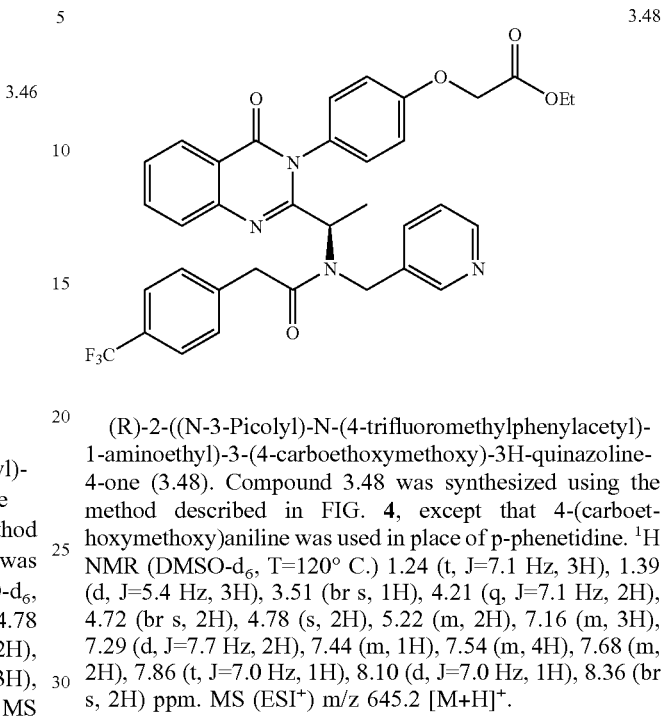

3.48

(R)-2-((N-3-Picolyl)-N-(4-trifluoromethylphenylacetyl)-1-aminoethyl)-3-(4-carboethoxymethoxy)-3H-quinazoline-4-one (3.48). Compound 3.48 was synthesized using the method described in FIG. 4, except that 4-(carboethoxymethoxy)aniline was used in place of p-phenetidine. $^1$H NMR (DMSO-$d_6$, T=120° C.) 1.24 (t, J=7.1 Hz, 3H), 1.39 (d, J=5.4 Hz, 3H), 3.51 (br s, 1H), 4.21 (q, J=7.1 Hz, 2H), 4.72 (br s, 2H), 4.78 (s, 2H), 5.22 (m, 2H), 7.16 (m, 3H), 7.29 (d, J=7.7 Hz, 2H), 7.44 (m, 1H), 7.54 (m, 4H), 7.68 (m, 2H), 7.86 (t, J=7.0 Hz, 1H), 8.10 (d, J=7.0 Hz, 1H), 8.36 (br s, 2H) ppm. MS (ESI$^+$) m/z 645.2 [M+H]$^+$.

Synthesis of Compound 3.49

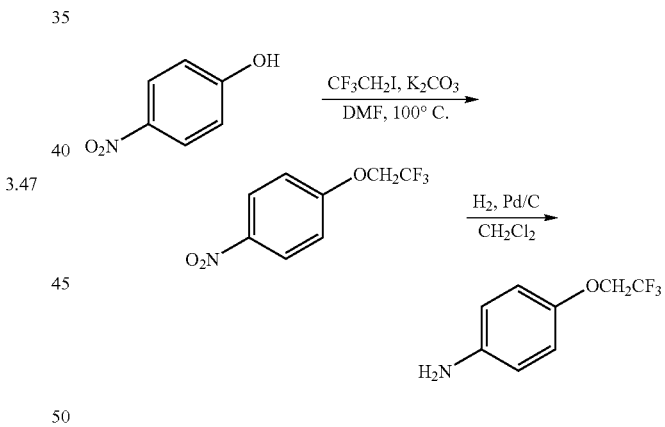

4-(2,2,2-trifluoroethoxy)aniline. To a mixture of 4-nitrophenol (1.39 g, 10 mmol, 1.0 equiv), and K$_2$CO$_3$ (1.8 g, 13 mmol, 1.3 equiv) in 10 mL of dry DMF was added 1-iodo-2,2,2-trifluoroethane (2.31 g, 11 mmol, 1.1 equiv). The mixture was heated in an oil bath at 100° C. for 24 h. Half of the initial amount of K$_2$CO$_3$ and 1-iodo-2,2,2-trifluoroethane were added. The mixture was stirred for another 24 h at 100° C. This was repeated once more on the third day. At the end of this 72 h reaction, the mixture was cooled to room temperature and poured into 40 mL of water. The mixture was extracted twice with 20 mL of diethyl ether. The combined ether extract was washed once with 40 mL of brine, dried over anhydrous Na2SO4, filtered to remove drying agent, and evaporated in vacuo to yield 1.6 g of a crude product as light yellow solid. $^1$H NMR (DMSO-$d_6$) 4.98 (q, J=8.8 Hz, 2H), 7.30 (d, J=9.2 Hz, 2H), 8.26 ((d, J=9.2 Hz, 2H) ppm.

To a solution of the crude 4-(2,2,2-trifluoroethoxy)nitrobenzene (1.6 g, 7.2 mmol, 1.0 equiv) in 40 mL of dichloromethane was added 0.4 g of a 5% palladium on activated carbon (0.19 mmol, 0.026 equiv). Hydrogen gas was introduced using a balloon while the mixture was stirred vigorously for 48 h at room temperature. After all starting material had been consumed, the mixture was filtered through a pad of Celite to remove the palladium catalyst. The filtrate was evaporated in vacuo to give a crude product as a brown liquid. This crude product was purified by distillation at reduced pressure to give 1.3 g of pure 4-(2,2,2-trifluoroethoxy)aniline as a colorless liquid, which solidified upon cooling to 0° C. b.p. 81–83° C. at 0.5 torr;. ¹H NMR (DMSO-d₆) δ 4.53 (q, J=9.1 Hz, 2H), 4.76 (br s, 2H), 6.52 (d, J=7.6 Hz, 2H), 6.76 (d, J=7.6 Hz, 2H) ppm.

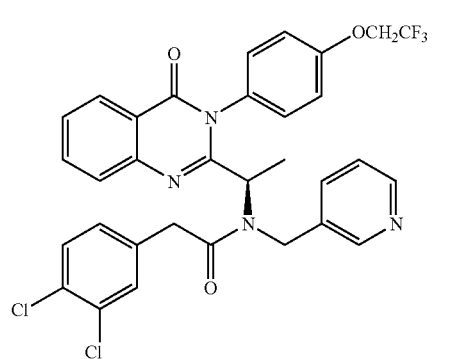

3.49

(R)-2-((N-3-Picolyl)-N-(3,4-dichlorophenylacetyl)-1-aminoethyl)-3-(4-(2,2,2-trifluoroethoxy)phenyl)-3H-quinazoline-4-one trifluoroacetate (3.49.CF₃COOH). The trifluoroacetic acid salt of compound 3.49 was synthesized using the method described in FIG. 4, except that 4-(2,2,2-trifluoroethoxy)aniline was used in place of p-phenetidine, and that 3,4-dichlorophenylacetic acid was used in place of 4-trifluoromethylphenylacetic acid. ¹H NMR (DMSO-d₆, T=120° C.) δ 1.42 (br s, 3H), 3.50 (m, 1H), 4.75 (m, 5H), 5.22 (m, 1H), 7.03 (d, J=7.9 Hz, 1H), 7.27 (m, 5H), 7.43 (d, J=8.2 Hz, 1H), 7.50 (m, 1H), 7.56 (t, J=7.4 Hz, 1H), 7.67 (t, J=8.4 Hz, 2H), 7.87 (t, 1H), 8.11 (d, J=7.6 Hz, 1H), 8.42 (br s, 2H) ppm. MS (ESI⁺) m/z 641.2 [M+H]⁺.

Synthesis of Compound 3.50

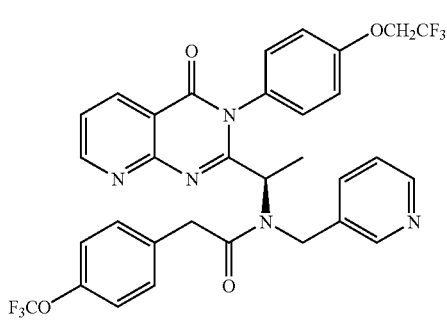

3.50

(R)-2-((N-3-Picolyl)-N-(4-trifluoromethoxyphenylacetyl)-1-aminoethyl)-3-(4-(2,2,2-trifluoroethoxy)phenyl)-3H-8-azaquinazoline-4-one (5). Compound 3.50 was synthesized using the method described in FIG. 13, except that 4-(2,2,2-trifluoroethoxy)aniline was used in place of p-phenetidine. ¹H NMR (DMSO-d₆, T=120° C.) δ 1.42 (m, 3H), 3.51 (m, 1H), 4.17 (m, 1H), 4.77 (q, J=8.7 Hz, 2H), 4.89 (m, 2H), 5.25 (m, 1H), 7.18 (m, 4H), 7.28 (m, 3H), 7.47 (m, 1H), 7.59 (m, 2H), 7.90 (m, 1H), 8.50 (m, 3H), 9.01 (m, 1H) ppm. MS (ESI⁺) m/z 658.2 [M+H]⁺.

Synthesis of Compound 3.51

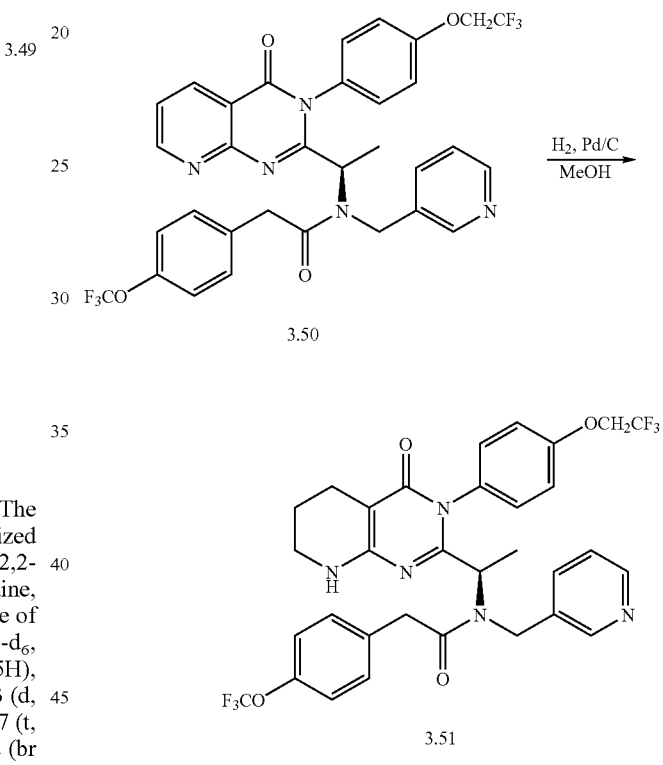

(R)-2-((N-3-Picolyl)-N-(4-trifluoromethoxyphenylacetyl)-1-aminoethyl)-3-(4-(2,2,2-trifluoroethoxy)phenyl)-3H-5,6,7,8-tetrahydro-8-azaquinazoline-4-one (3.51). To a solution of compound 3.50 (10 mg, 15 μmol, 1.0 equiv) in 1.0 mL of MeOH, was added 10% Pd on activated carbon (2 mg, 1.9 μmol, 0.13 equiv). Hydrogen was introduced using a balloon. The mixture was stirred vigorously for 16 h at room temperature. The mixture was diluted with 5 mL of dichloromethane and filtered to removed catalyst. The filtrated was evaporated in vacuo to give crude 6, which was purified by silica gel chromatography to give 7.3 mg 3.51 as a white solid. ¹H NMR (DMSO-d₆, T=120° C.) δ 1.26 (d, J=6.5 Hz, 3H), 1.79 (m, 2H), 2.34 (t, J=6.1 Hz, 2H), 2.88 (m, 1H), 3.29 (m, 3H), 4.62 (m, 2H), 4.70 (q, J=8.8 Hz, 2H), 5.07 (m, 1H), 6.43 (s, 1H), 7.00 (m, 1H), 7.16 (m, 6H), 7.29 (m, 2H), 7.51(d, 1H), 8.41(m, 2H ppm. MS (ESI⁺) m/z 662.2 [M+H]⁺.

Synthesis of Compound 3.52

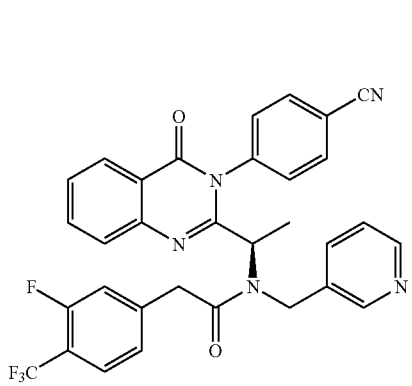

3.52

N-{1-[3-(4-Cyano-phenyl)-4-oxo-3,4-dihydro-quinazolin-2-yl]-ethyl}-2-(3-fluoro-4-trifluoromethyl-phenyl)-N-pyridin-3-ylmethyl-acetamide Compound 3.52, white solid. $^1$H NMR (DMSO, T=120° C.) 8.37–8.41(m, 2H), 8.12 (d, 1H, J=7.2 Hz), 7.99 (m, 2H), 7.89 (m, 1H), 7.79 (m, 1H), 7.69 (d, 1H, J=7.0 Hz), 7.53–7.61 (m, 4H), 7.09–7.23 (m, 3H), 5.23 (m, 1H), 4.68–4.81 (m, 2H), 3.65–3.70 (m, 1H), 2.96–3.22 (m, 1H), 1.40 (m, 3H). MS (ESI$^+$) 586.2 (MH$^+$).

Synthesis of Compound 3.53

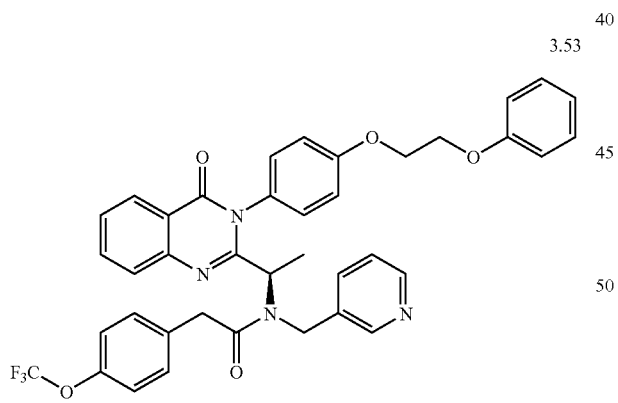

3.53

N-(1-{4-Oxo-3-[4-(2-phenoxy-ethoxy)-phenyl]-3,4-dihydro-quinazolin-2-yl}-ethyl)-N-pyridin-3-ylmethyl-2-(4-trifluoromethoxy-phenyl)-acetamide Compound 3.53, white solid. $^1$H NMR (DMSO, T=120° C.) 8.35 (m, 2H), 8.10 (d, 1H, J=6.9 Hz), 7.86 (t, 1H, J=7.0 Hz), 7.70 (m, 1H), 7.41–7.31 (m, 3H), 7.29 (m, 2H), 7.16 (m, 8H), 6.94–7.00 (m, 3H), 5.26 (m, 1H), 4.71 (m, 2H), 4.36–4.41 (m 4H), 3.44 (m, 1H), 3.05 (m, 1H), 1.39 (m, 3H). MS (ESI$^+$) 695.2 (MH$^+$).

Synthesis of Compound 3.54

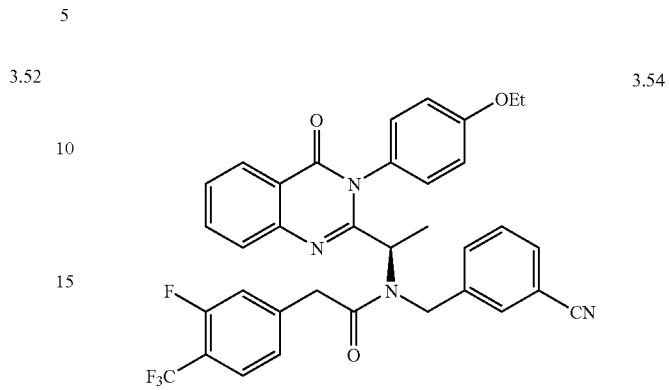

3.54

N-(3-Cyano-benzyl)-N-{1-[3-(4-ethoxy-phenyl)-4-oxo-3,4-dihydro-quinazolin-2-yl]-ethyl}-2-(3-fluoro-4-trifluoromethyl-phenyl)-acetamide Compound 3.54, white solid. $^1$H NMR (DMSO, T=120° C.) 8.10 (d, 1H, J=7.5 Hz), 7.86 (t, 1H, J=7.1 Hz), 7.40–7.71 (m, 9H), 7.10 (m, 4H), 5.25 (m, 1H), 4.77 (m, 2H), 4.12 (q, 2H, J=7.0 Hz), 3.61 (m, 1H), 3.05 (m, 1H), 1.43 (m, 3H), 1.36 (t, 3H, J=7.0 Hz). MS (ESI$^+$) 629.2 (MH$^+$).

Synthesis of Compound 3.55

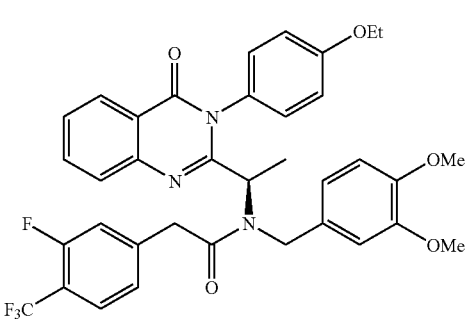

3.55

N-(3,4-Dimethoxy-benzyl)-N-{1-[3-(4-ethoxy-phenyl)-4-oxo-3,4-dihydro-quinazolin-2-yl]-ethyl}-2-(3-fluoro-4-trifluoromethyl-phenyl)-acetamide Compound 3.55, white solid. $^1$H NMR (DMSO, T=120° C.) 8.10 (d, 1H, J=8.0 Hz), 7.86 (t, 1H, J=7.2 Hz), 7.71 (m, 1H), 7.54–7.60 (m, 2H), 7.37 (m, 1H), 7.03–7.11 (m, 5H), 6.76 (m, 1H), 6.70 (m, 2H), 5.28 (m, 1H), 4.61–4.63 (m, 2H), 4.10 (q, 2H, J=7.0 Hz), 3.70 (s, 3H), 3.65 (m, 1H), 3.59 (s, 3H), 2.95 (m, 1H), 1.43 (m, 3H), 1.36 (q, 3H, J=7.0). MS (ESI$^+$) 664.2 (MH$^+$).

Synthesis of Compound 3.56

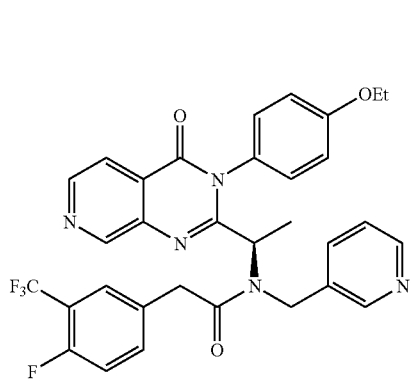

3.56

N-{1-[3-(4-Ethoxy-phenyl)-4-oxo-3,4-dihydro-pyrido[3,4-d]pyrimidin-2-yl]-ethyl}-2-(4-fluoro-3-trifluoromethyl-phenyl)-N-pyridin-3-ylmethyl-acetamide Compound 3.56, white solid. $^1$H NMR (DMSO, T=120° C.) 9.06 (s, 1H), 8.70 (d, 1H, J=5.1 Hz), 8.35–8.37 (m, 2H), 7.90 (d, 1H, J=5.1 Hz), 7.55 (m, 1H), 7.41 (m, 3H), 7.28–7.33 (m, 1H), 7.07–7.19 (m, 4H), 5.28 (m, 1H), 4.74 (m, 2H), 4.10 (q, 2H, J=7.0 Hz), 3.60 (m, 1H), 2.86 (m, 1H), 1.45 (m, 3H), 1.35 (t, 3H, J=7.0 Hz). MS (ESI$^+$) 606.2 (MH$^+$).

Synthesis of Compound 3.57

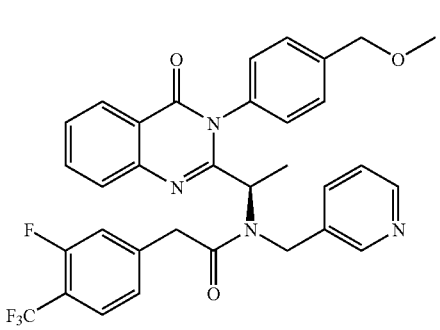

3.57

2-(3-Fluoro-4-trifluoromethyl-phenyl)-N-{1-[3-(4-methoxymethyl-phenyl)-4-oxo-3,4-dihydro-quinazolin-2-yl]-ethyl}-N-pyridin-3-ylmethyl-acetamide Compound 3.57, white solid. $^1$H NMR (DMSO, T=120° C.) 8.36 (m, 2H), 8.10 (s, 1H, J=8.1 Hz), 7.87 (t, 1H, J=7.0 Hz), 7.71 (m, 1H), 7.47–7.61 (m, 6H), 7.07–7.19 (m, 4H), 5.23 (m, 1H), 4.71 (m, 2H), 4.50 (s, 2H), 3.58 (m, 1H), 3.37 (s, 3H), 2.90 (m, 1H), 1.43 (m, 3H). MS (ESI$^+$) 605.3 (MH$^+$).

Synthesis of Compound 3.58

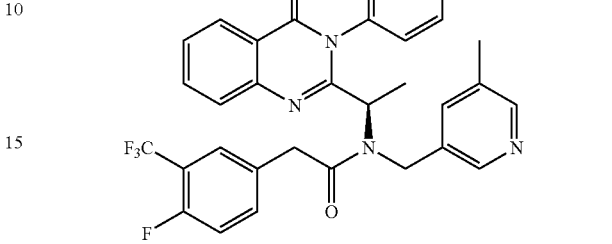

3.58

N-{1-[3-(4-Ethoxy-phenyl)-4-oxo-3,4-dihydro-quinazolin-2-yl]-ethyl}-2-(4-fluoro-3-trifluoromethyl-phenyl)-N-(5-methyl-pyridin-3-ylmethyl)-acetamide Compound 3.58, white solid. $^1$H NMR (DMSO, T=120° C.) 8.20 (d, 1H, J=1.0 Hz), 8.17 (s, 1H), 8.09 (m, 1H), 7.87 (m, 1H), 7.72 (m, 1H), 7.56 t, 1H, J=7.2 Hz), 7.38–7.40 (m, 3H), 7.29–7.34 (m, 1H), 7.17 (m, 1H), 7.03–7.11 (m, 3H), 5.27 (m, 1H), 4.68–4.71 (m, 2H), 4.09 (q, 2H, J=7.0 Hz), 3.52–3.58 (m, 1H), 2.90 (m, 1H), 2.07 (s, 3H), 1.44–1.47 (m, 3H), 1.34 (t, 3H, J=7.0 Hz). MS (ESI$^+$) 619.2 (MH$^+$).

Synthesis of Compound 3.59

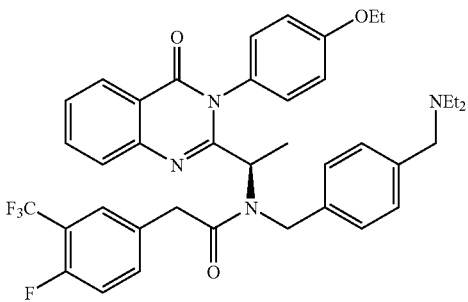

3.59

N-(4-Diethylaminomethyl-benzyl)-N-{1-[3-(4-ethoxy-phenyl)-4-oxo-3,4-dihydroquinazolin-2-yl]-ethyl}-2-(4-fluoro-3-trifluoromethyl-phenyl)-acetamide Compound 3.59, white solid. $^1$H NMR (DMSO, T=120° C.) 8.07 (d, 1H, J=8.0 Hz), 7.85 (t, 1H, J=6.9 Hz), 7.70 (m, 1H), 7.54 (m, 1H), 7.27–7.38 (m, 4H), 7.04–7.09 (m, 7H), 5.28 (m, 1H), 4.68 (m, 2H), 4.09 q, 2H, J=6.9 Hz), 3.49–3.58 (m, 3H), 2.90 (m, 1H), 2.46–2.51 (m, 4H), 1.43 (m, 3H), 1.35 (t, 3H, J=6.9 Hz), 0.96 (t, 6H, J=7.0 Hz). MS (ESI$^+$) 688.5 (MH$^+$).

115
Synthesis of Compound 3.60

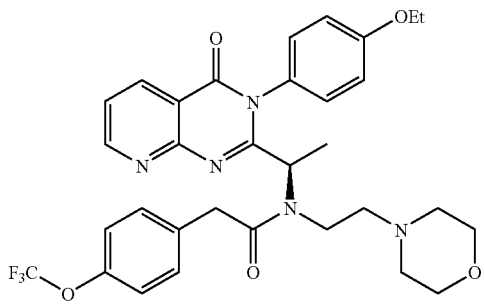

N-{1-[3-(4-Ethoxy-phenyl)-4-oxo-3,4-dihydro-pyrido[2,3-d]pyrimidin-2-yl]-ethyl}-N-(2-morpholin-4-yl-ethyl)-2-(4-trifluoromethoxy-phenyl)-acetamide 3.60

Compound 3.60 was prepared as outlined in Scheme 11, below. White solid. $^1$H NMR (DMSO, T=120° C.) 9.00 (m, 1H), 8.51 (m, 1H), 7.58 (m, 1H), 7.41 (m, 1H), 7.18–7.26 (m, 5H), 7.04–7.10 (m, 2H), 5.16 (m, 1H), 4.11 (q, 2H, J=7.0 Hz), 3.40–3.50 (m, 7H), 2.90 (m, 1H), 2.30–2.40 (m, 6H), 1.46 (m, 3H), 1.36 (t, 3H, J=7.0 Hz). MS (ESI$^+$) 626.4 (MH$^+$).

Scheme II

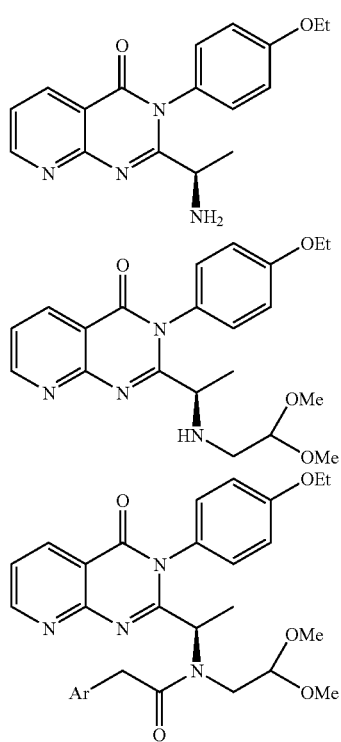

116

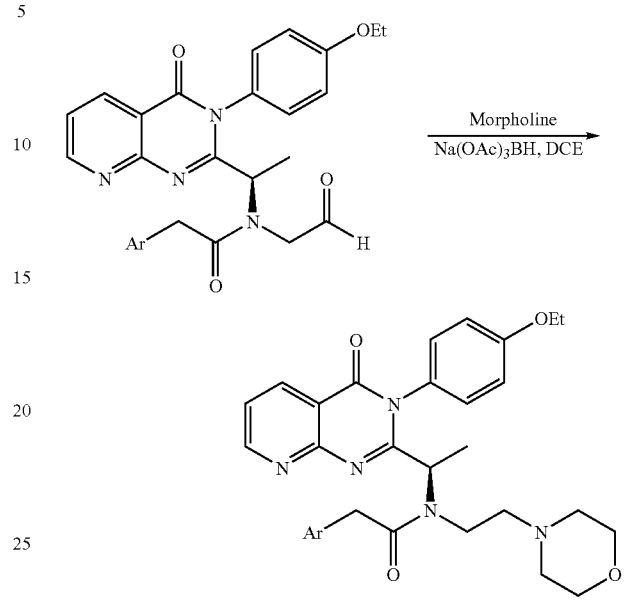

Synthesis of Compound 3.61

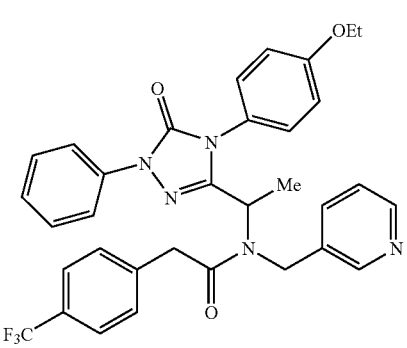

3.61

N-{1-[4-(4-Ethoxy-phenyl)-5-oxo-1-phenyl-4,5-dihydro-1H-[1,2,4]triazol-3-yl]-ethyl}-N-pyridin-3-ylmethyl-2-(4-trifluoromethyl-phenyl)-acetamide 3.61 was synthesized following the generic synthetic scheme for the synthesis of triazolinones (FIG. 9) to yield a colorless solid. $^1$H NMR (d$_6$-DMSO; T=120° C.) δ 8.57 (d, J=14 Hz, 2H), 7.91 (s, 1H), 7.90 (d, J=8.0 Hz, 2H), 7.58 (s, 1H), 7.57 (d, J=8.4 Hz, 2H), 7.41 (t, J=7.6 Hz, 2H), 7.35 (d, J=8.4 Hz, 2H), 7.27 (t, J=7.6 Hz, 1H), 7.24 (d, J=7.6 Hz, 2H), 7.09 (d, J=8.8 Hz, 2H), 5.50 (s, 1H), 4.73 (d, J=16.8 Hz, 1H), 4.63 (d, J=16.8 Hz, 1H), 4.12 (q, J=6.8 Hz, 2H), 3.67 (d, J=16.0 Hz, 1H), 3.31 (br s, 1H), 1.48 (d, J=6.8 Hz, 3H), 1.37 (t, J=6.8 Hz, 3H) ppm. MS(ESI$^+$) 602.2 (MH$^+$).

Synthesis of Compound 3.62

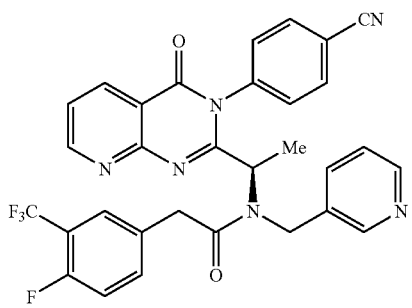

(R)-N-{1-[3-(4-Cyano-phenyl)-4-oxo-3,4-dihydro-pyrido[2,3-d]pyrimidin-2-yl]-ethyl}-2-(4-fluor-3-trifluoromethyl-phenyl)-N-pyridin-3-ylmethyl-acetamide 3.62 was synthesized following the synthetic scheme for 8-azaquinazolinones (FIG. 13) to yield a faint yellow solid. $^1$H NMR (d$_6$-DMSO; T=120° C.) 9.02 (dd, J$_1$=2.0 Hz, J$_2$=4.4 Hz, 1H), 8.57 (br s, 1H), 8.51 (br s, 1H), 8.50 (dd, J$_1$=1.6 Hz, J$_2$=8.0 Hz, 1H), 8.02 (m, 2H), 7.94 (br s, 1H), 7.83 (br s, 1H), 7.67 (br s, 1H), 7.60 (dd, J$_1$=4.4 Hz, J$_2$=7.6 Hz, 1H), 7.50 (br s, 1H), 7.44 (d, J=8.4 Hz, 1H), 7.42 (d, J=6.8 Hz, 1H), 7.30 (dd, J$_1$=J$_2$=8.8 Hz, 1H), 5.23 (q, J=6.4 Hz, 1H), 4.96 (d, J=18.0 Hz, 1H), 4.86 (d, J=18.0 Hz, 1H), 3.70 (d, J=16.4 Hz, 1H), 3.39 (br s, 1H), 1.42 (d, J=6.4 Hz, 3H) ppm. MS(ESI$^+$) 587.3 (MH$^+$).

Synthesis of Compound 3.63

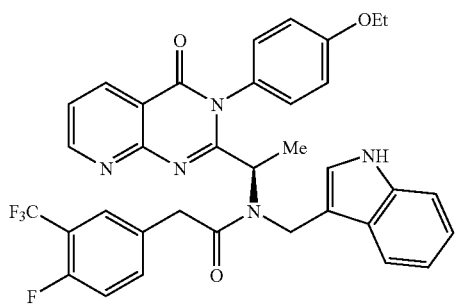

N-{1-[3-(4-Ethoxy-phenyl)-4-oxo-3,4-dihydro-pyrido[2,3-d]pyrimidin-2-yl]-ethyl}-2-(4-fluoro-3-trifluoromethyl-phenyl)-N-(1H-indol-3-ylmethyl)-acetamide Compound 3.63 was synthesized following the synthetic scheme for 8-azaquinazolinones (FIG. 13) to yield a colorless solid. $^1$H NMR (d$_6$-DMSO; T=120° C.) δ 9.01 (dd, J$_1$=1.6 Hz, J$_2$=4.4 Hz, 1H), 8.44 (dd, J$_1$=1.6 Hz, J$_2$=7.6 Hz, 1H), 7.55 (dd, J$_1$=4.8 Hz, J$_2$=8.0 Hz, 1H), 7.48 (d, J=8.0 Hz, 1H), 7.35–7.44 (m, 3H), 7.32 (d, J=8.4 Hz, 1H), 7.27 (d, J=8.8 Hz, 1H), 6.93–7.12 (m, 5H), 6.87 (dd, J$_1$=J$_2$=4.0 Hz, 1H), 5.25 (q, J=6.4 Hz, 1H), 4.82 (d, J=16.4 Hz, 1H), 4.71 (d, J=16.8 Hz, 1H), 4.09 (q, J=7.2 Hz, 2H), 3.64 (d, J=15.6 Hz, 1H), 2.98 (br m, 1H), 1.49 (d, J=6.8 Hz, 3H), 1.35 (t, J=6.8 Hz, 3H) ppm. MS(ESI$^+$) 666.2 (MNa$^+$).

Synthesis of Compound 3.64

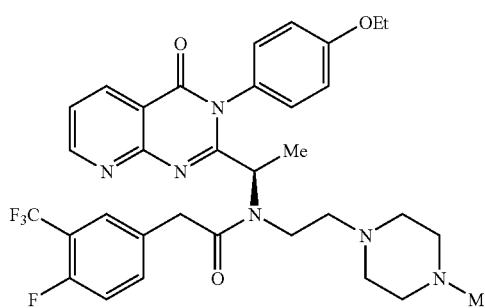

(R)-N-{1-[3-(4-Ethoxy-phenyl)-4-oxo-3,4-dihydro-pyrido[2,3-d]pyrimidin-2-yl]-ethyl}-2-(4-fluoro-3-trifluoromethyl-phenyl)-N-[2-(4-methyl-piperazin-1-yl)-ethyl]-acetamide Compound 3.64 was synthesized following the synthetic scheme for 8-azaquinazolinones (FIG. 13) to yield a yellow glassy solid. $^1$H NMR (d$_6$-DMSO; T=120° C.) δ 9.02 (dd, J$_1$=1.6 Hz, J$_2$=4.4 Hz, 1H), 8.52 (dd, J$_1$=2.0 Hz, J$_2$=8.0 Hz, 1H), 7.59 (dd, J$_1$=4.4 Hz, J$_2$=7.6 Hz, 1H), 7.38–7.52 (m, 3H), 7.32 (dd, J$_1$=J$_2$=10.4 Hz, 1H), 7.28 (d, J=9.2 Hz, 1H), 6.90–7.04 (m, 2H), 5.14 (q, J=6.4 Hz, 1H), 4.09 (q, J=6.8 Hz, 2H), 3.48–3.72 (br m, 3H), 3.02–3.17 (br m, 4H), 2.77–2.98 (br m, 5H), 2.67 (s, 3H), 1.51 (d, J=6.4 Hz, 3H), 1.35 (t, J=6.8 Hz, 3H) ppm. MS(ESI$^+$) 641.3 (MH$^+$).

Synthesis of Compound 3.65

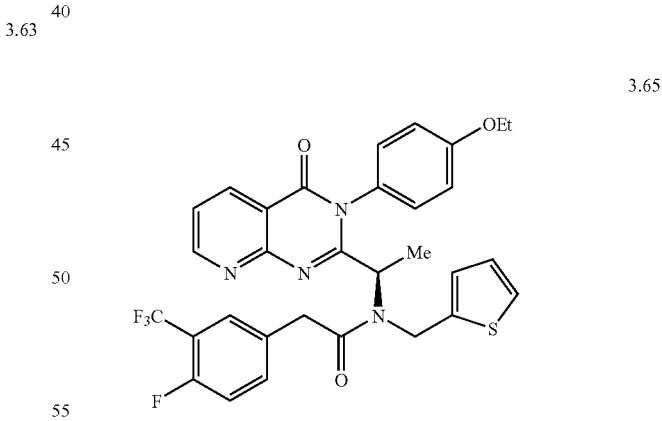

(R)-N-{1-[3-(4-Ethoxy-phenyl)-4-oxo-3,4-dihydro-pyrido[2,3-d]pyrimidin-2-yl]-ethyl}-2-(4-fluoro-3-trifluoromethyl-phenyl)-N-thiophen-2-ylmethyl-acetamide Compound 3.65 was synthesized following the synthetic scheme for the generic synthesis of 8-azaquinazolinones (FIG. 13) to yield a colorless solid. $^1$H NMR (d$_6$-DMSO; T=120° C.) δ 9.03 (d, J=2.8, 1H), 8.50 (dd, J$_1$=1.6 Hz, J$_2$=7.6 Hz, 1H), 7.59 (dd, J$_1$=4.8 Hz, J$_2$=7.6 Hz, 1H), 7.43 (d, J=8.4 Hz, 1H), 7.38 (d, J=6.4 Hz, 1H), 7.34–7.47 (m, 1H), 7.09 (d, J=8.0 Hz, 1H), 6.99 (d, J=7.2 Hz, 1H), 6.66–6.92 (m, 3H), 5.26 (br s, 1H), 4.83 (br s, 2H), 4.08 (q, J=7.2 Hz, 2H), 3.56 (br s, 1H), 2.98 (br s, 1H), 1.52 (d, J=6.8 Hz, 3H), 1.33 (t, J=6.8 Hz, 3H) ppm. MS(ESI$^+$) 611.2 (MH$^+$), 633.2 (MNa$^+$).

Synthesis of Compound 3.66

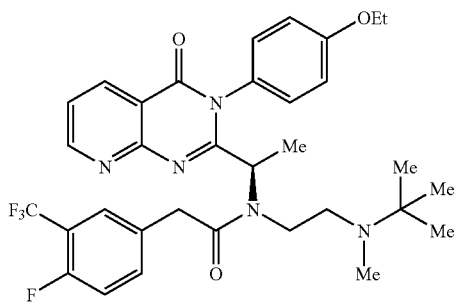

3.66

(R)-N-[2-(tert-Butyl-methyl-amino)-ethyl]-N-{1-[3-(4-ethoxy-phenyl)-4-oxo-3,4-dihydro-pyrido[2,3-d]pyrimidin-2-yl]-ethyl}-2-(4-fluoro-3-trifluoromethyl-phenyl)-acetamide Compound 3.66 was synthesized following the synthetic scheme for the generic synthesis of 8-azaquinazolinones (FIG. 13) to yield a yellow glassy solid. $^1$H NMR (d$_6$-DMSO; T=120° C.) δ 9.00 (d, J=2.4 Hz, 1H), 8.52 (d, J=7.6 Hz, 1H), 7.90 (dd, J$_1$=4.4 Hz, J$_2$=7.6 Hz, 1H), 7.41–7.54 (m, 3H), 7.37 (d, J=11.6 Hz, 1H), 7.32 (dd, J$_1$=J$_2$=9.2 Hz, 1H), 7.04–7.18 (m, 2H), 5.10 (br s, 1H), 4.12 (q, J=7.2 Hz, 2H), 3.90–4.06 (m, 1H), 3.62–3.84 (m, 1H), 3.40–3.60 (m, 1H), 2.96–3.14 (m, 1H), 2.74 (s, 3H), 1.52 (d, J=6.4 Hz, 3H), 1.36 (s, 9H), 1.34 (t, J=7.2 Hz, 3H) ppm. MS(ESI$^+$) 628.4 (MH$^+$).

Synthesis of Compound 3.67

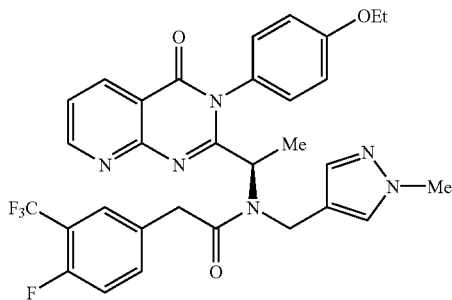

3.67

(R)-N-{1-[3-(4-Ethoxy-phenyl)-4-oxo-3,4-dihydro-pyrido[2,3-d]pyrimidin-2-yl]-ethyl}-2-(4-fluoro-3-trifluoromethyl-phenyl)-N-(1-methyl-1H-pyrazol-4-ylmethyl)-acetamide Compound 3.67 was synthesized following the synthetic scheme for the generic synthesis of 8-azaquinazolinones (FIG. 13) to yield a colorless solid. $^1$H NMR (d$_6$-DMSO; T=120° C.) δ 9.04 (dd, J$_1$=1.6 Hz, J$_2$=4.4 Hz, 1H), 8.50 (dd, J$_1$=2.0 Hz, J$_2$=7.6 Hz, 1H), 7.58 (dd, J$_1$=4.4 Hz, J$_2$=8.0 Hz, 1H), 7.40 (d, J=6.8 Hz, 2H), 7.36–7.45 (m, 1H), 7.30 (dd, J$_1$=J$_2$=10.4 Hz, 1H), 7.27–7.34 (m, 1H), 7.08 (d, J=8.4 Hz, 2H), 7.02 (d, J=6.8 Hz, 1H), 5.23 (br s, 1H), 4.50 (d, J=15.6 Hz, 1H), 4.43 (d, J=15.6 Hz, 1H), 4.09 (q, J=6.8 Hz, 1H), 3.67 (s, 3H), 2.93 (br s, 2H), 1.49 (d, J=6.4 Hz, 3H), 1.35 (t, J=6.8 Hz, 3H) ppm. MS(ESI$^+$) 609.3 (MH$^+$), 631.2 (MNa$^+$).

Synthesis of Compound 3.68

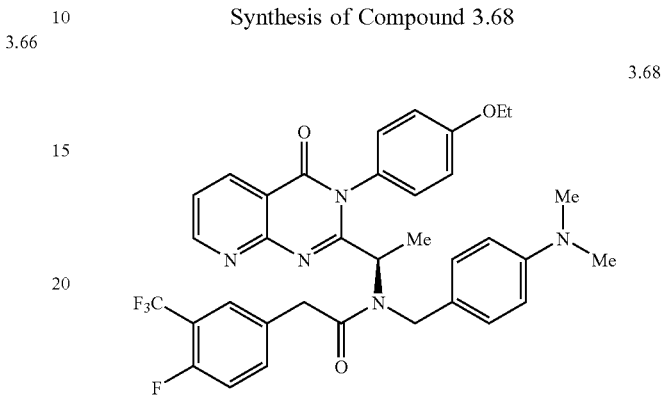

3.68

(R)-N-(4-Dimethylamino-benzyl)-N-{1-[3-(4-ethoxy-phenyl)-4-oxo-3,4-dihydro-pyrido[2,3-d]pyrimidin-2-yl]-ethyl}-2-(4-fluoro-3-trifluoromethyl-phenyl)-acetamide Compound 3.68 was synthesized following the synthetic scheme for the generic synthesis of 8-azaquinazolinones (FIG. 13) to yield a yellow glassy solid. $^1$H NMR (d$_6$-DMSO; T=120° C.) δ 9.00 (dd, J$_1$=2.0 Hz, J$_2$=4.4 Hz, 1H), 8.44 (dd, J$_1$=2.4 Hz, J$_2$=8.4 Hz, 1H), 7.56 (dd, J$_1$=4.8 Hz, J$_2$=8.0 Hz, 1H), 7.33–7.44 (m, 3H), 7.28 (dd, J$_1$=J$_2$=10.4 Hz, 1H), 7.06 (dd, J$_1$=J$_2$=8.8 Hz, 1H), 7.05 (d, J=5.2 Hz, 2H), 6.95 (d, J=8.4 Hz, 2H), 6.52 (d, J=7.2 Hz, 2H), 5.27 (q, J=6.4 Hz, 1H), 4.65 (d, J=16.4 Hz, 1H), 4.48 (d, J=16.4 Hz, 1H), 4.10 (q, J=6.8 Hz, 2H), 3.58 (d, J=15.2 Hz, 1H), 2.90 (br s, 1H), 2.82 (s, 3H), 1.45 (d, J=6.4 Hz, 3H), 1.35 (t, J=6.8 Hz, 3H) ppm. MS(ESI$^+$) 670.3 (MNa$^+$).

Synthesis of Compound 3.69

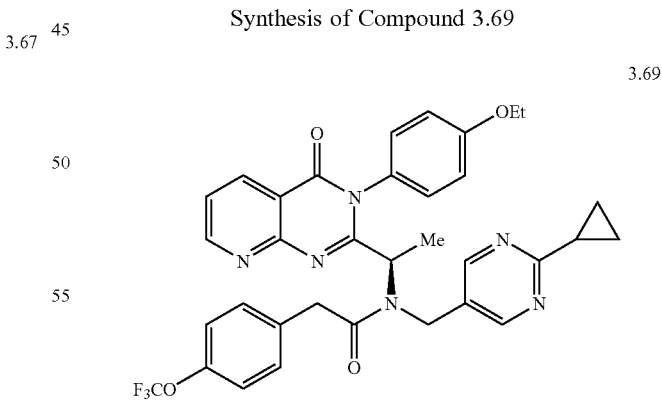

3.69

(R)-N-(2-Cyclopropyl-pyrimidin-5-ylmethyl)-N-{1-[3-(4-ethoxy-phenyl)-4-oxo-3,4-dihydro-pyrido[2,3-d]pyrimidin-2-yl]-ethyl}-2-(4-trifluoromethoxy-phenyl)-acetamide Comopund 3.69 was synthesized following the synthetic scheme for the generic synthesis of 8-azaquinazolinones (FIG. 13) to yield a colorless solid. $^1$H NMR (d$_6$-DMSO; T=120° C.) δ 9.01 (dd, J$_1$=2.0 Hz, J$_2$=4.4 Hz, 1H), 8.47 (dd, J$_1$=2.0 Hz, J$_2$=8.0 Hz, 1H), 8.36 (s, 2H), 7.58 (dd, J$_1$=4.4 Hz, J$_2$=8.0 Hz, 1H), 7.2 Hz, 1H), 7.08–7.22 (m, 7H), 5.26 (q, J=6.8 Hz, 1H), 4.68 (br s, 2H), 4.13 (q, J=7.2 Hz, 2H), 2.89 (br s, 2H), 2.11 (tt, J$_1$=J$_2$=4.4 Hz, 1H), 1.43 (d, J=6.8 Hz, 3H), 1.36 (t, J=7.2 Hz, 3H), 0.84–1.00 (m, 4H) ppm. MS(ESI$^+$) 645.3 (MH$^+$).

Synthesis of Compound 3.70

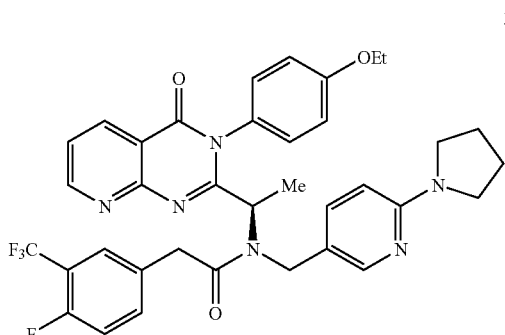

3.70

(R)-N-{1-[3-(4-Ethoxy-phenyl)-4-oxo-3,4-dihydro-pyrido[2,3-d]pyrimidin-2-yl]-ethyl}-2-(4-fluoro-3-trifluoromethyl-phenyl)-N-(6-pyrrolidin-1-yl-pyridin-3-ylmethyl)-acetamide Compound 3.70 was synthesized following the synthetic scheme for the generic synthesis of 8-azaquinazolinones (FIG. 13) to yield a colorless solid. $^1$H NMR (d$_6$-DMSO; T=120° C.) δ 8.09 (d, J=7.6 Hz, 1H), 7.87 (dd, J$_1$=J$_2$=6.8 Hz, 1H), 7.82 (s, 1H), 7.73 (d, J=8.4 Hz, 1H), 7.56 (dd, J$_1$=J$_2$=7.2 Hz, 1H), 7.38 (d, J=6.8 Hz, 2H), 7.30 (dd, J$_1$=J$_2$=10.4 Hz, 1H), 7.22 (d, J=8.0 Hz, 1H), 7.22 (d, J=8.0 Hz, 1H), 7.08 (d, J=7.6 Hz, 1H), 7.03 (d, J=7.6 Hz, 1H), 6.21 (d, J=8.4 Hz, 1H), 5.23 (q, J=6.4 Hz, 1H), 4.48 (br s, 2H), 4.09 (q, J=6.8 Hz, 2H), 3.54 (d, J=15.2 Hz, 1H), 3.30 (br s, 1H), 2.88 (br s, 4H), 1.91–1.94 (m, 4H), 1.44 (d, J=6.4 Hz, 3H), 1.34 (t, J=6.8 Hz, 3H) ppm. MS(ESI$^+$) 674.3 (MH$^+$).

Synthesis of Compound 3.71

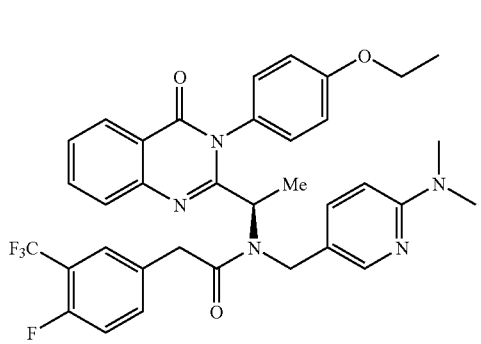

3.71

(-)-(R)-N-(6-Dimethylamino-pyridin-3-ylmethyl)-N-[3-(4-ethoxy-phenyl)-4-oxo3,4-dihydro-quinazolin-2-yl]ethyl}-2-(4-fluoro-3-trifluoromethyl-phenyl)-acetamide Compound 3.71 was prepared like compound 3.16a, with the pyridyl side chain prepared from 2,5-dibromopyridine.

White solid. $^1$H NMR (DMSO, 120° C.) δ 8.10 (d, 1H, J=8.0 Hz), 7.86 (m, 2H), 7.73 (d, 1H, J=8.0 Hz), 7.56 (dd, 1H, J$_1$=J$_2$=8.0 Hz), 7.38 (d, 3H, J=6.8 Hz), 7.31 (d, 1H, J=10.4 Hz), 7.25 (d, 1H, J=8.4 Hz), 7.18 (s, 1H), 7.08 (m, 2H), 7.04 (m, 1H), 6.41 (d, 1H, J=8.4 Hz), 5.23 (broad s, 1H), 4.49 (s, 2H), 4.12 (q, 1H, J=8.0 Hz) 4.09 (q, 2H, J=7.5 Hz), 3.54 (d, 1H, J=13.2 Hz), 2.95 (s, 6H), 1.44 (d, 3H, J=6.4 Hz), 1.36 (t, 3H, J=8.0 Hz), 1.28 (s, 1H) ppm. MS (ESI$^+$): expected 648.26 (MH$^+$), found 648.3.

Synthesis of Compound 3.72

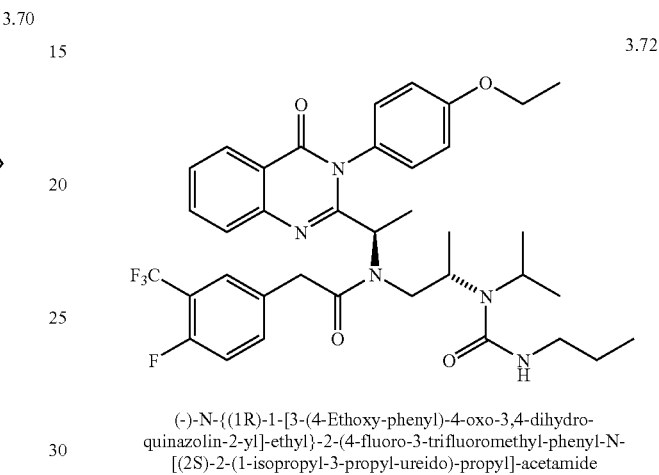

3.72

(-)-N-{(1R)-1-[3-(4-Ethoxy-phenyl)-4-oxo-3,4-dihydro-quinazolin-2-yl]-ethyl}-2-(4-fluoro-3-trifluoromethyl-phenyl-N-[(2S)-2-(1-isopropyl-3-propyl-ureido)-propyl]-acetamide White solid. $^1$H NMR (DMSO, 120° C.) δ 8.13 (d, 1H, J=8.0 Hz), 7.85 (dd, 1H, J$_1$=J$_2$=7.6 Hz), 7.67 (d, 1H, J=8.0 Hz), 7.55 (dd, 1H, J$_1$=J$_2$=7.6 Hz), 7.44 (m, 2H), 7.34 (d, 1H, J=12.4 Hz), 7.30 (dd, 1H, J$_1$=J$_2$=9.6 Hz), 7.23 (d, 1H, J=8.0 Hz), 7.05 (m, 2H), 5.66 (broad s, 1H), 5.19 (broad s, 1H), 4.08 (q, 2H, J=6.6 Hz), 3.77 (hept, 1H, J=6.6 Hz), 3.66 (m, 2H), 3.31 (m, 1H), 3.01 (m, 2H), 2.94 (m, 1H), 1.49 (d, 3H, J=6.8 Hz), 1.43 (tq, 2H, J=7.2 Hz), 1.35 (t, 3H, J=6.8 Hz), 1.21 (t, 3H, J=7.0 Hz), 1.17 (s, 1H), 1.09 (d, 3H, J=6.8 Hz), 0.99 (d, 3H, J=5.2 Hz), 0.83 (t, 3H, J=7.4 Hz) ppm. MS (ESI$^+$): expected 698.34 (MH$^+$), found 698.3.

Synthesis of Compound 3.73

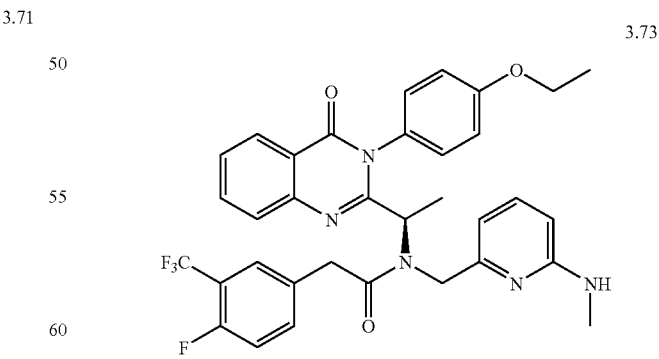

3.73

(-)-(R)-N-{1-[3-(4-Ethoxy-phenyl)-4-oxo-3,4-dihydro-quinazolin-2-yl]-ethyl}-2-(4-fluoro-3-trifluoromethyl-phenyl)-N-(6-methylamino-pyridin-2-ylmethyl)-acetamide Compound 3.73 was synthesized in the usual fashion, with the pyridyl fragment coming from 2,6-dibromopyridine. White solid. $^1$H NMR (DMSO, 120° C.) δ 8.09 (d, 1H, J=8.0 Hz), 7.83 (d, 1H, $J_1$=$J_2$=7.8 Hz), 7.68 (d, 1H, J=8.0 Hz), 7.53 (dd, 1H, $J_1$=$J_2$=7.6 Hz), 7.40 (d, 2H, J=6.4 Hz), 7.27 (m, 3H), 7.15 (d, 1H, $J_1$=$J_2$=7.6 Hz), 7.03 (m, 1H), 6.98 (m, 1H), 6.24 (d, 2H, J=7.6 Hz), 5.91 (broad s, 1H), 5.35 (s, 1H), 4.56 (q, 2H, J=16.4 Hz), 4.08 (d, 2H, J=6.8 Hz), 3.80 (s, 2H), 2.94 (s, 3H), 2.72 (s, 3H), 1.35 (t, 3H, J=6.8 Hz) ppm. MS (ESI$^+$): expected 634.25 (MH$^+$), found 634.2.

Synthesis of Compound 3.74

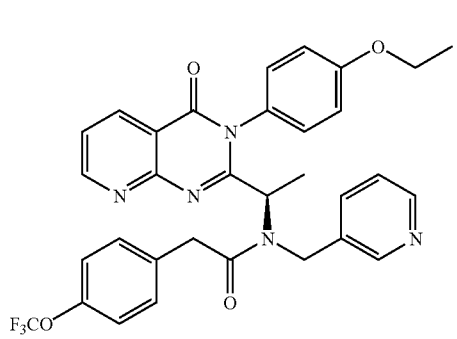

3.74

Figure 13:
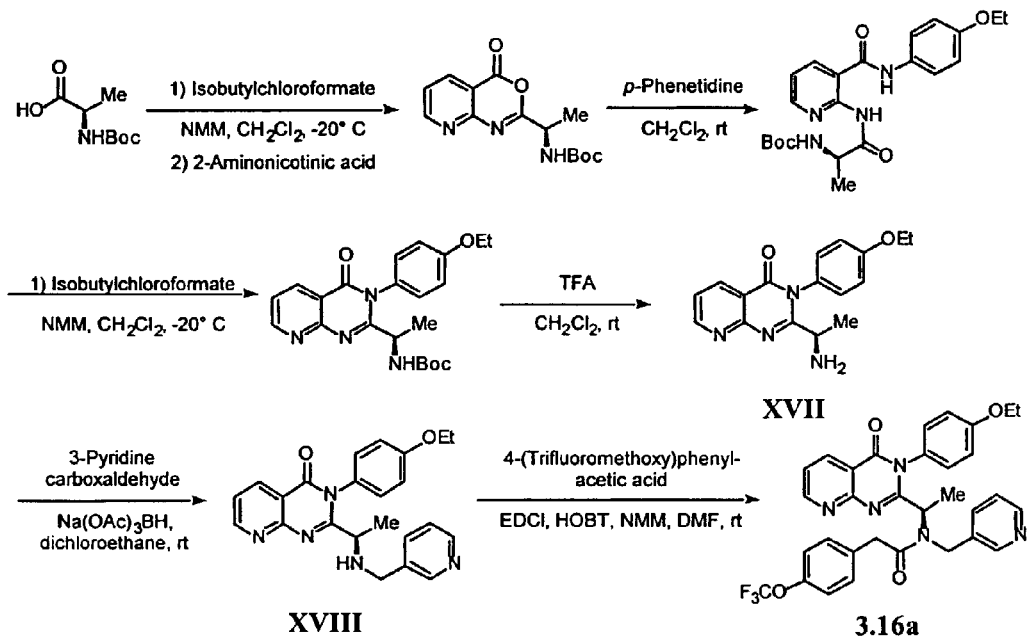
FIG. 13 illustrates a representative synthesis of 8-azaquinazolinones of the invention.

(+)-(S)-N-{1-[3-(4-Ethoxy-phenyl)-4-oxo-3,4-dihydro-pyrido[2,3-d]pyrimidin-2-yl]-ethyl}-N-pyridin-3-ylmethyl-2-(4-trifluoromethoxy-phenyl)-acetamide Compound 3.74 was synthesized as shown in FIG. 13, starting with the L-alanine derivative rather than the D-Ala. White solid. $^1$H NMR (DMSO, 120° C.) δ 9.02 (d, 1H, J=3.6 Hz), 8.46 (dd, 1H, $J_1$=7.8 Hz, $J_2$=1.8 Hz), 8.35 (s, 2H), 7.57 (dd, 1H, $J_1$=8.0 Hz, $J_2$=4.4 Hz), 7.53 (d, 1H, J=6.8 Hz), 7.43 (d, 1H, J=6.8 Hz), 3.46 (broad m, 8H), 5.29 (d, 1H, J=6.0 Hz), 4.76 (s, 2H), 4.13 (q, 2H, J=6.8 Hz), 3.46 (broad s, 1H), 2.91 (s, 4H), 1.42 (d, 3H, J=6.8 Hz), 1.36 (t, 3H, J=7.0 Hz) ppm. MS (ESI$^+$): expected 604.22 (MH$^+$), found 604.3.

Example 4

Synthesis of Compound 4.01

The synthesis of compound 4.01 in four steps from commercially available starting materials provides another example of a 3H-quinazolin-4-one synthesis in racemic form. Scheme 12 provides an overview of the synthetic route, for which the experimental details follow.

Scheme 12

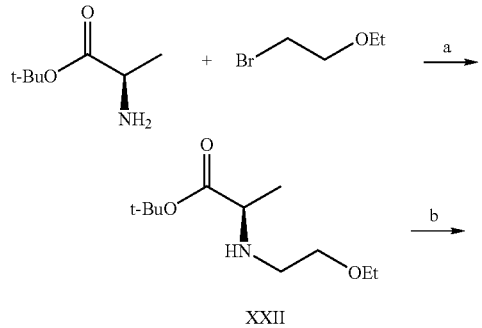

XXII

-continued

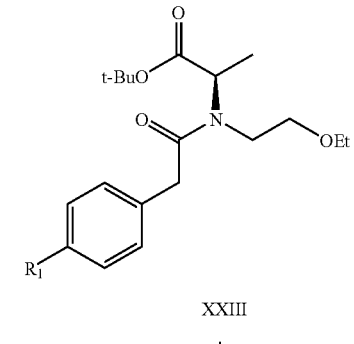

XXIII

↓c

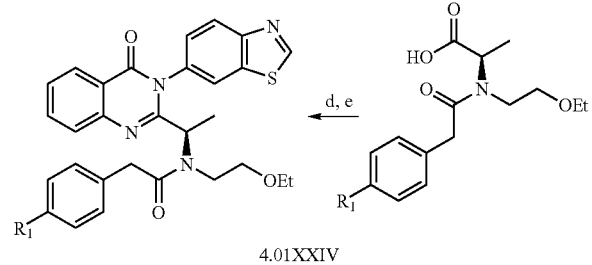

4.01 XXIV a. KI, $K_2CO_3$, DMF;
b. 4-phenylphenylacetic acid, EDC, HOBT, NMM, $CH_2Cl_2$;
c. $CF_3COOH$, $Et_3SiH$, $CH_2Cl_2$;
d. anthranilic acid, P(OPh)3, pyridine;
e. 6-aminobenothiazole.

(R)-t-Butyl 2-(N-2-Ethoxyethyl)aminopropionate (XXII). To a solution of D-alanine t-butyl ester hydrochloride (3.15 g, 17.3 mmol, 1.0 equiv), and 2-bromoethyl ethyl ether (2.79 g, 18.2 mmol, 1.05 equiv) in 14 mL of DMF, was added KI (1.44 g, 8.7 mmol, 0.50 equiv), followed by $K_2CO_3$ (2.40 g, 17.3 mmol, 1.0 equiv). After stirred at 55° C. for 16 h, the reaction mixture was poured into a mixture of 70 mL of water and 10 mL of 10% $Na_2CO_3$. The resulting mixture was extracted three times with 50 mL of EtOAc. The organic layer was washed with 50 mL of brine, dried over $Na_2SO_4$ and concentrated in vacuo to give a yellow oil, which was passed through a short silica gel column, eluted with EtOAc. The eluent was concentrated in vacuo to give 3.13 g of the crude XXII as a brown oil, which was used in subsequent step without further purification. $^1$H NMR (CDCl$_3$) δ 1.20 (t, J=8.0 Hz, 3H), 1.27 (d, J=7.2 Hz, 3H), 1.46 (s, 9H), 1.95 (br, 1H), 2.65 (m, 1H), 2.83 (m, 1H), 3.23 (q, J=7.2 Hz, 1H), 3.40–3.56 (m, 4H) ppm. MS (ESI$^+$) m/z 218.1 [M+H]$^+$.

(R)-t-Butyl 2-(N-2-Ethoxyethyl)-(N-4-phenylphenylacetyl)amino-propionate (XXIII) To a solution of crude XXII (5.0 g, 23 mmol, 1.0 equiv), and 4-phenylphenylacetic acid (4.88 g, 23 mmol, 1.0 equiv) in 40 mL of dichloromethane, was added EDC (5.51 g, 29 mmol, 1.25 equiv), HOBT (3.89 g, 29 mmol, 1.25 equiv), and N-methylmorpholine (2.79 g, 28 mmol, 1.2 equiv) at room temperature. The mixture was stirred at room temperature for 4 h. The reaction mixture was poured into a 30 mL of 5% aqueous H₃PO₄, and extracted twice with 20 mL of EtOAc. The combined EtOAc extract was washed twice with 20 mL of 10% aqueous NaHCO₃, and once with 30 mL of brine. The organic layer was dried over Na₂SO₄ and evaporated in vacuo to give a brown oil, which was purified by silica gel chromatography to give 5.05 g of compound XXIII as a light yellow oil. ¹H NMR (CDCl₃) δ 1.20 (t, J=8.0 Hz, 3H), 1.27 (d, J=7.2 Hz, 3H), 1.46 (s, 9H), 1.95 (br, 1H), 2.65 (m, 1H), 2.83 (m, 1H), 3.23 (q, J=7.2 Hz, 1H), 3.40–3.56 (m, 4H) ppm. MS (ESI⁺) m/z 218.1 [M+H]⁺.

(R)-2-(N-2-Ethoxyethyl)-(N-4-phenylphenylacetyl)aminopropionic acid (XXIV) To a solution of compound XXIII (5.05 g, 12.3 mmol, 1.0 equiv) in 25 mL of dichloromethane, was added triethylsilane (3.57 g, 30.7 mmol, 2.5 equiv), and trifluoroacetic acid (18 g, 160 mmol, 13 equiv) at room temperature. The mixture was stirred at room temperature for 8 h. The reaction mixture was evaporated in vacuo to give a brown residue, which was dissolved in 60 mL of EtOAc and washed once with 50 mL of 0.5 M aqueous KH₂PO₄, followed by 40 mL of brine. The organic layer was dried over Na₂SO₄ and evaporated in vacuo to give a brown oil, which was purified by silica gel chromatography to give 3.69 g of compound XXIV as a colorless oil, which solidified into a cream colored solid upon standing at room temperature. At room temperature the product exists as mixture of cis/trans amide rotamers, ca. 4.4:1 molar ratio in DMSO. For the major rotamer, ¹H NMR (DMSO-d₆) δ 1.12 (t, J=7.0 Hz, 3H), 1.34 (d, J=6.8 Hz, 3H3.40–3.60 (m, 6H), 3.78 (s, 2H), 4.16 (q, J=6.8 Hz, 1H), 7.29 (d, J=8.0 Hz, 2H), 7.35 (t, J=7.2 Hz, 1H), 7.46 (t, J=7.4 Hz, 2H), 7.59 (d, J=8.0 Hz, 2H), 7.65 (d, J=7.8 Hz, 2H) ppm. For the minor rotamer ¹H NMR (DMSO-d₆) δ 4.77 (q, J=6.8 Hz, 1H) ppm. MS (ESI⁻) m/z 354.2 [M−H]⁻.

2-((N-2-Ethoxyethyl)-N-(4-phenylphenylacetyl)-1-aminoethyl)-3-(6-benzothiazolyl)-3H-quinazoline-4-one (4.01). To a solution of anthranilic acid (69 mg, 0.50 mmol, 1.0 equiv) and compound XXIV (178 mg, 0.50 mmol, 1.0 equiv) in 1.0 mL of anhydrous pyridine was added 127 µL of triphenylphosphite (155 mg, 0.50 mmol, 1.0 equiv) at room temperature. The resulting yellow solution was stirred at reflux for 2 h. 6-Aminobenzothiazole (75 mg, 0.50 mmol, 1.0 equiv) was added via syringe. The reaction mixture was stirred for another 3 h at 100° C., cooled to room temperature, and evaporated in vacuo to give a brown residue. This residue was dissolved in 20 mL of ether. The mixture was washed successively twice with 5 mL of 5% aqueous phosphoric acid, twice with 5 mL of 1 M NaOH, once with 5 mL of pH 7 phosphate buffer (0.5 M KH₂PO₄ and 0.5 M K₂HPO₄), and once with 10 mL of brine. The organic layer was dried over Na₂SO₄ and evaporated in vacuo to give a brown residue, which was purified by preparative TLC to give 19 mg of compound 4.01 as a light yellow solid. At room temperature, this compound exists as a mixture of cis/trans amide rotamers, and diastereomers, ca. 0.33:0.30:1 molar ratio in DMSO. ¹H NMR (DMSO-d₆, T=25° C.) δ 4.92 (q, J=6.8 Hz, 1H), 5.05 (q, J=6.8 Hz, 1H), & 5.27 (q, J=6.8 Hz, 1H) ppm. MS (ESI⁺) m/z 589.3 [M+H]⁺.

Synthesis of Compound 4.03

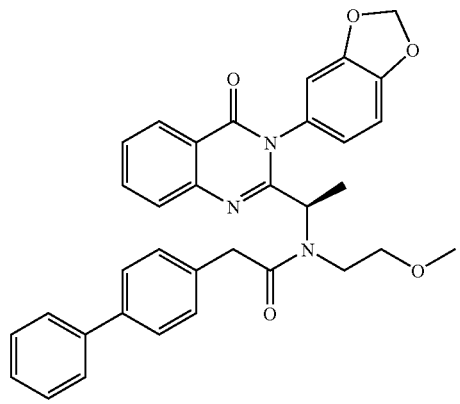

4.03

N-[1-(3-Benzo[1,3]dioxol-5-yl-4-oxo-3,4-dihydro-quinazolin-2-yl)-ethyl]-2-biphenyl-4-yl-N-(2-methoxy-ethyl)-acetamide Compound 4.03 was prepared following the synthesis of compound 4.01. Yellow solid, mixture of cis/trans amide rotamers (1.5/1), determined by ¹H NMR (CDCl₃) 1.20 (t, 3H, J=7.0 Hz), 1.26 (t, 3H, J=7.0 Hz). MS(ESI⁺) 577.3 (MH⁺).

Example 5

Synthesis of Compound 5.01

Synthesis of the biphenyl compound 5.01 was achieved via a four-step reaction sequence, commencing with a Suzuki coupling of 1-ethyl-2-iodo-benzene and 4-ethoxyphenylboronic acid to form the biphenyl unit. The remaining transformations install the amino alkyl and acetyl groups.

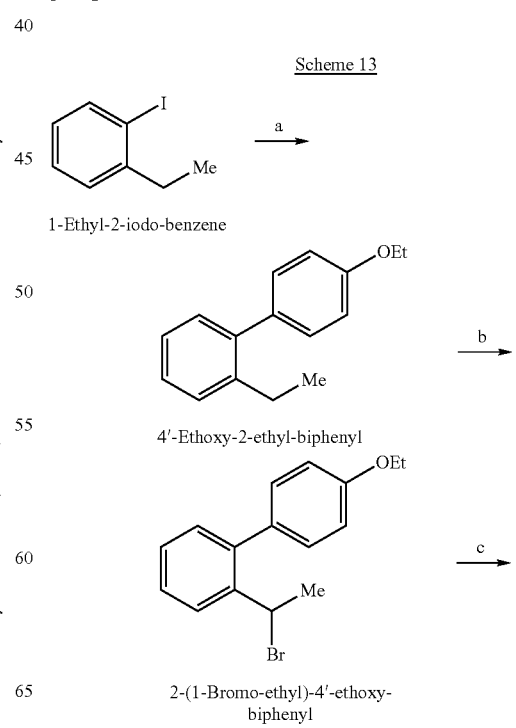

Scheme 13

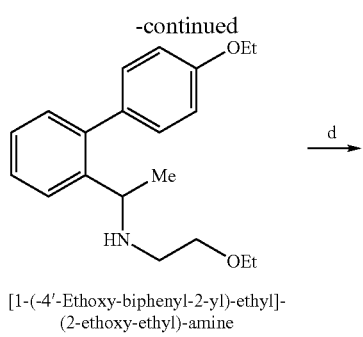

[1-(-4'-Ethoxy-biphenyl-2-yl)-ethyl]-
(2-ethoxy-ethyl)-amine

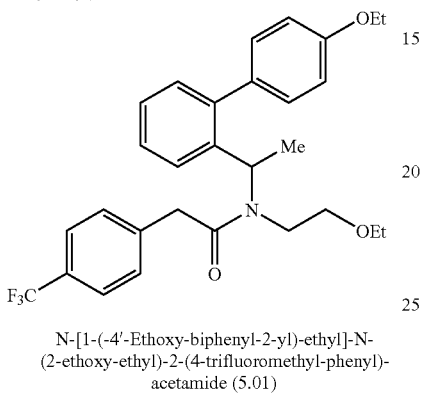

N-[1-(-4'-Ethoxy-biphenyl-2-yl)-ethyl]-N-
(2-ethoxy-ethyl)-2-(4-trifluoromethyl-phenyl)-
acetamide (5.01)

(a) 4-ethoxyphenylboronic acid, cat. Pd(PPh$_3$)$_4$, toluene-2M Na$_2$CO$_3$ aq., 100° C.
(b) NBS, cat. AIBN, hv, CCl$_4$, reflux.
(c) 2-ethoxy-1-aminoethane, ethanol, reflux.
(d) 4'-(trifluoromethyl)phenylacetic acid, EDC, cat. HOBT, CH$_2$Cl$_2$, RT.

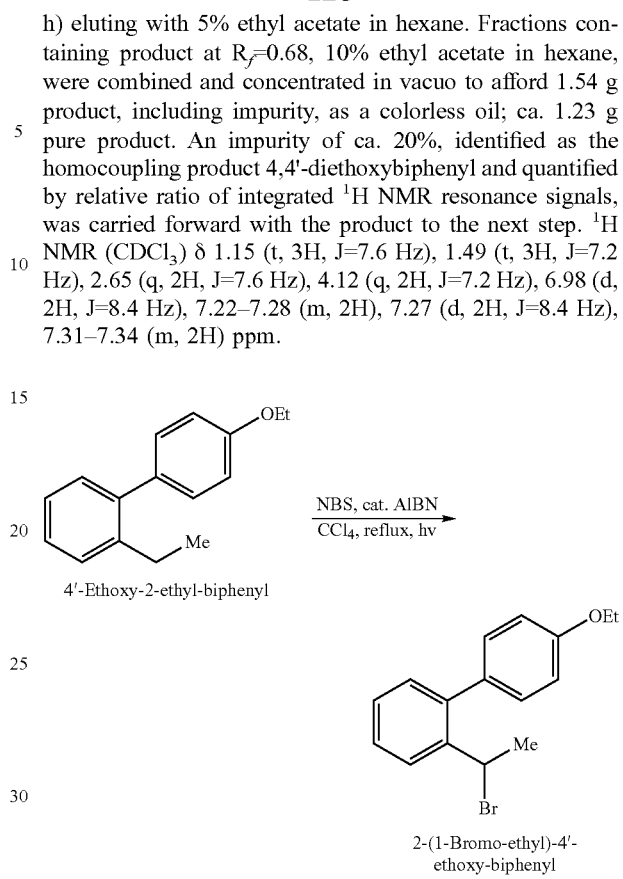

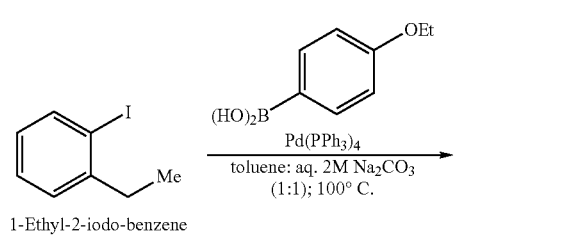

4'-Ethoxy-2-ethyl-biphenyl

4'-Ethoxy-2-ethyl-biphenyl. A degassed (3× freeze-thaw cycles) mixture of 1.00 mL 1-ethyl-2-iodo-benzene (6.97 mmol, 1.00 equiv), 3.47 g 4-ethoxyphenylboronic acid (20.9 mmol, 3.00 equiv), and 402 mg tetrakis(triphenylphosphine)palladium(0) (0.349 mmol, 0.0501 equiv) was dissolved in 8.0 mL toluene and 8.0 mL aqueous 2M sodium carbonate solution and the biphasic mixture heated to 100° C. (external temperature, oil bath). After 16 h the reaction was cooled to room temperature and the organic phase separated. The aqueous layer was extracted with 50% ethyl acetate in hexane (2×25 mL) and the combined organic separations dried over magnesium sulfate, filtered, and concentrated in vacuo to yield a yellow oil. The crude material was purified by column chromatography on silica gel (3.5 cm o.d.×20 cm h) eluting with 5% ethyl acetate in hexane. Fractions containing product at R$_f$=0.68, 10% ethyl acetate in hexane, were combined and concentrated in vacuo to afford 1.54 g product, including impurity, as a colorless oil; ca. 1.23 g pure product. An impurity of ca. 20%, identified as the homocoupling product 4,4'-diethoxybiphenyl and quantified by relative ratio of integrated $^1$H NMR resonance signals, was carried forward with the product to the next step. $^1$H NMR (CDCl$_3$) δ 1.15 (t, 3H, J=7.6 Hz), 1.49 (t, 3H, J=7.2 Hz), 2.65 (q, 2H, J=7.6 Hz), 4.12 (q, 2H, J=7.2 Hz), 6.98 (d, 2H, J=8.4 Hz), 7.22–7.28 (m, 2H), 7.27 (d, 2H, J=8.4 Hz), 7.31–7.34 (m, 2H) ppm.

2-(1-Bromo-ethyl)-4'-ethoxy-biphenyl from 4'-ethoxy-2-ethyl-biphenyl. A mixture of 673 mg 4'-ethoxy-2-ethyl-biphenyl (2.98 mmol, 1.00 equiv), 556 mg N-bromosuccinimide (3.13 mmol, 1.05 equiv), and 49 mg 2,2'-azobisisobutyronitrile (0.30 mmol, 0.10 equiv) dissolved in 15 mL carbon tetrachloride was heated to reflux in the presence of a high intensity incandescent light for 1.5 h. The reaction was cooled to 0° C. and the resulting precipitate removed by filtration. The concentrated filtrate was subjected to iterative triturations with cold hexane (3×50 mL) to afford 890 mg product as a colorless oil. The 4,4'-diethoxybiphenyl impurity, ca. 20% quantitated by relative ratio of integrated $^1$H NMR resonance signals, was carried forward to the next step with the product. $^1$H NMR (CDCl$_3$) δ 1.48 (t, 3H, J=6.8 Hz), 1.99 (d, 3H, J=7.2 Hz), 4.12 (q, 2H, J=6.8 Hz), 5.33 (q, 1H, J=6.8 Hz), 7.00 (d, 2H, J=8.8 Hz), 7.21 (d, 1H, J=7.6 Hz), 7.30–7.34 (m, 3H), 7.42 (dd, 1H, J$_1$=J$_2$=7.6 Hz), 7.77 (d, 1H, J=8.0 Hz)

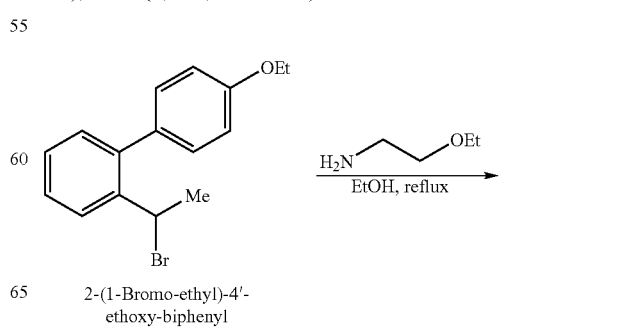

2-(1-Bromo-ethyl)-4'-
ethoxy-biphenyl

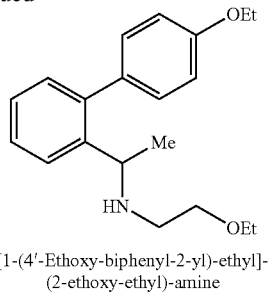

[1-(4'-Ethoxy-biphenyl-2-yl)-ethyl]-
(2-ethoxy-ethyl)-amine ppm.

[1-(4'-Ethoxy-biphenyl-2-yl)-ethyl]-(2-ethoxy-ethyl)-amine from 2-(1-bromo-ethyl)-4'-ethoxy-biphenyl. A mixture of 135 mg 2-(1-bromo-ethyl)-4'-ethoxy-biphenyl (0.442 mmol, 1.00 equiv) and 115 µL 2-ethoxy-1-aminoethane (1.10 mmol, 2.50 equiv) dissolved in 3.0 mL ethanol was heated to reflux for 20 h and then concentrated in vacuo to remove the solvent. The concentrated reaction product was adsorbed directly onto a column of silica gel (3.5 cm o.d.×12 cm h) and eluted with 3% methanol in chloroform. Fractions containing product at $R_f$=0.30, 10% methanol in chloroform, were combined and concentrated in vacuo to afford 13.5 mg purified product as a yellow oil. $^1$H NMR (CDCl$_3$) δ 1.17 (t, 3H, J=7.2 Hz), 1.34 (d, 3H, J=6.8 Hz), 1.47 (t, 3H, J=7.2 Hz), 2.55 (t, 2H, J=5.6 Hz), 3.37–3.50 (m, 2H), 4.01 (q, 1H, J=6.4 Hz), 4.10 (q, 2H, J=6.8 Hz), 6.94 (d, 2H, J=8.8 Hz), 7.15–7.22 (m, 3H), 7.27 (dd, 1H, J$_1$=J$_2$=7.6 Hz), 7.39 (dd, 1H, J$_1$=J$_2$=7.6 Hz), 7.63 (d, 1H, J=7.6 Hz) ppm. MS (ESI, positive mode) 314.1

A mixture of 13.5 mg [1-(4'-ethoxy-biphenyl-2-yl)-ethyl]-(2-ethoxy-ethyl)-amine (43.1 µmol, 1.00 equiv), 10.5 mg 4'-(trifluoromethyl)phenylacetic acid (51.7 µmol, 1.20 equiv), 9.9 mg EDC (51.7 µmol, 1.20 equiv), and 1.0 mg HOBT (7.4 µmol, 0.18 equiv) dissolved in 2.0 mL dichloromethane was stirred at room temperature for 2 h. To the reaction solution was added 5 mL aqueous saturated sodium bicarbonate solution. The aqueous layer was diluted with water to 15 mL and extracted with dichloromethane (2×20 mL). The combined organic separations were dried over magnesium sulfate, filtered, and concentrated in vacuo to yield a yellow oil. The crude product was adsorbed onto a column of silica gel (3.5 cm o.d.×10 cm h) and eluted with 17% to 25% ethyl acetate gradient in hexane. Fractions containing product were combined and concentrated in vacuo to afford 12.8 mg purified product as a colorless oil. $^1$H NMR (d$_6$-DMSO; T=140° C.) δ 1.04 (t, 3H, J=6.8 Hz), 1.34 (t, 3H, J=6.8 Hz), 1.44 (d, 3H, J=7.2 Hz), 3.00–3.06 (m, 1H), 3.17–3.36 (m, 6H), 3.49 (d, 1H, J=16.0 Hz), 4.07 (q, 2H, J=6.8 Hz), 5.43 (q, 1H, J=7.2 Hz), 6.92–6.96 (m, 2H), 7.13–7.18 (m, 3H), 7.22–7.26 (m, 2H), 7.34 (ddd, 1H, J$_1$=1.2 Hz, J$_2$=7.6 Hz, J$_3$=8.4 Hz), 7.39 (ddd, 1H, J$_1$=2.0 Hz, J$_2$=7.6 Hz, J$_3$=9.2 Hz), 7.53–7.59 (m, 3H) ppm. At room temperature, compound exists as a mixture of cis/trans amide rotamers in ca. 2:1 ratio as determined by integration of characteristic $^1$H NMR signals (CDCl$_3$; T=25° C.) δ$_{major}$ 5.19 (q, 2.1H, J=7.2 Hz) and δ$_{minor}$ 5.89 (q, 1.0H, J=7.6 Hz) ppm. MS (ESI, positive mode) 500.1 [MH]$^+$ Example 6

Synthesis of Compound 6.01

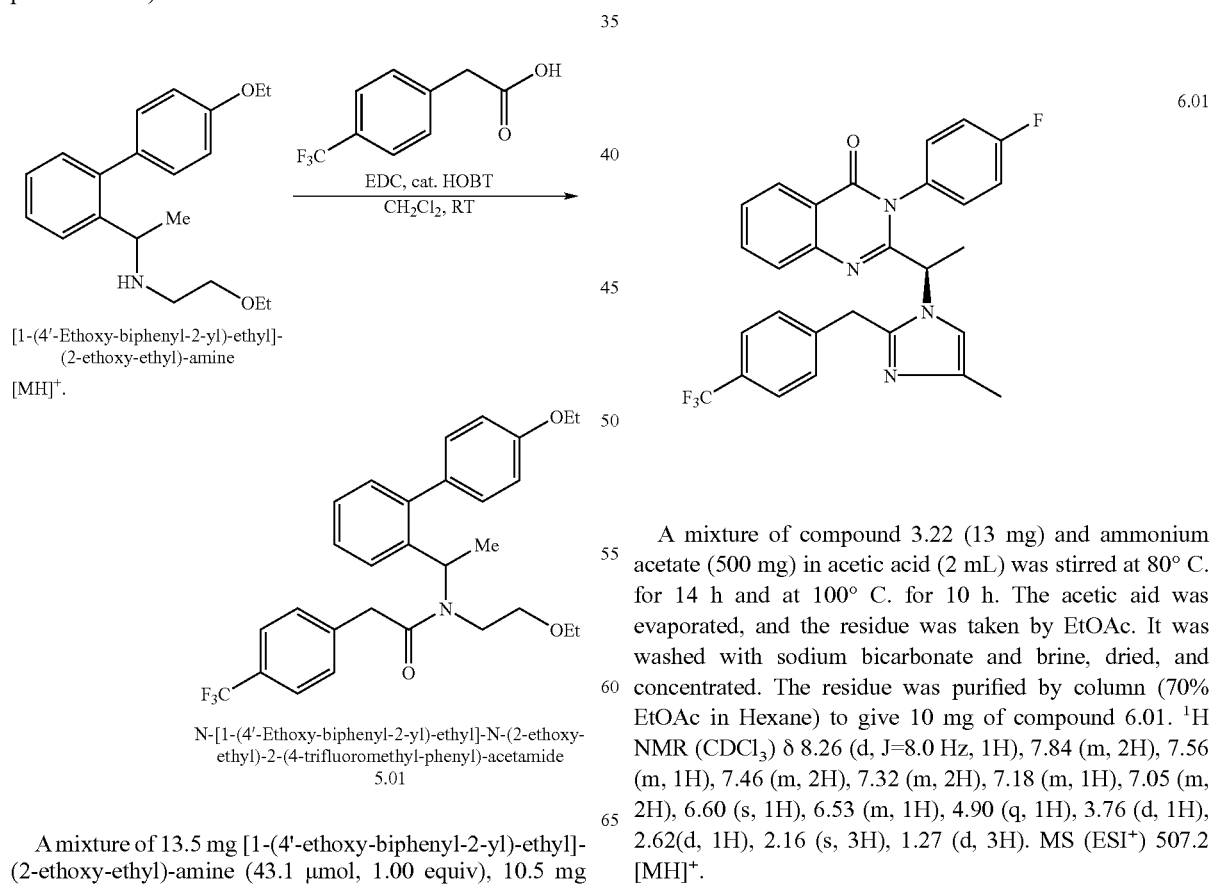

A mixture of compound 3.22 (13 mg) and ammonium acetate (500 mg) in acetic acid (2 mL) was stirred at 80° C. for 14 h and at 100° C. for 10 h. The acetic aid was evaporated, and the residue was taken by EtOAc. It was washed with sodium bicarbonate and brine, dried, and concentrated. The residue was purified by column (70% EtOAc in Hexane) to give 10 mg of compound 6.01. $^1$H NMR (CDCl$_3$) δ 8.26 (d, J=8.0 Hz, 1H), 7.84 (m, 2H), 7.56 (m, 1H), 7.46 (m, 2H), 7.32 (m, 2H), 7.18 (m, 1H), 7.05 (m, 2H), 6.60 (s, 1H), 6.53 (m, 1H), 4.90 (q, 1H), 3.76 (d, 1H), 2.62(d, 1H), 2.16 (s, 3H), 1.27 (d, 3H). MS (ESI$^+$) 507.2 [MH]$^+$.

Synthesis of Compound 6.02

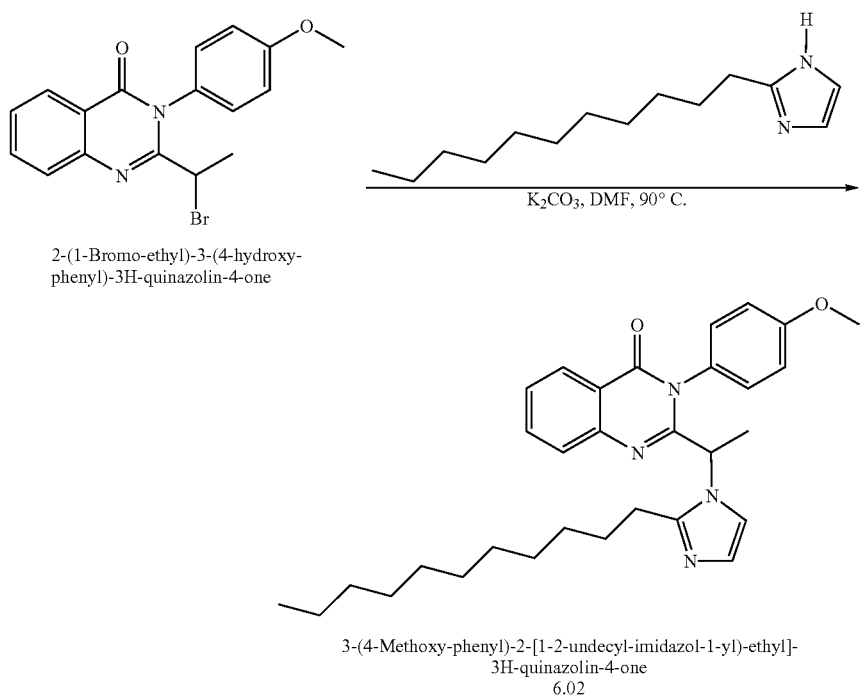

2-(1-Bromo-ethyl)-3-(4-hydroxy-phenyl)-3H-quinazolin-4-one 3-(4-Methoxy-phenyl)-2-[1-2-undecyl-imidazol-1-yl)-ethyl]-3H-quinazolin-4-one
6.02

Into a mixture of bromide (0.557 mmol, 0.20 g) and K₂CO₃ (0.89 mmol, 0.123 g) in 3 mL of DMF was added 2-undecyl-1-H-imidazole (0.557 mmol, 0.124 g). The reaction mixture was heated to 90° C. for 10 h. After evaporating the solvent, the residue was dissolved in CH₂Cl₂, the organic layer was washed by water, brine, dried over NaSO₄ and removed in vacuo to give a sticky oil which was purified by chromatography to afford a yellow solid (0.16 g). ¹H NMR (CDCl₃) 0.89 (t, 3H, J=7.0 Hz), 1.25 (m, 16H), 1.60 (br m, 3H), 1.73 (d, 3H, J=6.7 Hz), 1.83 (m, 1H), 3.84 (s, 3H), 5.09 (q, 1H, J=6.7 Hz), 6.35 (m, 1H), 6.84–6.90 (m, 3H), 7.05 (m, 1H), 7.20 (m, 1H), 7.55 (m, 1H), 7.82 (m, 2H), 8.28 (dd, 1H, J₁=1.1 Hz, J₂=7.9 Hz). MS(ESI⁺) 501.2 (MH⁺). Anal. (C₃₁H₄₀N₄O₂) cal. C, 74.22; H, 8.05, N, 11.19. Found C, 74.22, H, 8.14, N, 11.03.

Preparation of Compound 6.03

Figure 16:
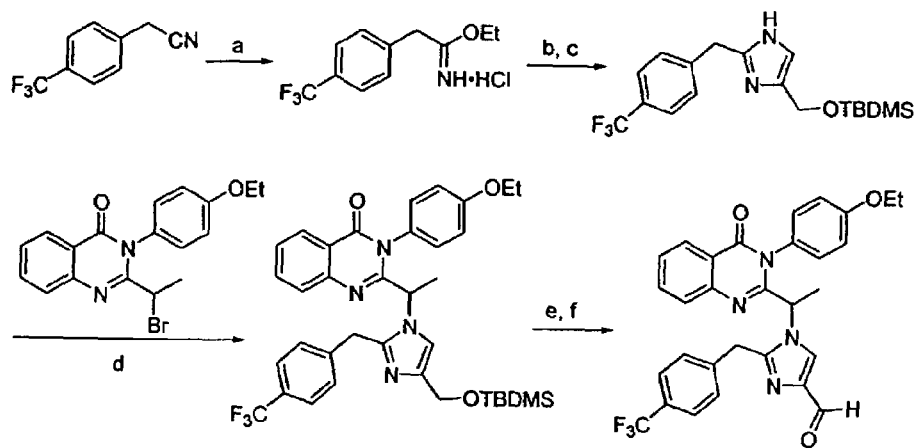
Figure 16:
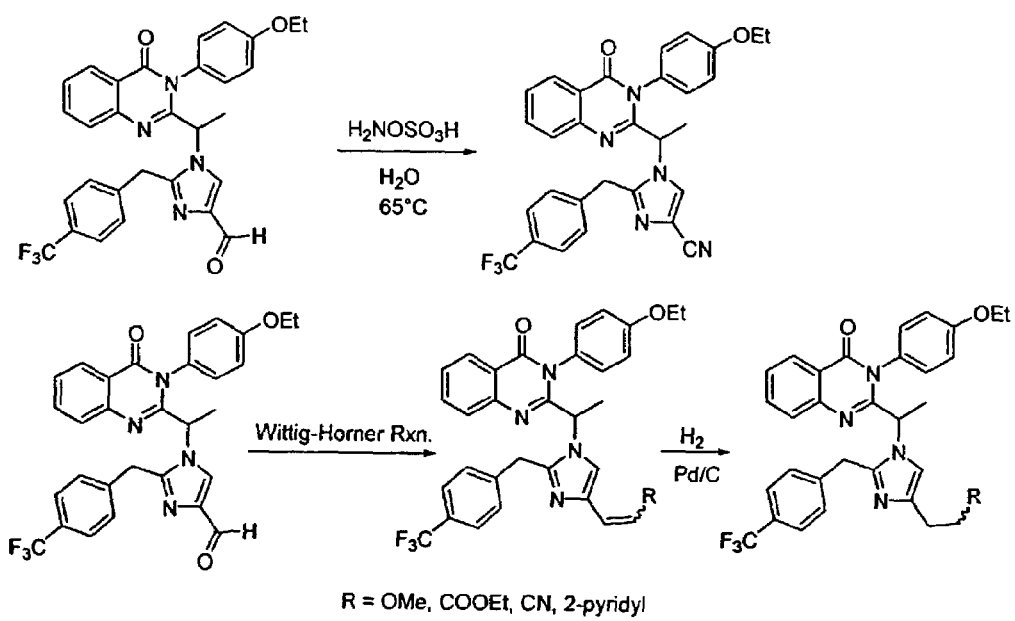

The synthesis of compound 6.03 is shown in FIG. 16. ¹H NMR (CDCl₃) δ 8.27 (d, J=8.0 Hz, 1H), 7.80 (m, 2H), 7.74 (s, 1H), 7.57 (m, 1H), 7.48 (m, 2H), 7.21 (m, 2H), 7.02 (m, 3H), 6.64 (m, 1H), 5.10 (q, J=6.8 Hz, 1H), 4.12 (q, 2H), 3.83 (d, J=16.4 Hz, 1H), 2.95 (d, J=16.2 Hz, 1H), 1.49 (t, 3H), 1.32 (d, J=6.7 Hz, 3H). MS (ESI⁺) 544.2 [MH]⁺.

Preparation of Compound 6.04

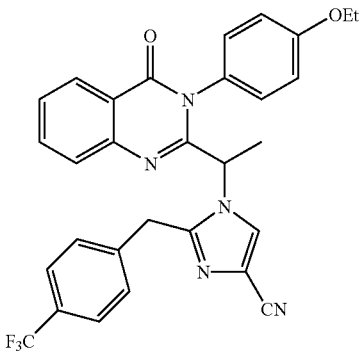

6.03

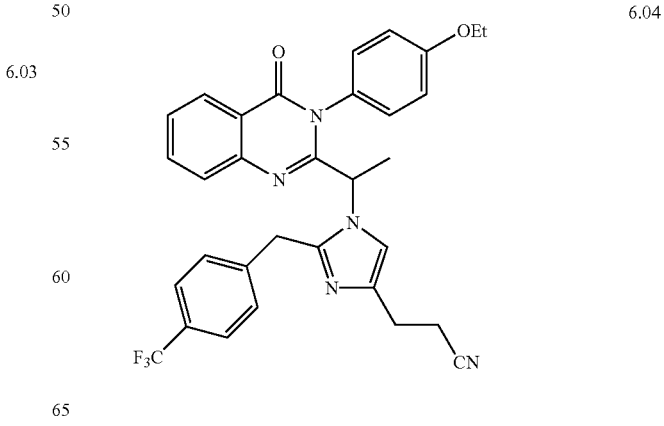

6.04

The synthesis of compound 6.04 is shown in FIG. 16. ¹H NMR (CDCl₃) δ 8.26 (d, J=8.0 Hz, 1H), 7.80 (m, 2H), 7.54 (m, 1H), 7.47 (m, 2H), 7.18 (m, 2H), 7.03 (m, 2H), 6.96 (m, 1H), 6.87 (s, 1H), 6.56 (m, 1H), 5.01 (q, J=6.8 Hz, 1H), 4.11 (q, 2H), 3.71 (d, J=16.4 Hz, 1H), 2.83 (m, 2H), 2.76 (d, J=16.2 Hz, 1H), 2.69 (m, 2H), 1.47 (t, 3H), 1.27 (d, J=6.7 Hz, 3H). MS (ESI⁺) 572.3 [MH]⁺.

Preparation of Compound 6.05

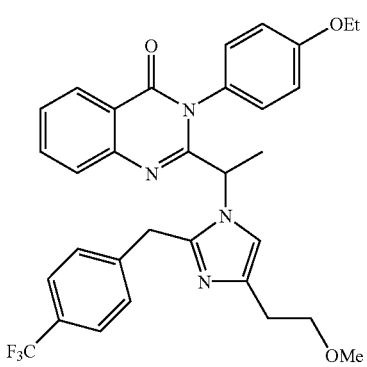

6.05

The synthesis of compound 6.05 is shown in FIG. 16. ¹H NMR (CDCl₃) δ 8.26 (d, J=8.0 Hz, 1H), 7.80 (m, 2H), 7.54 (m, 1H), 7.47 (m, 2H), 7.18 (m, 2H), 7.06 (m, 2H), 6.96 (m, 1H), 6.78 (s, 1H), 6.52 (m, 1H), 5.01 (q, J=6.8 Hz, 1H), 4.11 (m, 3H), 3.64 (m, 2H), 3.34 (s, 3H), 2.81 (m, 2H), 2.68 (d, J=16.2 Hz, 1H), 1.47 (t, 3H), 1.24 (d, J=6.7 Hz, 3H). MS (ESI⁺) 577.1 [MH]⁺.

Preparation of Compound 6.06

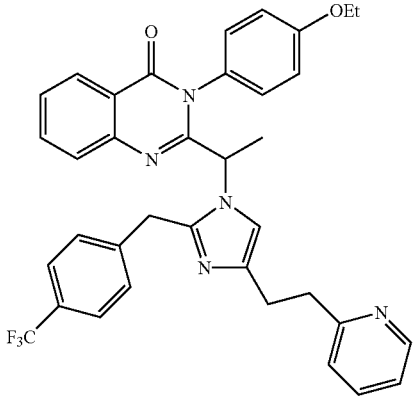

6.06

The synthesis of compound 6.06 is shown in FIG. 16. ¹H NMR (CDCl₃) δ 8.36 (m, 1H), 8.27 (d, J=8.0 Hz, 1H), 7.80 (m, 2H), 7.56 (m, 1H), 7.47 (m, 3H), 7.16 (m, 2H), 7.04 (m, 3H), 6.92 (m, 2H), 6.50 (s, 1H), 6.29 (m, 1H), 4.92 (q, J=6.8 Hz, 1H), 4.11 (q, 2H), 3.74 (d, J=16.4 Hz, 1H), 3.08 (m, 2H), 2.98 (m, 2H), 2.59 (d, J=16.2 Hz, 1H), 1.47 (t, 3H), 1.17 (d, J=6.7 Hz, 3H). MS (ESI⁺) 624.2 [MH]⁺.

Preparation of Compound 6.07

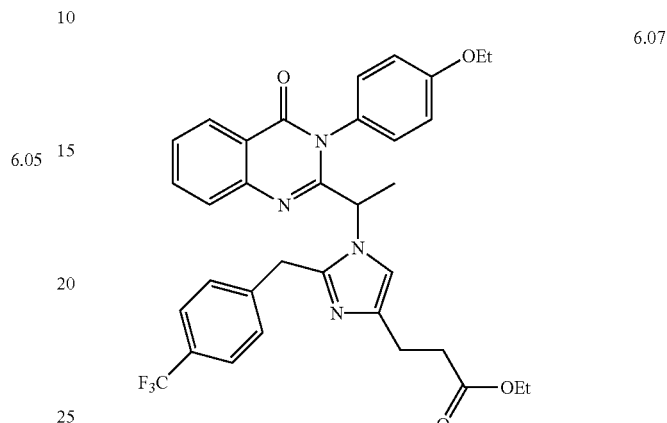

6.07

The synthesis of compound 6.07 is shown in FIG. 16. ¹H NMR (CDCl₃) δ 8.26 (d, J=8.0 Hz, 1H), 7.80 (m, 2H), 7.54 (m, 1H), 7.47 (m, 2H), 7.18 (m, 2H), 7.05 (m, 2H), 6.96 (m, 1H), 6.72 (s, 1H), 6.48 (m, 1H), 5.00 (q, J=6.8 Hz, 1H), 4.11 (q, 2H), 4.04 (q, 2H), 3.80 (d, J=16.4 Hz, 1H), 2.85 (m, 2H), 2.65 (m, 3H), 1.47 (t, 3H), 1.23 (d, J=6.7 Hz, 3H), 1.14 (t, 3H). MS (ESI⁺) 619.1 [MH]⁺.

Preparation of Compound 6.08

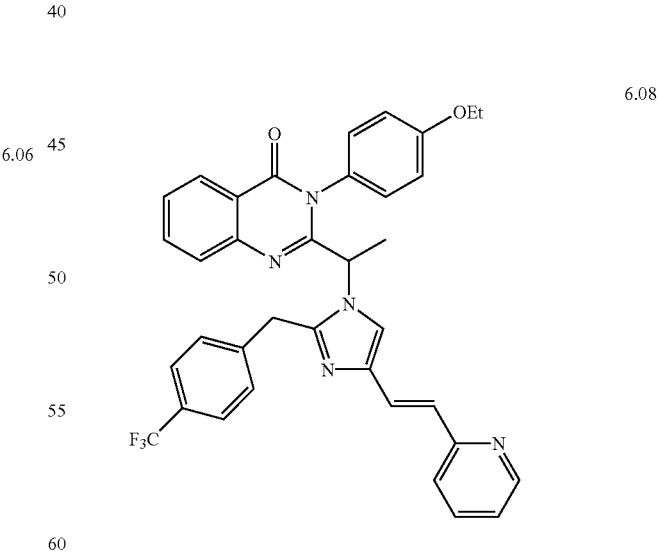

6.08

The synthesis of 6.08 is shown in FIG. 16. ¹H NMR (CDCl₃) δ 8.53 (m, 1H), 8.26 (d, J=8.0 Hz, 1H), 7.80 (m, 2H), 7.50 (m, 5H), 7.26 (m, 5H), 7.07 (m, 3H), 7.00 (m, 1H), 6.61 (m, 1H), 5.03 (q, J=6.8 Hz, 1H), 4.11 (q, 2H), 3.89 (d, J=16.4 Hz, 1H), 2.81 (d, J=16.2 Hz, 1H), 1.47 (t, 3H), 1.27 (d, J=6.7 Hz, 3H). MS (ESI⁺) 622.1 [MH]⁺.

Preparation of Compound 6.09

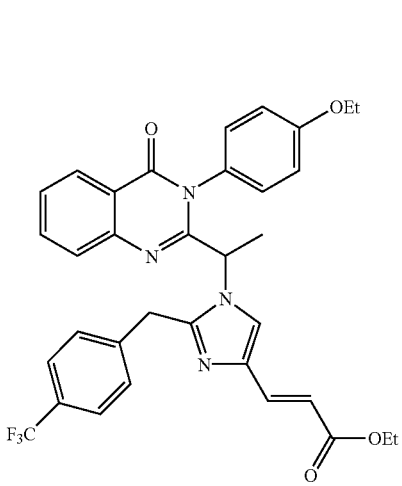

6.09

The synthesis of compound 6.09 is shown in FIG. 16. $^1$H NMR (CDCl$_3$) δ 8.27 (d, J=8.0 Hz, 1H), 7.80 (m, 2H), 7.53 (m, 1H), 7.48 (m, 3H), 7.25 (s, 1H), 7.20 (m, 2H), 7.05 (m, 2H), 7.00 (m, 1H), 6.58 (m, 1H), 6.50 (d, J=15.8 Hz, 1H), 5.04 (q, J=6.8 Hz, 1H), 4.21 (q, 2H), 4.12 (q, 2H), 3.83 (d, J=16.4 Hz, 1H), 2.80 (d, J=16.2 Hz, 1H), 1.48 (t, 3H), 1.28 (d, J=6.7 Hz, 3H). MS (ESI$^+$) 617.2 [MH]$^+$.

Preparation of Compound 6.10

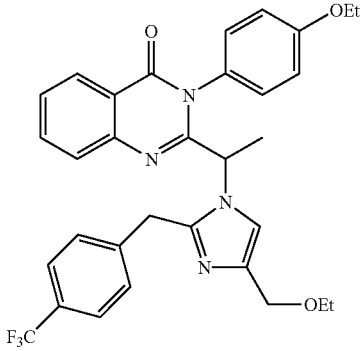

6.10

The synthesis of compound 6.10 is shown in FIG. 16. $^1$H NMR (CDCl$_3$) δ 8.26 (d, J=8.0 Hz, 1H), 7.80 (m, 2H), 7.54 (m, 1H), 7.47 (m, 2H), 7.19 (m, 2H), 7.06 (m, 3H), 6.96 (m, 1H), 6.59 (m, 1H), 5.04 (q, J=6.8 Hz, 1H), 4.44 (s, 2H), 4.11 (m, 3H), 3.60 (m, 2H), 2.70 (d, J=16.2 Hz, 1H), 1.47 (t, 3H), 1.24 (d, J=6.7 Hz, 3H). MS (ESI$^+$) 577.5 [MH]$^+$.

Preparation of Compound 6.11

6.11

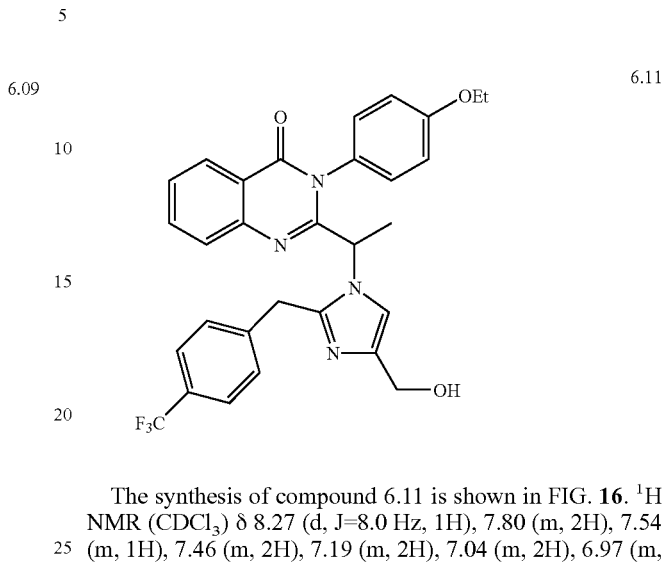

The synthesis of compound 6.11 is shown in FIG. 16. $^1$H NMR (CDCl$_3$) δ 8.27 (d, J=8.0 Hz, 1H), 7.80 (m, 2H), 7.54 (m, 1H), 7.46 (m, 2H), 7.19 (m, 2H), 7.04 (m, 2H), 6.97 (m, 2H), 6.54 (m, 1H), 5.03 (q, J=6.8 Hz, 1H), 4.53 (s, 2H), 4.11 (q, 2H), 3.75 (d, J=16.4 Hz, 1H), 2.73 (d, J=16.2 Hz, 1H), 1.47 (t, 3H), 1.27 (d, J=6.7 Hz, 3H). MS (ESI$^+$) 549.5 [MH]$^+$.

Example 7

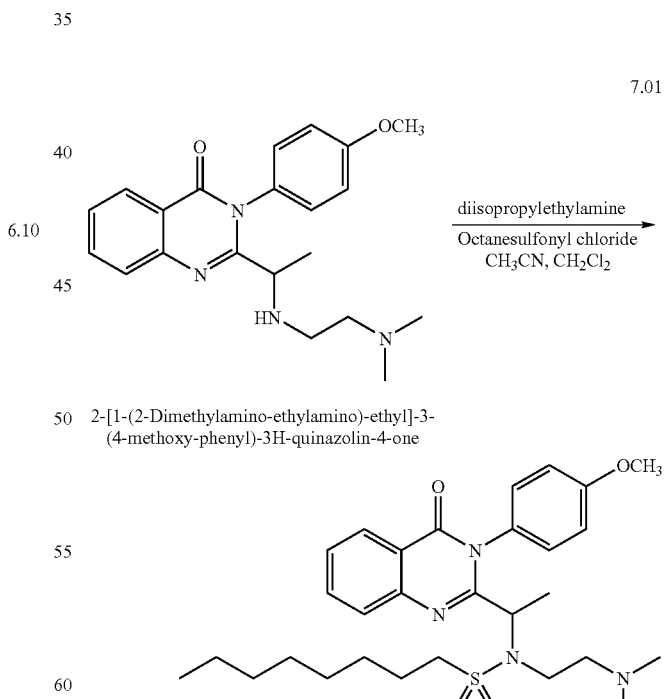

2-[1-(2-Dimethylamino-ethylamino)-ethyl]-3-(4-methoxy-phenyl)-3H-quinazolin-4-one Octane-1-sulfonic acid(2-dimethylamino-ethyl)-{1-[3-(4-methoxy-phenyl)-4-oxo-3,4-dihydro-quinazolin-2-yl]-ethyl}-amide Compound 7.01. To a solution of the amine (1 mmol, 0.37 g) and diisopropylethylamine (1.2 mmol, 0.16 g) in acetonitrile (3 mL) and methylene chloride (3 mL) was added octanesulfonyl chloride (1.2 mmol, 0.26 g). The reaction mixture was stirred at room temperature overnight. Sodium carbonate (15%) was added and the aqueous layer was extracted with methylene chloride. The organic layer was washed with water, brine, dried over NaSO$_4$ and concentrated in vacuo to give a yellow oil, which was purified by chromatography on silica gel (eluent: CHCl$_3$/MeOH=10/1.5) to afford a light yellow glassy oil (0.22 g). $^1$H NMR (CDCl$_3$) 0.86 (t, 3H, J=7.2 Hz), 1.17–1.25 (m, 10H), 1.46 (d, 3H, J=6.9 Hz), 1.70 (m, 2H), 2.19 (s, 6H), 2.45 (m, 2H), 2.73–2.90 (m, 2H), 3.62–3.78 (m, 2H), 3.87 (s, 3H), 4.88(q, 1H, J=6.9 Hz), 7.04–7.14 (m, 3H), 7.31–7.34 (m, 1H), 7.49 (dt, 1H, J$_1$=1.3 Hz, J$_2$=8 Hz), 7.68 (d, 1H, J=7.3 Hz), 7.77 (dd, 1H, J$_1$=2.1 Hz, J$_2$=8 Hz), 8.27 (dd, 1H, J$_1$=1.2 Hz, J$_2$=8 Hz). MS(ESI$^+$) 544.2 (MH$^+$). Anal. (C$_{29}$H$_{42}$N$_4$O$_4$S) cal. C, 64.18; H, 7.80, N, 10.32, S, 5.91. Found C, 64.36, H, 7.81, N, 10.08, S, 5.78.

Example 8

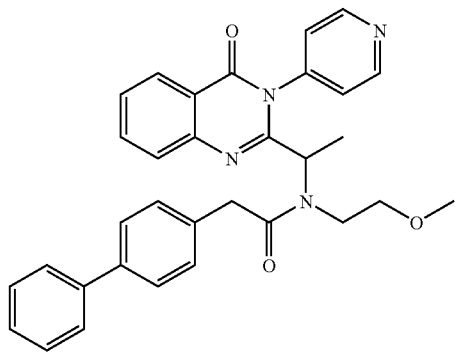

8.01

Compound 8.01. Compound 8.01 was prepared using the similar condition for synthesis of compound 4.01. Oil. Mixture of cis/trans amide rotamers (1/6), determined by $^1$H NMR (CDCl$_3$) 4.18 (q, 1H, J=7.0 Hz), 4.69 (q, 1H, J=7.0 Hz). MS(ESI$^+$) 533.2 (MH$^+$).

Example 9

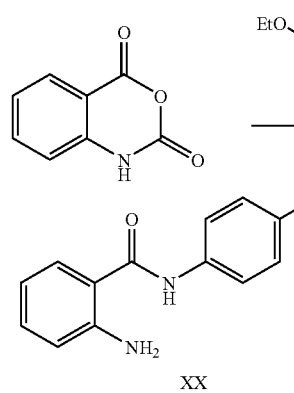

XX

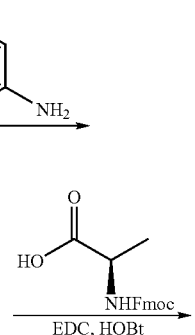

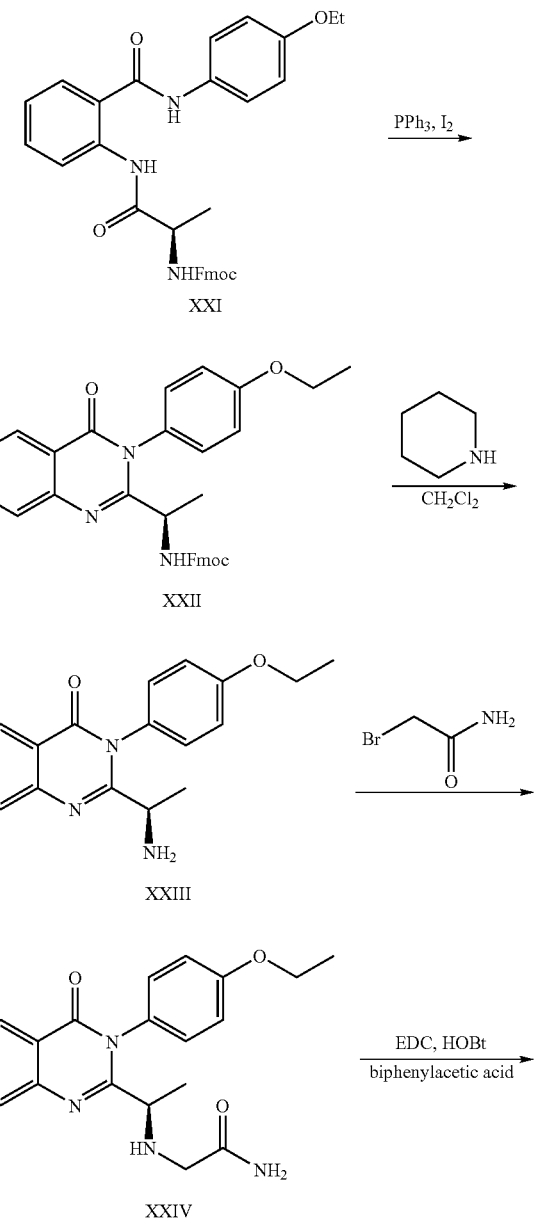

XXI

XXII

XXIII

XXIV

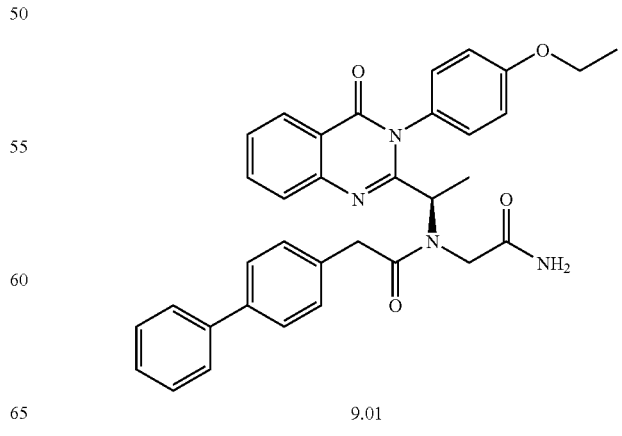

9.01

2-Amino-N-(4-ethoxy-phenyl)benzamide (XX). A mixture of isotoic anhydride (16.3 g, 100 mmol) and p-phenetidine (13.7 g, 100 mmol) was heated at 120° C. for 4 h. The reaction mixture after cooling was triturated with ether. The resulting solid was collected by suction to give compound XX, $^1$H NMR (CD$_3$OD) 1.37 (t, 3H, J=7.0 Hz), 4.01 (q, 2H, J=7.0 Hz), 6.67 (t, 1H, J=7.0 Hz), 6.78 (dd, 1H, J$_1$=1.2 Hz, J$_2$=8.2 Hz), 6.89 (m, 2H), 7.20 (dt, 1H, J$_1$=1.4 Hz, J$_2$=8.2 Hz), 7.47 (m, 2H), 7.56 (dd, 1H, J$_1$=1.4 Hz, J$_2$=9.3 Hz). MS(ESI$^+$) 257.3 (MH$^+$).

Synthesis of o-diamide XXI. To a mixture of compound XX (7.68 g, 30 mmol) and N-(9-fluorenylmethyloxycarbonyl)-D-alanine (10.26 g, 33 mmol) in CH$_2$Cl$_2$ (150 mL), was added EDAC (8.63 g, 45 mmol) and HOBt (1.38 g, 9 mmol). After stirring at room temperature overnight, the resulting solid was filtered and washed with ethyl ether to yield compound XXI (14.50 g). $^1$H NMR (CDCl$_3$) 1.37 (t, 3H, J=7.0 Hz), 1.48 (d, 3H, J=7.2 Hz), 3.89 (m, 2H), 4.26 (m, 2H), 4.45 (m, 2H), 5.50 (m, 1H), 6.76 (m, 2H), 7.17 (t, 1H, J=7.3 Hz), 7.25–7.76 (m, 12H), 8.62 (d, 1H, J=8.8 Hz), 11.43 (s, 1H). MS(ESI$^+$) 550.3 (MH$^+$).

4-Oxoquinazoline XXII. To a solution of diamide XXI (7.27 g, 13.27 mmol) in CH$_2$Cl$_2$, was added PPh$_3$ (17.40 g, 66.39 mmol), I$_2$ (16.52 g, 65.02 mmol) and N,N-diisopropylethylamine(17.12 g, 132.7 mmol). The reaction mixture was stirred at room temperature overnight. The resulting solid was filtered and washed with ethyl ether to yield compound XXII (4.83 g). $^1$H NMR (CDCl$_3$) 1.43 (t, 3H, J=7.0 Hz), 1.52 (d, 3H, J=7.2 Hz), 4.03 (m, 2H), 4.23 (m, 1H), 4.43 (m, 2H), 4.66 (m, 1H), 5.58 (m, 2H), 6.88 (m, 2H), 7.23–7.78 (m, 13H), 8.46 (d, 1H, J=8.8 Hz). MS(ESI$^+$) 532.3 (MH$^+$).

Compound XXIII. Piperidine (15 ml) was added to a solution of compound XXII (2.68 g, 5.05 mmol) in DMF (100 ml). After stirring at room temperature for 1 h, the mixture was poured into 150 ml of water, the aqueous layer was extracted with CH$_2$Cl$_2$, the combined organic extracts was dried over Na$_2$SO$_4$, filtered and concentrated. The residue was purified by chromatography to give a white solid (0.80 g). $^1$H NMR (CDCl$_3$) 1.30 (d, 3H, J=6.6 Hz), 1.46 (t, 3H, J=6.3 Hz), 3.82 (m, 1H), 4.10 (q, 2H, J=6.6 Hz), 7.03 (dd, 2H, J$_1$=1.9 Hz, J$_2$=7.0 Hz ), 7.18 (m, 2H), 7.47 (m, 1H), 7.75 (m, 2H), 8.26 (d, 1H, J=8 Hz). MS(ESI$^+$) 310.1 (MH$^+$).

Compound XXIV. To a mixture of compound XXIII (0.06 g, 0.19 mmol) and bromoacetamide (0.032 g, 0.23 mmol) in DMF (3 mL), was added K$_2$CO$_3$ (0.079 g, 0.57 mmol) and NaI (0.086 g, 0.57 mmol). After stirring at room temperature overnight, evaporated the solvent, the residue was dissolved in CH$_2$Cl$_2$, the organic layer was washed by water, brine, dried over NaSO$_4$ and removed in vacuo to give a yellow solid which was purified by chromatography to afford a white solid. $^1$H NMR (CDCl$_3$) 1.26 (t, 3H, J=7.2 Hz), 1.38(d, 3H, J=6.6 Hz), 3.46 9 br, 1H), 3.58 (br, 1H), 3.82 (m, 1H), 4.11 (m, 2H), 5.68 (br, 1H), 7.04 (m, 2H), 7.14 (m, 2H), 7.50 (m, 1H), 7.75 (m, 2H), 8.30 (d, 1H, J=8 Hz). MS(ESI$^+$) 367.3 (MH$^+$).

Synthesis of Compound 9.01

Compound 9.01 was prepared using the similar condition for synthesis of compound 3.02, white solid, mixture of cis/trans amide rotamers (1/5), determined by $^1$H NMR (CDCl$_3$) 4.85 (q, 1H, J=7.3 Hz), 5.35 (q, 1H, J=7.3 Hz). MS(ESI$^+$) 561.2 (MH$^+$).

Synthesis of Compound 9.02

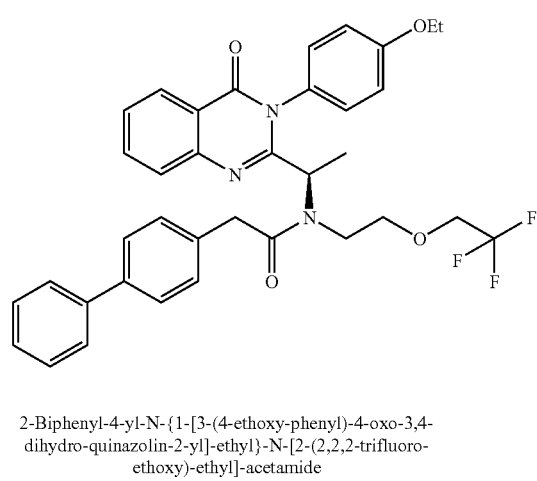

2-Biphenyl-4-yl-N-{1-[3-(4-ethoxy-phenyl)-4-oxo-3,4-dihydro-quinazolin-2-yl]-ethyl}-N-[2-(2,2,2-trifluoro-ethoxy)-ethyl]-acetamide Compound 9.02 was prepared following the synthesis of compound 9.01, oil, mixture of cis/trans amide rotamers (1/1), determined by $^1$H NMR (CDCl$_3$) 4.95 (m, 1H), 5.35 (m, 1H). MS(ESI$^+$) 630.2 (MH$^+$).

Synthesis of Compound 9.03

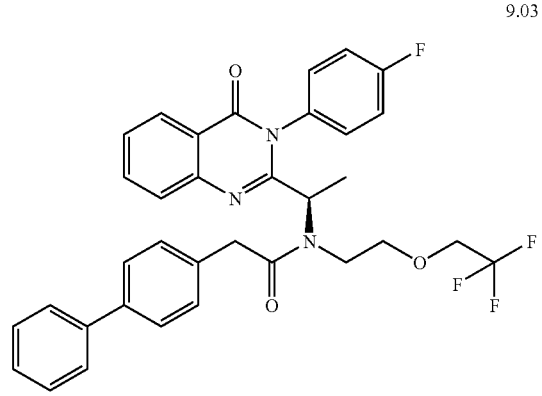

2-Biphenyl-4-yl-N-{1-[3-(4-fluoro-phenyl)-4-oxo-3,4-dihydro-quinazolin-2-yl]-ethyl}-N-[2-(2,2,2-trifluoro-ethoxy)-ethyl]-acetamide Compound 9.03 was prepared following the synthesis of compound 9.01. Yellow solid, m.p. 167.9° C., mixture of cis/trans amide rotamers (1/2), determined by $^1$H NMR (CDCl$_3$) 4.85 (q, 1H, J=7.0 Hz), 5.26 (q, 1H, J=7.0 Hz). MS(ESI$^+$) 604.2 (MH$^+$). Anal. (C$_{34}$H$_{29}$F$_4$N$_3$O$_3$) cal. C, 67.65; H, 4.84; N, 6.96. Found C, 67.80, H, 4.98, N, 6.97.

Synthesis of Compound 9.04

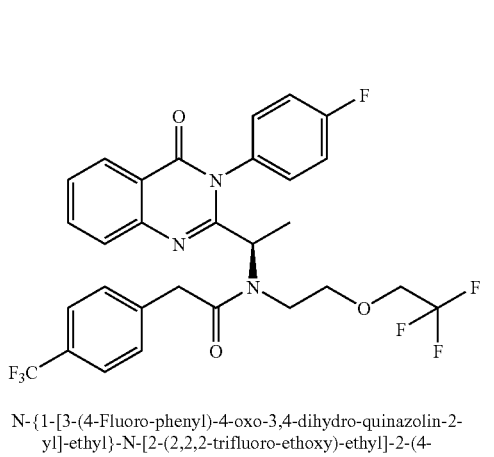

N-{1-[3-(4-Fluoro-phenyl)-4-oxo-3,4-dihydro-quinazolin-2-yl]-ethyl}-N-[2-(2,2,2-trifluoro-ethoxy)-ethyl]-2-(4-trifluoromethyl-phenyl)-acetamide Compound 9.04 was prepared following the synthesis of compound 9.01. white solid, m.p. 156.2° C. $^1$H NMR (DMSO, T=140° C.) 1.45(d, 3H, J=6.8 Hz), 3.59–3.73 (m, 6H), 3.92 (m, 2H), 5.14(q, 1H, J=6.8 Hz), 7.33 (m, 5H), 7.69 (m, 4H), 7.72 (d, 1H, J=8 Hz), 7.86 (m 1H), 8.14 (dd, 1H, $J_1$=1.2 Hz, $J_1$=8.4 Hz), At room temperature, mixture of cis/trans amide rotamers (1/2), determined by $^1$H NMR (CDCl$_3$) 4.88 (q, 1H, J=6.8 Hz), 5.27 (q, 1H, J=6.8 Hz). MS(ESI$^+$) 604.2 (MH$^+$). Anal. (C$_{29}$H$_{24}$F$_7$N$_3$O$_3$) cal. C, 58.49; H, 4.06; N, 7.06. Found C, 58.53, H, 4.18, N, 7.05.

Synthesis of Compound 9.05

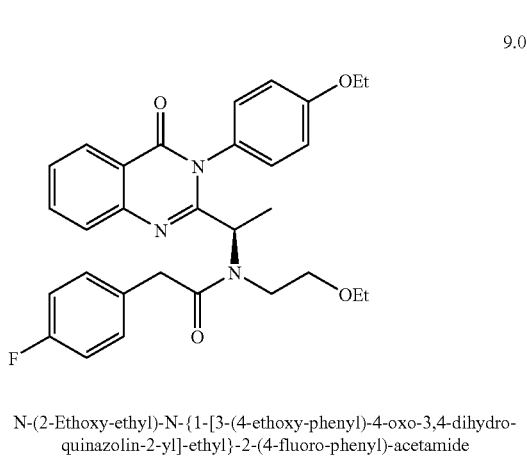

N-(2-Ethoxy-ethyl)-N-{1-[3-(4-ethoxy-phenyl)-4-oxo-3,4-dihydro-quinazolin-2-yl]-ethyl}-2-(4-fluoro-phenyl)-acetamide Compound 9.05 was prepared following the synthesis of compound 9.01. Yellow solid, mixture of cis/trans amide rotamers (1/1), determined by $^1$H NMR (CDCl$_3$) 4.88 (q, 1H, J=7.0 Hz), 5.35 (q, 1H, J=7.0 Hz). MS(ESI$^+$) 518.3 (M$^+$). Anal. (C$_{30}$H$_{32}$FN$_3$O$_4$) cal. C, 69.62; H, 6.23; N, 8.12. Found C, 69.40, H, 6.26, N, 7.98.

Synthesis of Compound 9.06

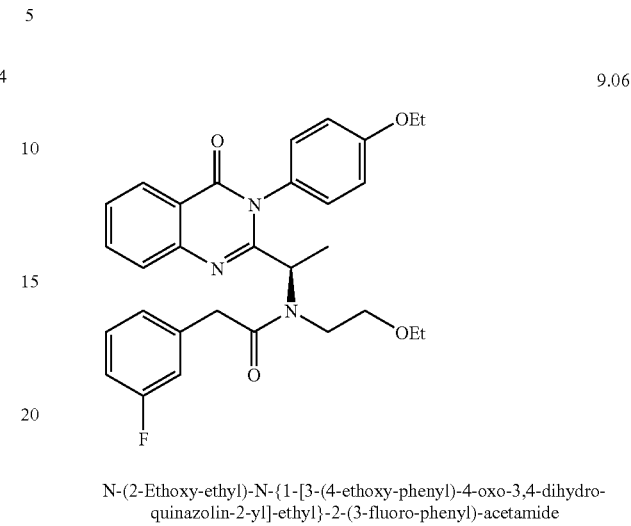

N-(2-Ethoxy-ethyl)-N-{1-[3-(4-ethoxy-phenyl)-4-oxo-3,4-dihydro-quinazolin-2-yl]-ethyl}-2-(3-fluoro-phenyl)-acetamide Compound 9.06 was prepared following the synthesis of compound 9.01. Yellow solid, mixture of cis/trans amide rotamers (1/1), determined by $^1$H NMR (CDCl$_3$) 4.90 (q, 1H, J=7.0 Hz), 5.35 (q, 1H, J=7.0 Hz). MS(ESI$^+$) 518.3 (MH$^+$). Anal. (C$_{30}$H$_{32}$FN$_3$O$_4$) cal. C, 69.62; H, 6.23; N, 8.12. Found C, 69.33, H, 6.20, N, 8.06.

Synthesis of Compound 9.07

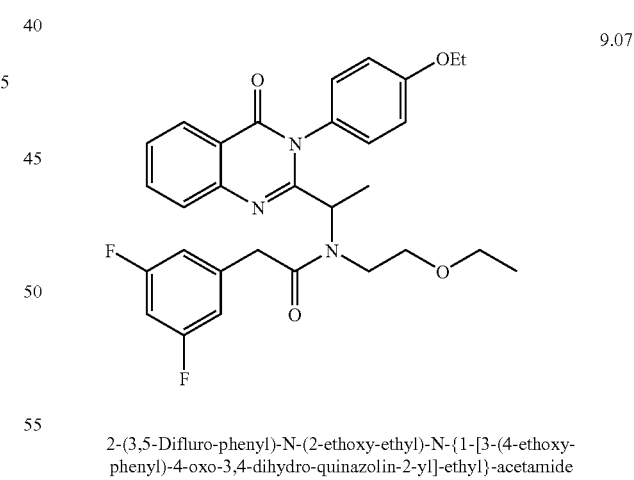

2-(3,5-Difluro-phenyl)-N-(2-ethoxy-ethyl)-N-{1-[3-(4-ethoxy-phenyl)-4-oxo-3,4-dihydro-quinazolin-2-yl]-ethyl}-acetamide Compound 9.07 was prepared following the synthesis of compound 9.01. Yellow solid, mixture of cis/trans amide rotamers (1/1), determined by $^1$H NMR (CDCl$_3$) 4.88 (q, 1H, J=7.0 Hz ), 5.37 (q, 1H, J=7.0 Hz ). MS(ESI$^+$) 536.3 (MH$^+$). Anal. (C$_{30}$H$_{31}$F$_2$N$_3$O$_4$) cal. C, 67.28; H, 5.83; N, 7.85. Found C, 67.28, H, 5.80, N, 7.78.

Synthesis of Compound 9.08

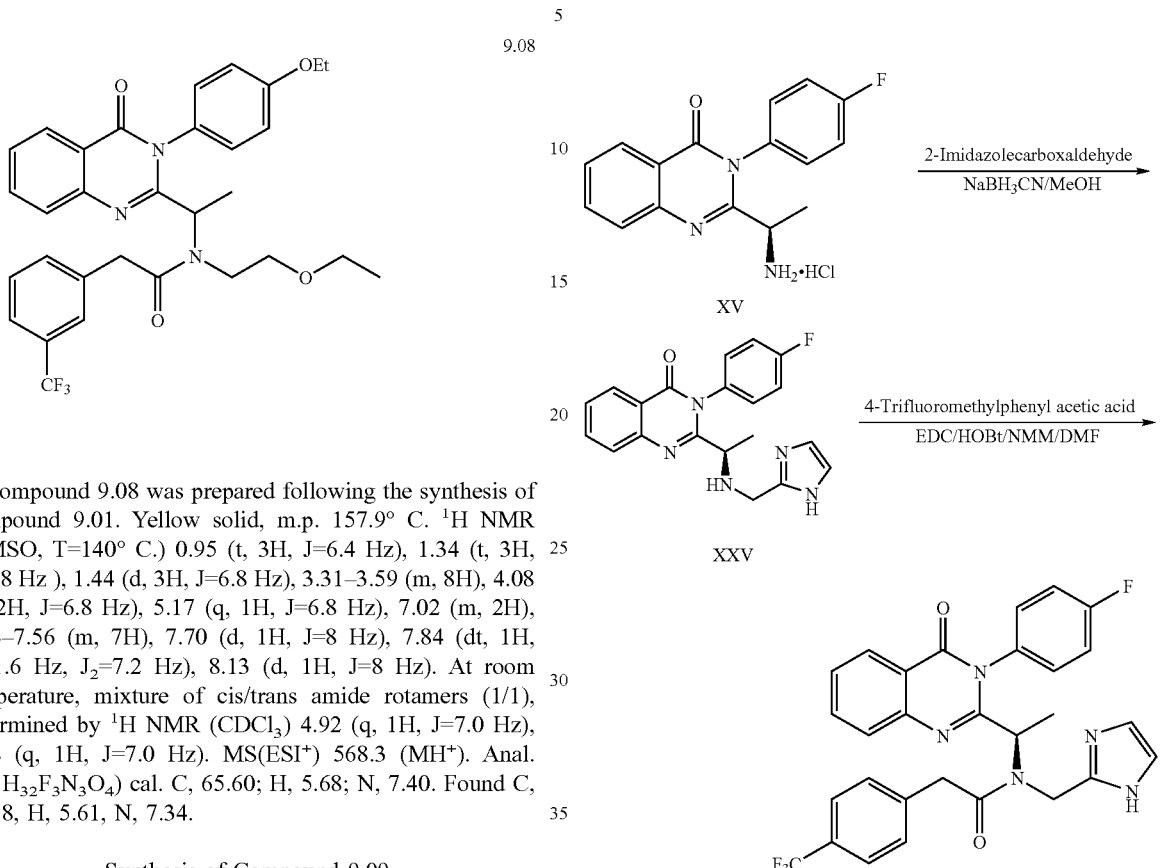

Compound 9.08 was prepared following the synthesis of compound 9.01. Yellow solid, m.p. 157.9° C. $^1$H NMR (DMSO, T=140° C.) 0.95 (t, 3H, J=6.4 Hz), 1.34 (t, 3H, J=6.8 Hz ), 1.44 (d, 3H, J=6.8 Hz), 3.31–3.59 (m, 8H), 4.08 (q, 2H, J=6.8 Hz), 5.17 (q, 1H, J=6.8 Hz), 7.02 (m, 2H), 7.24–7.56 (m, 7H), 7.70 (d, 1H, J=8 Hz), 7.84 (dt, 1H, $J_1$=1.6 Hz, $J_2$=7.2 Hz), 8.13 (d, 1H, J=8 Hz). At room temperature, mixture of cis/trans amide rotamers (1/1), determined by $^1$H NMR (CDCl$_3$) 4.92 (q, 1H, J=7.0 Hz), 5.38 (q, 1H, J=7.0 Hz). MS(ESI$^+$) 568.3 (MH$^+$). Anal. (C$_{31}$H$_{32}$F$_3$N$_3$O$_4$) cal. C, 65.60; H, 5.68; N, 7.40. Found C, 65.38, H, 5.61, N, 7.34.

Synthesis of Compound 9.09

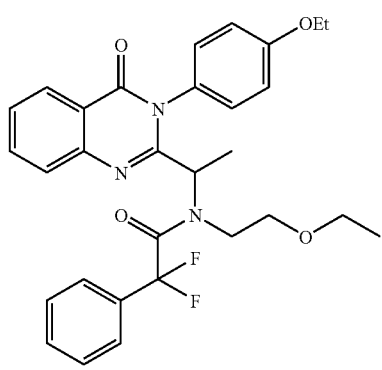

N-(2-Ethoxy-ethyl)-N-{1-[3-(4-ethoxy-phenyl)-4-oxo-3,4-dihydro-quinazolin-2-yl]-ethyl}-2,2-difluoro-2-phenyl-acetamide Compound 9.09 was prepared following the synthesis of compound 9.01. Colorless oil, $^1$H NMR (CDCl$_3$) 1.04 (t, 3H, J=6.9 Hz), 1.46 (m, 6H), 3.30 (m, 2H), 3.42 (m, 2H), 3.62 (m, 2H), 4.08 (q, 2H, J=7.0 Hz), 5.15 (q, 1H, J=7.0 Hz), 7.02 (m, 2H), 7.18 (m, 1H), 7.42–7.54 (m, 8H), 7.75 (m, 1H), 8.28 (d, 1H, J=7.8 Hz) MS(ESI$^+$) 536.3 (MH$^+$).

Example 10

Synthesis of Compound 10.01

A mixture of compound XV (160 mg, 0.5 mmol) and 2-imidazolcarboxaldehyde (58 mg, 0.6 mmol) in methanol (10 mL) was stirred at room temperature for 20 minutes. Then sodium cyanoborohydride (38 mg, 0.6 mmol) was added. The mixture was stirred at room temperature for 6 h. The reaction mixture was treated with EtOAc, and it was washed with sodium bicarbonate and brine, dried, and concentrated. The residue was purified by column (5% methanol and 1% conc. NH$_4$OH in 3:7 EtOAc/DCM) to give 120 mg of compound XXV. $^1$H NMR (CDCl$_3$) δ 8.25 (d, J=8.0 Hz, 1H), 7.78 (t, J=8.0 Hz, 1H), 7.70 (d, J=7.7 Hz, 1H), 7.49 (t, J=8.0 Hz, 1H), 7.20–7.05 (m, 4H), 6.93 (s, 2H), 3.94 (d, J=14.8 Hz, 1H), 3.77 (d, J=14.8 Hz, 1H), 3.38 (q, J=6.6 Hz, 1H), 1.25 (d, J=6.6 Hz, 3H).

EDC (123 mg, 0.64 mmol) was added to a mixture of compound XXV (115 mg, 0.32 mmol), 4-trifluoromethylphenyl acetic acid (65 mg, 0.32 mmol), HOBt (43 mg, 0.32 mmol), and NMM (0.07 mL, 0.64 mmol) in DMF (3 mL). The mixture was stirred at room temperature for 14 h. The reaction mixture was treated with EtOAc, and it was washed with sodium bicarbonate and brine, dried, and concentrated. The residue was purified by column (5% methanol and 1% conc. NH$_4$OH in 3:7 EtOAc/DCM) to give 100 mg of compound 10.01. MS (ESI$^+$) 550.2 [MH]$^+$.

Synthesis of Compound 10.02

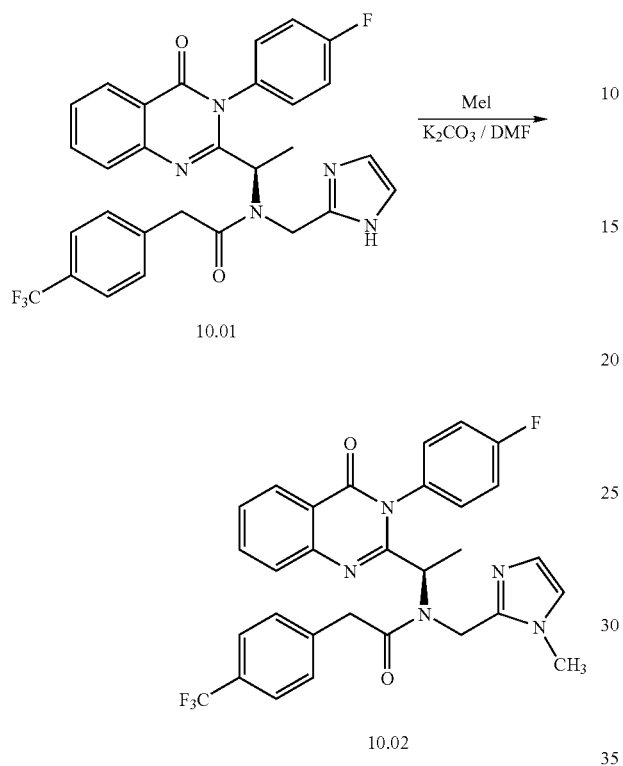

Potassium carbonate (97 mg, 0.7 mmol) was added to a mixture of compound 10.01 (38 mg, 0.07 mmol) and iodomethane (0.044 mL, 0.7 mmol) in DMF (2 mL). The mixture was stirred at room temperature for two days. DMF was evaporated under high vacuum, and the residue was taken by EtOAc. It was washed with brine, dried, and concentrated. The residue was purified by column (2% methanol and 0.5% conc. NH$_4$OH in 3:7 EtOAc/DCM) to give 15 mg of compound 10.02. MS (ESI$^+$) 564.2 [MH]$^+$.

Synthesis of 10.03

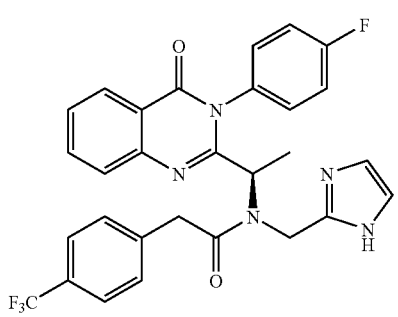

Compound 10.03 was prepared following the synthetic procedure for compound 10.01, described above. MS (ESI$^+$) 550.2 [MH]$^+$.

Synthesis of Compound 10.04

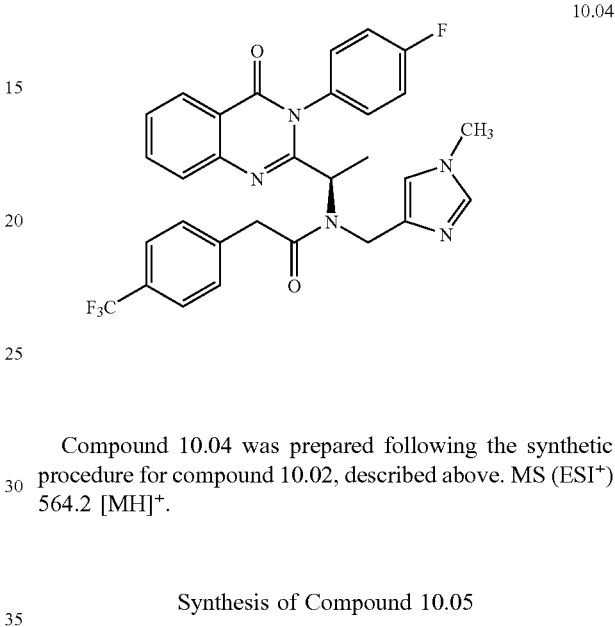

Compound 10.04 was prepared following the synthetic procedure for compound 10.02, described above. MS (ESI$^+$) 564.2 [MH]$^+$.

Synthesis of Compound 10.05

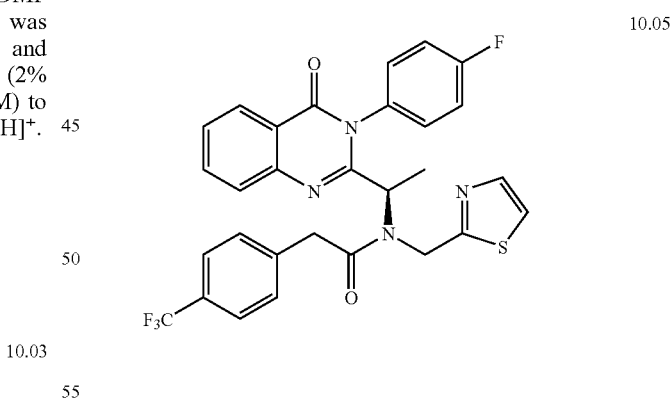

Compound 10.05 was prepared following the synthetic procedure of compound 10.01, described above. $^1$H NMR (d$_6$-DMSO, T=140° C.) δ 8.11 (d, J=8.0 Hz, 1H), 7.82 (t, J=8.1 Hz, 1H), 7.68 (d, J=8.1 Hz, 1H), 7.60–7.40 (m, 6H), 7.38–7.15 (m, 5H), 5.33 (bs, 1H), 5.02 (dd, J=11.4 Hz, 2H), 3.60 (bm, 2H), 1.45 (d, J=7.0 Hz, 3H). m.p. 173–174° C. MS (ESI$^+$) 567.2 [MH]$^+$. Anal. Calcd. for C$_{29}$H$_{22}$F$_4$N$_4$O$_2$S: C, 61.48; H, 3.91; N, 9.89. Found: C, 61.36; H, 4.08; N, 9.75.

Example 11

Preparation of Compound 11.01

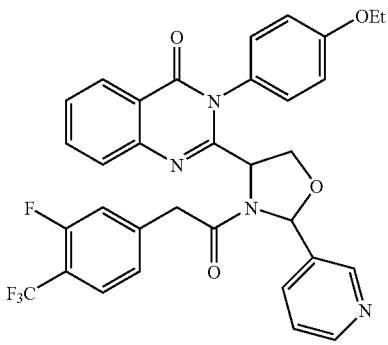

Figure 14:
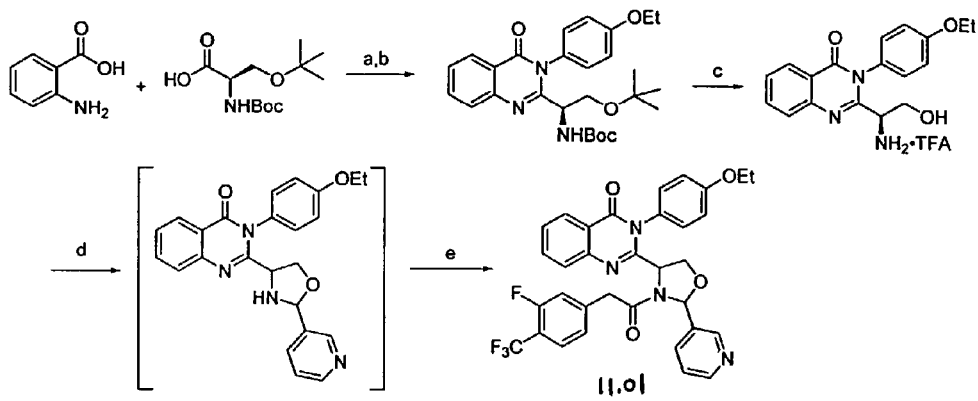
FIGS. 14–18 illustrate synthetic routes for exemplary compounds of the invention.
Figure 15:
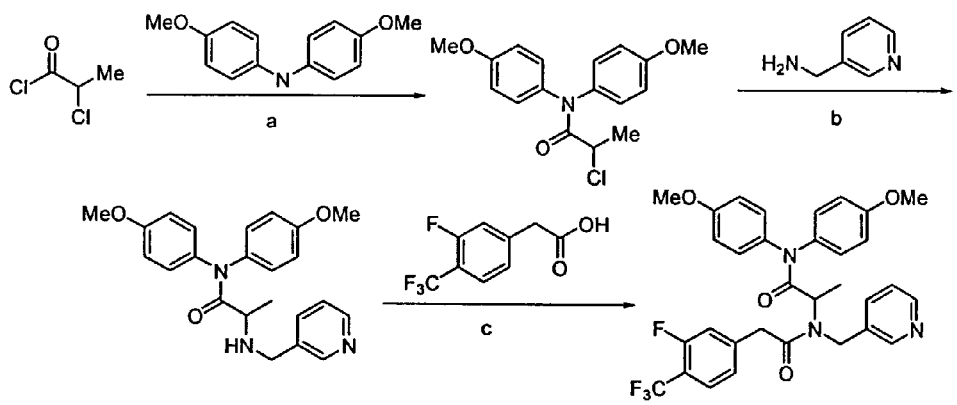

The synthesis of compound 11.01 is shown in FIG. 14. $^1$H NMR (d$_6$-DMSO, T=120° C.) δ 8.8–7.0 (m, 17H), 6.35 (s, 1H), 5.00 (m, 1H), 4.35 (m, 1H), 4.25–4.00 (m, 4H), 3.65 (m, 1H), 1.40 (t, 3H). MS (ESI$^+$) 619.1 [MH]$^+$.

Preparation of Compound 11.02

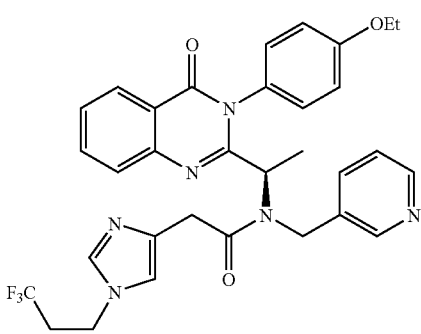

Figure 17:
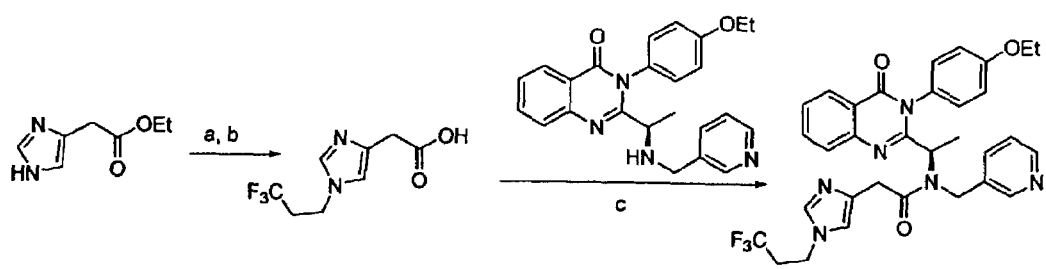

The synthesis of compound 11.02 is shown in FIG. 17. $^1$H NMR (d$_6$-DMSO, T=150° C.) δ 8.38 (m, 2H), 8.09 (m, 1H), 7.84 (m, 2H), 7.68 (m, 1H), 7.54 (m, 2H), 7.40–7.00 (m, 6H), 5.25 (m, 1H), 4.74 (m, 2H), 4.25 (m, 1H), 4.14 (m, 3H), 3.62 (m, 1H), 3.31 (m, 1H), 2.78 (m, 2H), 1.37 (m, 6H). MS (ESI$^+$) 605.3 [MH]$^+$.

Preparation of Compound 11.03

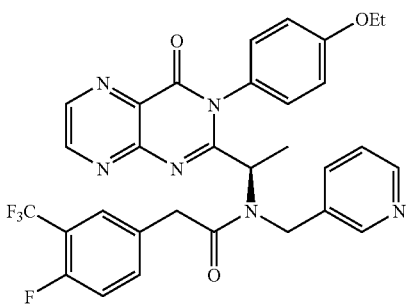

Figure 18:
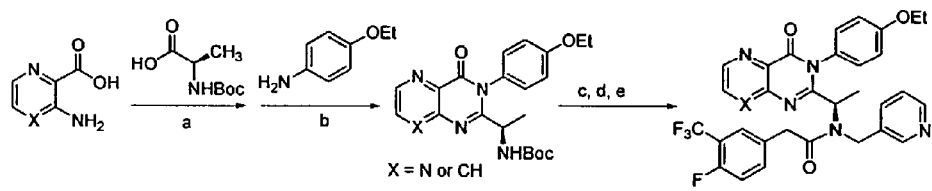

The synthesis of compound 11.03 is shown in FIG. 18. $^1$H NMR (d$_6$-DMSO, T=150° C.) δ 9.02 (s, 1H), 8.85 (s, 1H), 8.40 (s, 1H), 8.38 (m, 1H), 7.57 (m, 1H), 7.41 (m, 3H), 7.33–7.15 (m, 5H), 5.30 (q, 1H), 4.80 (dd, 2H), 4.13 (q, 2H), 3.64 (d, 1H), 3.21 (bs, 1H), 1.46 (d, 3H), 1.37 (t, 3H). MS (ESI$^+$) 607.2 [MH]$^+$.

Preparation of Compound 11.04

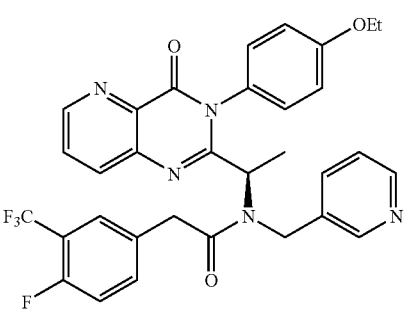

The synthesis of compound 11.04 is shown in FIG. 18. $^1$H NMR (d$_6$-DMSO, T=150° C.) δ 8.81 (d, 1H), 8.38 (s, 1H), 8.35 (m, 1H), 8.03 (m, 1H), 7.81 (m, 1H), 7.54 (m, 1H), 7.40 (m, 3H), 7.33–7.05 (m, 5H), 5.28 (q, 1H), 4.75 (dd, 2H), 4.13 (q, 2H), 3.60 (d, 1H), 3.19 (bs, 1H), 1.44 (d, 3H), 1.37 (t, 3H). MS (ESI$^+$) 606.2 [MH]$^+$.

Preparation of Compound 11.05

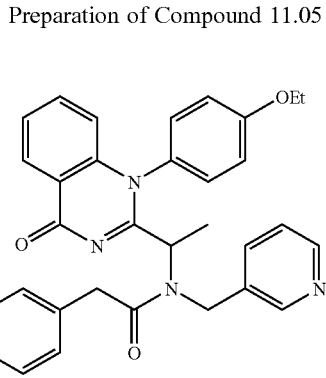

Figure 11:
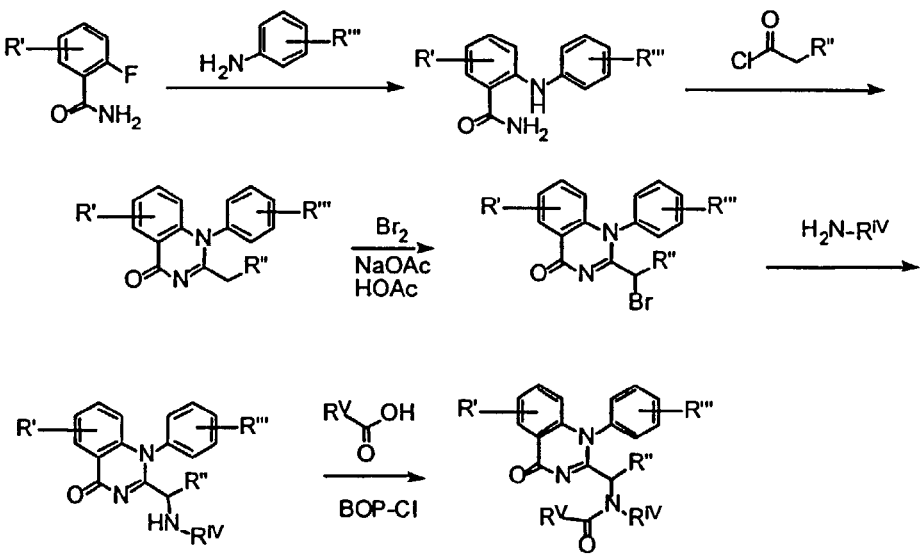
FIG. 11 illustrates the generic synthesis of regioisomeric (see FIG. 1) substituted quinazolinones of the invention.
Figure 12:
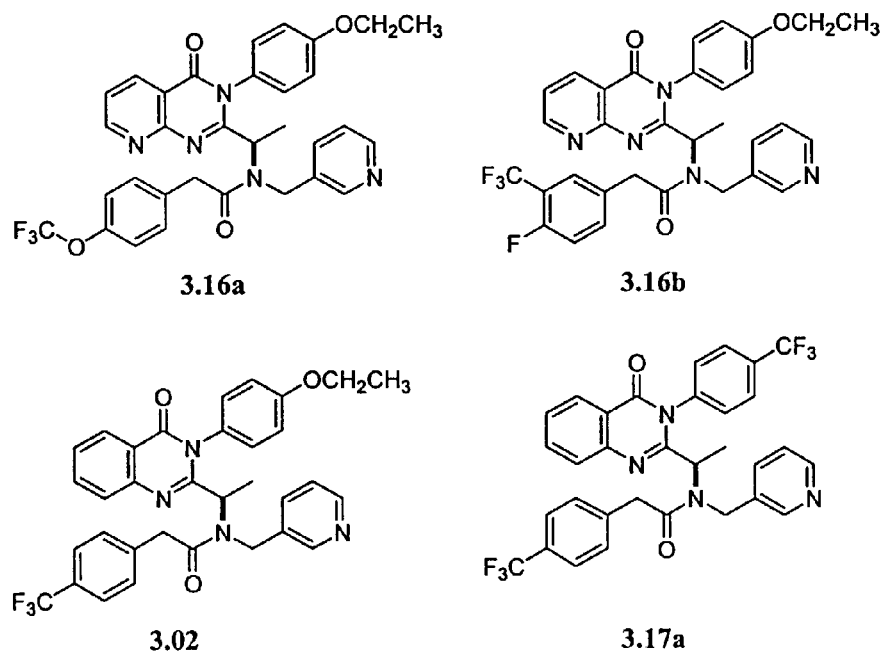
FIG. 12 illustrates exemplary structures for certain compounds of the invention.

The synthesis of compound 11.05 is shown in FIG. 11. $^1$H NMR (d$_6$-DMSO, T=150° C.) δ 8.47 (s, 1H), 8.37 (d, 1H), 8.13 (d, 1H), 7.66–7.25 (m, 7H), 7.25–7.10 (m, 6H), 6.59 (d, 1H), 5.25 (q, 1H), 4.86 (dd, 2H), 4.18 (q, 2H), 3.70 (d, 1H), 3.31 (bd, 1H), 1.41 (m, 6H). MS (ESI$^+$) 605.2 [MH]$^+$.

Preparation of Compound 11.06

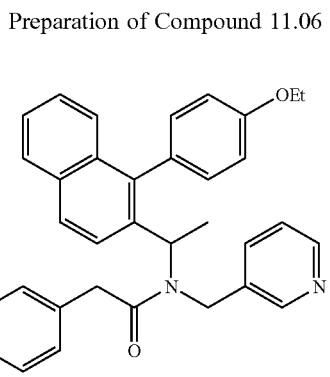

Figure 3:
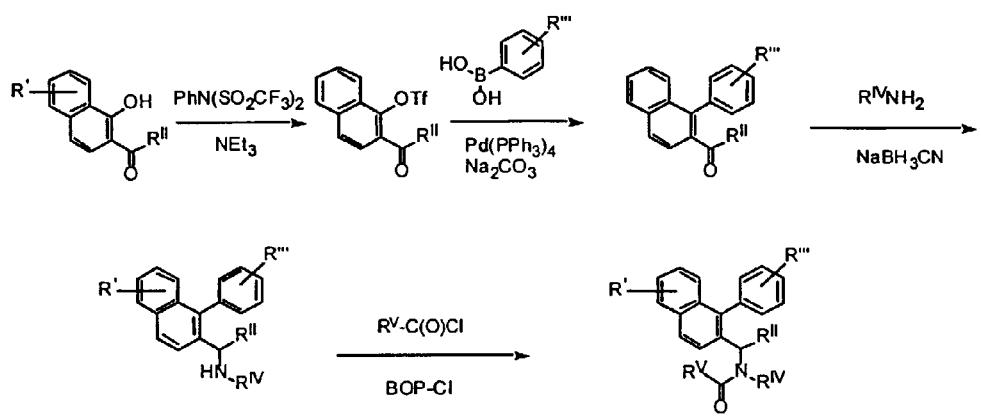
FIG. 3 illustrates the generic synthesis of substituted naphthalenes of the invention.
Figure 4:
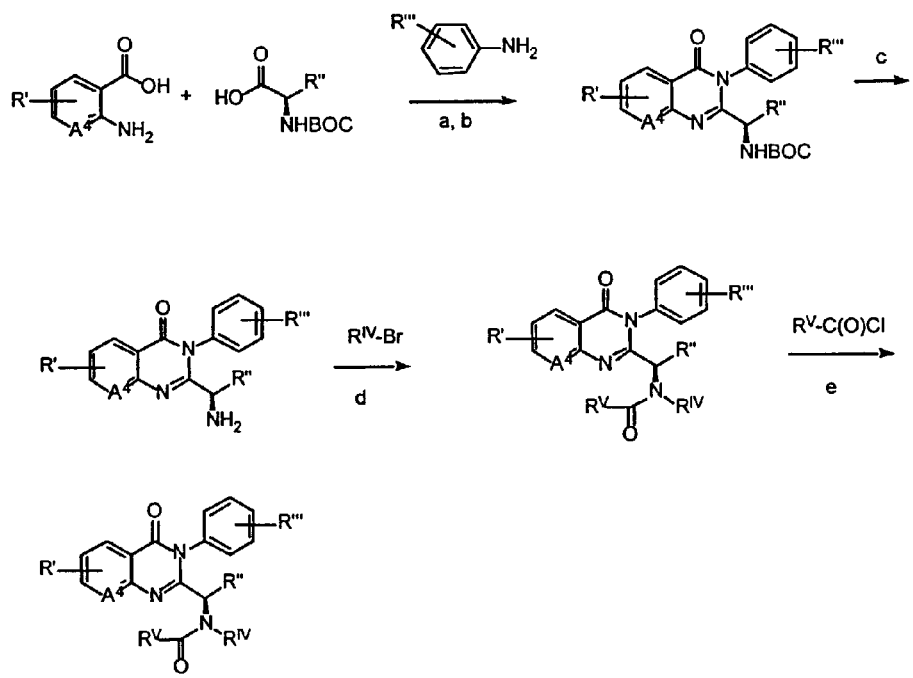
FIG. 4 illustrates the generic synthesis of enantiomerically enriched substituted quinazolinones and 8-azaquinazolinones of the invention.
Figure 5:
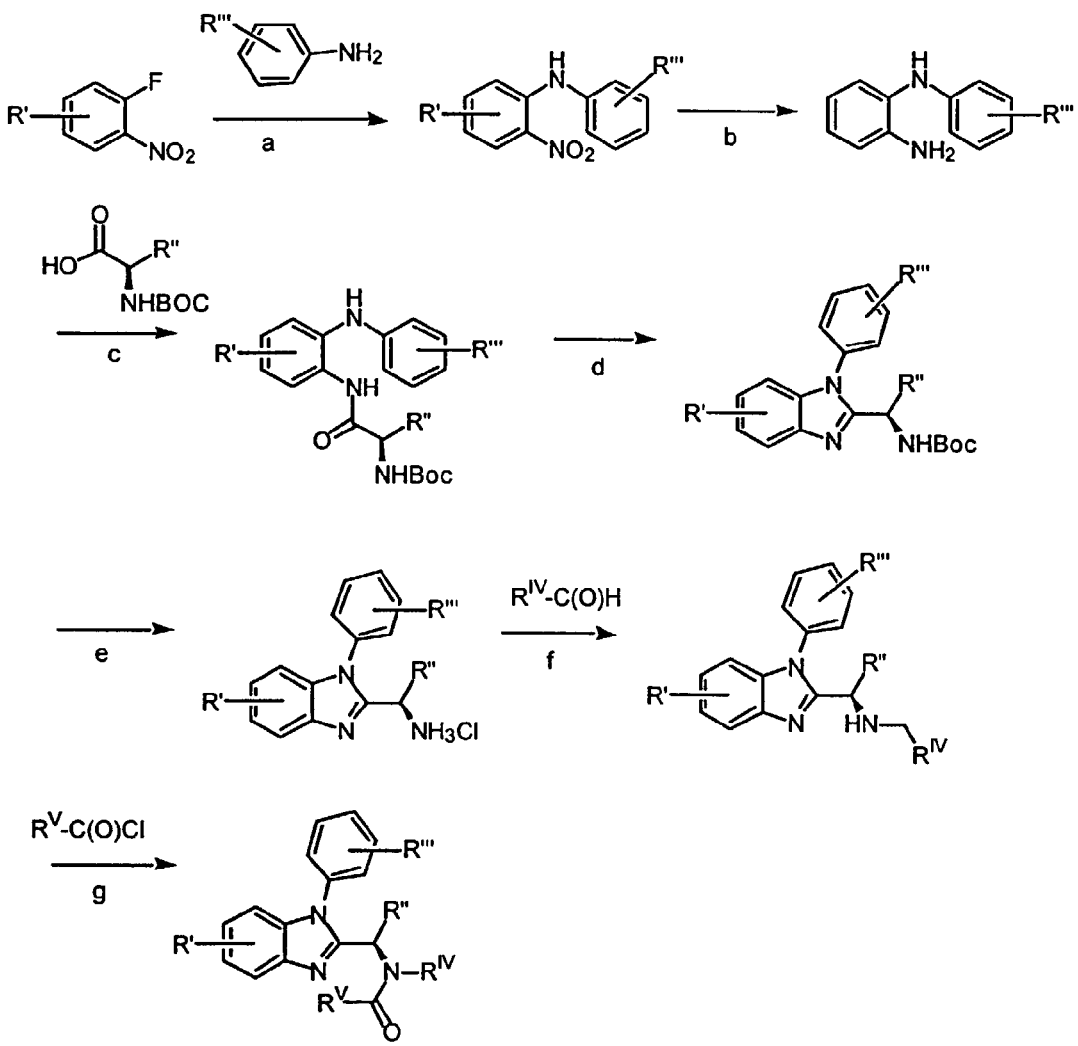
FIG. 5 illustrates the generic synthesis of substituted benzimidazoles of the invention.
Figure 6:
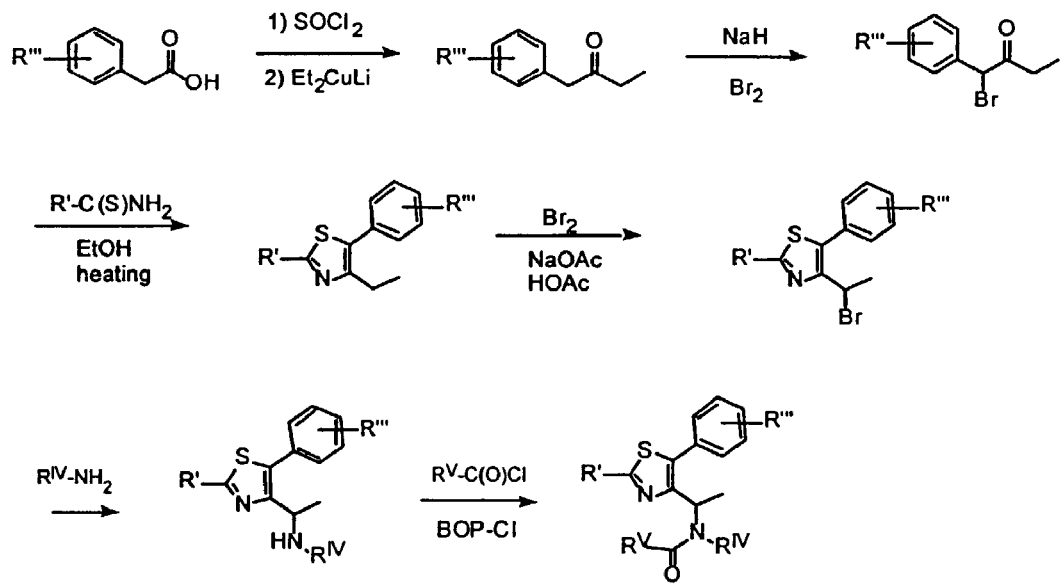
FIG. 6 illustrates the synthesis of two regioisomeric substituted thiazoles of the invention.
Figure 6:
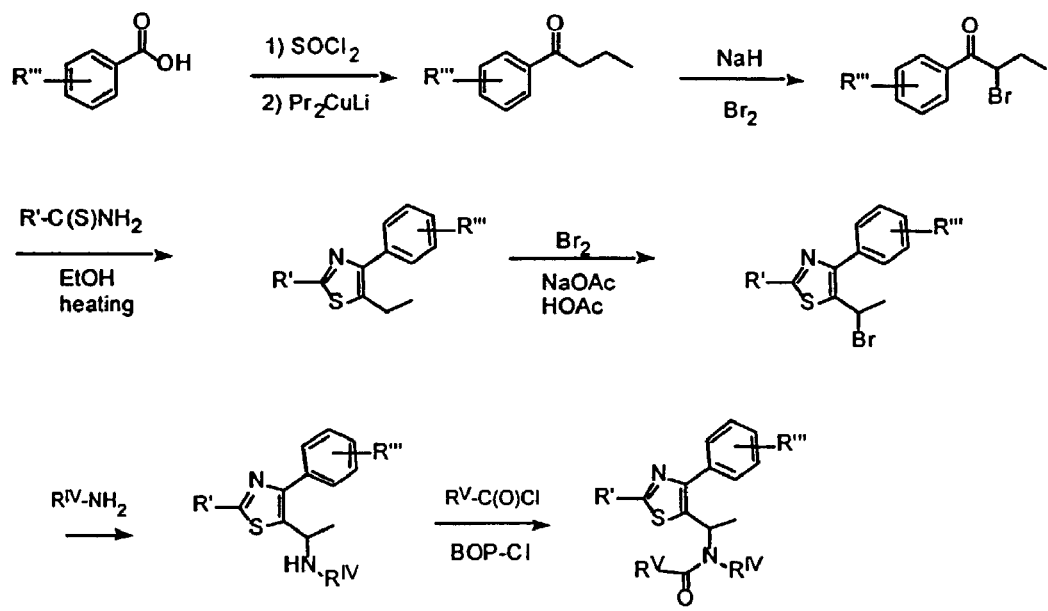
Figure 7:
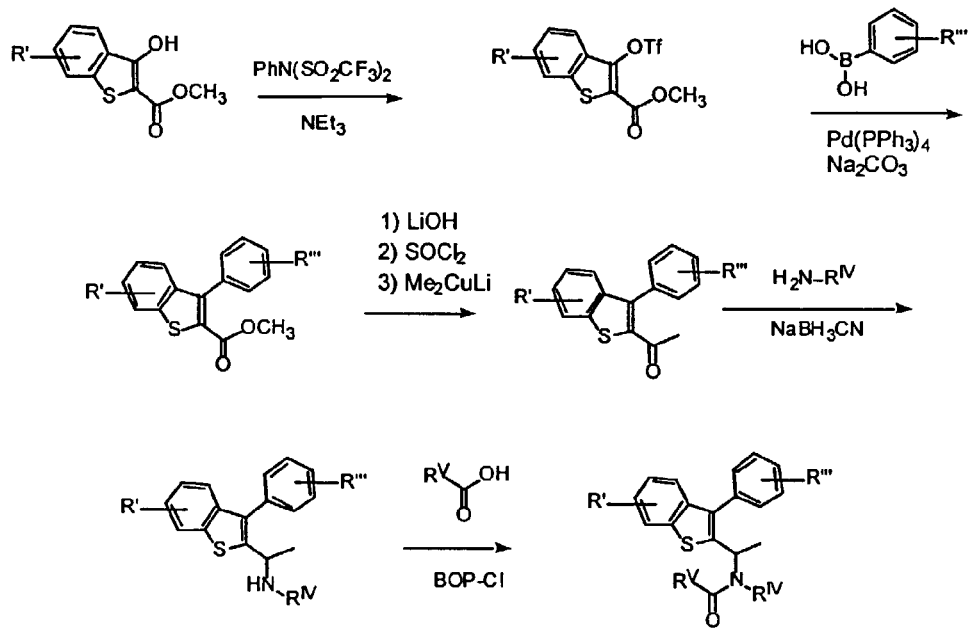
FIG. 7 illustrates the generic synthesis of substituted benzothiophenes of the invention.
Figure 8:
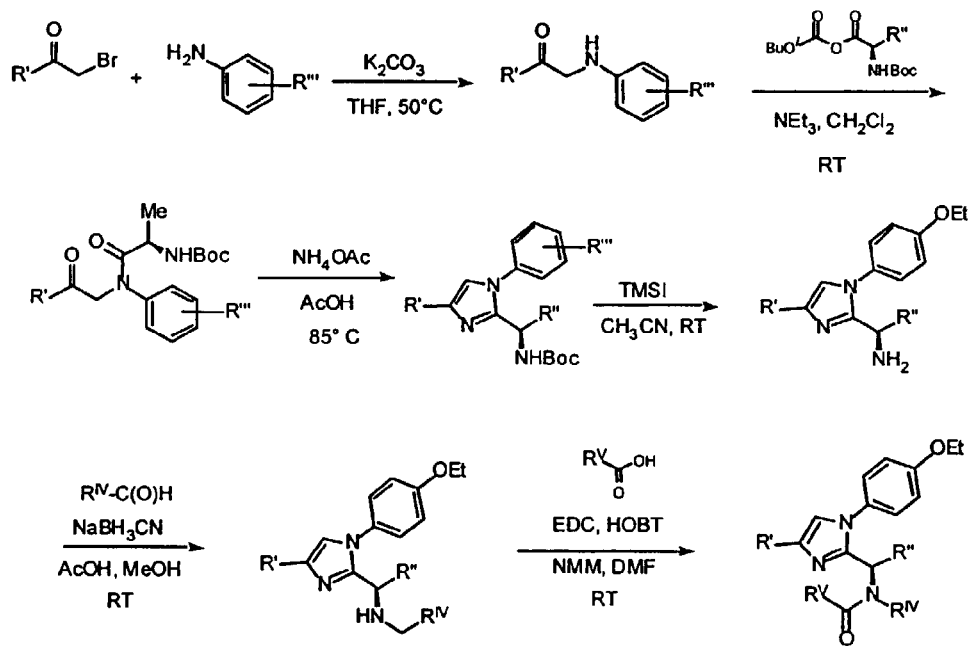
FIG. 8 illustrates the generic synthesis of substituted imidazoles of the invention.
Figure 9:
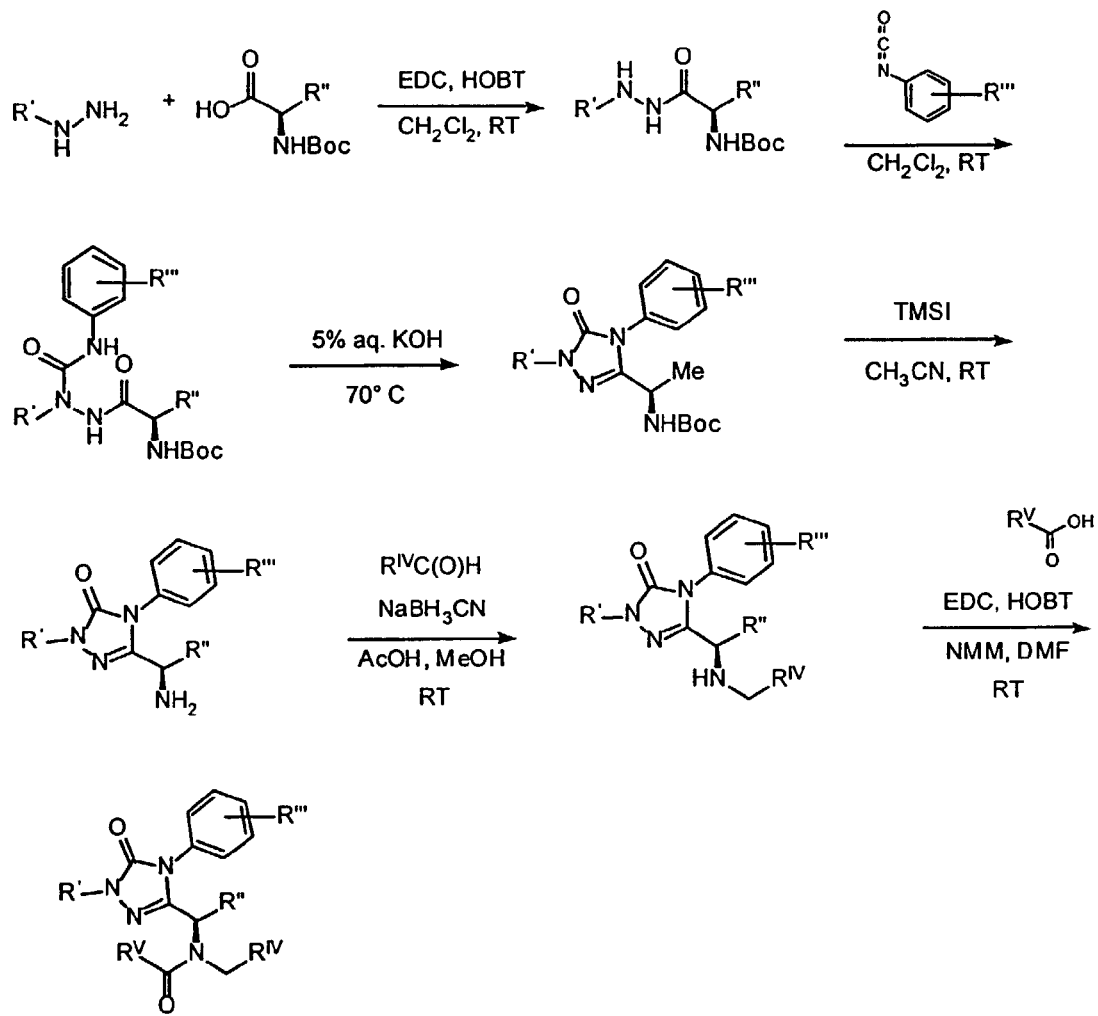
FIG. 9 illustrates the generic synthesis of substituted triazolinones of the invention.
Figure 10:
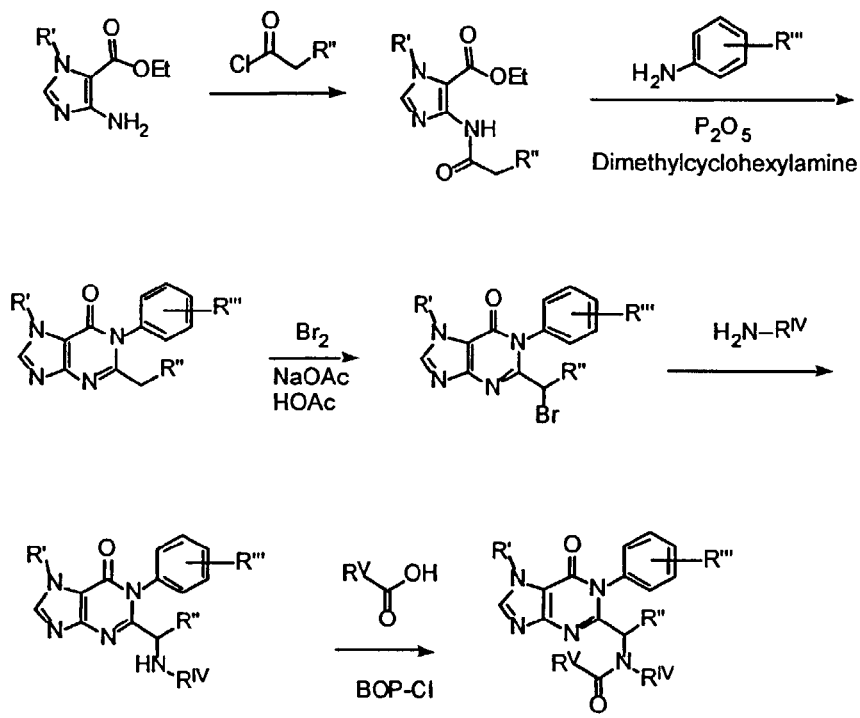
FIG. 10 illustrates the generic synthesis of substituted purine-6-ones of the invention.

The synthesis of compound 11.06 is shown in FIG. 3. $^1$H NMR (d$_6$-DMSO, T=150° C.) δ 8.30 (m, 1H), 8.22 (s, 1H), 7.95 (m, 2H), 7.83 (m, 1H), 7.57 (m, 1H), 7.48 (m, 1H), 7.36 (m, 2H), 7.24 (m, 2H), 7.15–6.95 (m, 6H), 5.45 (q, 1H), 4.50 (dd, 2H), 4.14 (q, 2H), 3.57 (d, 1H), 3.05 (bd, 1H), 1.54 (d, 3H), 1.38 (t, 3H). MS (ESI$^+$) 587.3 [MH]$^+$.

Preparation of Compound 11.07

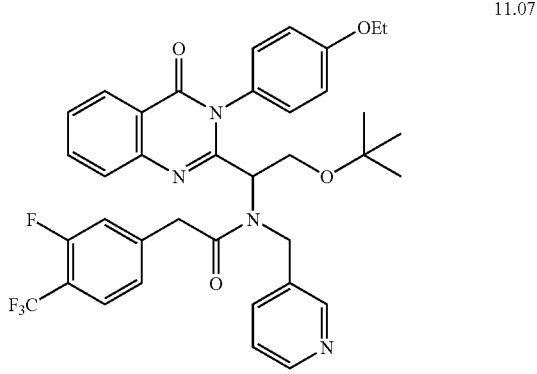

11.07

The synthesis of compound 11.07 is shown in FIG. 1. $^1$H NMR (CDCl$_3$) δ 8.30 (m, 3H), 7.85 (m, 2H), 7.52 (m, 3H), 7.23 (m, 1H), 7.11 (m, 1H), 7.03 (m, 2H), 6.82 (d, 1H), 6.75 (d, 1H), 6.54 (m, 1H), 5.07 (q, 1H), 4.60 (dd, 2H), 4.05 (m, 3H), 3.82 (m, 2H), 1.85 (d, 1H), 1.45 (t, 3H), 1.17 (s, 9H). MS (ESI$^+$) 677.3 [MH]$^+$.

Example 12

This example illustrates a CXCR3 binding assay that can be used for evaluating the compounds of the present invention.

Unless otherwise noted, all reagents used are available from commercial sources (e.g., Sigma). Test compounds are diluted in DMSO to a concentration that is 40-times the intended final assay concentration; 5 μL are transferred to each well of a 96-well flat-bottomed polypropylene plate (e.g., from Greiner, Inc.). CXCR3-expressing cells obtained from ChemoCentryx were used in the assays to generate the data set forth in the table provided in FIG. 19. The cells were resuspended in assay buffer (25 mM Hepes, 80 mM NaCl, 1 mM CaCl2, 5 mM MgCl2, 0.2% bovine serum albumin, pH 7.1, stored at 4° C.) at 5 million cells per mL; 100 μL of this cell suspension is then transferred to each well of a 96-well plate containing the diluted test compounds. 125I-labelled chemokine (purchased from commercial sources, e.g., Amersham, PE Life Sciences) is diluted in assay buffer to a concentration of approximately 60 pM; 100 μL of this chemokine solution is transferred to each well of a 96-well plate containing compounds and cell suspension. The plates are sealed with commercially available foil plate seals (e.g., from E&K Scientific), and stored at 4° C. for 2 to 4 h, shaking gently. At the end of this incubation period, the contents of the assay plates are transferred to GF/B filter plates (Packard) that have been pre-coated by dipping into a solution containing 0.3% polyethyleneimine (Sigma), using a cell harvester (Packard), and washing twice with wash buffer (25 mM Hepes, 500 mM NaCl, 1 mM CaCl2, 5 mM MgCl2, pH 7.1, stored at room temperature). The filter plates are sealed on the bottom with plate seals (Packard), 50 μL of Microscint-20 scintillation fluid (Packard) is added to each well, and the top of the plates are sealed with clear plastic (TopSeal A, Packard). The plates are counted on a scintillation counter, such as a Packard TopCount. To measure non-specific binding, 4 wells containing unlabelled "cold" chemokine were included on each 96-well plate. To measure maximum binding, 4 wells containing 5 μL of DMSO, 100 μL of cell suspension and 100 μL of 125I-labelled chemokine solution were included on each 96-well plate. Data were analyzed using commercially available software (e.g., Excel from Microsoft, Prism from GraphPad Software Inc.).

Other assays may be used to identify compounds that modulate CXCR3 chemokine receptor activity, for example, binding assays (see, e.g., Weng et al. (1998) *J. Biol. Chem.* 273:18288–18291, Campbell et al. (1998) *J. Cell Biol.* 141:1053–1059, Endres et al. (1999) *J. Exp. Med.* 189: 1993–1998 and Ng et al. (1999) *J. Med. Chem.* 42:4680–4694), calcium flux assays (see, e.g., Wang et al. (2000) *Mol. Pharm.* 57:1190–1198 and Rabin et al. (1999) *J. Immunol.* 162:3840–3850) and chemotaxis assays (see, e.g., Albanesi et al. (2000) *J. Immunol.* 165:1395–1402 and Loetscher et al. (1998) *Eur. J. Immunol.* 28:3696–3705).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula:

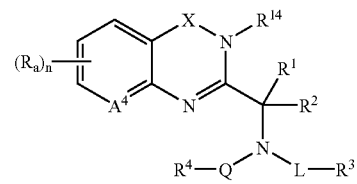

or a pharmaceutically acceptable salt, racemate, diastereomer or geometric isomer thereof wherein A$_4$ is C;

X is —C(O)—;

R$^1$ and R$^2$ are each members independently selected from the group consisting of H, and (C1–C4) alkyl;

R$^3$ is selected from the group consisting of substituted or unsubstituted pyridyl and substituted or unsubstituted imidazolyl;

R$^4$ is a member selected from the group consisting of (C$_1$–C$_{20}$)alkyl, (C$_2$–C$_{20}$)heteroalkyl, heteroaryl, aryl, heteroaryl(C$_1$–C$_6$)alkyl, heteroaryl(C$_2$–C$_6$)heteroalkyl, aryl(C$_1$–C$_6$)alkyl and aryl(C$_2$–C$_6$)heteroalkyl;

R$^{14}$ is substituted or unsubstituted aryl or substituted or unsubstituted heteroaryl;

Q is —C(O)—;

L is (C$_1$–C$_8$)alkylene;

the subscript n is an integer of from 0 to 4; and each R$_a$ is independently selected from the group consisting of halogen, —OR', —OC(O)R', —NR'R", —SR', —R', —CN, —NO$_2$, —CO$_2$R', —CONR'R", —C(O)

R', —OC(O)NR'R'', —NR''C(O)R', —NR''C(O)$_2$R', —NR'—C(O)NR''R''', —NH—C(NH$_2$)=NH, —NR'C(NH$_2$)=NH, —NH—C(NH$_2$)=NR', —S(O)R', —S(O)$_2$R', —S(O)$_2$NR'R'', —N$_3$, —CH(Ph)$_2$, perfluoro(C$_1$–C$_4$)alkoxy, and perfluoro(C$_1$–C$_4$)alkyl, wherein R', R'' and R''' are each independently selected from the group consisting of H, (C$_1$–C$_8$)alkyl, (C$_2$–C$_8$) heteroalkyl, unsubstituted aryl, unsubstituted heteroaryl, (unsubstituted aryl)-(C$_1$–C$_4$)alkyl, and (unsubstituted aryl)oxy-(C$_1$–C$_4$)alkyl.

2. The compound of claim 1, wherein R$^4$ is heteroaryl (C$_1$–C$_6$)alkyl or aryl(C$_1$–C$_6$)alkyl.

3. The compound of claim 1, wherein R$^4$ is substituted or unsubstituted benzyl, wherein said substituents are selected from the group consisting of halogen, halo(C$_1$–C$_4$)alkyl, halo(C$_1$–C$_4$)alkoxy, cyano, nitro, and phenyl.

4. The compound of claim 1, wherein R$^{14}$ is a substituted or unsubstituted member selected from the group consisting of phenyl, pyridyl, thiazolyl, thienyl, and pyrimidinyl.

5. The compound of claim 1, wherein R$^{14}$ is a substituted or unsubstituted member selected from the group consisting of phenyl, pyridyl, thiazolyl, thienyl, and pyrimidinyl and R$^3$ is selected from the group consisting of substituted or unsubstituted pyridyl and substituted or unsubstituted imidazolyl.

6. The compound of claim 1, wherein R$^{14}$ is selected from the group consisting of substituted phenyl, substituted pyridyl, substituted thiazolyl and substituted thienyl, wherein the substituents are selected from the group consisting of cyano, halogen, (C$_1$–C$_8$)alkoxy, (C$_1$–C$_8$)alkyl, (C$_2$–C$_8$)heteroalkyl, CONH$_2$, methylenedioxy and ethylenedioxy.

7. The compound of claim 1, wherein R$^{14}$ is substituted phenyl, wherein the substituents are selected from the group consisting of cyano, halogen, (C$_1$–C$_8$)alkoxy, (C$_1$–C$_8$)alkyl, (C$_2$–C$_8$)heteroalkyl, CONH$_2$, methylenedioxy and ethylenedioxy.

8. The compound of claim 1, wherein R$^4$ is substituted or unsubstituted benzyl, wherein said substituents are selected from the group consisting of halogen, halo(C$_1$–C$_4$)alkyl, halo(C$_1$–C$_4$)alkoxy, cyano, nitro, and phenyl, and R$^{14}$ is substituted phenyl, wherein the substituents are selected from the group consisting of cyano, halogen, (C$_1$–C$_8$)alkoxy, (C$_1$–C$_8$)alkyl, (C$_2$–C$_8$)heteroalkyl, CONH$_2$, methylenedioxy and ethylenedioxy.

9. The compound of claim 1, wherein R$^1$ is selected from the group consisting of methyl, ethyl and propyl, and R$^2$ is hydrogen.

10. The compound of claim 1, wherein R$^1$ and R$^2$ are each methyl.

11. The compound of claim 1, wherein L is (C$_1$–C$_4$)alkylene.

12. The compound of claim 1, wherein R$^1$ and R$^2$ are each independently selected from the group consisting of H, methyl and ethyl; R$^{14}$ is phenyl; L is methylene, ethylene or propylene; and R$^4$ is substituted or unsubstituted benzyl, wherein said substituents are selected from the group consisting of halogen, halo(C$_1$–C$_4$)alkyl, halo(C$_1$–C$_4$)alkoxy, cyano, nitro, and phenyl.

13. The compound of claim 1, wherein R$^1$ and R$^2$ are each members independently selected from the group consisting of H, methyl and ethyl; R$^4$ substituted or unsubstituted benzyl wherein said substituents are selected from the group consisting of halogen, halo(C$_1$–C$_4$)alkyl, halo(C$_1$–C$_4$) alkoxy, cyano, nitro, and phenyl; R$^{14}$ is substituted or unsubstituted phenyl; and L is methylene, ethylene or propylene.

14. The compound of claim 1 which is selected from the group consisting of:

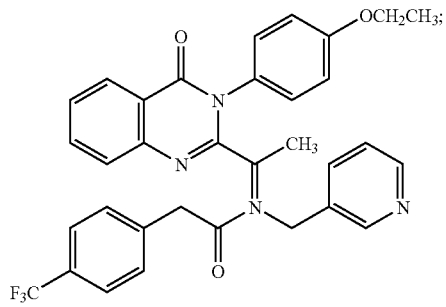

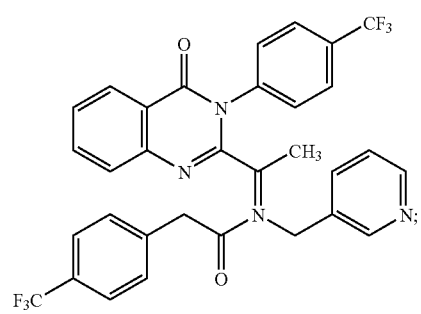

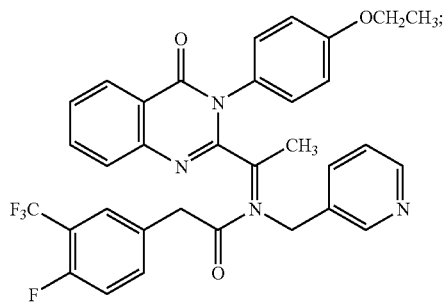

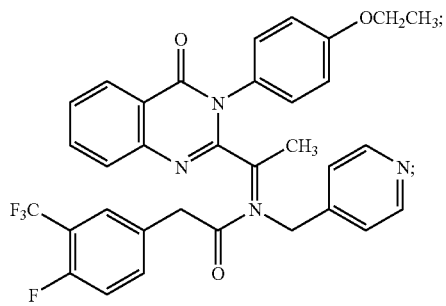

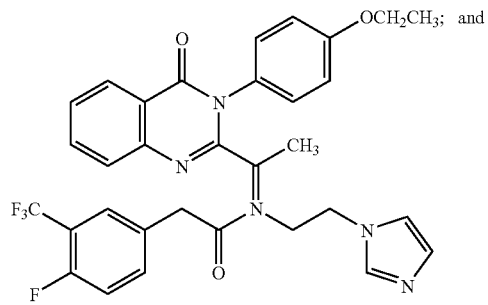

-continued

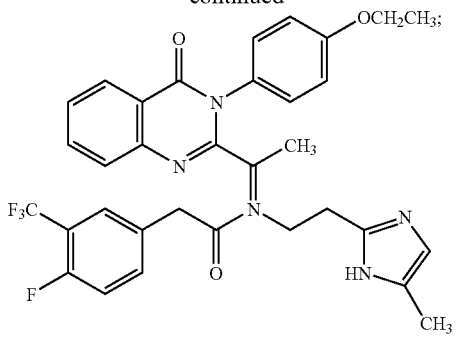

or a pharmaceutically acceptable salt, racemate, diastereomer or geometric isomer thereof.

15. A pharmaceutical composition comprising the compound of claim 1 or 14, and a pharmaceutically acceptable carrier or diluent.

16. A composition comprising the compound of claim 1 or 14, and a carrier or diluent.

17. A method for the modulation of CXCR3 function in a cell, comprising contacting said cell with a compound of claim 1 or 14.

18. A method for the modulation of CXCR3 function, comprising contacting a CXCR3 protein with a compound of claim 1 or 14.

* * * * *